US007285269B2

(12) United States Patent
Babcook et al.

(10) Patent No.: US 7,285,269 B2
(45) Date of Patent: Oct. 23, 2007

(54) ANTIBODIES DIRECTED TO TUMOR NECROSIS FACTOR

(75) Inventors: John S. Babcook, Vancouver (CA); Jaspal S. Kang, Surrey (CA); Orit Foord, Foster-City, CA (US); Larry Green, San Francisco, CA (US); Xiao Feng, Union City, CA (US); Scott Klakamp, Fremont, CA (US); Mary Haak-Frendscho, Newark, CA (US); Palaniswami Rathanaswami, Vancouver (CA); Craig Pigott, Cambridge (GB); Meina Liang, Danville, CA (US); Yen-Wah Lee, Newark, CA (US); Kathy Manchulenko, Port Coquitlam (CA); Raffaella Faggioni, Pleasanton, CA (US); Giorgio Senaldi, Dublin, CA (US); Qiaojuan Jane Su, San Jose, CA (US)

(73) Assignee: Amgen Fremont, Inc., Fremont, CA (US)

(*) Notice: Subject to any disclaimer, the term of this patent is extended or adjusted under 35 U.S.C. 154(b) by 137 days.

(21) Appl. No.: 10/727,155

(22) Filed: Dec. 2, 2003

(65) Prior Publication Data

US 2005/0049402 A1 Mar. 3, 2005

Related U.S. Application Data

(60) Provisional application No. 60/430,729, filed on Dec. 2, 2002.

(51) Int. Cl.
*A61K 39/395* (2006.01)
*C07K 16/24* (2006.01)

(52) U.S. Cl. .............. 424/142.1; 424/183.1; 424/181.1; 424/145.1; 530/388.23; 530/388.73; 530/388.75

(58) Field of Classification Search .................. None
See application file for complete search history.

(56) References Cited

U.S. PATENT DOCUMENTS

| | | | |
|---|---|---|---|
| 4,309,418 A | 1/1982 | Green | |
| 4,390,468 A | 6/1983 | Sasaki et al. | |
| 4,447,355 A | 5/1984 | Sakamoto et al. | |
| 4,457,916 A | 7/1984 | Hayashi et al. | |
| 4,495,282 A | 1/1985 | Ohnishi et al. | |
| 4,529,594 A | 7/1985 | Hayashi et al. | |
| 4,603,106 A | 7/1986 | Cerami et al. | |
| 4,650,674 A | 3/1987 | Aggarwal et al. | |
| 4,656,132 A | 4/1987 | Ben-Bassat et al. | |
| 4,677,063 A | 6/1987 | Mark et al. | |
| 4,677,064 A | 6/1987 | Mark et al. | |
| 4,677,197 A | 6/1987 | Lin et al. | |
| 4,678,773 A | 7/1987 | Usami et al. | |
| 4,684,623 A | 8/1987 | Larrick et al. | |
| 4,736,020 A | 4/1988 | Hillen et al. | |
| 4,770,995 A | 9/1988 | Rubin et al. | |
| 4,777,241 A | 10/1988 | Irikura et al. | |
| 4,777,242 A | 10/1988 | Nelles | |
| 4,791,101 A | 12/1988 | Adolf | |
| 4,822,605 A | 4/1989 | Power | |
| 4,822,776 A | 4/1989 | Cerami et al. | |
| 4,863,727 A | 9/1989 | Zimmerman et al. | |
| 4,870,163 A | 9/1989 | Rubin et al. | |
| 4,871,663 A | 10/1989 | Oshima et al. | |
| 4,879,226 A | 11/1989 | Wallace et al. | |
| 4,880,915 A | 11/1989 | Kajihara et al. | |
| 4,894,225 A | 1/1990 | Zimmerman | |
| 4,894,334 A | 1/1990 | Ben-Bassat et al. | |
| 4,894,439 A | 1/1990 | Dorin et al. | |
| 4,900,724 A | 2/1990 | Kato et al. | |
| 4,948,875 A | 8/1990 | Tanaka et al. | |
| 4,990,455 A | 2/1991 | Yamagishi et al. | |
| 5,002,876 A | 3/1991 | Sreekrishna et al. | |
| 5,028,420 A | 7/1991 | Masegi et al. | |
| 5,043,271 A | 8/1991 | Yamada et al. | |
| 5,059,530 A | 10/1991 | Oshima et al. | |
| 5,075,236 A | 12/1991 | Yone et al. | |
| 5,081,021 A | 1/1992 | Mizuno et al. | |
| 5,110,913 A | 5/1992 | Coan et al. | |

(Continued)

FOREIGN PATENT DOCUMENTS

EP 0350690 1/1990

(Continued)

OTHER PUBLICATIONS

Benjamini et al., Immunology, 4th Ed., Wiley Liss Publishers, p. 60 (2000).*

(Continued)

Primary Examiner—Phillip Gambel
Assistant Examiner—Zachary Skelding
(74) Attorney, Agent, or Firm—Knobbe Martens Olson & Bear LLP

(57) ABSTRACT

Antibodies directed to the antigen TNFα and uses of such antibodies. In particular, fully human monoclonal antibodies directed to the antigen TNFα. Nucleotide sequences encoding, and amino acid sequences comprising, heavy and light chain immunoglobulin molecules, particularly sequences corresponding to contiguous heavy and light chain sequences spanning the framework regions and/or complementarity determining regions (CDR's), specifically from FR1 through FR4 or CDR1 through CDR3. Hybridomas or other cell lines expressing such immunoglobulin molecules and monoclonal antibodies.

35 Claims, 13 Drawing Sheets

U.S. PATENT DOCUMENTS

| | | |
|---|---|---|
| 5,158,871 A | 10/1992 | Rossomando et al. |
| 5,160,483 A | 11/1992 | Postlethwaite et al. |
| 5,162,430 A | 11/1992 | Rhee et al. |
| 5,180,811 A | 1/1993 | Doerper et al. |
| 5,182,196 A | 1/1993 | Allet et al. |
| 5,183,657 A | 2/1993 | Buurman |
| 5,215,743 A | 6/1993 | Singh et al. |
| 5,223,395 A | 6/1993 | Gero |
| 5,223,408 A | 6/1993 | Goeddel et al. |
| 5,231,024 A | 7/1993 | Moeller et al. |
| 5,247,070 A | 9/1993 | Yamada et al. |
| 5,252,479 A | 10/1993 | Srivastava |
| 5,256,769 A | 10/1993 | Kato et al. |
| 5,262,309 A | 11/1993 | Nakamura et al. |
| 5,278,284 A | 1/1994 | Lusk et al. |
| 5,288,852 A | 2/1994 | Yamada et al. |
| 5,324,655 A | 6/1994 | Kriegler et al. |
| 5,334,380 A | 8/1994 | Kilbourn et al. |
| 5,360,716 A | 11/1994 | Ohmoto et al. |
| 5,395,760 A | 3/1995 | Smith et al. |
| 5,422,104 A | 6/1995 | Fiers et al. |
| 5,425,940 A | 6/1995 | Zimmerman et al. |
| 5,436,154 A | 7/1995 | Barbanti et al. |
| 5,447,851 A | 9/1995 | Beutler et al. |
| 5,474,930 A | 12/1995 | Barnes |
| 5,486,463 A | 1/1996 | Lesslauer et al. |
| 5,487,984 A | 1/1996 | Allet et al. |
| 5,504,005 A | 4/1996 | Bloom et al. |
| 5,510,121 A | 4/1996 | Rhee et al. |
| 5,519,119 A | 5/1996 | Yamada et al. |
| 5,593,858 A | 1/1997 | Fleer et al. |
| 5,597,899 A | 1/1997 | Banner et al. |
| 5,602,025 A | 2/1997 | Barnes |
| 5,606,023 A | 2/1997 | Chen et al. |
| 5,616,321 A | 4/1997 | Hector et al. |
| 5,626,843 A | 5/1997 | Skurkovich et al. |
| 5,627,052 A | 5/1997 | Schrader |
| 5,633,145 A | 5/1997 | Feldmann et al. |
| 5,633,146 A | 5/1997 | Fleer et al. |
| 5,635,399 A | 6/1997 | Kriegler et al. |
| 5,641,670 A | 6/1997 | Treco et al. |
| 5,644,034 A | 7/1997 | Rathjen et al. |
| 5,650,150 A | 7/1997 | Gillies |
| 5,652,130 A | 7/1997 | Kriegler et al. |
| 5,652,353 A | 7/1997 | Fiers et al. |
| 5,653,974 A | 8/1997 | Jung et al. |
| 5,654,407 A | 8/1997 | Boyle et al. |
| 5,656,272 A | 8/1997 | Le et al. |
| 5,658,570 A | 8/1997 | Newman et al. |
| 5,658,803 A | 8/1997 | Kuo |
| 5,672,347 A | 9/1997 | Aggarwal et al. |
| 5,672,510 A | 9/1997 | Eglitis et al. |
| 5,677,182 A | 10/1997 | Kriegler et al. |
| 5,679,260 A | 10/1997 | Boos et al. |
| 5,686,259 A | 11/1997 | Kriegler et al. |
| 5,698,195 A | 12/1997 | Le et al. |
| 5,698,419 A | 12/1997 | Wolpe et al. |
| 5,700,466 A | 12/1997 | Wolpe et al. |
| 5,702,705 A | 12/1997 | Kriegler et al. |
| 5,705,364 A | 1/1998 | Etcheverry et al. |
| 5,733,742 A | 3/1998 | Landon |
| 5,741,488 A | 4/1998 | Feldman et al. |
| 5,750,373 A | 5/1998 | Garrard et al. |
| 5,753,499 A | 5/1998 | Meruelo et al. |
| 5,763,733 A | 6/1998 | Whitlow et al. |
| 5,773,582 A | 6/1998 | Shin et al. |
| 5,795,967 A | 8/1998 | Aggarwal et al. |
| 5,821,047 A | 10/1998 | Garrard et al. |
| 5,833,975 A | 11/1998 | Paoletti et al. |
| 5,837,242 A | 11/1998 | Holliger et al. |
| 5,849,586 A | 12/1998 | Kriegler et al. |
| 5,859,413 A | 1/1999 | Kim et al. |
| 5,866,131 A | 2/1999 | Ramshaw et al. |
| 5,866,136 A | 2/1999 | Ramshaw et al. |
| 5,874,077 A | 2/1999 | Kriegler et al. |
| 5,876,691 A | 3/1999 | Chester et al. |
| 5,877,302 A | 3/1999 | Hanson et al. |
| 5,885,793 A | 3/1999 | Griffiths et al. |
| 5,888,814 A | 3/1999 | Kriegler et al. |
| 5,889,156 A | 3/1999 | Kriegler et al. |
| 5,891,679 A | 4/1999 | Lucas et al. |
| 5,895,649 A | 4/1999 | De Lacharriere et al. |
| 5,917,123 A | 6/1999 | McTiernan et al. |
| 5,919,452 A | 7/1999 | Le et al. |
| 5,958,409 A | 9/1999 | Turk et al. |
| 5,959,085 A | 9/1999 | Garrone et al. |
| 5,959,087 A | 9/1999 | Rathjen et al. |
| 5,965,379 A | 10/1999 | Tamarkin et al. |
| 5,968,735 A | 10/1999 | Stein et al. |
| 5,994,510 A | 11/1999 | Adair et al. |
| 6,001,569 A | 12/1999 | Plevy et al. |
| 6,015,557 A | 1/2000 | Tobinick et al. |
| 6,015,558 A | 1/2000 | Hotamisligil et al. |
| 6,022,737 A | 2/2000 | Niven et al. |
| 6,028,106 A | 2/2000 | Garfield et al. |
| 6,071,512 A | 6/2000 | Kriegler et al. |
| 6,080,382 A | 6/2000 | Lee et al. |
| 6,090,382 A | 7/2000 | Salfeld et al. |
| 6,090,923 A | 7/2000 | Wallach et al. |
| 6,099,847 A | 8/2000 | Tobin et al. |
| 6,127,528 A | 10/2000 | Hirai et al. |
| 6,136,599 A | 10/2000 | Cho |
| 6,172,202 B1 | 1/2001 | Marcucci et al. |
| 6,177,077 B1 | 1/2001 | Tobinick |
| 6,193,969 B1 | 2/2001 | Landon et al. |
| 6,207,153 B1 | 3/2001 | Dan et al. |
| 6,210,963 B1 | 4/2001 | Haddada et al. |
| 6,217,912 B1 | 4/2001 | Park et al. |
| 6,218,180 B1 | 4/2001 | Kurtzman et al. |
| 6,232,446 B1 | 5/2001 | Wallach et al. |
| 6,235,281 B1 | 5/2001 | Stenzel et al. |
| 6,258,562 B1 | 7/2001 | Salfeld et al. |
| 6,261,834 B1 | 7/2001 | Srivastava |
| 6,262,239 B1 | 7/2001 | Wallach et al. |
| 6,265,189 B1 | 7/2001 | Paoletti et al. |
| 6,268,212 B1 | 7/2001 | Simonet |
| 6,270,766 B1 | 8/2001 | Feldman et al. |
| 6,277,368 B1 | 8/2001 | Hiserodt et al. |
| 6,277,969 B1 | 8/2001 | Le et al. |
| 6,284,471 B1 | 9/2001 | Le et al. |
| 6,284,519 B1 | 9/2001 | Young et al. |
| 6,287,588 B1 | 9/2001 | Shih et al. |
| 6,309,640 B1 | 10/2001 | Cerami et al. |
| 6,315,999 B1 | 11/2001 | Sadoff et al. |
| 6,346,274 B1 | 2/2002 | Koll et al. |
| 6,379,924 B1 | 4/2002 | Sleep |
| 6,399,331 B2 | 6/2002 | Mather et al. |
| 6,407,218 B1 | 6/2002 | Tamarkin et al. |
| 6,410,033 B1 | 6/2002 | Cochran |
| 6,416,757 B1 | 7/2002 | Rathjen et al. |
| 6,419,927 B1 | 7/2002 | Cerami et al. |
| 6,440,693 B1 | 8/2002 | Hauptmann et al. |
| 6,448,380 B2 | 9/2002 | Rathjen et al. |
| 6,451,983 B2 | 9/2002 | Rathjen et al. |
| 6,455,045 B1 | 9/2002 | Zagury et al. |
| 6,476,214 B1 | 11/2002 | Eagles et al. |
| 6,479,652 B1 | 11/2002 | Crameri et al. |
| 6,492,123 B1 | 12/2002 | Holliger et al. |
| 6,498,237 B2 | 12/2002 | Rathjen et al. |
| 6,503,499 B1 | 1/2003 | Meruelo et al. |
| 6,509,015 B1 | 1/2003 | Salfeld et al. |
| 6,518,239 B1 | 2/2003 | Kuo et al. |
| 6,524,572 B1 | 2/2003 | Li |
| 6,524,856 B1 | 2/2003 | Pati et al. |

| | | |
|---|---|---|
| 6,531,120 B2 | 3/2003 | Gehlsen |
| 6,534,263 B1 | 3/2003 | Plevy et al. |
| 6,534,323 B1 | 3/2003 | Sabbadini |
| 6,537,594 B1 | 3/2003 | Paoletti et al. |
| 6,541,610 B1 | 4/2003 | Smith |

FOREIGN PATENT DOCUMENTS

| | | |
|---|---|---|
| EP | 0791360 | 8/1997 |
| WO | WO96/08516 | 3/1996 |
| WO | WO97/29131 | 8/1997 |
| WO | WO 01/00229 | 1/2001 |
| WO | WO 01/30369 | 5/2001 |
| WO | WO 01/37874 | 5/2001 |
| WO | WO 01/43773 | 6/2001 |
| WO | WO 01/58473 | 8/2001 |
| WO | WO 01/94585 | 12/2001 |
| WO | WO 02/12502 | 2/2002 |

OTHER PUBLICATIONS

Rudikoff et al., Proc. Natl. Acad. Sci. USA 79:1979-1983 (1982).*
Janeway et al., Immunobiology, 6th Ed., Garland Science, pp. 110-112 (2004).*
Vargas-Madrazo et al., J. Mol. Biol. 254: 497-504 (1995).*
MacCallum et al., J. Mol. Biol. 262: 732-745 (1996).*
Feldman, M. Development of Anti-TNF Therapy for Rheumatoid Arthritis *Nature Publishing Group*, 2(5):364-371 (2002).
Michie, et al. Tumour Necrosis Factor and Bacterial Sepsis *British Journal Surgery* 76:670-671 (1989).
Liang, et al. Production and Characterization of Monoclonal Antibodies Against Recombinant Human Tumor Necrosis Factor/Cachectin *Biochemical and Biophysical Research Communications* 137(2):847-854 (1986).
Meager, et al. Preparation and Characterizaion of Monoclonal Antibodies Directed Against Antigenic Determinants of Recombinant Human Tumour Necrosis Factor (rTNF) *Hybridoma* 6(3):305-311 (1987).
Fendly, et al. Murine Monoclonal Antibodies Defining Neutralizing Epitopes on Tumor Necrosis Factor *Hybridoma* 6(4):359-370 (1987).
Hirai, et al. Production and Characterization of Monoclonal Antibodies to Human Tumor Necrosis Factor *Journal of Immunological Methods* 96:57-62 (1987).
Möeller, et al. Monoclonal Antibodies to Human Tumor Necrosis Factor α: In Vitor and In Vivo Appliation *Cytokine* 2(3):162-169 (1990).
Bringman, et al. Monoclonal Antibodies to Human Tumor Necrosis Factors Alpha and Beta Application for Affinity Purification, Immunoassays, and as Structural Probes *Hybridoma* 6(5):489-507 (1987).
Beutler, et al. Passive Immuniation Against Cachectin/Tumor Necrosis Factor Protects Mice From Lethal Effect of Endotoxin *Science* 30:869-871 (1985).
Tracey, et al. Anti-Cachectin/TNF Monoclonal Antibodies Prevent Septic Shock During Lethal Bacteraemia *Nature* 330:662-664 (1987).
Mathison, et al. Participation of Tumor Necrosis Factor in the Mediation of Gram Negative Bacterial Lipopolysaccharide-Inducted Injury in Rabbits *Journal of Clinical Investigation* 81:1925-1937 (1988).
Shimamoto, et al. Monoclonal Antibodies Against Human Recombinant Tumor Necrosis Factor: Prevention of Endotoxic Shock *Immunology Letters* 17:311-318 (1988).
Opal et al. Efficacy of a Monoclonal Antibody Directed Against Tumor Necrosis Factor in Protecting Neutropenic Rats From Lethal Infection with *Pseudomanas aeruginosa The Journal of Infectious Diseases* 161:1148-1152 (1990).
Silva, et al. Monoclonal Antibody to Endotoxin Core Protects Mice from *Escherichia coli* Sepsis by a Mechanism Independent of Tumor Necrosis Factor and Interleukin-6 *The Journal of Infectious Diseases* 162:454-459 (1990).
Hinshaw, et al. Survival of Primates in LD100 Septic Shock Following Therapy With Antibody to Tumor Necrosis Factor (TNFα) *Circulatory Shock* 30:279-292 (1990).
Kumar, et al. Universal T Helper Cell Determinants Enhance Immunogenicity of a Plasmodium Falciparum Merozoite Surface Antigen Peptide *The Journal of Immunology* 148(5):1499-1505 (1992).
Babcook, et al. A Novel Strategy for Generating Monoclonal Antibodies From single, Isolated Lymphocytes Producing Antibodies of Defined Specificities *Proceedings of the National Academy of Sciencesl* 93:7843-7848 (1996).
Jones, et al. Crystal Structure of TNF *Tumor Necrosis Factors: Structure, Function, and Mechanism of Action* 5:93-127 (1992).
Lehmann, et al. Lethal Toxicity of Lipopolysacchardie and Tumor Necrosis Factor in Normal and D-Galactosamine-Treated Mice *Journal of Experimental Medicine* 165:657-663 (1987).
Leist, et al. Tumor Necrosis Factor-Induced Hepatocyte Apoptosis Precedes Liver Failure in Experimental Murine Shock Models *American Journal of Pathology* 146(5):1220-1234 (1995).
Nowak, et al. LPS-induced Liver Injury in D-Galactosamine-Sensitized Mice Required Secreted TNF-α and the TNF-p55 Receptor *American Journal of Physiological Society* 278:R1202-R1209 (2000).
Benigni, et al. TNF Receptor p55 Plays a Major Role in Centrally Mediated Increases of Serum IL-6 and Corticosterone After Intracerebroventricular Injection of TNF 1 *The American Association of Immunologists* 0022-1767:5563-5568 (1996).
Chothia, et al. Canonical Structures for the Hypervariable Regions of Immunoglobulins *Journal of Molecular Biology* 96:901-917 (1987).
Chothia, et al. Conformations of Immunoglobulin Hypervariable Regions *Nature Publishing Group* 342:877-883 (1989).
Martin, et al. Structural Families in Loops of Homologous Proteins: Automatic Classification, Modeling and Application to Antibodies *Journal Molecular Biology* 263:800-815 (1996).
Ostade, et al. Human TNF Mutants With Selective Activity on the p55 Receptor *Nature* 361:266-269 (1993).
Ostade, et al. Localization of the Active Site of Human Tumor Necrosis Factor (hTNF) by Mutational Analysis *The EMBO Journal* 10(4):827-836 (1991).
Hochberg et al., 2003, *Ann. Rheum. Dis.*, vol. 62 (Suppl. II):ii13-ii16.
Enbrel® (etanercept) package insert. Document No. 10662-10. Immunex Corporation. pp. 1-28. 2002.
Griffiths et al. "Human anti-self antibodies with high specificity from phage libraries," *The EMBO Journal*. 12(2):725-734 (1993).
Hove et al. "Infliximab Treatment Induces Apoptosis of Lamina Propria T Lymphocytes in Crohn's Disease." *Gut*. 50:206-211 (2002).
Jespers et al. "Guiding the selection of human antibodies from phage display repertoires to a single epitope of an antigen." *Biotechnology*. 12:899-903 (1994).
Möller et al. "Monoclonal antibodies to human tumor necrosis factor α: In vitro and in vivo application." *Cytokine*. 2(3):162-169 (1990).
Remicade® Infliximab Recombinant for IV injection package insert. Revised Mar. 2002.
Santora et al. "Characterization of Noncovalent Complexes of Recombinant Human Monoclonal Antibody and Antigen Using Cation Exchange, Size Exclusion Chromatography, and BIAcore." *Analytical Biochemistry*. 299:119-129 (2001).
Scallon et al. "Binding and Functional Comparisons of Two Types of Tumor Necrosis Factor Antagonists." *The Journal of Pharmacology and Experimental Therapeutics*. 301(2):418-426 (2002)/.
Scallon et al. "Chimeric Anti-TNF-α Monoclonal Anti-Body cA2 Binds Recombinant Transmembrane TNF-α and Activates Immune Effector Functions." *Cytokine*. 7(3)251-259 (1995).
Siegel et al. "The Mouse/Human Chimeric Monoclonal Antibody cA2 Neutralizes TNF In Vitro and Protects Transgenic Mice from Cachexia and TNF Lethality In Vivo." *Cytokine*. 7(1):15-25 (1995).
Tracey et al. "Anti-cachetin/TNF monoclonal antibodies prevent septic shock during lethal bacteraemia." *Nature*. 330:662-664 (1987).

* cited by examiner

Binding to human soluble recombinant TNF

Binding to soluble cynomolgus macaque recombinant TNF.

Inhibition of TNF-α Induced Apoptosis of WM266 Cells

TNF-Induced IL-8 in human whole blood

TNF-Induced Liver Damage

TNF-induced IL-6 levels in mice

ANTIBODIES DIRECTED TO TUMOR NECROSIS FACTOR

RELATED APPLICATIONS

This application claims priority under 35 U.S.C §119(e) to U.S. Provisional Application No. 60/430,729, filed Dec. 2, 2002, which is hereby expressly incorporated by reference in its entirety.

FIELD

The present invention relates to antibodies directed to the antigen Tumor Necrosis Factor alpha (hereinafter TNFα) and uses of such antibodies. More specifically, the present invention relates to fully human monoclonal antibodies directed to the antigen TNFα and uses of these antibodies. Aspects of the invention also relate to hybridomas or other cell lines expressing such antibodies. The antibodies herein are useful as diagnostics and as treatments for diseases associated with the activity and/or overproduction of TNFα.

BACKGROUND

TNFα has been demonstrated to be involved in infectious diseases, immune disorders, autoimmune pathologies, graft vs host disease (GVHD), neoplasia/cancer and cancer-associated cachexia. See, Feldman M., 2002 *Nat. Rev. Immunol.*, 2:364. In particular, TNFα levels are dramatically induced in gram negative sepsis, endotoxic shock (See, Michie et al., 1989 *Br. J. Surg.* 76:670) Crohn's disease, and rheumatoid arthritis. The implications of TNFα in such a wide variety of indications highlights the importance of developing specific biological therapeutics targeting this inflammatory cytokine.

Several investigators report the characterization of monoclonal antibodies against TNFα which neutralize its activity in vitro. See, Liang C M, et al., 1986, *Biochem. Biophys Res. Commun.*, 137:847, and Meager A, et al., 1987 *Hybridoma* 6:305. Some of these antibodies were used to map epitopes of human TNFα and develop enzyme immunoassays and to assist in the purification of recombinant TNFα. See Fendly B M, et al., 1987 *Hybridoma*, 6:359; Hirai M, et al., 1987 *J. Immunol Methods*, 96:57; Moller A, et al., 1990 *Cytokine*, 2:162; Bringman T S and Aggarwal B B, 1987, *Hybridoma*, 6:489. Unfortunately, the antibodies generated for these studies would not be useful as therapeutic neutralizing TNFα antibodies for treating human patients since they were derived from non-human species and lack specificity for TNFα.

Neutralizing antisera or mAbs to TNFα have shown efficacy in non-human mammals by abrogating adverse pathophysiological events and preventing death after lethal challenge in experimental endotoxemia. These effects have been demonstrated in rodent and non-human primate model systems. See, Beutler B, et al., 1985 *Science*, 229:869; Tracey K J, et al., 1987 *Nature*, 330:662; Mathison J C, et al., 1988 *J. Clin. Invest.*, 81:1925; Shimamoto Y, et al., 1988, *Immunol. Lett.*, 17:311; Opal S M, et al., 1990, *J. Infect. Dis.*, 161:1148; Silva A T, et al., 1990, *J. Infect. Dis.*, 162:454; Hinshaw L B, et al., 1990, *Circ. Shock*, 30:279.

Various forms of neutralizing antibodies currently exist and are reviewed by Feldman. See, Feldman M, 2002, *Nat. Rev. Immunol.*, 2:364. As described in this review, a great deal of effort has been expended to create a neutralizing antibody that would yield a therapeutically suitable antibody for chronic administration to humans. Currently, antibody/TNFR fusion (fcIg/TNFR) proteins (Enbrel) have shown some utility, but are challenged by a short half-life in the serum leading to frequent administration (e.g., twice weekly) of the drug. A neutralizing therapeutic antibody to TNFα for chronic treatment would exceed the half-life issue (one injection per 3-4 weeks) as long as the antibody itself was not immunogenic. Others have attempted to create neutralizing antibodies to TNFα which have the desired characteristics of low/no immunogenicity and a half life typical of their endogenous counterparts without success. Examples of such antibodies include mouse/human chimeras, such as Infliximab (cA2 or Remicade), and the humanized antibody CDP571 or Adalimumab (D2E7 or Humira). These represent attempts to create neutralizing therapeutic antibodies which closely resemble their human counterparts.

Unfortunately, the full potential of these drugs may not be realized due to their inherent potential immunogenicity, compromised half-life and/or reduced avidity/affinity for TNFα. Host immune responses induced by these chimeric antibodies can lead to clearance of the antibodies from the circulation and make repeated administration unsuitable for therapy due to loss of efficacy. These problems ultimately reduce the therapeutic benefit to the patient. Additional problems in scale-up and manufacturing may also be encountered using antibodies or fragments thereof, such as those mentioned above.

Thus, for the above reasons, there exists a need in the art to provide an alternative to patients in clinically indicated populations where TNFα is responsible for the pathophysiology of a particular disease. Fully human, high affinity, neutralizing monoclonal antibodies, or fragments thereof, for chronic administration provide the desired characteristics of a non-immunogenic therapeutic option with a half-life suitable for less frequent administration.

SUMMARY

Embodiments of the invention relate to human monoclonal antibodies that specifically bind to Tumor Necrosis Factor-α and have a heavy chain complementarity determining region 1 (CDR1) having an amino acid sequence of "Ser Tyr Asp Met His" SEQ ID NO: 321). Antibodies described herein can also include a heavy chain complementarity determining region 2 (CDR2) having an amino acid sequence of "Val lie Trp Ser Asp Gly Ser Ile Lys Tyr Tyr Ala Asp Ser Val Lys Gly" (SEQ ID NO: 322), a heavy chain complementarity determining region 3 (CDR3) having an amino acid sequence of "Glu Val Glu Ser Ala Met Gly Gly Phe Tyr Tyr Asn Gly Met Asp Val" (SEQ ID NO: 323), a heavy chain amino acid comprising the amino acid sequence shown in SEQ ID NO: 70, and a heavy chain amino acid comprising the amino acid sequence shown in SEQ ID NO: 74.

Further embodiments include human monoclonal antibodies having a light chain complementarity determining region 1 (CDR 1) having an amino acid sequence of "Arg Ala Ser Gln Gly Ile Arg Ile Asp Leu Gly" (SEQ ID NO: 324). Antibodies herein can also include a light chain complementarity determining region 2 (CDR2) having an amino acid sequence of "Ala Ala Ser Thr Leu Gln Ser" (SEQ ID NO: 325), a light chain complementarity determining region 3 (CDR3) having an amino acid sequence of "Leu Gln His Lys Ser Tyr Pro Leu Thr" (SEQ ID NO: 326), a light chain amino acid comprising the amino acid sequence shown in SEQ ID NO: 72.

In other embodiments, the invention provides human monoclonal antibodies that specifically bind to Tumor Necrosis Factor-α and comprise a light chain complementarity determining region 1 (CDR1) having an amino acid sequence of "Arg Ala Ser Gln Gly Ile Arg Ile Asp Leu Gly" (SEQ ID NO: 324), a light chain complementarity determining region 2 (CDR2) having an amino acid sequence of "Ala Ala Ser Thr Leu Gln Ser" (SEQ ID NO: 325), and a light chain complementarity determining region 3 (CDR3) having an amino acid sequence of "Leu Gln His Lys Ser Tyr Pro Leu Thr" (SEQ ID NO: 326).

Still further embodiments include human monoclonal antibodies having a heavy chain complementarity determining region 1 (CDR1) having an amino acid sequence of "Ser Tyr Asp Met His" (SEQ ID NO: 321), a heavy chain complementarity determining region 2 (CDR2) having an amino acid sequence of "Val Ile Trp Ser Asp Gly Ser lie Lys Tyr Tyr Ala Asp Ser Val Lys Gly" (SEQ ID NO: 322), and a heavy chain complementarity determining region 3 (CDR3) having an amino acid sequence of "Glu Val Glu Ser Ala Met Gly Gly Phe Tyr Tyr Asn Gly Met Asp Val" (SEQ ID NO: 323).

In other embodiments the invention includes human monoclonal antibodies that specifically bind to Tumor Necrosis Factor-α and include a VH3-33 heavy chain gene, or conservative variants thereof. Antibodies described herein can also include an A30VK1 light chain gene.

Further embodiments of the invention include human monoclonal antibodies that specifically bind to Tumor Necrosis Factor-α, wherein the antibodies comprise a heavy chain complementarity determining region 1 (CDR1) corresponding to canonical class 1. The antibodies provided herein can also include a heavy chain complementarity determining region 2 (CDR2) corresponding to canonical class 3, a light chain complementarity determining region 1 (CDR1) corresponding to canonical class 2, a light chain complementarity determining region 2 (CDR2) corresponding to canonical class 1, and a light chain complementarity determining region 3 (CDR3) corresponding to canonical class 1.

In other embodiments, the invention provides human monoclonal antibodies that specifically bind to Tumor Necrosis Factor-α and include a heavy chain complementarity determining region 1 (CDR1) having an amino acid sequence of "Arg Asn Tyr Met Ser" (SEQ ID NO: 327). Antibodies can further include a heavy chain complementarity determining region 2 (CDR2) having an amino acid sequence of "Val Ile Tyr Ser Gly Asp Arg Thr Tyr Tyr Ala Asp Ser Val Lys Gly" (SEQ ID NO: 328), a heavy chain complementarity determining region 3 (CDR3) having an amino acid sequence of "Gly Glu Gly Gly Phe Asp Tyr" (SEQ ID NO: 329), and a heavy chain amino acid having the amino acid sequence shown in SEQ ID NO: 50.

In further embodiments of the invention, human monoclonal antibodies can include a light chain complementarity determining region 1 (CDR1) having an amino acid sequence of "Arg Ala Ser Gin Ser Val Ser Ser Asn Leu Ala" (SEQ ID NO: 330), a light chain complementarity determining region 2 (CDR2) having an amino acid sequence of "Gly Ala Ser Ile Arg Ala Thr" (SEQ ID NO: 331), a light chain complementarity determining region 3 (CDR3) having an amino acid sequence of "Gln Gln Tyr Asn Tyr Trp Trp Thr" (SEQ ID NO: 332), and a light chain amino acid comprising the amino acid sequence shown in SEQ ID NO: 52.

In still further embodiments, the invention includes human monoclonal antibodies that specifically bind to Tumor Necrosis Factor-α and have a light chain complementarity determining region 1 (CDR1) having an amino acid sequence of "Arg Ala Ser Gln Ser Val Ser Ser Asn Leu Ala" (SEQ ID NO: 330), a light chain complementarity determining region 2 (CDR2) having an amino acid sequence of "Gly Ala Ser Ile Arg Ala Thr" (SEQ ID NO: 331), a light chain complementarity determining region 3 (CDR3) having an amino acid sequence of "Gln Gln Tyr Asn Tyr Trp Trp Thr" (SEQ ID NO: 332), a heavy chain complementarity determining region 1 (CDR1) having an amino acid sequence of "Arg Asn Tyr Met Ser" (SEQ ID NO: 327), a heavy chain complementarity determining region 2 (CDR2) having an amino acid sequence of "Val Ile Tyr Ser Gly Asp Arg Thr Tyr Tyr Ala Asp Ser Val Lys Gly" (SEQ ID NO: 328), and a heavy chain complementarity determining region 3 (CDR3) having an amino acid sequence of "Gly Glu Gly Gly Phe Asp Tyr" (SEQ ID NO: 329).

In other embodiments, the invention provides human monoclonal antibodies that specifically bind to Tumor Necrosis Factor-α and have a VH3-53 heavy chain gene, or conservative variant thereof. Antibodies herein can also include an L2VK3 light chain gene.

In additional embodiments, the invention includes human monoclonal antibodies that specifically bind to Tumor Necrosis Factor-α, wherein the antibodies comprise a heavy chain complementarity determining region 1 (CDR1) corresponding to canonical class 1. The antibodies herein can also include a heavy chain complementarity determining region 2 (CDR2) corresponding to canonical class 1, a light chain complementarity determining region 1 (CDR1) corresponding to canonical class 2, a light chain complementarity determining region 2 (CDR2) corresponding to canonical class 1, and a light chain complementarity determining region 3 (CDR3) corresponding to canonical class 3.

The invention further provides methods for assaying the level of tumor necrosis factor alpha (TNFα) in a patient sample, comprising contacting an anti-TNFα antibody with a biological sample from a patient, and detecting the level of binding between said antibody and TNFα in said sample. In more specific embodiments, the biological sample is blood.

In other embodiments the invention provides compositions, including an antibody or functional fragment thereof, and a pharmaceutically acceptable carrier.

Still further embodiments of the invention include methods of effectively treating an animal suffering from a neoplastic disease, including selecting an animal in need of treatment for a neoplastic disease, and administering to said animal a therapeutically effective dose of a fully human monoclonal antibody that specifically binds to tumor necrosis factor alpha (TNFα).

Treatable neoplastic diseases can include breast cancer, ovarian cancer, bladder cancer, lung cancer, glioblastoma, stomach cancer, endometrial cancer, kidney cancer, colon cancer, pancreatic cancer, and prostrate cancer.

Further methods of the invention relate to effectively treating an immuno-mediated inflammatory disease. These methods include selecting an animal in need of treatment for an inflammatory condition, and administering to said animal a therapeutically effective dose of a fully human monoclonal antibody, wherein said antibody specifically binds to tumor necrosis factor alpha (TNFα). Treatable immuno-mediated inflammatory diseases include rheumatoid arthritis, glomerulonephritis, atherosclerosis, psoriasis, restenosis, autoimmune disease, Crohn's disease, graft-host reactions, septic shock, cachexia, anorexia, ankylosing spondylitis and multiple sclerosis.

Additional embodiments of the invention include methods of inhibiting tumor necrosis factor alpha (TNFα) induced apoptosis in an animal. These methods include selecting an animal in need of treatment for TNFα induced apoptosis, and administering to said animal a therapeutically effective dose of a fully human monoclonal antibody wherein said antibody specifically binds to TNFα.

Further embodiments of the invention include the use of an antibody of in the preparation of medicament for the treatment of neoplastic disease in an animal, wherein said monoclonal antibody specifically binds to tumor necrosis factor (TNFα). Treatable neoplastic diseases can include breast cancer, ovarian cancer, bladder cancer, lung cancer, glioblastoma, stomach cancer, endometrial cancer, kidney cancer, colon cancer, pancreatic cancer, and prostrate cancer.

Further uses of the antibodies herein can be for the preparation of a medicament for the effective treatment of immuno-mediated inflammatory diseases in an animal, wherein said monoclonal antibody specifically binds to tumor necrosis factor (TNFα). Treatable immuno-mediated inflammatory diseases can include rheumatoid arthritis, glomerulonephritis, atherosclerosis, psoriasis, restenosis, autoimmune disease, Crohn's disease, graft-host reactions, septic shock, cachexia, anorexia, and multiple sclerosis.

In still further embodiments, the antibodies described herein can be used for the preparation of a medicament for the effective treatment of tumor necrosis factor induced apoptosis in an animal, wherein said monoclonal antibody specifically binds to tumor necrosis factor (TNFα).

Embodiments of the invention described herein related to monoclonal antibodies that bind TNFα and affect TNFα function. Other embodiments relate to fully human anti-TNFα antibodies and anti-TNFα antibody preparations with desirable properties from a therapeutic perspective, including strong binding affinity for TNFα, the ability to neutralize TNFα in vitro and in vivo, and the ability to inhibit TNFα induced apoptosis.

In a preferred embodiment, antibodies described herein bind to TNFα with very high affinities (Kd). For example a human, rabbit, mouse, chimeric or humanized antibody that is capable of binding TNFα with a Kd less than, but not limited to, $10^{-7}$, $10^{-8}$, $10^{-9}$, $10^{-10}$, $10^{-11}$, $10^{-12}$, $10^{-13}$ or $10^{-14}$ M, or any range or value therein. The rabbit antibody R014, described herein, possesses a measured affinity in the $10^{-13}$ (fM) range. Antibody 299 V.1 and 299 V.2 were shown to possess affinities in the $10^{-13}$ or low $10^{-12}$ (M) range. Affinity and/or avidity measurements can be measured by KinExA® and/or BIACORE®, as described herein.

Accordingly, one embodiment described herein includes isolated antibodies, or fragments of those antibodies, that bind to TNFα. As known in the art, the antibodies can advantageously be, for example, monoclonal, chimeric and/or fully human antibodies. Embodiments of the invention described herein also provide cells for producing these antibodies.

Another embodiment of the invention is a fully human antibody that binds to TNFα and comprises a heavy chain amino acid sequence having the complementarity determining region (CDR) with one of the sequences shown in Tables 31-34. It is noted that CDR determinations can be readily accomplished by those of ordinary skill in the art. See for example, Kabat et al., *Sequences of Proteins of Immunological Interest*, Fifth Edition, NIH Publication 91-3242, Bethesda Md. [1991], vols. 1-3.

Yet another embodiment is an antibody that binds to TNFα and comprises a light chain amino acid sequence having a CDR comprising one of the sequences shown in Tables 32 and 34. In certain embodiments the antibody is a fully human monoclonal antibody.

A further embodiment is an antibody that binds to TNFα and comprises a heavy chain amino acid sequence having one of the CDR sequences shown in Tables 31 and 33 and a light chain amino acid sequence having one of the CDR sequences shown in Tables 32 and 34. In certain embodiments the antibody is a fully human monoclonal antibody.

Another embodiment of the invention is a fully human antibody that binds to other TNFα family members including, but not limited to, TNFβ. A further embodiment herein is an antibody that cross-competes for binding to TNFβ with the fully human antibodies of the invention.

It will be appreciated that embodiments of the invention are not limited to any particular form of an antibody or method of generation or production. For example, the anti-TNFα antibody may be a full-length antibody (e.g., having an intact human Fc region) or an antibody fragment (e.g., a Fab, Fab' or F(ab')$_2$). In addition, the antibody may be manufactured from a hybridoma that secretes the antibody, or from a recombinantly produced cell that has been transformed or transfected with a gene or genes encoding the antibody.

Other embodiments of the invention include isolated nucleic acid molecules encoding any of the antibodies described herein, vectors having an isolated nucleic acid molecules encoding anti-TNFα antibodies or a host cell transformed with any of such nucleic acid molecules. In addition, one embodiment of the invention is a method of producing an anti-TNFα antibody by culturing host cells under conditions wherein a nucleic acid molecule is expressed to produce the antibody followed by recovering the antibody.

A further embodiment herein includes a method of producing high affinity antibodies to TNFα by immunizing a mammal with human TNFα, or a fragment thereof, and one or more orthologous sequences or fragments thereof.

Other embodiments are based upon the generation and identification of isolated antibodies that bind specifically to TNFα. TNFα is expressed at elevated levels in neoplastic diseases, such as tumors, and other inflammatory diseases. Inhibition of the biological activity of TNFα can prevent inflammation and other desired effects, including TNFα induced apoptosis.

Another embodiment of the invention includes a method of diagnosing diseases or conditions in which an antibody prepared as described herein is utilized to detect the level of TNFα in a patient sample. In one embodiment, the patient sample is blood or blood serum. In further embodiments, methods for the identification of risk factors, diagnosis of disease, and staging of disease is presented which involves the identification of the overexpression of TNFα using anti-TNFα antibodies.

Another embodiment of the invention includes a method for diagnosing a condition associated with the expression of TNFα in a cell by contacting the cell with an anti-TNFα antibody, and thereafter detecting the presence of TNFα. Preferred conditions include, but are not limited to, neoplastic diseases including, without limitation, tumors, cancers, such as breast, ovarian, stomach, endometrial, salivary gland, lung, kidney, colon, colorectal, thyroid, pancreatic, prostate and bladder cancer. In another embodiment, an anti-TNFα antibody can be used to diagnose an inflammatory condition including, but is not limited to, atherosclerosis, restenosis, autoimmune disease, immuno-mediated inflammatory diseases (IMIDs) including but not limited to rheumatoid arthritis, psoriasis, uveitis (e.g., childhood and seronegative), lupus and other diseases mediated by immune complexes such as pemphigus and glomerulonephritis, congential hyperthyroidism (CH), delayed type hypersensitivity (DTH) such as contact hypersensitivity, sarcoidosis, Behcet's disease, chronic arthritis, psoriatic arthritis, ankylosing spondylitis, adult still disease, primary Sjögren's disease, scleroderma, giant cell arteritis, SAPHO syndrome, primary biliary cirrhosis (PBC), sarcoidosis, myelodysplastic syndromes, Wegener's syndrome and other vasculitis, hematologic malignancies, cochleovestibular disorders, macrophage activation syndrome, asthma, interstitial lung disease, Hepatitis C, pulmonary fibrosis, ovulation induction, myelodysplastic syndromes, Crohn's disease, graft-host reactions, septic shock, cachexia, anorexia, and multiple sclerosis. Other conditions the antibodies can diagnose are disclosed in U.S. Pat. No. 6,090,382 to Salfeld et al., and U.S. Pat. No. 5,436,154 to Barbanti, et al. both of which are incorporated by reference in their entireties.

In another embodiment, the invention includes an assay kit for detecting TNFα and TNFα family members in mammalian tissues or cell' to screen for neoplastic diseases or inflammatory conditions. The kit includes an antibody that binds to TNFα and a means for indicating the reaction of the antibody with TNFα, if present. Preferably the antibody is a monoclonal antibody. In one embodiment, the antibody that binds TNFα is labeled. In another embodiment the antibody is an unlabeled first antibody and the kit further includes a means for detecting the first antibody. In one embodiment, the means includes a labeled second antibody that is an anti-immunoglobulin. Preferably the antibody is labeled with a marker selected from the group consisting of a fluorochrome, an enzyme, a radionuclide and a radiopaque material.

Other embodiments of the invention include pharmaceutical compositions having an effective amount of an anti-TNFα antibody in admixture with a pharmaceutically acceptable carrier or diluent. In yet other embodiments, the anti-TNFα antibody, or a fragment thereof, is conjugated to a therapeutic agent. The therapeutic agent can be, for example, a toxin or a radioisotope. Preferably, such antibodies can be used for the treatment of diseases, including for example, tumors, cancers, such as breast, ovarian, stomach, endometrial, salivary gland, lung, kidney, colon, colorectal, thyroid, pancreatic, prostate and bladder cancer, as well as other inflammatory conditions including but not limited to, atherosclerosis, restenosis, autoimmune disease, immuno-mediated inflammatory diseases (IMIDs) including but not limited to rheumatoid arthritis, psoriasis, uveitis (e.g., childhood and seronegative), lupus and other diseases mediated by immune complexes such as pemphigus and glomerulonephritis, congenital hyperthyroidism (CH), delayed type hypersensitivity (DTH) such as contact hypersensitivity, sarcoidosis, Behcet's disease, chronic arthritis, psoriatic arthritis, ankylosing spondylitis, adult still disease, primary Sjögren's disease, scleroderma, giant cell arteritis, SAPHO syndrome, primary biliary cirrhosis (PBC), sarcoidosis, myelodysplastic syndromes, Wegener's syndrome and other vasculitis, hematologic malignancies, cochleovestibular disorders, macrophage activation syndrome, asthma, interstitial lung disease, Hepatitis C, pulmonary fibrosis, ovulation inductionmyelodysplastic syndromes, Crohn's disease, graft-host reactions, septic shock, cachexia, anorexia, and multiple sclerosis. Other conditions the antibodies can treat are disclosed in U.S. Pat. No. 6,090,382 to Salfeld et al., and U.S. Pat. No. 5,436,154 to Barbanti, et al., both of which are incorporated by reference in their entireties.

Yet another embodiment includes methods for treating diseases or conditions associated with the expression of TNFα in a patient, by administering to the patient an effective amount of an anti-TNFα antibody. The method can be performed in vivo and the patient is preferably a human patient. In a preferred embodiment, the method concerns the treatment of tumors, tumors, cancers, such as breast, ovarian, stomach, endometrial, salivary gland, lung, kidney, colon, colorectal, thyroid, pancreatic, prostate and bladder cancer. In another embodiment, the inflammatory condition includes, but is not limited to, atherosclerosis, restenosis, autoimmune disease, immuno-mediated inflammatory diseases (IMIDs) including but not limited to rheumatoid arthritis, psoriasis, uveitis (e.g., childhood and seronegative), lupus and other diseases mediated by immune complexes such as pemphigus and glomerulonephritis, congential hyperthyroidism (CH), delayed type hypersensitivity (DTH) such as contact hypersensitivity, sarcoidosis, Behcet's disease, chronic arthritis, psoriatic arthritis, ankylosing spondylitis, adult still disease, primary Sjögren's disease, scleroderma, giant cell arteritis, SAPHO syndrome, primary biliary cirrhosis (PBC), sarcoidosis, myelodysplastic syndromes, Wegener's syndrome and other vasculitis, hematologic malignancies, cochleovestibular disorders, macrophage activation syndrome, asthma, interstitial lung disease, Hepatitis C, pulmonary fibrosis, ovulation induction, myelodysplastic syndromes, Crohn's disease, graft-host reactions, septic shock, cachexia, anorexia, and multiple sclerosis. Other conditions the antibodies can treat are disclosed in U.S. Pat. No. 6,090,382 to Salfeld et al., and U.S. Pat. No. 5,436,154 to Barbanti, et al. both of which are incorporated by reference in their entireties.

In another embodiment, the invention provides an article of manufacture including a container. The container includes a composition containing an anti-TNFα antibody, and a package insert or label indicating that the composition can be used to treat neoplastic or inflammatory diseases characterized by the overexpression of TNFα.

In some embodiments, the anti-TNFα antibody is administered to a patient, followed by administration of a clearing agent to remove excess circulating antibody from the blood.

In some embodiments, anti-TNFα antibodies can be modified to enhance their capability of fixing complement and participating in complement-dependent cytotoxicity (CDC). In one embodiment, anti-TNFα antibodies can be modified, such as by an amino acid substitution, to alter their clearance from the body. Alternatively, some other amino acid substitutions may slow clearance of the antibody from the body.

Yet another embodiment is the use of an anti-TNFα antibody in the preparation of a medicament for the treatment of diseases such as neoplastic diseases and inflammatory conditions. In one embodiment, the neoplastic diseases include tumors and cancers, such as breast, ovarian, stomach, endometrial, salivary gland, lung, kidney, colon, colorectal, thyroid, pancreatic, prostate and bladder cancer. In another embodiment, the inflammatory condition includes, but is not limited to, atherosclerosis, restenosis, autoimmune disease, immuno-mediated inflammatory diseases (IMIDs) including but not limited to rheumatoid arthritis, psoriasis, uveitis (e.g., childhood and seronegative), lupus and other diseases mediated by immune complexes such as pemphigus and glomerulonephritis, congenital hyperthyroidism (CH), delayed type hypersensitivity (DTH) such as contact hypersensitivity, sarcoidosis, Behcet's disease, chronic arthritis, psoriatic arthritis, ankylosing spondylitis, adult still disease, primary Sjögren's disease, scleroderma, giant cell arteritis, SAPHO syndrome, primary biliary cirrhosis (PBC), sarcoidosis, myelodysplastic syndromes, Wegener's syndrome and other vasculitis, hematologic malignancies, cochleovestibular disorders, macrophage activation syndrome, asthma, interstitial lung disease, Hepatitis C, pulmonary fibrosis, ovulation induction, myelodysplastic syndromes, Crohn's disease, graft-host reactions, septic shock, cachexia, anorexia, and multiple sclerosis. Other conditions the antibodies can treat are disclosed in U.S. Pat. No. 6,090,382 to Salfeld et al., and U.S. Pat. No. 5,436,154 to Barbanti, et al. both of which are incorporated by reference in their entireties.

DETAILED DESCRIPTION

Figure 1:
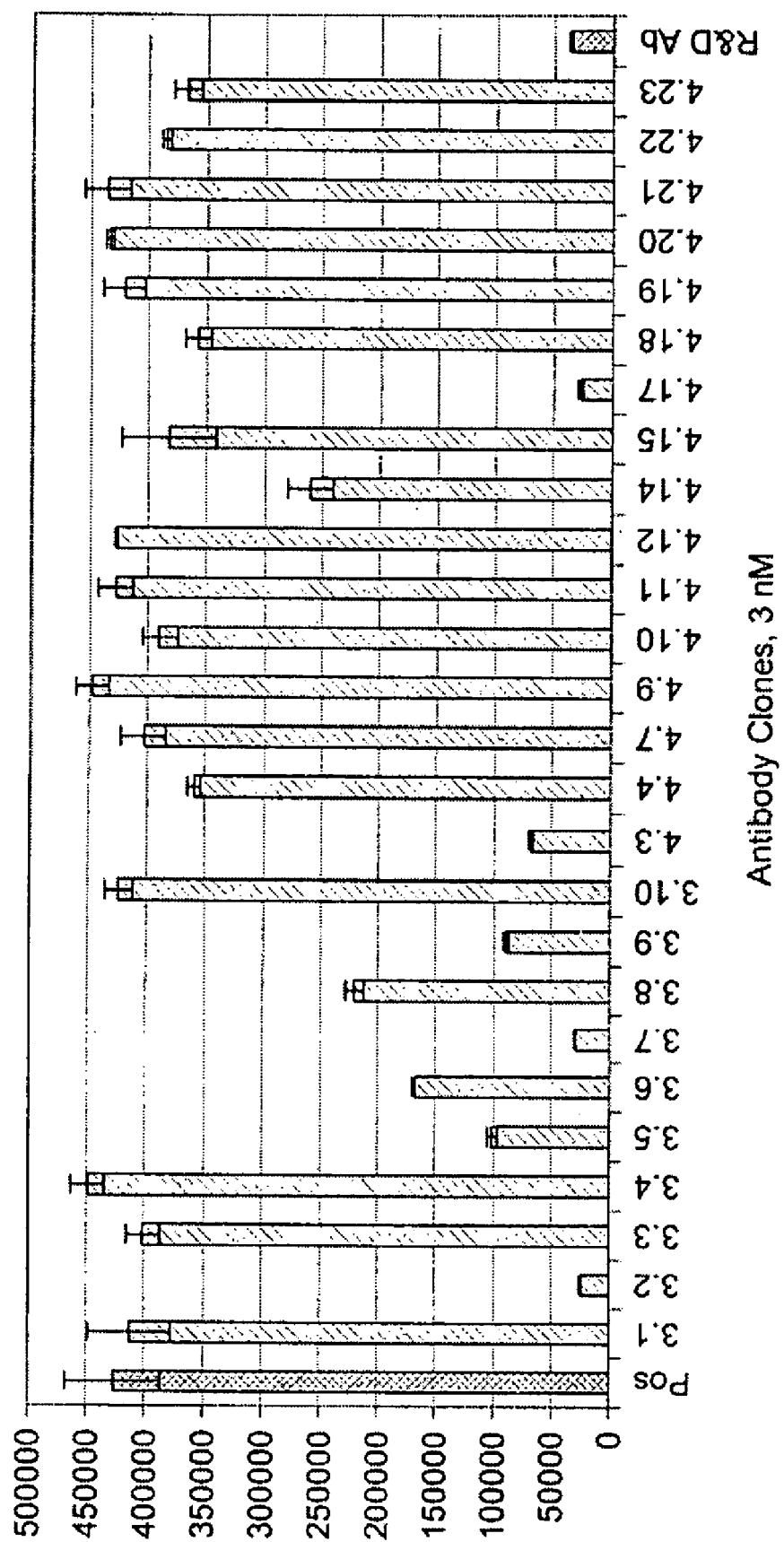
FIG. 1 is a bar graph which illustrates the effect that various hybridoma derived, human anti-TNFα binding antibodies have on neutralizing TNFα induced cell apoptosis in human WM 266 cells. The graph shows caspase activity as a measure of TNFα induced apoptosis.

Embodiments of the invention described herein relate to monoclonal antibodies that bind to TNFα. In some embodiments, the antibodies bind to TNFα and affect TNFα function. Other embodiments provide fully human anti-TNFα antibodies and anti-TNFα antibody preparations with desirable properties from a therapeutic perspective, including strong binding affinity for TNFα, the ability to neutralize TNFα in vitro, the ability to inhibit TNFα-induced hepatic injury in vivo, and the ability to inhibit TNFα-induced IL-6 production in vivo.

Accordingly, embodiments of the invention include isolated antibodies, or fragments of those antibodies, that bind to TNFα. As known in the art, the antibodies can advantageously be fully human monoclonal antibodies. Embodiments of the invention also provide cells for producing these antibodies.

In addition, embodiments of the invention provide for using these antibodies as a diagnostic tool or for treatment of a disease. For example, embodiments of the invention provide methods and antibodies for inhibiting expression of TNFα associated with infectious diseases, immune disorders, autoimmune pathologies, graft vs. host disease (GVHD), neoplasia, cancer associated cachexia, gram negative sepsis, endotoxic shock, Crohn's disease, and rheumatoid arthritis. Preferably, the antibodies are used to treat cancers, such as breast, ovarian, stomach, endometrial, salivary gland, lung, kidney, colon, colorectal, thyroid, pancreatic, prostate and bladder cancer, as well as other inflammatory conditions, including, but not limited to, rheumatoid arthritis, glomerulonephritis, atherosclerosis, psoriasis, organ transplants, restenosis and autoimmune diseases. In association with such treatment, articles of manufacture including antibodies as described herein are provided. Additionally, an assay kit having antibodies as described herein is provided to screen for tumors and inflammatory conditions.

Additionally, the nucleic acids described herein, and fragments and variants thereof, may be used, by way of nonlimiting example, (a) to direct the biosynthesis of the corresponding encoded proteins, polypeptides, fragments and variants as recombinant or heterologous gene products, (b) as probes for detection and quantification of the nucleic acids disclosed herein, (c) as sequence templates for preparing antisense molecules, and the like. Such uses are described more fully in the following disclosure.

Furthermore, the proteins and polypeptides described herein, and fragments and variants thereof, may be used in ways that include (a) serving as an immunogen to stimulate the production of an anti-TNFα antibody, (b) a capture antigen in an immunogenic assay for such an antibody, (c) as a target for screening for substances that bind to a TNFα polypeptide described herein, and (d) a target for a TNFα specific antibody such that treatment with the antibody affects the molecular and/or cellular function mediated by the target.

Further embodiments, features, and the like regarding the anti-TNFα-antibodies are provided in additional detail below.

Sequence Listing

The heavy chain and light chain variable region nucleotide and amino acid sequences of representative human anti-TNFα antibodies are provided in the sequence listing, the contents of which are summarized in Table 1 below.

TABLE 1

| mAb ID No.: | Sequence | SEQ ID NO: |
|---|---|---|
| 2 | Nucleotide sequence encoding the variable region of the heavy chain | 1 |
|  | Amino acid sequence encoding the variable region of the heavy chain | 2 |
|  | Nucleotide sequence encoding the variable region of the light chain | 3 |
|  | Amino acid sequence encoding the variable region of the light chain | 4 |
| 15 | Nucleotide sequence encoding the variable region of the heavy chain | 5 |
|  | Amino acid sequence encoding the variable region of the heavy chain | 6 |
|  | Nucleotide sequence encoding the variable region of the light chain | 7 |
|  | Amino acid sequence encoding the variable region of the light chain | 8 |
| 25 | Nucleotide sequence encoding the variable region of the heavy chain | 9 |
|  | Amino acid sequence encoding the variable region of the heavy chain | 10 |
|  | Nucleotide sequence encoding the variable region of the light chain | 11 |
|  | Amino acid sequence encoding the variable region of the light chain | 12 |
| 28 | Nucleotide sequence encoding the variable region of the heavy chain | 13 |
|  | Amino acid sequence encoding the variable region of the heavy chain | 14 |
|  | Nucleotide sequence encoding the variable region of the light chain | 15 |
|  | Amino acid sequence encoding the variable region of the light chain | 16 |
| 70 k/ 69 g | Nucleotide sequence encoding the variable region of the heavy chain | 17 |
|  | Amino acid sequence encoding the variable region of the heavy chain | 18 |
|  | Nucleotide sequence encoding the variable region of the light chain | 19 |
|  | Amino acid sequence encoding the variable region of the light chain | 20 |
| 95 | Nucleotide sequence encoding the variable region of the heavy chain | 21 |
|  | Amino acid sequence encoding the variable region of the heavy chain | 22 |
|  | Nucleotide sequence encoding the variable region of the light chain | 23 |
|  | Amino acid sequence encoding the variable region of the light chain | 24 |
| 123 | Nucleotide sequence encoding the variable region of the heavy chain | 25 |
|  | Amino acid sequence encoding the variable region of the heavy chain | 26 |
|  | Nucleotide sequence encoding the variable region of the light chain | 27 |
|  | Amino acid sequence encoding the variable region of the light chain | 28 |
| 131 | Nucleotide sequence encoding the variable region of the heavy chain | 29 |
|  | Amino acid sequence encoding the variable region of the heavy chain | 30 |
|  | Nucleotide sequence encoding the variable region of the light chain | 31 |
|  | Amino acid sequence encoding the variable region of the light chain | 32 |

TABLE 1-continued

| mAb ID No.: | Sequence | SEQ ID NO: |
|---|---|---|
| 145 k/ 140 g | Nucleotide sequence encoding the variable region of the heavy chain | 33 |
|  | Amino acid sequence encoding the variable region of the heavy chain | 34 |
|  | Nucleotide sequence encoding the variable region of the light chain | 35 |
|  | Amino acid sequence encoding the variable region of the light chain | 36 |
| 148 | Nucleotide sequence encoding the variable region of the heavy chain | 37 |
|  | Amino acid sequence encoding the variable region of the heavy chain | 38 |
|  | Nucleotide sequence encoding the variable region of the light chain | 39 |
|  | Amino acid sequence encoding the variable region of the light chain | 40 |
| 234 | Nucleotide sequence encoding the variable region of the heavy chain | 41 |
|  | Amino acid sequence encoding the variable region of the heavy chain | 42 |
|  | Nucleotide sequence encoding the variable region of the light chain | 43 |
|  | Amino acid sequence encoding the variable region of the light chain | 44 |
| 250 | Nucleotide sequence encoding the variable region of the heavy chain | 45 |
|  | Amino acid sequence encoding the variable region of the heavy chain | 46 |
|  | Nucleotide sequence encoding the variable region of the light chain | 47 |
|  | Amino acid sequence encoding the variable region of the light chain | 48 |
| 263 | Nucleotide sequence encoding the variable region of the heavy chain | 49 |
|  | Amino acid sequence encoding the variable region of the heavy chain | 50 |
|  | Nucleotide sequence encoding the variable region of the light chain | 51 |
|  | Amino acid sequence encoding the variable region of the light chain | 52 |
| 269 | Nucleotide sequence encoding the variable region of the heavy chain | 53 |
|  | Amino acid sequence encoding the variable region of the heavy chain | 54 |
|  | Nucleotide sequence encoding the variable region of the light chain | 55 |
|  | Amino acid sequence encoding the variable region of the light chain | 56 |
| 280 | Nucleotide sequence encoding the variable region of the heavy chain | 57 |
|  | Amino acid sequence encoding the variable region of the heavy chain | 58 |
|  | Nucleotide sequence encoding the variable region of the light chain | 59 |
|  | Amino acid sequence encoding the variable region of the light chain | 60 |
| 282 | Nucleotide sequence encoding the variable region of the heavy chain | 61 |
|  | Amino acid sequence encoding the variable region of the heavy chain | 62 |
|  | Nucleotide sequence encoding the variable region of the light chain | 63 |
|  | Amino acid sequence encoding the variable region of the light chain | 64 |
| 291 | Nucleotide sequence encoding the variable region of the heavy chain | 65 |
|  | Amino acid sequence encoding the variable region of the heavy chain | 66 |
|  | Nucleotide sequence encoding the variable region of the light chain | 67 |
|  | Amino acid sequence encoding the variable region of the light chain | 68 |
| 299v1 | Nucleotide sequence encoding the variable region of the heavy chain | 69 |
|  | Amino acid sequence encoding the variable region of the heavy chain | 70 |

TABLE 1-continued

| mAb ID No.: | Sequence | SEQ ID NO: |
|---|---|---|
| | Nucleotide sequence encoding the variable region of the light chain | 71 |
| | Amino acid sequence encoding the variable region of the light chain | 72 |
| 299v2 | Nucleotide sequence encoding the variable region of the heavy chain | 73 |
| | Amino acid sequence encoding the variable region of the heavy chain | 74 |
| | Nucleotide sequence encoding the variable region of the light chain | 71 |
| | Amino acid sequence encoding the variable region of the light chain | 72 |
| 313 | Nucleotide sequence encoding the variable region of the heavy chain | 75 |
| | Amino acid sequence encoding the variable region of the heavy chain | 76 |
| | Nucleotide sequence encoding the variable region of the light chain | 77 |
| | Amino acid sequence encoding the variable region of the light chain | 78 |
| R014 | Nucleotide sequence encoding the variable region of the heavy chain | 79 |
| | Amino acid sequence encoding the variable region of the heavy chain | 80 |
| | Nucleotide sequence encoding the variable region of the light chain | 81 |
| | Amino acid sequence encoding the variable region of the light chain | 82 |
| 1.1 | Nucleotide sequence encoding the variable region of the heavy chain | 83 |
| | Amino acid sequence encoding the variable region of the heavy chain | 84 |
| | Nucleotide sequence encoding the variable region of the light chain | 85 |
| | Amino acid sequence encoding the variable region of the light chain | 86 |
| 2.1 | Nucleotide sequence encoding the variable region of the heavy chain | 87 |
| | Amino acid sequence encoding the variable region of the heavy chain | 88 |
| | Nucleotide sequence encoding the variable region of the light chain | 89 |
| | Amino acid sequence encoding the variable region of the light chain | 90 |
| 2.2 | Nucleotide sequence encoding the variable region of the heavy chain | 91 |
| | Amino acid sequence encoding the variable region of the heavy chain | 92 |
| | Nucleotide sequence encoding the variable region of the light chain | 93 |
| | Amino acid sequence encoding the variable region of the light chain | 94 |
| 2.3 | Nucleotide sequence encoding the variable region of the heavy chain | 95 |
| | Amino acid sequence encoding the variable region of the heavy chain | 96 |
| | Nucleotide sequence encoding the variable region of the light chain | 97 |
| | Amino acid sequence encoding the variable region of the light chain | 98 |
| 2.4 | Nucleotide sequence encoding the variable region of the heavy chain | 99 |
| | Amino acid sequence encoding the variable region of the heavy chain | 100 |
| | Nucleotide sequence encoding the variable region of the light chain | 101 |
| | Amino acid sequence encoding the variable region of the light chain | 102 |
| 2.5 | Nucleotide sequence encoding the variable region of the heavy chain | 103 |
| | Amino acid sequence encoding the variable region of the heavy chain | 104 |
| | Nucleotide sequence encoding the variable region of the light chain | 105 |
| | Amino acid sequence encoding the variable region of the light chain | 106 |

TABLE 1-continued

| mAb ID No.: | Sequence | SEQ ID NO: |
|---|---|---|
| 2.6 | Nucleotide sequence encoding the variable region of the heavy chain | 107 |
| | Amino acid sequence encoding the variable region of the heavy chain | 108 |
| | Nucleotide sequence encoding the variable region of the light chain | 109 |
| | Amino acid sequence encoding the variable region of the light chain | 110 |
| 2.7 | Nucleotide sequence encoding the variable region of the heavy chain | 111 |
| | Amino acid sequence encoding the variable region of the heavy chain | 112 |
| | Nucleotide sequence encoding the variable region of the light chain | 113 |
| | Amino acid sequence encoding the variable region of the light chain | 114 |
| 2.8 | Nucleotide sequence encoding the variable region of the heavy chain | 115 |
| | Amino acid sequence encoding the variable region of the heavy chain | 116 |
| | Nucleotide sequence encoding the variable region of the light chain | 117 |
| | Amino acid sequence encoding the variable region of the light chain | 118 |
| 2.9 | Nucleotide sequence encoding the variable region of the heavy chain | 119 |
| | Amino acid sequence encoding the variable region of the heavy chain | 120 |
| | Nucleotide sequence encoding the variable region of the light chain | 121 |
| | Amino acid sequence encoding the variable region of the light chain | 122 |
| 2.10 | Nucleotide sequence encoding the variable region of the heavy chain | 123 |
| | Amino acid sequence encoding the variable region of the heavy chain | 124 |
| | Nucleotide sequence encoding the variable region of the light chain | 125 |
| | Amino acid sequence encoding the variable region of the light chain | 126 |
| 2.13 | Nucleotide sequence encoding the variable region of the heavy chain | 127 |
| | Amino acid sequence encoding the variable region of the heavy chain | 128 |
| | Nucleotide sequence encoding the variable region of the light chain | 129 |
| | Amino acid sequence encoding the variable region of the light chain | 130 |
| 2.14 | Nucleotide sequence encoding the variable region of the heavy chain | 131 |
| | Amino acid sequence encoding the variable region of the heavy chain | 132 |
| | Nucleotide sequence encoding the variable region of the light chain | 133 |
| | Amino acid sequence encoding the variable region of the light chain | 134 |
| 2.15 | Nucleotide sequence encoding the variable region of the heavy chain | 135 |
| | Amino acid sequence encoding the variable region of the heavy chain | 136 |
| | Nucleotide sequence encoding the variable region of the light chain | 137 |
| | Amino acid sequence encoding the variable region of the light chain | 138 |
| 2.16 | Nucleotide sequence encoding the variable region of the heavy chain | 139 |
| | Amino acid sequence encoding the variable region of the heavy chain | 140 |
| | Nucleotide sequence encoding the variable region of the light chain | 141 |
| | Amino acid sequence encoding the variable region of the light chain | 142 |
| 2.17 | Nucleotide sequence encoding the variable region of the heavy chain | 143 |
| | Amino acid sequence encoding the variable region of the heavy chain | 144 |

TABLE 1-continued

| mAb ID No.: | Sequence | SEQ ID NO: |
|---|---|---|
| | Nucleotide sequence encoding the variable region of the light chain | 145 |
| | Amino acid sequence encoding the variable region of the light chain | 146 |
| 2.18 | Nucleotide sequence encoding the variable region of the heavy chain | 147 |
| | Amino acid sequence encoding the variable region of the heavy chain | 148 |
| | Nucleotide sequence encoding the variable region of the light chain | 149 |
| | Amino acid sequence encoding the variable region of the light chain | 150 |
| 2.19 | Nucleotide sequence encoding the variable region of the heavy chain | 151 |
| | Amino acid sequence encoding the variable region of the heavy chain | 152 |
| | Nucleotide sequence encoding the variable region of the lambda light chain | 153 |
| | Amino acid sequence encoding the variable region of the lambda light chain | 154 |
| | Nucleotide sequence encoding the variable region of the kappa light chain | 155 |
| | Amino acid sequence encoding the variable region of the kappa light chain | 156 |
| 2.21 | Nucleotide sequence encoding the variable region of the heavy chain | 157 |
| | Amino acid sequence encoding the variable region of the heavy chain | 158 |
| | Nucleotide sequence encoding the variable region of the light chain | 159 |
| | Amino acid sequence encoding the variable region of the light chain | 160 |
| 3.1 | Nucleotide sequence encoding the variable region of the heavy chain | 161 |
| | Amino acid sequence encoding the variable region of the heavy chain | 162 |
| | Nucleotide sequence encoding the variable region of the light chain | 163 |
| | Amino acid sequence encoding the variable region of the light chain | 164 |
| 3.2 | Nucleotide sequence encoding the variable region of the heavy chain | 165 |
| | Amino acid sequence encoding the variable region of the heavy chain | 166 |
| | Nucleotide sequence encoding the variable region of the light chain | 167 |
| | Amino acid sequence encoding the variable region of the light chain | 168 |
| 3.4 | Nucleotide sequence encoding the variable region of the heavy chain | 169 |
| | Amino acid sequence encoding the variable region of the heavy chain | 170 |
| | Nucleotide sequence encoding the variable region of the light chain | 171 |
| | Amino acid sequence encoding the variable region of the light chain | 172 |
| 3.5 | Nucleotide sequence encoding the variable region of the heavy chain | 173 |
| | Amino acid sequence encoding the variable region of the heavy chain | 174 |
| | Nucleotide sequence encoding the variable region of the light chain | 175 |
| | Amino acid sequence encoding the variable region of the light chain | 176 |
| 3.6 | Nucleotide sequence encoding the variable region of the heavy chain | 177 |
| | Amino acid sequence encoding the variable region of the heavy chain | 178 |
| | Nucleotide sequence encoding the variable region of the light chain | 179 |
| | Amino acid sequence encoding the variable region of the light chain | 180 |
| 3.8 | Nucleotide sequence encoding the variable region of the heavy chain | 181 |
| | Amino acid sequence encoding the variable region of the heavy chain | 182 |
| | Nucleotide sequence encoding the variable region of the light chain | 183 |
| | Amino acid sequence encoding the variable region of the light chain | 184 |
| 3.9 | Nucleotide sequence encoding the variable region of the heavy chain | 185 |
| | Amino acid sequence encoding the variable region of the heavy chain | 186 |
| | Nucleotide sequence encoding the variable region of the light chain | 187 |
| | Amino acid sequence encoding the variable region of the light chain | 188 |
| 4.3 | Nucleotide sequence encoding the variable region of the heavy chain | 189 |
| | Amino acid sequence encoding the variable region of the heavy chain | 190 |
| | Nucleotide sequence encoding the variable region of the light chain | 191 |
| | Amino acid sequence encoding the variable region of the light chain | 192 |
| 4.4 | Nucleotide sequence encoding the variable region of the heavy chain | 193 |
| | Amino acid sequence encoding the variable region of the heavy chain | 194 |
| | Nucleotide sequence encoding the variable region of the light chain | 195 |
| | Amino acid sequence encoding the variable region of the light chain | 196 |
| 4.7 | Nucleotide sequence encoding the variable region of the heavy chain | 197 |
| | Amino acid sequence encoding the variable region of the heavy chain | 198 |
| | Nucleotide sequence encoding the variable region of the light chain | 199 |
| | Amino acid sequence encoding the variable region of the light chain | 200 |
| 4.8 | Nucleotide sequence encoding the variable region of the heavy chain | 201 |
| | Amino acid sequence encoding the variable region of the heavy chain | 202 |
| | Nucleotide sequence encoding the variable region of the light chain | 203 |
| | Amino acid sequence encoding the variable region of the light chain | 204 |
| 4.9 | Nucleotide sequence encoding the variable region of the heavy chain | 205 |
| | Amino acid sequence encoding the variable region of the heavy chain | 206 |
| | Nucleotide sequence encoding the variable region of the light chain | 207 |
| | Amino acid sequence encoding the variable region of the light chain | 208 |
| 4.10 | Nucleotide sequence encoding the variable region of the heavy chain | 209 |
| | Amino acid sequence encoding the variable region of the heavy chain | 210 |
| | Nucleotide sequence encoding the variable region of the light chain | 211 |
| | Amino acid sequence encoding the variable region of the light chain | 212 |
| 4.11 | Nucleotide sequence encoding the variable region of the heavy chain | 213 |
| | Amino acid sequence encoding the variable region of the heavy chain | 214 |
| | Nucleotide sequence encoding the variable region of the light chain | 215 |
| | Amino acid sequence encoding the variable region of the light chain | 216 |
| 4.12 | Nucleotide sequence encoding the variable region of the heavy chain | 217 |
| | Amino acid sequence encoding the variable region of the heavy chain | 218 |
| | Nucleotide sequence encoding the variable region of the light chain | 219 |
| | Amino acid sequence encoding the variable region of the light chain | 220 |

TABLE 1-continued

| mAb ID No.: | Sequence | SEQ ID NO: |
|---|---|---|
| 4.13 | Nucleotide sequence encoding the variable region of the heavy chain | 221 |
| | Amino acid sequence encoding the variable region of the heavy chain | 222 |
| | Nucleotide sequence encoding the variable region of the light chain | 223 |
| | Amino acid sequence encoding the variable region of the light chain | 224 |
| 4.14 | Nucleotide sequence encoding the variable region of the heavy chain | 225 |
| | Amino acid sequence encoding the variable region of the heavy chain | 226 |
| | Nucleotide sequence encoding the variable region of the light chain | 227 |
| | Amino acid sequence encoding the variable region of the light chain | 228 |
| 4.15 | Nucleotide sequence encoding the variable region of the heavy chain | 229 |
| | Amino acid sequence encoding the variable region of the heavy chain | 230 |
| | Nucleotide sequence encoding the variable region of the light chain | 231 |
| | Amino acid sequence encoding the variable region of the light chain | 232 |
| 4.16 | Nucleotide sequence encoding the variable region of the heavy chain | 233 |
| | Amino acid sequence encoding the variable region of the heavy chain | 234 |
| | Nucleotide sequence encoding the variable region of the light chain | 235 |
| | Amino acid sequence encoding the variable region of the light chain | 236 |
| 4.17 | Nucleotide sequence encoding the variable region of the heavy chain | 237 |
| | Amino acid sequence encoding the variable region of the heavy chain | 238 |
| | Nucleotide sequence encoding the variable region of the light chain | 239 |
| | Amino acid sequence encoding the variable region of the light chain | 240 |
| 4.18 | Nucleotide sequence encoding the variable region of the heavy chain | 241 |
| | Amino acid sequence encoding the variable region of the heavy chain | 242 |
| | Nucleotide sequence encoding the variable region of the light chain | 243 |
| | Amino acid sequence encoding the variable region of the light chain | 244 |
| 4.19 | Nucleotide sequence encoding the variable region of the heavy chain | 245 |
| | Amino acid sequence encoding the variable region of the heavy chain | 246 |
| | Nucleotide sequence encoding the variable region of the light chain | 247 |
| | Amino acid sequence encoding the variable region of the light chain | 248 |
| 4.20 | Nucleotide sequence encoding the variable region of the heavy chain | 249 |
| | Amino acid sequence encoding the variable region of the heavy chain | 250 |
| | Nucleotide sequence encoding the variable region of the light chain | 251 |
| | Amino acid sequence encoding the variable region of the light chain | 252 |
| 4.21 | Nucleotide sequence encoding the variable region of the heavy chain | 253 |
| | Amino acid sequence encoding the variable region of the heavy chain | 254 |
| | Nucleotide sequence encoding the variable region of the light chain | 255 |
| | Amino acid sequence encoding the variable region of the light chain | 256 |
| 4.22 | Nucleotide sequence encoding the variable region of the heavy chain | 257 |
| | Amino acid sequence encoding the variable region of the heavy chain | 258 |
| | Nucleotide sequence encoding the variable region of the light chain | 259 |
| | Amino acid sequence encoding the variable region of the light chain | 260 |
| 4.23 | Nucleotide sequence encoding the variable region of the heavy chain | 261 |
| | Amino acid sequence encoding the variable region of the heavy chain | 262 |
| | Nucleotide sequence encoding the variable region of the light chain | 263 |
| | Amino acid sequence encoding the variable region of the light chain | 264 |

Definitions

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (2d ed., Cold Spring Harbor Laboratory Press, Cold Spring Harbor, N.Y. (1989)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "TNFα" refers to the cytokine, Tumor Necrosis Factor-alpha (Pennica, D. et al., 1984, *Nature* 312:724-729). TNFα is also known in the art as cachectin.

The term "neutralizing" when referring to an antibody relates to an antibody's ability to eliminate or significantly reduce an effector function of a target antigen to which is binds. Accordingly, a "neutralizing" anti-TNFα antibody is capable of eliminating or significantly reducing an effector function, such as TNFα activity.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g. free of murine proteins, (3) is expressed by a cell from a different species, or (4) does not occur in nature.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules and the human kappa light chain immunoglobulin molecules, as well as antibody molecules formed by combinations comprising the heavy chain immunoglobulin molecules with light chain immunoglobulin molecules, such as the kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described that are in a relationship permitting them to function in their intended manner. For example, a control sequence "operably linked" to a coding sequence is connected in such a way that expression of the coding sequence is achieved under conditions compatible with the control sequences.

The term "control sequence" as used herein refers to polynucleotide sequences which are necessary to effect the expression and processing of coding sequences to which they are connected. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably, oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoroamidate, and the like. See e.g., LaPlanche et al. *Nucl. Acids Res*. 14:9081 (1986); Stec et al. *J Am. Chem. Soc*. 106:6077 (1984); Stein et al. *Nucl. Acids Res*. 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "selectively hybridize" referred to herein means to detectably and specifically bind. Polynucleotides, oligonucleotides and fragments thereof selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, or antibody fragments and a nucleic acid sequence of interest will be at least 80%, and more typically with preferably increasing homologies of at least 85%, 90%, 95%, 99%, and 100%.

Two amino acid sequences are "homologous" if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least about 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in *Atlas of Protein Sequence and Structure*, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence.

In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison. A reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least about 18 contiguous nucleotide positions or about 6 amino acids wherein the polynucleotide sequence or amino acid sequence is compared to a reference sequence of at least 18 contiguous nucleotides or 6 amino acid sequences and wherein the portion of the polynucleotide sequence in the comparison window may include additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), GENEWORKS™, or MACVECTOR® software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or amino acid residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more preferably at least 99 percent sequence identity, as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See *Immunology—A Synthesis* (2$^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99% sequence identity to the antibodies or immunoglobulin molecules described herein. In particular, conservative amino acid replacements are contemplated. Conservative replacements are those that take place within a family of amino acids that have related side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253:164 (1991). Thus, the foregoing examples demonstrate that those of skill in the art can recognize sequence motifs and structural conformations that may be used to define structural and functional domains in accordance with the antibodies described herein.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et at. *Nature* 354:105 (1991), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to a TNFα, under suitable binding conditions, (2) ability to block appropriate TNFα binding, or (3) ability to inhibit TNFα activity. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, *J. Adv. Drug Res.* 15:29 (1986); Veber and Freidinger TINS p.392 (1985); and Evans et al. *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —CH$_2$NH—, —CH$_2$S—, —CH$_2$—CH$_2$—, —CH=CH—(cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

"Antibody" or "antibody peptide(s)" refer to an intact antibody, or a binding fragment thereof, that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a receptor to a counterreceptor when an excess of antibody reduces the quantity of receptor bound to counterreceptor by at least about 20%, 40%, 60% or 80%, and more usually greater than about 85% (as measured in an in vitro competitive binding assay).

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is $\leq 1$ µM, preferably $\leq 100$ nM and most preferably $\leq 10$ nM.

The term "agent" is used herein to denote a chemical compound, a mixture of chemical compounds, a biological macromolecule, or an extract made from biological materials.

"Active" or "activity" in regard to a TNFα polypeptide refers to a portion of a TNFα polypeptide which has a biological or an immunological activity of a native TNFα polypeptide. "Biological" when used herein refers to a biological function that results from the activity of the native TNFα polypeptide. A preferred TNFα biological activity includes, for example, TNFα induced apoptosis.

"Mammal" when used herein refers to any animal that is considered a mammal. Preferably, the mammal is human.

Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in the a $F(ab')_2$ fragment in which the two arms of the antibody molecule remain linked and comprise two-antigen binding sites. The $F(ab')_2$ fragment has the ability to crosslink antigen.

"Fv" when used herein refers to the minimum fragment of an antibody that retains both antigen-recognition and antigen-binding sites.

"Fab" when used herein refers to a fragment of an antibody which comprises the constant domain of the light chain and the CH1 domain of the heavy chain.

The term "mAb" refers to monoclonal antibody.

The description of XENOMAX® antibody sequences is coded as follows: "AB"-referring to antibody, "TNFα"-referring to antibody's binding specificity, "X" referring to XENOMOUSE® derived, "G1"-referring to IgG1 isotype or "G2" referring to IgG2 isotype, the last three digits referring to the single cell number from which the antibody was derived, for example: AB-TNFα-XG1-015.

The term "SC" refers to single cell and a particular XENOMAX® derived antibody may be referred to as SC followed by three digits, or just three digits, referring to the single cell number from which the antibody was derived herein.

The description of hybridoma derived antibody sequences is coded as follows: "AB"-referring to antibody, "TNFα"-refers to the antibody's binding specificity, "X" refers to XENOMOUSE® derived, "G1"-refers to IgG1 isotype or "G2" refers to IgG2 isotype, "K" refers to kappa, "L" refers to lambda. the last three digits referring to the clone from which the antibody was derived, for example: AB-TNFα-XG2K-4.17

"Liposome" when used herein refers to a small vesicle that may be useful for delivery of drugs that may include the TNFα polypeptide of the invention or antibodies to such a TNFα polypeptide to a mammal.

"Label" or "labeled" as used herein refers to the addition of a detectable moiety to a polypeptide, for example, a radiolabel, fluorescent label, enzymatic label chemiluminescent labeled or a biotinyl group. Radioisotopes or radionuclides may include $^3H$, $^{14}C$, $^{15}N$, $^{35}S$, $^{90}Y$, $^{99}Tc$, $^{111}In$, $^{125}I$, $^{131}I$, fluorescent labels may include rhodamine, lanthanide phosphors or FITC and enzymatic labels may include horseradish peroxidase, β-galactosidase, luciferase, alkaline phosphatase.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), (incorporated herein by reference).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "patient" includes human and veterinary subjects.

The term "SLAM®" refers to the "Selected Lymphocyte Antibody Method" (Babcook et al., *Proc. Natl. Acad. Sci. USA*, i93:7843-7848 (1996), and Schrader, U.S. Pat. No. 5,627,052), both of which are incorporated by reference in their entireties.

The term "XENOMAX®" refers use of to the use of the "Selected Lymphocyte Antibody Method" (Babcook et al., *Proc. Natl. Acad. Sci. USA*, i93:7843-7848 (1996)), when used with XENOMOUSE® animals.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J. Mol. Biol.* 196:901-917 (1987); Chothia et al. *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann *Clin. Exp. Immunol.* 79: 315-321 (1990), Kostelny et al. *J. Immunol.* 148:1547-1553 (1992). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Human Antibodies and Humanization of Antibodies

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of human antibody function into a rodent so that the rodent produces fully human antibodies.

One method for generating fully human antibodies is through the use of XENOMOUSE® strains of mice which have been engineered to contain 245 kb and 190 kb-sized germline configuration fragments of the human heavy chain locus and kappa light chain locus. See Green et al. *Nature Genetics* 7:13-21 (1994). The XENOMOUSE® strains are available from Abgenix, Inc. (Fremont, Calif.).

The production of the XENOMOUSE® is further discussed and delineated in U.S. patent application Ser. Nos. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, filed Ser. No. 08/031, 801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759,620, filed Dec. 3, 1996 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also Mendez et al. *Nature Genetics* 15:146-156 (1997) and Green and Jakobovits *J. Exp. Med.* 188:483-495 (1998). See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. Nos. 5,591,669 and 6,023,010 to Krimpenfort and Berns, U.S. Pat. Nos. 5,612,205, 5,721,367, and 5,789, 215 to Berns et al., and U.S. Pat. No. 5,643,763 to Choi and Dunn, and GenPharm International U.S. patent application Ser. No. 07/574,748, filed Aug. 29, 1990, Ser. No. 07/575, 962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209, 741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against TNFα in order to vitiate concerns and/or effects of HAMA or HACA response.

Antibody Therapeutics

As discussed herein, the function of the TNFα antibody appears important to at least a portion of its mode of operation. By function, is meant, by way of example, the activity of the TNFα antibody in operation with TNFα. Accordingly, in certain respects, it may be desirable in connection with the generation of antibodies as therapeutic candidates against TNFα that the antibodies be capable of fixing complement and participating in CDC. There are a number of isotypes of antibodies that are capable of the same, including, without limitation, the following: murine IgM, murine IgG2a, murine IgG2b, murine IgG3, human IgM, human IgG1, and human IgG3. It will be appreciated that antibodies that are generated need not initially possess such an isotype but, rather, the antibody as generated can possess any isotype and the antibody can be isotype switched thereafter using conventional techniques that are well known in the art. Such techniques include the use of direct recombinant techniques (see e.g., U.S. Pat. No. 4,816, 397), cell-cell fusion techniques (see e.g., U.S. Pat. Nos. 5,916,771 and 6,207,418), among others.

In the cell-cell fusion technique, a myeloma or other cell line is prepared that possesses a heavy chain with any desired isotype and another myeloma or other cell line is prepared that possesses the light chain. Such cells can, thereafter, be fused and a cell line expressing an intact antibody can be isolated.

By way of example, the TNFα antibody discussed herein is a human anti-TNFα IgG2 antibody. If such antibody possessed desired binding to the TNFα molecule, it could be readily isotype switched to generate a human IgM, human IgG1, or human IgG3 isotype, while still possessing the same variable region (which defines the antibody's specificity and some of its affinity). Such molecule would then be capable of fixing complement and participating in CDC.

Accordingly, as antibody candidates are generated that meet desired "structural" attributes as discussed above, they can generally be provided with at least certain of the desired "functional" attributes through isotype switching.

Design and Generation of other Therapeutics

In accordance with the present invention and based on the activity of the antibodies that are produced and characterized herein with respect to TNFα, the design of other therapeutic modalities beyond antibody moieties is facilitated. Such modalities include, without limitation, advanced antibody therapeutics, such as bispecific antibodies, immunotoxins, and radiolabeled therapeutics, generation of peptide therapeutics, gene therapies, particularly intrabodies, antisense therapeutics, and small molecules.

In connection with the generation of advanced antibody therapeutics, where complement fixation is a desirable attribute, it may be possible to sidestep the dependence on complement for cell killing through the use of bispecifics, immunotoxins, or radiolabels, for example.

For example, in connection with bispecific antibodies, bispecific antibodies can be generated that comprise (i) two antibodies one with a specificity to TNFα and another to a second molecule that are conjugated together, (ii) a single antibody that has. one chain specific to TNFα and a second chain specific to a second molecule, or (iii) a single chain antibody that has specificity to TNFα and the other molecule. Such bispecific antibodies can be generated using techniques that are well known; for example, in connection with (i) and (ii) see e.g., Fanger et al. *Immunol Methods* 4:72-81 (1994) and Wright and Harris, supra. and in connection with (iii) see e.g., Traunecker et al. *Int. J. Cancer (Suppl.)* 7:51-52 (1992). In each case, the second specificity can be made to the heavy chain activation receptors, including, without limitation, CD16 or CD64 (see e.g., Deo et al. 18:127 (1997)) or CD89 (see e.g., Valerius et al. *Blood* 90:4485-4492 (1997)). Bispecific antibodies prepared in accordance with the foregoing would be likely to kill cells expressing TNFα.

In connection with immunotoxins, antibodies can be modified to act as immunotoxins utilizing techniques that are well known in the art. See e.g., Vitetta *Immunol Today* 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in *Cancer Chemotherapy and Biotherapy* 655-686 (2d edition, Chafner and Longo, eds., Lippincott Raven (1996)).

See also U.S. Pat. Nos. 4,681,581, 4,735,210, 5,101,827, 5,102,990 (RE 35,500), 5,648,471, and 5,697,902. Each of immunotoxins and radiolabeled molecules would be likely to kill cells expressing TNFα.

Preparation of Antibodies

Antibodies, as described herein, were prepared through the utilization of the XENOMOUSE® technology, as described below. Such mice, then, are capable of producing human immunoglobulin molecules and antibodies and are deficient in the production of murine immunoglobulin molecules and antibodies. Technologies utilized for achieving the same are disclosed in the patents, applications, and references disclosed in the background section herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. *Nature Genetics* 15:146-156 (1997), the disclosure of which is hereby incorporated by reference.

Through use of such technology, fully human monoclonal antibodies to a variety of antigens have been produced. Essentially, XENOMOUSE® lines of mice are immunized with an antigen of interest (e.g. TNFα), lymphatic cells (such as B-cells) are recovered from the mice that expressed antibodies, and the recovered cell lines are fused with a myeloid-type cell line to prepare immortal hybridoma cell lines. These hybridoma cell lines are screened and selected to identify hybridoma cell lines that produced antibodies specific to the antigen of interest. Provided herein are methods for the production of multiple hybridoma cell lines that produce antibodies specific to TNFα. Further, provided herein are characterization of the antibodies produced by such cell lines, including nucleotide and amino acid sequence analyses of the heavy and light chains of such antibodies.

Alternatively, instead of being fused to myeloma cells to generate hybridomas, the recovered cells, isolated from immunized XENOMOUSE® lines of mice, are screened further for reactivity against the initial antigen, preferably TNFα protein. Such screening includes ELISA with TNFα protein, a competition assay with known antibodies that bind the antigen of interest, in vitro neutralization of TNFα induced apoptosis and in vitro binding to transiently transfected CHO cells expressing full length TNFα. Single B cells secreting antibodies of interest are then isolated using a TNFα-specific hemolytic plaque assay (Babcook et al., *Proc. Natl. Acad. Sci. USA*, i93:7843-7848 (1996)). Cells targeted for lysis are preferably sheep red blood cells (SRBCs) coated with the TNFα antigen. In the presence of a B cell culture secreting the immunoglobulin of interest and complement, the formation of a plaque indicates specific TNFα-mediated lysis of the target cells. The single antigen-specific plasma cell in the center of the plaque can be isolated and the genetic information that encodes the specificity of the antibody is isolated from the single plasma cell. Using reverse-transcriptase PCR, the DNA encoding the variable region of the antibody secreted can be cloned. Such cloned DNA can then be further inserted into a suitable expression vector, preferably a vector cassette such as a pcDNA, more preferably such a pcDNA vector containing the constant domains of immunoglobulin heavy and light chain. The generated vector can then be transfected into host cells, preferably CHO cells, and cultured in conventional nutrient media modified as appropriate for inducing promoters, selecting transformants, or amplifying the genes encoding the desired sequences. Herein, is described, the isolation of multiple single plasma cells that produce antibodies specific to TNFα. Further, the genetic material that encodes the specificity of the anti-TNFα antibody is isolated, and introduced into a suitable expression vector which is then transfected into host cells.

In general, antibodies produced by the above-mentioned cell lines possessed fully human IgG1 or IgG2 heavy chains with human kappa light chains. The antibodies possessed high affinities, typically possessing Kd's of from about $10^{-9}$ through about $10^{-13}$ M, when measured by either solid phase and solution phase.

As will be appreciated, anti-TNFα antibodies can be expressed in cell lines other than hybridoma cell lines. Sequences encoding particular antibodies can be used for transformation of a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. Cell lines of particular preference are selected through determining which cell lines have high expression levels and produce antibodies with constitutive TNFα binding properties.

Anti-TNFα antibodies are useful in the detection of TNFα in patient samples and accordingly are useful as diagnostics for disease states as described herein. In addition, based on their ability to significantly neutralize TNFα activity (as demonstrated in the Examples below), anti-TNFα antibodies will have therapeutic effects in treating symptoms and conditions resulting from TNFα. In specific embodiments, the antibodies and methods herein relate to the treatment of symptoms resulting from TNFα including: fever, muscle ache, lethargy, headache, nausea, and inflammation. Further embodiments involve using the antibodies and methods described herein to treat: cachexia, anorexia, rheumatic diseases such as arthritis, inflammatory diseases such as Crohn's disease, and auto-immune diseases, such as psoriasis, graft-host reactions, and septic shock.

Therapeutic Administration and Formulations

Biologically active anti-TNFα antibodies as described herein may be used in a sterile pharmaceutical preparation or formulation to reduce the level of serum TNFα thereby effectively treating pathological conditions where, for example, serum TNFα is abnormally elevated. Anti-TNFα antibodies preferably possess adequate affinity to potently suppress TNFα to within the target therapeutic range, and preferably have an adequate duration of action to allow for infrequent dosing. A prolonged duration of action will allow for less frequent and more convenient dosing schedules by alternate parenteral routes such as subcutaneous or intramuscular injection.

When used for in vivo administration, the antibody formulation must be sterile. This is readily accomplished, for example, by filtration through sterile filtration membranes, prior to or following lyophilization and reconstitution. The antibody ordinarily will be stored in lyophilized form or in solution. Therapeutic antibody compositions generally are placed into a container having a sterile access port, for example, an intravenous solution bag or vial having an adapter that allows retrieval of the formulation, such as a stopper pierceable by a hypodermic injection needle.

The route of antibody administration is in accord with known methods, e.g., injection or infusion by intravenous, intraperitoneal, intracerebral, intramuscular, intraocular, intraarterial, intrathecal, inhalation or intralesional routes, or by sustained release systems as noted below. The antibody is preferably administered continuously by infusion or by bolus injection.

An effective amount of antibody to be employed therapeutically will depend, for example, upon the therapeutic objectives, the route of administration, and the condition of the patient. Accordingly, it is preferred that the therapist titer the dosage and modify the route of administration as required to obtain the optimal therapeutic effect. Typically, the clinician will administer antibody until a dosage is reached that achieves the desired effect. The progress of this therapy is easily monitored by conventional assays or by the assays described herein.

Antibodies, as described herein, can be prepared in a mixture with a pharmaceutically acceptable carrier. This therapeutic composition can be administered intravenously or through the nose or lung, preferably as a liquid or powder aerosol (lyophilized). The composition may also be administered parenterally or subcutaneously as desired. When administered systemically, the therapeutic composition should be sterile, pyrogen-free and in a parenterally acceptable solution having due regard for pH, isotonicity, and stability. These conditions are known to those skilled in the art. Briefly, dosage formulations of the compounds described herein are prepared for storage or administration by mixing the compound having the desired degree of purity with physiologically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice as described in Remington: The Science and Practice of Pharmacy (20$^{th}$ ed, Lippincott Williams & Wilkens Publishers (2003)). For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

Suitable examples of sustained-release preparations include semipermeable matrices of solid hydrophobic polymers containing the polypeptide, which matrices are in the form of shaped articles, films or microcapsules. Examples of sustained-release matrices include polyesters, hydrogels (e.g., poly(2-hydroxyethyl-methacrylate) as described by Langer et al., *J. Biomed Mater. Res.*, (1981) 15:167-277 and Langer, *Chem. Tech.*, (1982) 12:98-105, or poly(vinylalcohol)), polylactides (U.S. Pat. No. 3,773,919, EP 58,481), copolymers of L-glutamic acid and gamma ethyl-L-glutamate (Sidman et al., *Biopolymers*, (1983) 22:547-556), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(-)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization may be achieved by modifying sulfhydryl residues, lyophilizing from acidic solutions, controlling moisture content, using appropriate additives, and developing specific polymer matrix compositions.

Sustained-released compositions also include preparations of crystals of the antibody suspended in suitable formulations capable of maintaining crystals in suspension. These preparations when injected subcutaneously or intraperitonealy can produce a sustain release effect. Other compositions also include liposomally entrapped antibodies. Liposomes containing such antibodies are prepared by methods known per se: U.S. Pat. No. DE 3,218,121; Epstein et al., *Proc. Natl. Acad. Sci. USA*, (1985) 82:3688-3692; Hwang et al., *Proc. Natl. Acad. Sci. USA*, (1980) 77:4030-4034; EP 52,322; EP 36,676; EP 88,046; EP 143,949; 142,641; Japanese patent application 83-118008; U.S. Pat. Nos. 4,485,045 and 4,544,545; and EP 102,324.

The dosage of the antibody formulation for a given patient will be determined by the attending physician taking into consideration various factors known to modify the action of drugs including severity and type of disease, body weight, sex, diet, time and route of administration, other medications and other relevant clinical factors. Therapeutically effective dosages may be determined by either in vitro or in vivo methods.

An effective amount of the antibodies, described herein, to be employed therapeutically will depend, for example, upon the therapeutic objectives, the route of administration, and the condition of the patient. Accordingly, it is preferred for the therapist to titer the dosage and modify the route of administration as required to obtain the optimal therapeutic effect. A typical daily dosage might range from about 0.001 mg/kg to up to 100 mg/kg or more, depending on the factors mentioned above. Typically, the clinician will administer the therapeutic antibody until a dosage is reached that achieves the desired effect. The progress of this therapy is easily monitored by conventional assays or as described herein.

It will be appreciated that administration of therapeutic entities in accordance with the compositions and methods herein will be administered with suitable carriers, excipients, and other agents that are incorporated into formulations to provide improved transfer, delivery, tolerance, and the like. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32(2):210-8 (2000), Wang W. "Lyophilization and development of solid protein pharmaceuticals." *Int. J. Pharm.* 203(1-2):1-60 (2000), Charman WN "Lipids, lipophilic drugs, and oral drug delivery-some emerging concepts." *J. Pharm Sci.* 89(8):967-78 (2000), Powell et al. "Compendium of excipients for parenteral formulations" *PDA J. Pharm Sci Technol.* 52:238-311 (1998) and the citations therein for additional information related to formulations, excipients and carriers well known to pharmaceutical chemists.

It is expected that the antibodies described herein will have therapeutic effect in treatment of symptoms and conditions resulting from TNFα. In specific embodiments, the antibodies and methods herein relate to the treatment of symptoms resulting from TNFα including: fever, muscle ache, lethargy, headache, nausea, and inflammation. Further embodiments, involve using the antibodies and methods described herein to treat: cachexia, anorexia, rheumatic diseases such as arthritis, inflammatory diseases such as Crohn's disease, auto-immune diseases, such as psoriasis, graft-host reactions, and septic shock.

EXAMPLES

The following examples, including the experiments conducted and results achieved are provided for illustrative purposes only and are not to be construed as limiting upon the teachings herein.

Example 1

Antigen Preparation

TNFα-KLH Antigen Preparation for Immunization of XENOMOUSE® Animals

Recombinant human TNFα was obtained from R&D Systems (Minneapolis, Minn. Cat. No. 210-TA/CF). The TNFα-KLH antigen, used for the immunization of XENOMOUSE® animals, was prepared as follows: human TNF-α(200 μg) (R&D) was mixed with 50 μg of keyhole limpet hemocyanin (KLH; Pierce, Rockford, Ill.) to a final volume of 165 μl using distilled water. 250 μl of conjugation buffer (0.1M MES, 0.9M NaCl, pH 4.7) was added and TNFα and KLH were crosslinked by the addition of 25 μl of 10 mg/mL stock solution of 1-ethyl-3-[3-dimethylaminopropyl]carbodiimide hydrochloride (EDC., Pierce, Rockford, Ill.). The conjugate was incubated for 2 hours at room temperature and the unreacted EDC was removed by centrifugation through a 1 kDa filter (Centrifugal filter; Millipore, Bedford, Mass.) using PBS pH 7.4.

TNFα-TCE Antigen Preparation for Immunization of XENOMOUSE® animals

Human TNFα was recombinantly generated as a fusion protein in frame with a universal T-cell epitope (TCE) (J. Immunol 1992 148(5):1499) for immunization of XENOMOUSE® animals.

Human TNFα was cloned from human peripheral mononuclear cells (PBMCs). mRNA was isolated from purified hPBMC's and cDNA was generated by reverse transcription. Human TNFα was specifically amplified by PCR and cloned in frame with a universal T-cell epitope (TCE) derived from Tetanus toxin in the expression vector pGEX (Amersham Pharmacia). The fusion protein was expressed in E. Coli, purified on Glutathione Sepharose beads (CAT# 17-0756-01, Amersham Pharmacia), cleaved with thrombin (Sigma) and eluted as described by the manufacturer (Amersham Pharmacia).

Example 2

Antibody Generation

Immunization

Human monoclonal antibodies against human TNFα were developed by sequentially immunizing XENOMOUSE® mice (XENOMOUSE® XMG2L3 or 3B-3L3 Abgenix, Inc. Fremont, Calif.).

To generate hybridomas, cohorts of XMG2L3 and 3B-L3 XENOMOUSE® mice were immunized with TNFα alone or TNFα with CPG via foot pad. The initial immunization was with 10 µg of antigen mixed 1:1 v/v with TITERMAX GOLD® (Sigma, Oakville, Oreg.) per mouse. A subsequent four boosts were performed with 10 µg of antigen mixed with alum (Sigma, Oakville, Oreg.), adsorbed overnight, per mouse, followed by one injection with TNFα in TITERMAX GOLD®, one injection with alum and then a final boost of 10 µg of TNFα in PBS per mouse.

Cohorts receiving TNFα with CPG were first immunized with TNFα and TITERMAX GOLD® as above, the next six boosts were with TNFα absorbed to Alum as previously stated along with CPG. The final boost was with TNFα in PBS and CPG. In particular, animals were immunized on days 0, 3, 9,16, 21, 25, 30 and 35. The animals were bled on days 28 and 39 to obtain sera for harvest selection as described below.

To generate mAbs by XENOMAX®, cohorts of XMG2 XENOMOUSE® mice were immunized with TNFα via foot pad (FP), TNFα-KLH (as prepared in Example 1) via base of the tail by subcutaneous injection and intraperitoneum (BIP), or with TNFα-TCE (as prepared in Example 1) via base of the tail by subcutaneous injection and intraperitoneum. For TNFα footpad immunizations, the initial immunization was with 2 µg of antigen mixed 1:1 v/v with TITERMAX GOLD® per mouse. A subsequent four boosts were performed with 2 µg of antigen mixed with alum (Sigma, Oakville, Oreg.), adsorbed overnight, per mouse, followed by one injection with TNFα in TITERMAX GOLD®, one injection with alum and then a final boost of 2 µg of TNFα in PBS per mouse. In particular, animals were immunized on days 0, 3, 7,10, 14, 17, 21 and 24. The animals were bled on day 19 to obtain sera for harvest selection as described below.

The initial BIP immunization with 2 or 5 µg TNFα-KLH or TNFα-TCE respectively was mixed 1:1 v/v with Complete Freund's Adjuvant (CFA, Sigma, Oakville, Oreg.) per mouse. Subsequent boosts were made first with 2 or 5 µg of antigen respectively, mixed 1:1 v/v with Incomplete Freund's Adjuvant (IFA, Sigma, Oakville, Oreg.) per mouse, followed by a final boost in PBS per mouse. The animals were immunized on days 0, 14, 28, 42, 56, and day 75 or 93 (final boost). The animals were bled on day 63 to obtain sera for harvest selection as described below.

To generate rabbit anti-hTNFα monoclonal antibodies by SLAM, a cohort of New Zealand white rabbits were immunized as follows. A primary boost consisting of 250 µg of TNFα-TCE, emulsified 1;1 v/v with complete freund's adjuvant (CFA), was given subcutaneously in four sites along the rabbit's dorsal body. These were followed by 3 immunizations with 125 µg of TNFα-TCE emulsified 1:1 v/v with incomplete freunds adjuvant (IFA) intramuscularly via the hind legs. Each of the boosts were separated by 21 days. The animals were bled prior to the fourth immunization for serology, see Table 9 below.

Selection of Animals for Harvest

Anti-hTNFα antibody titers were determined by ELISA. hTNFα was coated onto Costar Labcoat Universal Binding Polystyrene 96-well plates (Corning, Acton, Mass.) overnight at four degrees. The solution containing unbound TNFα was removed and the plates were treated with UV light (365 nm) for 4 minutes (4000 microjoules). The plates were washed five times with dH$_2$O. XENOMOUSE® sera from the TNFα immunized animals, or naïve XENOMOUSE® animals, were titrated in 2% milk/PBS at 1:2 dilutions in duplicate from a 1:100 initial dilution. The last well was left blank. The plates were washed five times with dH$_2$O. A goat anti-human IgG Fc-specific horseradish peroxidase (HRP, Pierce, Rockford, Ill.) conjugated antibody was added at a final concentration of 1 µg/mL for 1 hour at room temperature. The plates were washed five times with dH20. The plates were developed with the addition of TMB chromogenic substrate (Gaithersburg, Md.) for 30 minutes and the ELISA was stopped by the addition of 1 M phosphoric acid. The specific titer of individual XENOMOUSE® animals was determined from the optical density at 450 nm and are shown in Tables 2 to 8 The titer represents the reciprocal dilution of the serum and therefore the higher the number the greater the humoral immune response to hTNFα.

Rabbit anti-TNFα titers were determined as above, but for detection of primary antibody, a goat anti-rabbit IgG heavy and light chain-specific horseradish peroxidase (HRP, Pierce, Rockford, Ill.) reagent was used in place of the anti-human reagent, see Table 9.

TABLE 2

FP, 3B-3L3 mice, hTNFα G1 kλ

| Mouse ID | Titer | |
|---|---|---|
| | day 28 | day 39 |
| N472-3 | 400 | — |
| N473-11 | 310 | — |
| N474-3 | 1,100 | — |
| N543-3 | 8,000 | 6,500 |

TABLE 2-continued

FP, 3B-3L3 mice, hTNFα G1 kλ

| Mouse ID | Titer day 28 | day 39 |
|---|---|---|
| N574-5 | 16,000 | 16,000 |
| N638-7 | — | — |
| N638-8 | 40 | 50 |

All XENOMOUSE® animals in Table 2 were selected for harvest and generation of hybridomas.

TABLE 3

FP, 3B-3L3 mice, hTNFα + CpG G1 kλ

| Mouse ID | Titer day 28 | day 39 |
|---|---|---|
| N643-8 | 19,000 | 70,000 |
| N651-9 | 24,000 | 75,000 |
| N673-7 | 19,000 | 60,000 |
| N713-7 | 750 | 6,000 |
| N732-6 | 80 | 450 |

All XENOMOUSE® animals in Table 3 were selected for harvest and generation of hybridomas.

TABLE 4

FP, XMG2L3 mice, hTNFα G2 kλ

| Mouse ID | Titer day 28 | day 39 |
|---|---|---|
| N668-1 | 50,000 | — |
| N668-2 | 40,000 | — |
| N668-3 | 22,000 | — |
| N668-7 | 150,000 | 175,000 |
| N670-1 | 22,000 | 24,000 |
| N676-6 | 55,000 | 73,000 |
| N677-3 | 110,000 | 150,000 |

All XENOMOUSE® animals in Table 4 were selected for harvest and generation of hybridomas.

TABLE 5

FP, XMG2L3 mice, hTNFα + CpG G2 kλ

| Mouse ID | Titer day 28 | day 39 |
|---|---|---|
| N667-1 | 175,000 | 600,000 |
| N667-3 | 200,000 | 500,000 |
| N667-5 | 400,000 | 200,000 |
| N677-2 | 325,000 | 600,000 |
| N677-4 | 21,000 | 300,000 |
| N677-5 | 300,000 | 600,000 |

All XENOMOUSE® animals in Table 5 were selected for harvest and generation of hybridomas.

TABLE 6

FP, XMG2 mice, hTNFα IgG2/K

| Mouse ID | Titer Day 17 |
|---|---|
| O651-1 | 186 |
| O651-2 | 816 |
| O651-3 | 388 |
| O651-4 | 260 |
| O651-5 | 1342 |
| O651-6 | 373 |
| O651-7 | 314 |
| O651-8 | <100 @ OD 0.666 |
| O651-9 | 588 |
| O651-10 | 163 |

XENOMOUSE® animals (O651-2, O651-3, O651-5 and O651-9) were selected for XENOMAX® harvests based on the serology data in Table 6.

TABLE 7

BIP, XMG2 mice, hTNFα – KLH IgG2/K

| Mouse ID | Titer Day 63 |
|---|---|
| O797-1 | 1999 |
| O797-2 | 2586 |
| O797-3 | 1885 |
| O797-4 | >6400 @ OD 2.074 |
| O797-5 | 1492 |
| O797-6 | 4325 |
| O797-7 | >6400 @ OD 3.294 |
| O797-8 | 1314 |
| O797-9 | 3329 |
| O797-10 | 4829 |

XENOMOUSE® animals (O797-4, O797-6, O797-7 and O797-10) were selected for XENOMAX® harvests based on the serology data in Table 7.

TABLE 8

BIP, XMG2 mice, hTNFα – TCE IgG2/K

| Mouse ID | Titer Day 63 |
|---|---|
| O796-1 | 2677 |
| O796-2 | 5197 |
| O796-3 | 3143 |
| O796-4 | >6400 @ OD 2.034 |
| O796-5 | 1055 |
| O796-6 | 221 |
| O796-7 | >6400 @ OD 2.017 |
| O796-8 | >6400 @ OD 2.066 |
| O796-9 | 2145 |
| O796-10 | 4364 |

XENOMOUSE® animals (O796-2, O796-4, O796-7, O796-8 and O796-10) were selected for XENOMAX® harvests based on the serology data in Table 8.

TABLE 9

Rabbit IPI-5

| Rabbit ID | Titer Day 63 |
|---|---|
| IPI-5 | 500,000 |

Blood from rabbit IPI-5 was harvested for generating rabbit monoclonal antibodies by SLAM.

Example 3

Generation of Anti-human TNFα Antibodies

Generation of Anti-hTNFα Antibodies by Hybridoma.
Recovery of Lymphocytes, B-cell Isolations, Fusions and Generation of Hybridomas Immunized mice were sacrificed by cervical dislocation, and the lymph nodes harvested and pooled from each cohort. The lymphoid cells were dissociated by grinding in DMEM to release the cells from the tissues and the cells were suspended in DMEM. The cells were counted, and 0.9 mL DMEM per 100 million lymphocytes added to the cell pellet to resuspend the cells gently but completely. Using 100 μL of CD90$^+$ magnetic beads per 100 million cells, the cells were labeled by incubating the cells with the magnetic beads at 4° C. for 15 minutes. The magnetically labeled cell suspension containing up to $10^8$ positive cells (or up to $2 \times 10^9$ total cells) was loaded onto a LS$^+$ column and the column washed with DMEM. The total effluent was collected as the CD90-negative fraction (most of these cells are B cells).

P3 myeloma cells and B cell-enriched lymph node cells were combined in a ratio of 1:1 (myeloma:lymph nodes) into a 50 mL conical tube in DMEM. The combined cells were centrifuged at 800×g (2000 rpm) for 5-7 min. and the supernatant immediately removed from the resulting pellet. Two to four mL of Pronase solution (CalBiochem, Cat. #53702; 0.5 mg/mL in PBS) was added to the cells to resuspend the cell pellet gently. The enzyme treatment was allowed to proceed for no more than two minutes and the reaction stopped by the addition of 3-5 mL of FBS. Enough ECF solution was added to bring the total volume to 40 mL and the mixture was centrifuged at 800×g (2000 rpm) for 5-7 min. The supernatant was removed and the cell pellet gently resuspended with a small volume of ECF solution, followed by enough ECF solution to make a total volume of 40 mL. The cells were mixed well and counted, then centrifuged at 800×g (2000 rpm) for 5-7 min. The supernatant was removed and the cells resuspended in a small volume of ECF solution. Enough additional ECF solution was added to adjust the concentration to $2 \times 10^6$ cells/mL.

The cells were then placed in an Electro-Cell-Fusion (ECF) generator (Model ECM2001, Genetronic, Inc., San Diego, Calif.) and fused according to the manufacturer's instructions. After ECF, the cell suspensions were carefully removed from the fusion chamber under sterile conditions and transferred into a sterile tube containing the same volume of Hybridoma Medium in DMEM. The cells were incubated for 15-30 minutes at 37° C., then centrifuged at 400×g (1000 rpm) for five minutes. The cells were gently resuspended in a small volume of ½ HA medium (1 bottle of 50X HA from Sigma, Cat. #A9666 and 1 liter of Hybridoma Medium) and the volume adjusted appropriately with more ½ HA medium (based on $5 \times 10^6$ B cells per 96-well plate and 200 μL per well). The cells were mixed well and pipetted into 96-well plates and allowed to grow. On day 7 or 10, one-half the medium was removed, and the cells re-fed with HA ½ medium.

Selection of Candidate Antibodies by ELISA

After 14 days of culture, hybridoma supernatants were screened for TNFα-specific monoclonal antibodies. The ELISA plates (Fisher, Cat. No. 12-565-136) were coated with 50 μL/well of TNFα (2 μg/mL) in Coating Buffer (0.1 M Carbonate Buffer, pH 9.6, NaHCO$_{38.4}$ g/L), then incubated at 4° C. overnight. After incubation, the plates were washed with Washing Buffer (0.05% Tween 20 in PBS) 3 times. 200 μL/well Blocking Buffer (0.5% BSA, 0.1% Tween 20, 0.01% Thimerosal in 1× PBS) were added and the plates incubated at room temperature for 1 hour. After incubation, the plates were washed with Washing Buffer three times. 50 μL/well of hybridoma supernatants, and positive and negative controls were added and the plates incubated at room temperature for 2 hours.

After incubation, the plates were washed three times with Washing Buffer. 100 μL/well of goat anti-huIgGfc-HRP detection antibody (Caltag, Cat. #H10507), goat anti-hIg kappa-HRP (Southern Biotechnology, Cat. # 2060-05) and goat anti-hIg lambda (Southern Biotechnology, Cat. # 2070-05) were added and the plates were incubated at room temperature for 1 hour. After the incubation, the plates were washed three times with Washing Buffer. 100 ul/well of TMB (BioFX Lab. Cat. #TMSK-0100-01) were added and the plates allowed to develop for about 10 minutes (until negative control wells barely started to show color), then 50 ul/well stop solution (TMB Stop Solution (BioFX Lab. Cat. #STPR-0100-01) were added and the plates read on an ELISA plate reader at wavelength 450 nm. The number of positive wells is presented in Table 10.

TABLE 10

| Group # | hIgG/hkappa | hIgG/hlamda | Total # positive |
|---|---|---|---|
| fusion 1 + 2 (3B-3L3) | 9 | 9 | 18 |
| fusion 3 + 4 (xgm2L3) | 21 | 12 | 33 |

Secondary Screen to determine the Isotype and Light Chain Usage for the Anti-TNFα Hybridoma Supernatants Using Luminex The Luminex platform is a fluorescence bead based technology which enables one to run multiple assays at once. The Luminex reader is able to ascertain positive signaling events on different coded microspheres. This allows one to coat each bead separately, then mix the differentially coated microspheres together and then in one step assay antibody binding to each of the different microspheres. For isotyping antibodies, microspheres were coated in such a manner in that each bead was able to specifically bind a particular heavy chain or light chain isotype. The microspheres were then mixed together and hybridoma supernatant for each antibody was added. After a 20 minute incubation, the microspheres were washed, and the bound antibody was detected using a fluorescently labeled secondary antibody. The microspheres were then read using the Luminex reader. Table 10 shows number of each isotype found for the different fusion groups.

Neutralization of TNFα Induced Apoptosis Assays by Hybridoma Anti-TNFα Antibodies 47 anti-TNFα hybridoma antibodies were assayed for their ability to neutralize the biological effect of TNFα induced apoptosis on human WM 266.4 cells. IgG was first enriched from each hybridoma supernatant by purification on Swell-Gel protein A (Pierce), and then eluted, neutralized, and quantified. 20,000 WM266.6 cells were plated in 96-well plates in complete media (RPMI1640/10%FBS/Gln/P/S) and incubated at 37° C./10%$CO_2$ overnight. Media was removed and 50 μL of test antibodies and TNFα (pre-incubated for 30' at room temperature) were added in serum free media (RPMI1640/Gln/P/S). 50 μL cyclohexamide plates were incubated overnight as above under the following final assay conditions: V=100 μl, cyclohexamide=6 μg/mL, TNFα=600 pg/mL=11.4 pM as a trimer, test antibodies concentrations vary as described. 100 μL Caspase buffer and 0.3 μL Caspase substrate (APO-ONE, Promega) were added to each well.

Caspase activity was determined on a Victor Wallac plate reader with the excitation wavelength @ 485 nm and the emission wavelength @ 530 nm. An example of the neutralization of apoptosis by hybridoma derived antibodies is provided in FIG. 1. FIG. 1 shows a bar graph illustrating the effect that various TNFα antibodies had on neutralizing apoptosis in human WM 266.4 cells. A control (pos) shows the induction of apoptosis by TNFα in the presence of cyclohexamide alone. Another control shows inhibition of apoptosis by 6 nM mouse anti-hTNFα antibody (R&D). The Y-axis represents the relative amount of caspase 3/7 activity as an indication of TNFα induced apoptosis. As FIG. 1 illustrates, antibodies, including 3.2, 3.7 and 4.17 were very potent at neutralizing TNFα induced apoptosis at 3 nM.

Neutralization of Apoptosis by Propidium Iodide Incorporation Assay

The 47 anti-hTNFα hybridoma antibody supernatants were further assayed for their ability to neutralize the biological effect of TNFα induced apoptosis on human MCF-7 cells. 96-well plates were seeded at 5000 cells/well, 200 μl/well with phenol red free DMEM+10% FCS. The cells were incubated overnight at 37° C.+5% $CO_2$. On each plate a titration of hybridoma antibody (quantitated by capture ELISA, as described in Example 2, and compared to a standard curve control Ab) was assayed along-side Rabbit 014 control Ab from 10 μg/mL to a final concentration of 0.005 ng/mL (titrated 1:5) in apoptosis medium (2.5% FCS, 5 μg/mL CHX in phenol red free DMEM), in triplicate, at a constant concentration of 100 pg/mL (1.9 pM as a trimer) TNFα. Six well plates with TNFα alone and 6 wells with apoptosis medium alone were also included. TNFα+/− neutralizing antibody was pre-incubated for 1 hour at 37° C.+5% $CO_2$. 200 μL of antibody was then transferred to the cells and incubated overnight at 37° C.+5% $CO_2$.

Cells were stained with 0.5 μg/mL PI and 2.5 μg/mL Heochst 33342 for one hour. The percentage of apoptosis was determined by counting the number of dead cells (PI+ve) and dividing by the total number of cells (Heochst+ve). The ability of hybridoma derived, human anti-TNFα binding antibodies to neutralize TNFα induced apoptosis of MCF-7 cells was measured by propidium iodide uptake as a ratio of the number of total cells by Heochst 33342 staining. SLAM derived rabbit mAb, R014, as well as various other human mAbs, including 3.2, 4.17 and 3.7 were very potent at neutralizing TNFα induced apoptosis of MCF-7 cells.

Isotype Switching and Expression of IgG2 Hybridomas 4.1 7 and 3.2 mRNA was extracted from hybridomas 4.17 and 3.2. Reverse transcriptase PCR was conducted to generate cDNA. The cDNA encoding the variable heavy and light chains was specifically amplified using PCR. The variable heavy chain region was cloned into an IgG1 expression vector. This vector was generated by cloning the constant domain of human IgG1 into the multiple cloning site of pcDNA3.1+/Hygro (Invitrogen, Burlington, Oreg.). The variable light chain region was cloned into an IgK expression vector or Igλ. These vectors were generated by cloning the constant domain of human IgK or Igλ into the multiple cloning site of pcDNA3.1+/Neo (Invitrogen, Burlington, Oreg.). The heavy chain and the light chain expression vectors were then co-lipofected into a 60 mm dish of 70% confluent human embryonal kidney 293 cells and the transfected cells were allowed to secrete a recombinant antibody with the identical specificity as the original plasma cell for 24-72 hours. The supernatant (3 mL) was harvested from the HEK 293 cells and the secretion of an intact antibody was demonstrated with a sandwich ELISA to specifically detect human IgG. The specificity was assessed through binding of the recombinant antibody to TNFα using ELISA.

Generation of Anti-hTNFα Antibodies by XENOMAX®

Culture and Selection of B Cells

B-cells from the animals were harvested and cultured. Those secreting TNFα-specific antibodies were isolated as described in Babcook et al., Proc. Natl. Acad. Sci. USA, 93:7843-7848 (1996). ELISA was used to identify primary TNFα-specific wells. About 18 million B-cells were cultured from XENOMOUSE® animals in 480 96 well plates at 500 or 150 cells/well, and were screened on TNFα to identify the antigen-specific wells. 3,825 wells showed ODs significantly over background, a representative sample of which are shown in Table 11. Rabbit B-cells were also screened for their ability to secrete anti-TNFα antibodies and positives further assayed as described below.

TABLE 11

| | Positives above cut off OD of: | | | | | | | | | | | | | | | |
|---|---|---|---|---|---|---|---|---|---|---|---|---|---|---|---|---|
| Plates ID'S | >0 | 0.1 | 0.2 | 0.3 | 0.4 | 0.5 | 0.6 | 0.7 | 0.8 | 0.9 | 1 | 1.5 | 2 | 2.5 | 3 | 3.5 | 4 |
| Plates 191–230 | 3840 | 3110 | 313 | 158 | 136 | 117 | 109 | 105 | 101 | 97 | 93 | 77 | 60 | 49 | 44 | 27 | 1 |
| Plates 231–269 | 3744 | 2665 | 339 | 167 | 137 | 130 | 116 | 111 | 106 | 101 | 95 | 78 | 58 | 50 | 43 | 25 | 13 |
| Total | | | | 325 | | | | | | | | | | | | | |

Normalization of Antigen Specific Antibody Concentrations

Using an ELISA method, supernatants for concentration of antigen specific antibody were normalized. Using an anti-target (TNFα) antibody of known concentration titrated in parallel, a standard curve can be generated and the amount of antigen specific antibody in the supernatant can be compared to the standard and it's concentration determined, see Table 12 below.

Limited Antigen Analysis

B-cell culture supernatants were prepared having concentrations of antigen specific antibody ranging from 10 ng/mL

TABLE 12

|        | ELISA OD on Antigen |   |   |   | Extrapolated Concentration ng/mL * |   |   |   |   |
|--------|------|------|------|------|------|------|------|------|------|
| mab ID | 1:40 dilution | 1:80 dilution | 1:160 dilution | 1:320 dilution | Conc. At 1:40 | Conc. At 1:80 | Conc. At 1:160 | Conc. At 1:320 | Average |
| 439A3  | 2.1 | 1.5 | 0.9 | 0.5 |    | 112 | 103 | 101 | 105 |
| 460A12 | 1.7 | 1.1 | 0.6 | 0.4 |    | 69  | 63  |     | 66  |
| 401A7  | 1.6 | 1.1 | 0.6 | 0.4 |    | 66  | 62  |     | 64  |
| 327D12 | 2.4 | 1.7 | 1.1 | 0.7 |    |     | 131 | 129 | 130 |
| 402G10 | 1.1 | 0.6 | 0.4 | 0.3 | 36 | 28  |     |     | 32  |
| 360A5  | 2.4 | 1.6 | 1.1 | 0.7 |    |     | 130 | 138 | 134 |
| 436F1  | 2.3 | 1.6 | 1.1 | 0.7 |    |     | 145 | 134 | 139 |
| 410F1  | 1.3 | 0.8 | 0.5 | 0.3 | 46 | 46  |     |     | 46  |
| 356B4  | 1.7 | 1.1 | 0.7 | 0.4 |    | 65  | 66  |     | 66  |
| 433F4  | 0.5 | 0.3 | 0.2 | 0.2 | 12 |     |     |     | 12  |
| 454G7  | 1.9 | 1.3 | 0.7 | 0.4 |    | 88  | 75  |     | 81  |

* Data points outside the linear region of the ELISA reader were excluded.

Limited Antigen Assay

The limited antigen analysis is a method that affinity ranks the antigen-specific antibodies prepared in B-cell culture supernatants relative to all other antigen-specific antibodies. In the presence of a very low coating of antigen, only the highest affinity antibodies should be able to bind to any detectable level at equilibrium. (See, e.g., PCT Publication WO/03048730A2 entitled "IDENTIFICATION OF HIGH AFFINITY MOLECULES BY LIMITED DILUTION SCREENING" published on Jun. 12, 2003).

Biotinylated TNFα was bound to streptavidin plates at three concentrations; 1 ng/mL, 0.1 ng/mL and 0.0 ng/mL for 1 hour at room temperature on 96-well culture plates. Each plate was washed 5 times with dH$_2$O, before 45 µL of 1% milk in PBS with 0.05% sodium azide were added to the plate, followed by 5 µL of B cell supernatant added to each well. After 18 hours at room temperature on a shaker, the plates were again washed 5 times with dH$_2$O. To each well was added 50 µL of Gt anti-Human (Fc)-HRP at 1 µg/mL. After 1 hour at room temperature, the plates were again washed 5 times with dH$_2$O and 50 µL of TMB substrate were added to each well. The reaction was stopped by the addition of 5 µL of 1M phosphoric acid to each well and the plates were read at wavelength 450 nm to give the results shown in Table 13.

TABLE 13

Figure 2:
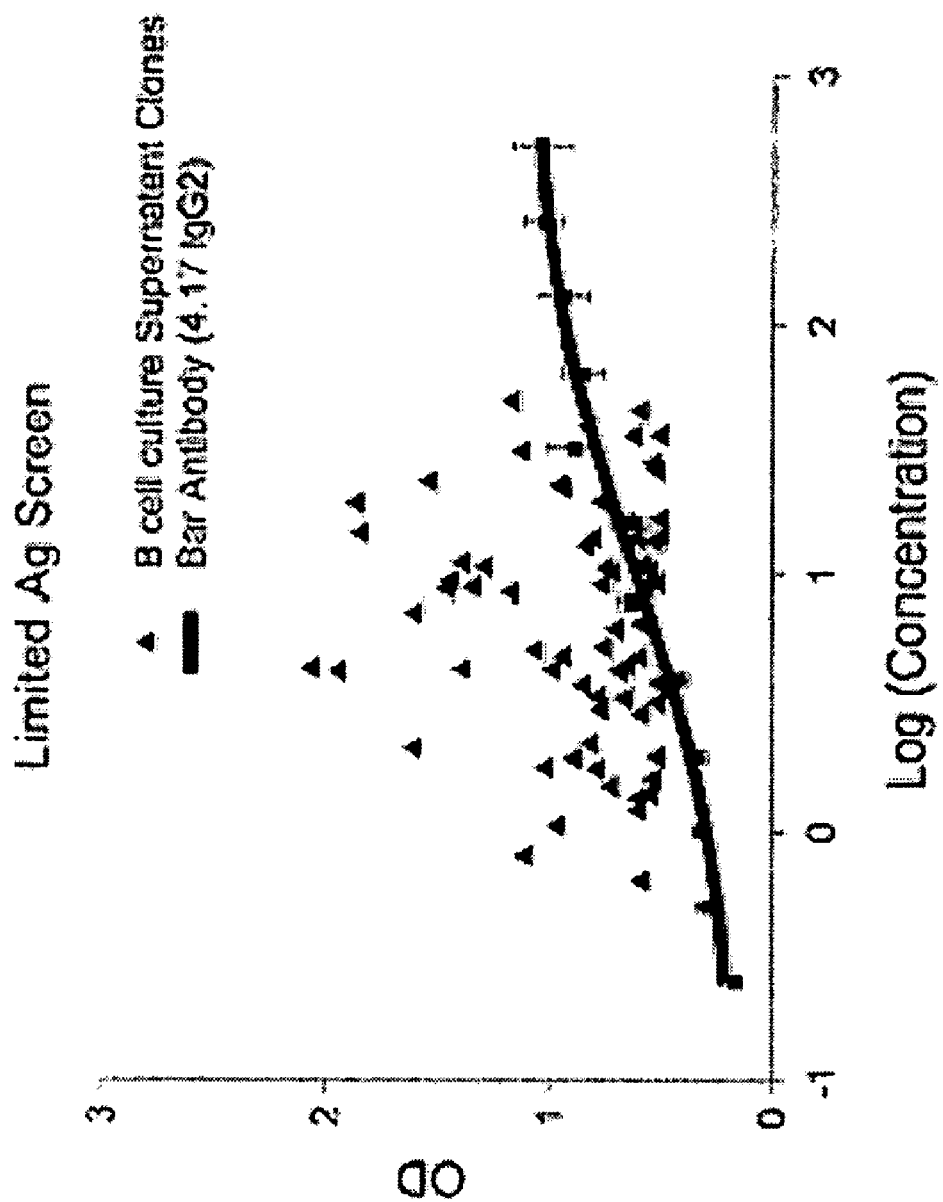
FIG. 2 is a point graph that compares the anti-TNFα limited antigen binding between antibodies in B-cell culture supernatants to that of a control antibody (4.17 IgG2) over a concentration range. The triangles represent the B-cell culture supernatant clones, and the blocks represent Bar Antibody (4.17 IgG2). B-cell culture supernatants clones with points above the bar antibody curve are ranked as having potentially higher affinity.

|      | 1' Screen | Coating Concentrations |   |   |
|------|------|------|------|------|
| Well | (OD) | 1 ng/ml | 0.1 ng/ml | 0.01 ng/ml |
| 401A7  | 2.92 | 1.94 | 0.33 | 0.19 |
| 433F4  | 2.96 | 1.12 | 0.24 | 0.20 |
| 337E7  | 2.53 | 0.97 | 0.47 | 0.19 |
| 164C7  | 1.97 | 0.81 | 0.24 | 0.16 |
| 356B4  | 2.87 | 0.69 | 0.17 | 0.15 |
| 402A4  | 2.33 | 0.61 | 0.35 | 0.18 |
| 286B9  | 2.56 | 0.32 | 0.32 | 0.27 |
| 203A2  | 2.33 | 0.23 | 0.15 | 0.19 |
| 286G8  | 2.06 | 0.21 | 0.19 | 0.19 |
| 286F11 | 2.93 | 0.18 | 0.23 | 0.19 |
| 286D12 | 0.78 | 0.18 | 0.21 | 0.25 |
| 286G1  | 0.82 | 0.17 | 0.16 | 0.18 |
| 286C4  | 0.75 | 0.17 | 0.17 | 0.19 |
| 286G6  | 0.97 | 0.16 | 0.18 | 0.14 |
| 287D1  | 0.58 | 0.16 | 0.19 | 0.16 | to 1000 ng/mL. The results generated from limited antigen analysis were compared to a titration of 4.17 hybridoma derived antibody. In this assay many of the antibodies were not able to give detectable binding, however there were a number of wells including 401A7 and 433F4, which were clearly superior as measured by O.D. to the other culture supernatants and recombinant antibodies at all concentrations (Table 13). The remaining clones were further analyzed by combining the high antigen data which measures specific antibody concentration, (see above for details) and the limited antigen output. In this way it was possible to compare antibodies in B-cell culture supernatants to that of the control antibody over a concentration range as shown in FIG. 2. FIG. 2 is a point graph that compares the anti-TNFα limited antigen binding between antibodies in B-cell culture supernatants to that of a control antibody (4.17 IgG2) over a concentration range. The triangles represent the B-cell culture supernatant clones, and the blocks represent Bar Antibody (4.17 IgG2). B-cell culture supernatant clones with points above the bar antibody curve are ranked as having potentially higher affinity. Neutralization of Apoptosis by Propidium Iodide Incorporation Assay All 1455 anti-hTNFα antibodies identified from B-cell culture well supernatants from foot-pad immunized mice were further assayed for their ability to neutralize the biological effect of TNFα induced apoptosis on human MCF-7 cells. In addition, after limited antigen analysis of all 2,370 anti-hTNFα identified from BIP immunized animals, 145 antibodies having the highest kinetic ranking were further analyzed for neutralizing TNFα activity. 96 well plates were seeded at 5000 cells MCF-7/well, 200 µL/well with phenol red free DMEM+10% FCS. Plates were incubated overnight at 37° C.+5% CO$_2$. On each plate B-cell culture antibody supernatant was assayed along-side the most potent neutralizing anti-TNFα hybridoma antibodies, 4.17 and 3.2 and/or Rabbit 014 control in apoptosis medium (2.5% FCS, 5 µg/mL CHX in phenol red free DMEM), at a constant concentration of 100 pg/mL (1.9 pM as a trimer) TNFα. Replicate wells with TNFα in apoptosis media and wells with apoptosis medium alone were included as controls. TNFα+/− test sample was pre-incubated for 1 hour at 37° C.+5% CO$_2$. 200 µL TNFα+/− was transferred to cells and incubated overnight at 37° C.+5% CO$_2$.

Figure 3:
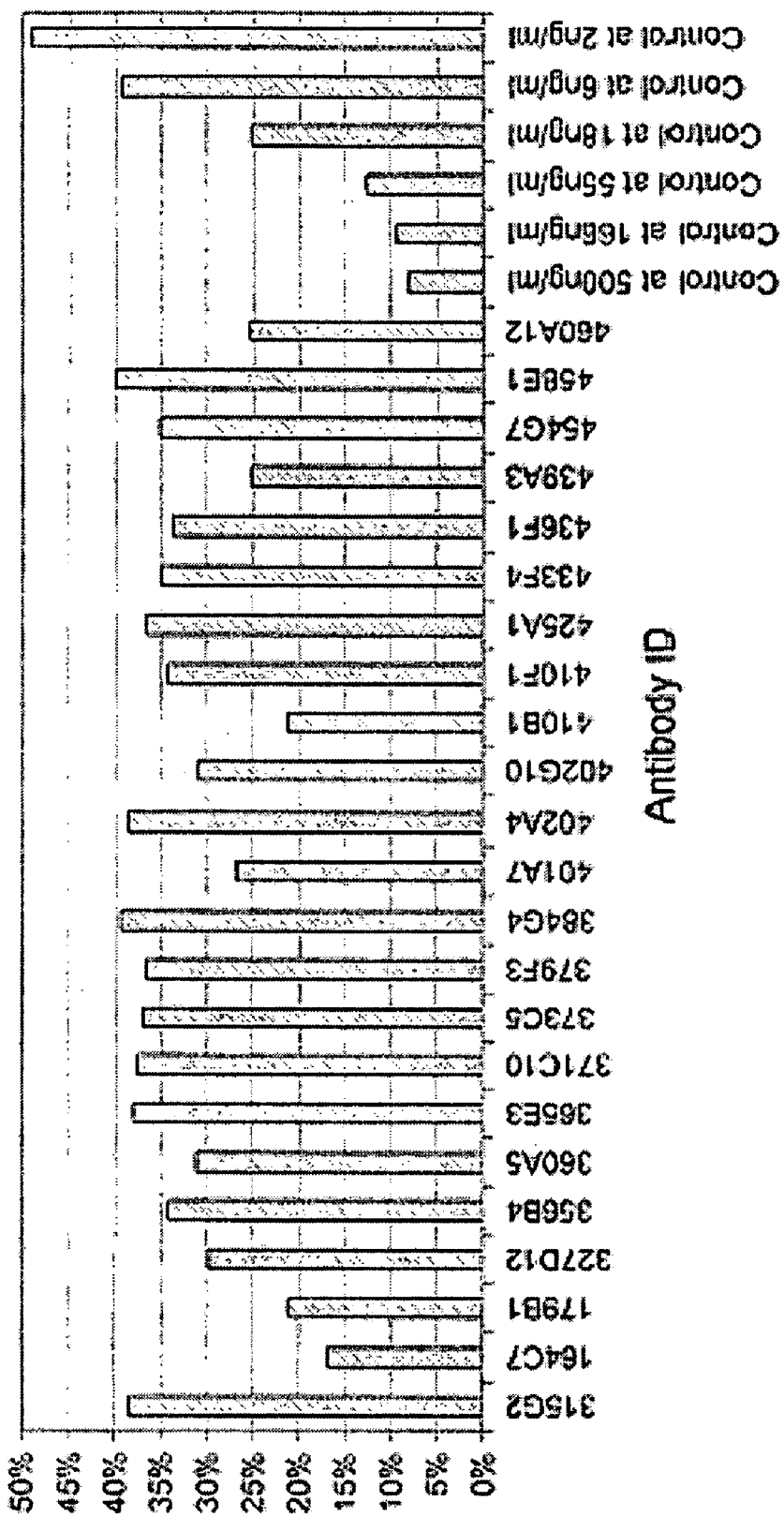
FIG. 3 is a representative bar graph that compares the effectiveness of various XENOMAX® B-cell culture supernatants at inhibiting TNFα induced cell apoptosis in human MCF-7 cells.

Cells were stained with 0.5 μg/mL PI and 2.5 μg/mL Heochst 33342 for one hour. Percentage of apoptosis was determined by counting the number of dead cells (PI+ve) and dividing by the total number of cells (Heochst+ve). An example is show in FIG. 3 which shows a representative bar graph that compares the effectiveness of various XENOMAX® B-cell culture supernatants at inhibiting TNFα induced cell apoptosis in human MCF-7 cells. A number of B-cell culture well supernatants showed the ability to neutralize TNFα induced apoptosis. These supernatants included: 164C7, 179B1, 401A7, 410B1, 439A3 and 460A12.

Neutralization Potency Determination of TNFα Induced Poptosis by Anti-hTNFα Antibodies in Polyclonal Solutions Using the extrapolated concentrations of antigen specific antibodies in polyclonal B-cell culture supernatants, the apparent potency of neutralization of TNFα induced apoptosis on MCF-7 cells was calculated. By performing the assay in parallel with a standard anti-target reagent, in this case the hybridoma derived antibody 3.2 IgG2, it was possible to set a potency bar and look for antibodies with higher potential potency than the standard.

Figure 4:
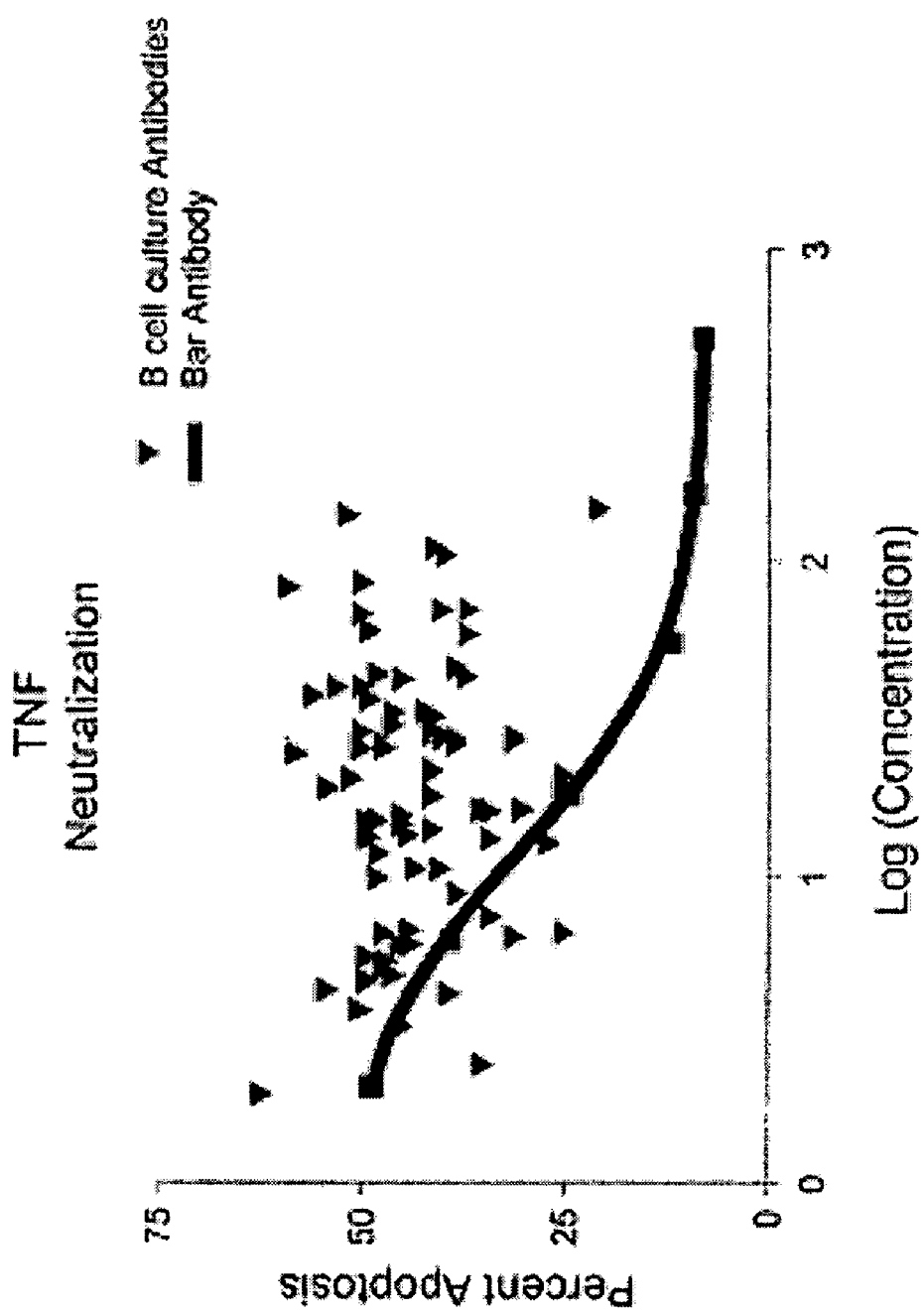
FIG. 4 is a representative point graph that shows calculated potency comparisons for neutralization of TNFα induced apoptosis on human MCF-7 cells by XENOMAX® B-cell culture supernatants. The triangles represent the potency of B-cell culture supernatants, while the squares represent the potency of a bar control, 3.2 IgG2.

An example of calculated potency comparisons for neutralization of TNFα induced apoptosis on MCF-7 cells is shown in FIG. 4. FIG. 4 is a representative point graph that shows calculated potency comparisons for neutralization of TNFα induced apoptosis on human MCF-7 cells by XENOMAX® B-cell culture supernatants. The triangles represent the potency of B-cell culture supernatants, while the squares represent the potency of a bar control, 3.2 IgG2. A number of B-cell culture supernatants showed greater neutralization of TNFα induced apoptosis at lower anti-TNFα antibody concentrations than that of the 3.2 control standard curve, indicating greater potency.

Inhibition of TNFα Binding to p55 (TNFα Receptor I) by Rabbit Antibodies

Rabbit anti-TNFα neutralizing antibodies were found by examining whether or not the antibodies from the B-cell culture supernatants were able to inhibit TNFα binding to its p55 receptor. The following procedure was followed. 96 well microtiter plates were coated overnight with TNFα. The following day, the plates were washed and incubated +/− anti-TNFα antibodies for 1 hr. Biotin-p55 was then spiked into the plates for 1 hr, washed with water and bound p55 was detected using Streptavidin-HRP. Plates were then washed and developed as done with other ELISAs described above. Antibodies which inhibited the binding of p55 were termed neutralizing, see Table 14.

TABLE 14

| Abs | Assay 1 | Assay 2 |
| --- | --- | --- |
| 9C10 | 0.32 | 1.26 |
| 10G8 | 0.23 | 0.59 |
| 11A1 | 0.52 | 0.55 |
| 7A4 | 0.08 | 0.39 |
| 6A1 | 0.4 | 0.42 |
| 4A11 | 0.67 | 0.56 |
| 2A12 | 0.37 | 1.19 |
| 6A6 | 0.29 | 0.92 |
| TNFα alone | 0.3 | 0.97 |

TNFα-specific Hemolytic Plaque Assay

A number of specialized reagents were used to conduct this assay. These reagents were prepared as follows.

Biotinylation of Sheep Red Blood Cells (SRBC)

SRBCs were stored in RPMI media as a 25% stock. A 250 μL SRBC packed-cell pellet was obtained by aliquoting 1.0 mL of SRBC to a fresh eppendorf tube. The SRBC were pelleted with a pulse spin at 8000 rpm (6800 rcf) in microfuge, the supernatant drawn off, the pellet re-suspended in 1.0 mL PBS at pH 8.6, and the centrifugation repeated. The wash cycle was repeated 2 times, then the SRBC pellet was transferred to a 15-mL falcon tube and made to 5 mL with PBS pH 8.6. In a separate 50 mL falcon tube, 2.5 mg of Sulfo-NHS biotin was added to 45 mL of PBS pH 8.6. Once the biotin had completely dissolved, the 5 mL of SRBCs were added and the tube rotated at RT for 1 hour. The SRBCs were centrifuged at 3000 rpm for 5 min and the supernatant drawn off. The Biotinylated SRBCs were transferred to an eppendorf tube and washed 3 times as above but with PBS pH 7.4 and then made up to 5 mL with immune cell media (RPMI 1640) in a 15 mL falcon tube (5% B-SRBC stock). Stock was stored at 4° C. until needed.

Streptavidin (SA) Coating of B-SRBC 1 mL of the 5% B-SRBC stock was transferred into a fresh eppendorf tube. The B-SRBC cells were washed 3 times as above and resuspended in 1.0 mL of PBS at pH 7.4 to give a final concentration of 5% (v/v). 10 μL of a 10 mg/mL streptavidin (CalBiochem, San Diego, Calif.) stock solution was added and the tube mixed and rotated at RT for 20 min. The washing steps were repeated and the SA-SRBC were re-suspended in 1 mL PBS pH 7.4 (5% (v/v)).

Human TNFα Coating of SA-SRBC

The SA-SRBCs were coated with biotinylated-TNFα at 10 μg/mL, mixed and rotated at RT for 20 min. The SRBC were washed twice with 1.0 mL of PBS at pH 7.4 as above. The TNFα-coated SRBC were re-suspended in RPMI (+10% FCS) to a final concentration of 5% (v/v).

Determination of the Quality of TNFα-SRBC by Immunofluorescence (IF)

10 μL of 5% SA-SRBC and 10 μL of 5% TNFα-coated SRBC were each added to a separate fresh 1.5 mL eppendorf tube containing 40 μL of PBS. A control human anti-TNFα antibody was added to each sample of SRBCs at 45 μg/mL. The tubes were rotated at RT for 25 min, and the cells were then washed three times with 100 μL of PBS. The cells were re-suspended in 50 μL of PBS and incubated with 40 μg/mL Gt-anti Human IgG Fc antibody conjugated to Alexa488 (Molecular Probes, Eugene, Oreg.). The tubes were rotated at RT for 25 min, and then washed with 100 μL PBS and the cells re-suspended in 10 μL PBS. 10 μL of the stained cells were spotted onto a clean glass microscope slide, covered with a glass coverslip, observed under fluorescent light, and scored on an arbitrary scale of 0-4.

Preparation of Plasma Cells

The contents of a single microculture well previously identified by various assays as containing a B cell clone secreting the immunoglobulin of interest were harvested. Using a 100-1000 μL pipetman, the contents of the well were recovered by adding 37° C. RPMI (10% FCS). The cells were re-suspended by pipetting and then transferred to a fresh 1.5 mL eppendorf tube (final vol. approx 500-700 μL). The cells were centrifuged in a microfuge at 2500 rpm (660 rcf) for 1 minute at room temperature, then the tube was rotated 180 degrees and spun again for 1 minutes at 2500 rpm. The freeze media was drawn off and the immune cells resuspended in 100 μL RPMI (10% FCS), then centrifuged. This washing with RPMI (10% FCS) was repeated and the cells re-suspended in 60 μL RPMI (10% FCS) and stored on ice until ready to use.

Plaque Assay

Glass slides (2×3 inch) were prepared in advance with silicone edges and allowed to cure overnight at RT. Before use the slides were treated with approx. 5 µL of SigmaCoat (Sigma, Oakville, Oreg.) wiped evenly over glass surface, allowed to dry and then wiped vigorously. To a 60 µL sample of cells was added 60 µL each of TNFα-coated SRBC (5% v/v stock), 4× guinea pig complement (Sigma, Oakville, Oreg.) stock prepared in RPMI (10% FCS), and 4× enhancing sera stock (1:150 in RPMI (10% FCS)). The mixture (−) was spotted (10-15 µL) onto the prepared slides and the spots covered with undiluted paraffin oil. The slides were incubated at 37° C. for a minimum of 45 minutes.

Plaque Assay Results

TNFα coated sheep red blood cells were used to identify antigen-specific plasma cells from the wells (see Table 15).

TABLE 15

| mAb ID | Number of Single Cells picked | Single Cell Numbers |
|---|---|---|
| 1F7 | 23 | 69 |
| 10F1 | 12 | 92 |
| 11A8 | 12 | 128 |
| 27A9 | 12 | 148 |
| 44G7 | 12 | 116 |
| 101F1 | 8 | 140 |
| 103H1 | 12 | 25 |
| 107A6 | 11 | 13 |
| 107G12 | 12 | 1 |
| 164C7 | 8 | 291 |
| 203A2 | 12 | 299 |
| 337E7 | 5 | 280 |
| 401A7 | 8 | 261 |
| 402G10 | 12 | 249 |
| 410F1 | 12 | 311 |
| 433F4 | 9 | 230 |
| 460A12 | 12 | 268 |

Expression of Recombinant anti-TNFα Antibodies

After isolation of the single plasma cells, mRNA was extracted and reverse transcriptase PCR was conducted to generate cDNA encoding the variable heavy and light chains. The human variable heavy chain region was cloned and isotype switched into an IgG1 expression vector. This vector was generated by cloning the constant domain of human IgG1 into the multiple cloning site of pcDNA3.1+/Hygro (Invitrogen, Burlington, Oreg.). The human variable light chain region was cloned into an IgK expression vector. These vectors were generated by cloning the constant domain of human IgK into the multiple cloning site of pcDNA3.1+/Neo (Invitrogen, Burlington, Oreg.). The heavy chain and the light chain expression vectors were then co-lipofected into a 60 mm dish of 70% confluent human embryonal kidney 293 cells and the transfected cells were allowed to secrete a recombinant antibody with the identical specificity as the original plasma cell for 24-72 hours. The supernatant (3 mL) was harvested from the HEK 293 cells and the secretion of an intact antibody was demonstrated with a sandwich ELISA to specifically detect human IgG (Table 16). Specificity was assessed through binding of the recombinant antibody to TNFα using ELISA.

TABLE 16

| Supernatant ID | Titer | |
|---|---|---|
| | total antibody | antigen binding |
| 11A8 | >1:64 | >1:64 |
| 27A9 | 1:16 | 1:64 |
| 103H1 | >1:64 | 1:64 |
| 107A6 | >1:64 | >1:64 |
| 107G12 | >1:64 | >1:64 |
| 164C7 | >1:64 | >1:64 |
| 203A2 | >1:64 | >1:64 |
| 401A1 | >1:64 | >1:64 |
| 402G10 | >1:64 | >1:64 |

The secretion ELISA tests were performed as follows. Control plates were coated with 2 mg/mL goat anti-human IgG H+L overnight as for binding plates, hTNFα was coated onto Costar Labcoat Universal Binding Polystyrene 96 well plates and held overnight at 4° C. The plates were washed five times with dH$_2$O. Recombinant antibodies were titrated 1:2 for 7 wells from the undiluted minilipofection supernatant. The plates were washed five times with dH$_2$O. A goat anti-human IgG Fc-specific HRP-conjugated antibody was added at a final concentration of 1 µg/mL for 1 hour at RT for the secretion and the two binding assays. The plates were washed five times with dH$_2$O. The plates were developed with the addition of TMB for 30 minutes and the ELISA was stopped by the addition of 1 M phosphoric acid. Each ELISA plate was analyzed to determine the optical density of each well at 450 nm.

Rabbit antibody genes were rescued, cloned and expressed as above, but were cloned into vectors containing rabbit IgG1 heavy constant or kappa constant regions. Cells from well 7A4 (Table 14) were isolated, cloned and expressed as a fully rabbit antibody, R014 (AB-TNFα-R014).

Purification of Recombinant Anti-TNFα Antibodies

For larger scale production, heavy and light chain expression vectors (2.5 µg of each chain/dish) were lipofected into ten 100 mm dishes that were 70% confluent with HEK 293 cells. The transfected cells were incubated at 37° C. for 4 days, the supernatant (6 mL) was harvested and replaced with 6 mL of fresh media. At day 7, the supernatant was removed and pooled with the initial harvest (120 mL total from 10 plates). Each antibody was purified from the supernatant using a Protein-A Sepharose (Amersham Biosciences, Piscataway, N.J.) affinity chromatography (1 mL). The antibody was eluted from the Protein-A column with 500 mcL of 0.1 M Glycine pH 2.5. The eluate was dialysed in PBS pH 7.4 and filter sterilized. The antibody was analyzed by non-reducing SDS-PAGE to assess purity and yield. Concentration was also measured by UV analysis at OD 250.

Example 4

Binding of Anti-TNFα Antibodies to Transmembrane TNFα

Both soluble and membrane-bound TNFα can interact with TNFα receptors and contribute to TNFα pro-inflammatory effects. Therefore, it was important to establish whether 299v2 and 263 can effectively bind to membrane-bound TNFα, in addition to the soluble version of the molecule. To this end, TNFα-transfected CHO cells were used as well as activated T cells.

Binding of anti-TNFα reagents to transmembrane mutant TNFα expressed on the surface of CHO cells was measured. Specifically, purified, quantitated IgG2 kappa and lambda hybridoma antibodies as well as isotype switched hybridoma and XENOMAX® derived IgG1 recombinant antibodies were assayed for their ability to bind transmembrane TNFα expressed on the surface of Chinese hamster ovary cells, CHO's. TNFα cDNA was mutated at various positions to prevent cleavage of TNFα from the surface of cells. The cDNA was then cloned into an expression vector. CHO cells were transfected and stable expressing cells were placed under drug selection to generate a DTNFα cell line. Anti-TNFα antibodies, as well as Etanercept, were titrated and added to DTNFα CHO cells on ice for 1 or 18 hours. Cells were washed in cold PBS and a secondary biotinylated anti-rabbit or human IgG was further incubated on ice for 10 minutes, washed and a tertiary SA-PE labeled antibody was added on ice for an additional 10 minutes. Fluorescence activated cell sorting (FACS) was used to determine binding and staining profiles with antibodies at various concentrations.

At low concentrations, the human antibodies, as well as chimeric Infliximab and rabbit R014, bound the transmembrane form of TNFα on cells, whereas Etanercept clearly showed a lower binding signal. 299v2, 263, Infliximab, Adalimumab and Etanercept were incubated 18 hours at 4 degrees C. on the DTNF-CHO cells at 0.1 ug/mL. With reference to the monoclonal antibodies, 299v2 and adalumimab apparently stained less than 263 and infliximab. The resulting data suggests that Fc mediated effects such as antibody-dependant cytotoxicity (CDC) and antibody-dependant cellular cytotoxicity (ADCC) should be observed on cells expressing transmembrane TNFα. A number of the generated antibodies can have more potent Fc mediated effects than Infliximab and Etanercept. This may be of particular benefit for the treatment of diseases where cell surface TNFα may play a patho-physiological role such as Crohn's or psoriasis.

For the treatment of disease indications where soluble forms of TNFα may mediate the majority of the disease state, an antibody with low Fc mediated effector function may be desirable. This could be achieved by expressing the anti-TNFα antibody as an IgG2 or IgG4 isotype.

Binding of anti-TNFα reagents to activated PBMC was also measured. PBMCs were isolated from a normal donor and incubated with an anti-CD3 antibody to activate T cells. T cell activation implies surface TNFα expression of membrane-bound TNFα. The ability of anti-TNFα reagents to bind to membrane-bound TNFα was again assessed at various concentrations by FACS analysis, gating on lymphocytes on the ground of light scattering and using a PE-conjugated anti-human IgG secondary antibody. The resulting staining data indicated that all the monoclonal antibodies 299v2, 263, Infliximab and adalumimab stained lymphocytes after T cell activation, while Etanercept does not. No anti-TNFα antibody stained lymphocytes if they were not subjected to T cell activation.

Example 5

Epitope Binning Assays

Epitope Mapping of Anti TNFα Antibodies

The following describes the method used to map epitopes of anti TNFα Antibodies. Chimeric TNFα proteins, using human and mouse TNFα, were constructed and expressed. An alignment of human and mouse TNFα is provided in Table 17.

TABLE 17

```
Human:
VRSSSRTPSDKPVAHVVANPQAEGQLQWLNRRANA

Mouse:
LRSSSQNSSDKPVAHVVANHQVEEQLEWLSQRANA

Human:
LLANGVELRDNQLVVPSEGLYLIYSQVLFKGQGCP

Mouse:
LLANGMDLKDNQLVVPADGLYLVYSQVLFKGQGCP

Human:
STHVLLTHTISRIAVSYQTKVNLLSAIKSPCQRE

Mouse:
DY-VLLTHTVSRFAISYQEKVNLLSAVKSPCPKD

Human:
TPEGAEAKPWYEPIYLGGVFQLEKGDRLSAEINR

Mouse:
TPEGAELKPWYEPIYLGGVFQLEKGDQLSAEVNL

Human:
PDYLDFAESGQVYFGIIAL                  SEQ ID NO:265

Mouse:
PKYLDFAESGQVYFGVIAL                  SEQ ID NO:266
```

Restriction cleavage sites common in human and murine TNFα-a genes were used for construction of in-frame fusion TNFα chimeric proteins. Seven constructs were made: human TNFα, mouse TNFα, H/M BglI, M/H BglI, H/M HincII, H/M PvuII, M/H PvuII. All proteins were expressed and secreted in detectable levels measured by an ELISA assay using polyclonal antibodies against human and mouse TNFα. Chimeric TNFα proteins: the amino acid joining points are at positions: BglI-36/37, HincII-90/92, PvuII-124/126. The difference on one amino acid in the last two cases is due to the absence of the histidine residue at position 73 in the murine TNFα sequence. An example of anti-TNFα antibodies binding to these proteins by ELISA is in Table 18.

TABLE 18

| Construct | Goat Anti-Mouse | Goat Anti-human | 3.2 Ab | 3.7 Ab | 4.17 Ab | Human residues |
|---|---|---|---|---|---|---|
| H-TNFα | + | +++ | + | + | + | 1–157 |
| M TNFα | + | + | – | – | – | None |
| H/MBgl1 | ++++ | +++ | – | – | + 1–36 | 1–36 |
| M/HuBgl1 | + | +++ | – | + 36–157 | – | 36–157 |
| Hu/M PVu11 | + | +++ | + | – | + | 1–125 |
| M/Hu PVu11 | ++ | + | – | – | – | 125–157 |
| Hu/M Hin C 11 | + | ++++ | ++ 1–91 | – | ++ | 1–91 |

In order to define the binding site for different antibodies, a number of residues of hTNFα were mutated using site directed mutagenesis. A panel of antibodies was screened for binding by an ELISA assay. Human residues were replaced with the murine residues at position 27, 31, and 131. Histidine at position 73 was deleted, an example is illustrated in Table 19.

TABLE 19

| Human Amino acid residues | 1-36 | 36-157 | 1-125 | 1-91 | 1-157 | R31Q mut | R31Q, Q27E mut | R131Q mut | His 73del |
|---|---|---|---|---|---|---|---|---|---|
| 250Ab | − | − | − | − | +++ | +++ | +++ | +++ | +++ |
| 263Ab | − | − | − | − | +++ | +++ | +++ | +++ | +++ |
| 269Ab | − | − | − | − | +++ | +++ | +++ | +++ | +++ |
| 282 Ab | − | −− | − | − | +++ | +++ | +++ | +++ | +++ |
| 283 Ab | − | − | − | − | +++ | +++ | +++ | +++ | +++ |
| 291 Ab | +++ | − | +++ | +++ | +++ | −− | − | +++ | +++ |
| 299v2Ab | +++ | − | +++ | +++ | +++ | − | − | +++ | +++ |
| 313 Ab | +++ | − | +++ | +++ | +++ | − | − | +++ | +++ |
| Infliximab | − | − | − | − | +++ | +++ | +++ | +++ | +++ |
| 3.2.1 | − | − | ++ | ++ | − | ++ | ++ | +++ | +++ |
| 3.7.1 | − | ++ | − | − | − | ++ | ++ | +++ | +++ |
| 4.17.1 | ++ | − | ++ | ++ | − | + | − | +++ | +++ |
| Rabbit R014 | +++ | − | +++ | +++ | +++ | +++ | +++ | +++ | +++ |

As illustrated by Table 19, the binding site for Rabbit 014, 4.17, SC291, SC299 and SC313 are located in the first 36 amino acid residues of human TNFα. Amino Acids 31-35 have been shown to be involved in receptor recognition and triggering of biological response (Jones, E. Y., Stuart, D. I., and Walker, NPC., (1992) in Tumor Necrosis Factors: Structure, Function and Mechanism of Action (Aggarwal, B. B., and Vilcek, J., eds) pp 93-127, Marcel Dekker, Inc., New-York a non-conservative change of Arg31 was introduced for further epitope mapping. The single amino acid change at position 31 was shown to knock out the binding of SC291, SC299 and SC313 completely, while mAb 4.17 lost only 80% of its binding activity, an additional change at position 27 was required for the block the activity of 4.17.

The Binding site of MAb 3.2. lies between residues 1-91. Although replacement of Gln27 and arg31 did not affect its binding to human TNFα, the N-terminus appears to be necessary for its binding activity. Mab 3.7 epitope lies between residues 36-157.

None of the chimeras could be neutralized using monoclonal antibodies SC250, SC263, SC269, SC282, SC283 and Infliximab. All these antibodies are highly specific for human TNFα, and their epitope is a constellation of residues located in a different, non contiguous position of the TNFα polypeptide. Gln27, Arg31, His73 and Arg131 are not involved in the neutralizing binding site.

Table 20 summarize the results of additional epitope mapping performed on 299v2, 263, etanercept, infliximab and Adalimumab. As shown in the Table 20, 299v2, etanercept, and adalimumab bind to the chimeric proteins containing the region of human TNF between aa 1 and aa 36, while 263 and infliximab do not bind any of the chimeric proteins. All the anti-TNF antibodies bind to human TNF, but none to murine TNF. These results indicate that the binding regions of 299v2, etanercept, and adalimumab are most likely comprised within the first 36 aa of TNF, while those of 263 and infliximab are scattered over the entire molecule. All anti-TNF antibodies bind protein-denaturation sensitive regions, indicating that their binding regions are conformational.

TABLE 20

| | Human aa Residues | | | | | | |
|---|---|---|---|---|---|---|---|
| | 1-36 | 1-91 | 1-125 | 36-157 | 125-157 | 1-157 | — |
| | Murine aa Residues | | | | | | |
| | 37-157 | 92-157 | 126-157 | 1-35 | 1-125 | — | 1-157 |
| Etanercept | + | + | + | − | − | + | − |
| 299v2 | + | + | + | − | − | + | − |
| Adalimumab | + | + | + | − | − | + | − |
| Infliximab | − | − | − | − | − | + | − |
| 263 | − | − | − | − | − | + | − |

The TNFα receptors p75-hFc and p55-hFc (Catalog number 372-RI-050 and 372-RI/CF from R&D) were further analyzed for binding to TNFα proteins as shown in Table 21.

TABLE 21

| Constructs | p55-hFc | p75s-hFc | Human amino acid residues |
|---|---|---|---|
| Hu TNFα | ++ | ++ | 1–157 |
| Hu/MBgl1 | ++ | ++ | 1–36 |
| M/HuBgl1 | − | − | 36–157 |
| Hu/M PVu11 | + | ++ | 1–125 |
| Hu/M Hin C l1 | ++ | ++ | 1–91 |
| M/Hu Hin CII | ++ | ++ | 91–157 |

Example 6

Anti-macaque TNFα Binding Cross-reactivity

Binding to Human and Monkey Soluble Recombinant TNFα

Figure 5:
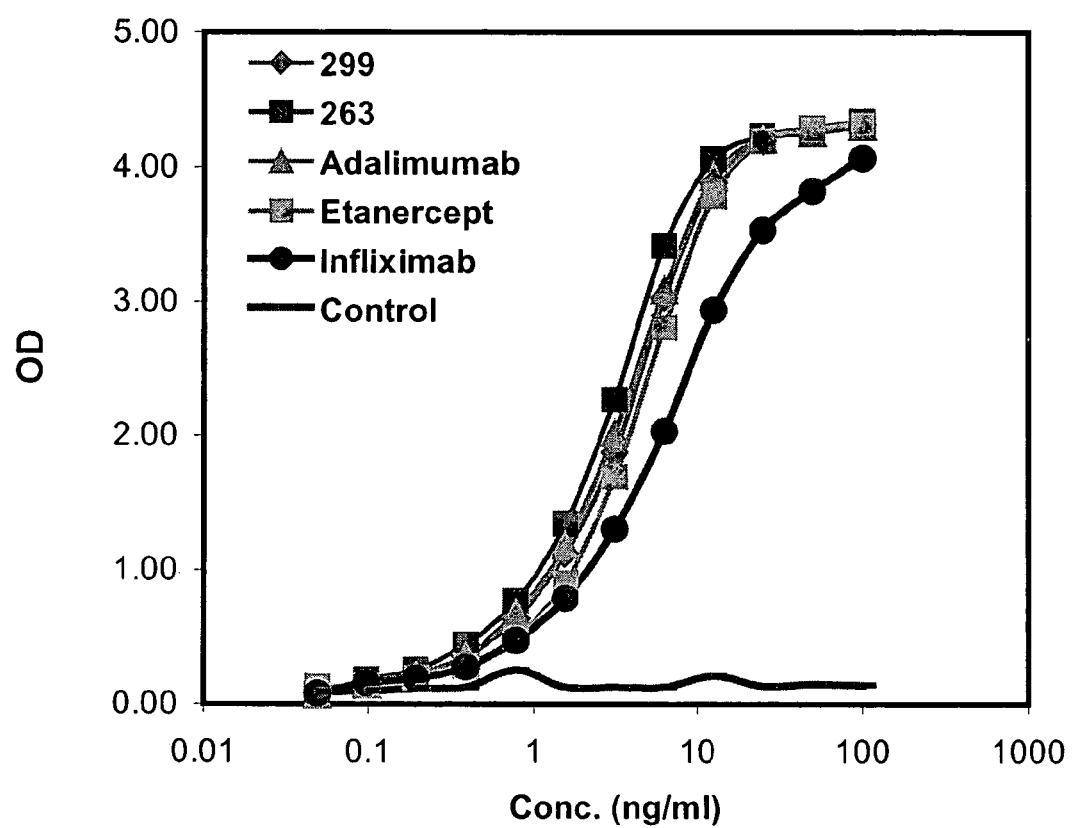
FIG. 5 is a line graph of anti-TNF reagents binding E. coli expressed soluble human TNF by ELISA.
Figure 6:
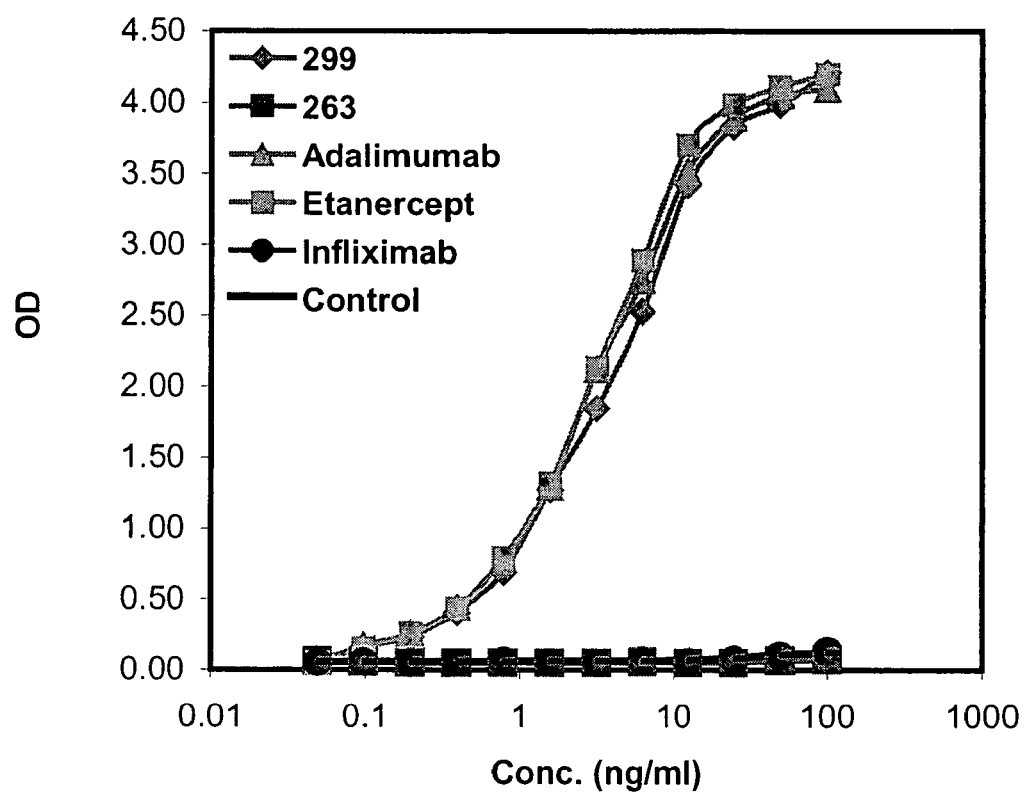
FIG. 6 is a line graph of anti-TNF reagents binding and cross-reacting to E. coli expressed soluble cynomolgous macaque monkey TNF by ELISA.

Anti-TNFα antibodies were also tested for their ability to bind to soluble recombinant TNFα. Human and monkey (cynomolgous macaque) TNFα were expressed in *E. coli* as fusion proteins with GST. Binding was assessed by ELISA. 299v2, 263, etanercept, infliximab, and adalumimab ("anti-TNFα antibodies") were incubated in 96-well plates coated overnight with 0.5 µg/ml of human GST-TNFα, 2 µg/ml of monkey GST-TNFα, and 10 µg/ml of GST. Bound antibody was detected using an HRP-conjugated goat anti-human IgG antibody. Results showed that anti-TNFα antibodies all bind to human TNFα with a similar dose-response (FIG. 5). Anti-TNFα antibodies differently bind to monkey TNFα. While 299v2, etanercept, and adalumimab bind cynomolgus macaque TNFα in a similar fashion, 263 and infliximab appear not to bind to cynomolgous macaque TNFα (FIG. 6).

Example 7

Kinetic Analysis

The kinetic measurements of the anti-TNFα antibodies were evaluated using KinExA® and BIACORE® technologies. The KinExA® method involves solution-based determination of formal affinity measurements at equilibrium. To measure the binding kinetics of each human anti-TNFα antibody, two experiments in replicates of three were performed. In both experiments a known concentration of antigen was titrated and a different antibody concentration was added to each antigen titration and allowed to reach binding equilibrium. To determine the $K_d$ measurements on human TNFα, the $K_d$ was calculated using a molar TNFα binding site concentration of one trimer (52.5 kDa), see Table 22, or three monomers (17.5 kDa), see Table 23. The results were analyzed by dual curve analysis. Kinetic measurements for the rabbit R014 antibody were essentially performed as above, however, the unknown antigen concentration method was performed using the known antibody concentration to calculate the $K_d$. In addition, to negate the possibility of avidity effects, Fab fragments were generated by papain cleavage and the kinetic analysis was repeated (see Table 24).

Additional kinetic constants were also calculated from BIACORE® data using the methods described in their product literature. An association rate constant ($k_a$) is the value that represents strength (extent) of binding of an antibody with target antigen as calculated based on antigen-antibody reaction kinetics. A dissociation rate constant ($k_d$) is the value that represents the strength (extent) of dissociation of this monoclonal antibody from target antigen as calculated based on antigen-antibody reaction kinetics. The dissociation constant ($K_d$) is the value obtained by dividing the dissociation rate constant ($k_d$) value from the association rate constant ($k_a$), see Table 25.

TABLE 22

| Ab | $K_d$ (M) | $K_d$ (M) High | $K_d$ (M) Low | % Error |
|---|---|---|---|---|
| 299 V1 | 6.3e−13 | 9.2e−13 | 4.3e−13 | 4.99 |
| 299v2 | 1.07e−12 | SD = 0.48 (n = 5) | | |
| 263 | 3.73e−12 | SD = 1.06 (n = 4) | | |
| 3.2 | 4.77e−12 | 7.6e−12 | 2.43e−12 | 4.7 |
| p75-hFc* | 4.10e−13 | SD = 0.15 (n = 4) | | >5%** |
| Infliximab | 4.70e−12 | 6.90e−12 | 2.93e−12 | 5.45 |
| Adulimumab | 3.90e−12 | 6.87e−12 | 1.64e−12 | 5.77 |

*A p75-hFc construct (R&D Systems) similar to etanercept (Enbrel) was used in these studies. When etanercept was used similar results were obtained (data not shown).
**Each experiment had errors between 6–7%.

TABLE 23

| mAb | $K_d$ (M) | $K_d$ (M) High | $K_d$ (M) Low | % Error |
|---|---|---|---|---|
| 299 V1 | 1.89e−12 | 2.76e−12 | 1.29e−12 | 4.99 |
| 299v2 | 3.20e−12 | SD = 1.44 (n = 5) | | |
| 263 | 1.12e−11 | SD = 3.17 (n = 4) | | |
| 3.2 | 1.43e−11 | 2.30e−11 | 7.30e−12 | 4.7 |
| p75-hFc* | 1.23e−12 | SD = 0.44 (n = 4) | | >5%** |
| Infliximab | 1.41e−11 | 2.07e−11 | 8.78e−12 | 5.45 |
| Adulimumab | 1.17e−11 | 2.06e−11 | 4.94e−12 | 5.77 |

*A p75-hFc construct (R&D Systems) similar to etanercept (Enbrel) was used in these studies. When etanercept was used similar results were obtained (data not shown).
**Each experiment had errors between 6–7%.

TABLE 24

| mAb | $K_d$ (M) | $K_d$ (M) High | $K_d$ (M) Low | % Error |
|---|---|---|---|---|
| Rabbit R014 | 7.87e−13 | 2.47e−12 | 1.56e−13 | 2.74 |
| Rabbit R014 Fab | 6.38e−13 | 1.94e−10 | 2.09e−15 | 16.9 |

TABLE 25

| mAb 299 v2 | Average | Standard Deviation (CV) | 95% Confidence Intervals |
|---|---|---|---|
| $k_a$ (M$^{-1}$s$^{-1}$) | 2.16 × 10$^6$ (N = 5) | +/− 9.38 × 10$^5$ (46%) | +/− 1.22 × 10$^6$ (56%) |
| $k_d$ (s$^{-1}$) | 1.03 × 10$^{-5}$ (N = 5) | +/− 5.48 × 10$^{-6}$ (53%) | +/− 6.81 × 10$^{-6}$ (66%) |
| $K_d$ (pM) | 5.7 | +/− 3.9 (68%) | +/− 4.8 (84%) |

The binding affinity of 299v2 for cynomolgus macaque TNFα was also measured, since this antibody had been found capable of binding monkey TNFa in an ELISA. The KinExA® method was also used to measure the $K_d$ describing this binding affinity. 299v2 bound to monkey TNFα with an affinity of 626 pM, considering TNFα as a monomer, which is therefore approximately 200 times lower than the affinity for human TNFα.

Example 8

In Vitro Anti-HTNFα Antibodies Characterization

Inhibition of TNFα Induced Apoptosis on Human MCF-7 Cells.

IgG2 kappa and lambda hybridomas were bulk cultured, purified and quantified as described previously. Isotype switched hybridoma and XENOMAX® derived IgG1 recombinant antibodies were expressed, purified and quantitated as described previously. Antibodies were further assayed for their ability to neutralize the biological effect of TNFα induced apoptosis on human MCF-7 cells. 96-well plates were seeded at 5000 cells MCF-7/well, 200 μL/well with phenol red free DMEM+10% FCS. The plates were incubated overnight at 37° C.+5% $CO_2$. On each plate, a titration of each antibody was assayed, in final concentrations from 0.005 ng/ml to 10 μg/ml. Anti-TNF reagents were diluted in apoptosis medium (2.5% FCS, 5 μg/mL CHX in phenol red free DMEM), in triplicate or up to replicates of six, at a constant concentration of 100 pg/mL (1.9 pM as a trimer) TNFα. 6 well plates with TNFα alone in apoptosis media and 6 well plates with apoptosis medium alone were also included. TNFα+/− neutralizing antibody was pre-incubated for 1 hour or for 18 hours at 37° C.+5% $CO_2$. 200 μL TNFα+/− neutralizing antibody was transferred to cells and incubated overnight at 37° C.+5% $CO_2$.

Figure 7:
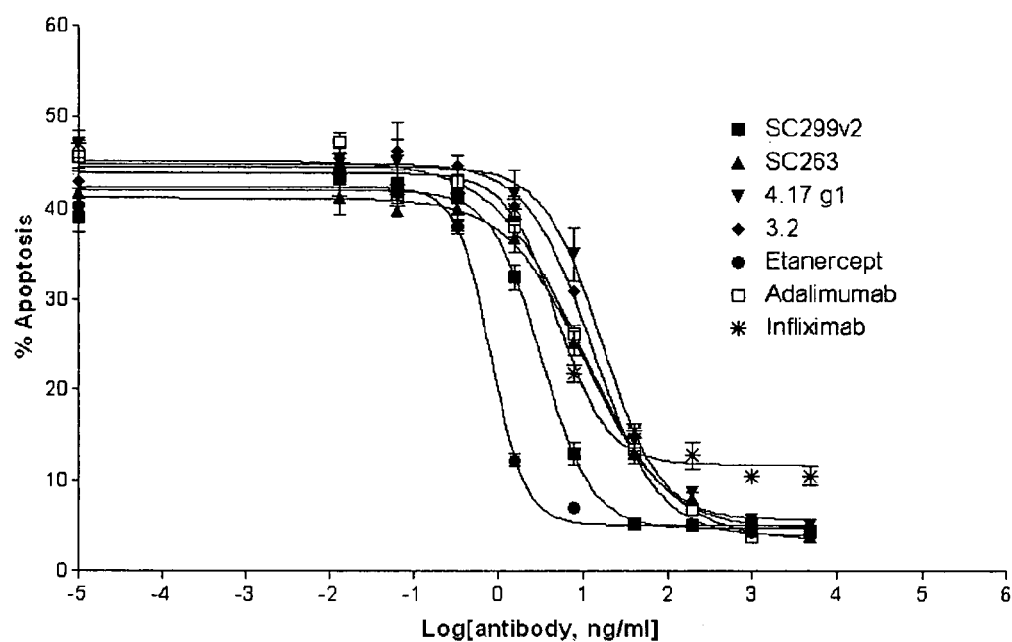
FIG. 7 is a representative line graph showing an example of neutralizing anti-TNFα antibody titration curves used to generate $IC_{50}$ values. Anti-TNFα reagents were pre-incubated with 100 pg/ml of TNFα for 1 hour at 37° C. Neutralization was assayed using MCF-7 cells and detected as a ratio of propidium iodide and Hoechst 33342 staining.
Figure 8:
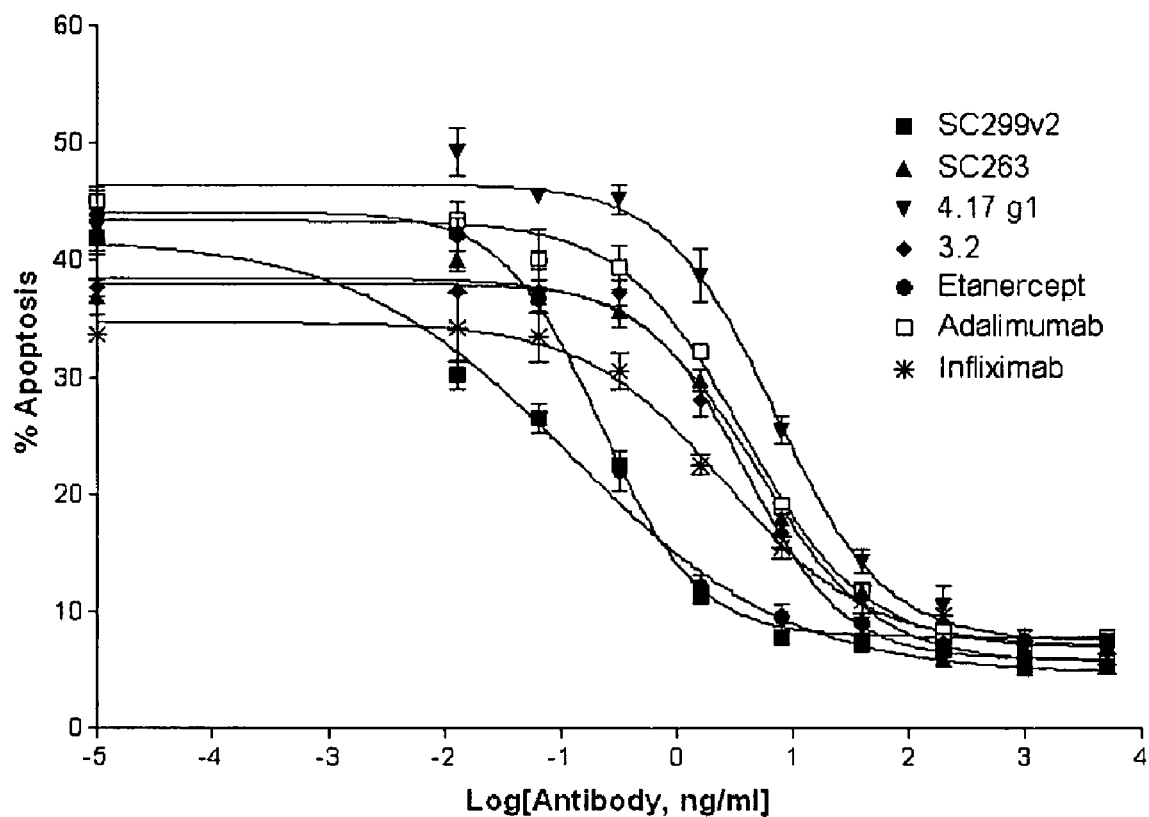
FIG. 8 is a representative line graph showing an example of neutralizing anti-TNFα reagents titration curves used to generate $IC_{50}$ values. Anti-TNFα antibodies were pre-incubated with 100 pg/ml of TNFα for 18 hours at 37° C. Neutralization was assayed using MCF-7 cells and detected as a ratio of propidium iodide and Hoechst 33342 staining.

Cells were stained with 0.5 μg/mL PI and 2.5 μg/mL Heochst 33342 for one hour. Percentage of apoptosis was determined by counting the number of dead cells (PI+ve) and dividing by the total number of cells (Heochst+ve). Neutralization was assayed using MCF-7 cells and detected as a ratio of propidium iodide and Heochst 33342 staining. An example of neutralizing antibody titration curves used to generate $IC_{50}$ values by four parameter curve fitting is provided in FIGS. 7 and 8, as line graphs.

Results shown in Table 26 are the averages of data obtained from different experiments of in vitro inhibition of TNF induced apoptosis in MCF-7 cells at a 1 hour or 18 hour antibody pre-incubation time point with TNF. The longer 18 hour preincubation may allow affinity differences to be seen more readily, as antibody-antigen binding is nearer to equilibrium. 299v2 demonstrated the lowest IC50s of any of the fully human mAbs as well as Infliximab. A strong correlation between affinity and neutralization potency is also observed.

TABLE 26

| mAb | IC50 1 hr Pre-incubation (pM) | | IC50 18 hr Pre-incubation (pM) | |
|---|---|---|---|---|
| | Average | St. Dev. | Average | St. Dev. |
| 299v2 | 18.6 | 4.2 | 1.6 | 1.3 |
| 263 | 59.5 | 13.4 | 37.0 | 4.3 |
| 4.17 g1 | 256.3 | 238.8 | 40.4 | 6.2 |
| 3.2 g1 | 93.8 | 11.0 | 38.6 | 12.1 |
| Infliximab | 32.4 | 1.5 | 31.7 | 20.4 |
| Adalimumab | 75.8 | 12.8 | 34.5 | 8.3 |
| Etanercept | 3.4 | 1.8 | 2.2 | 0.8 |

Figure 9:
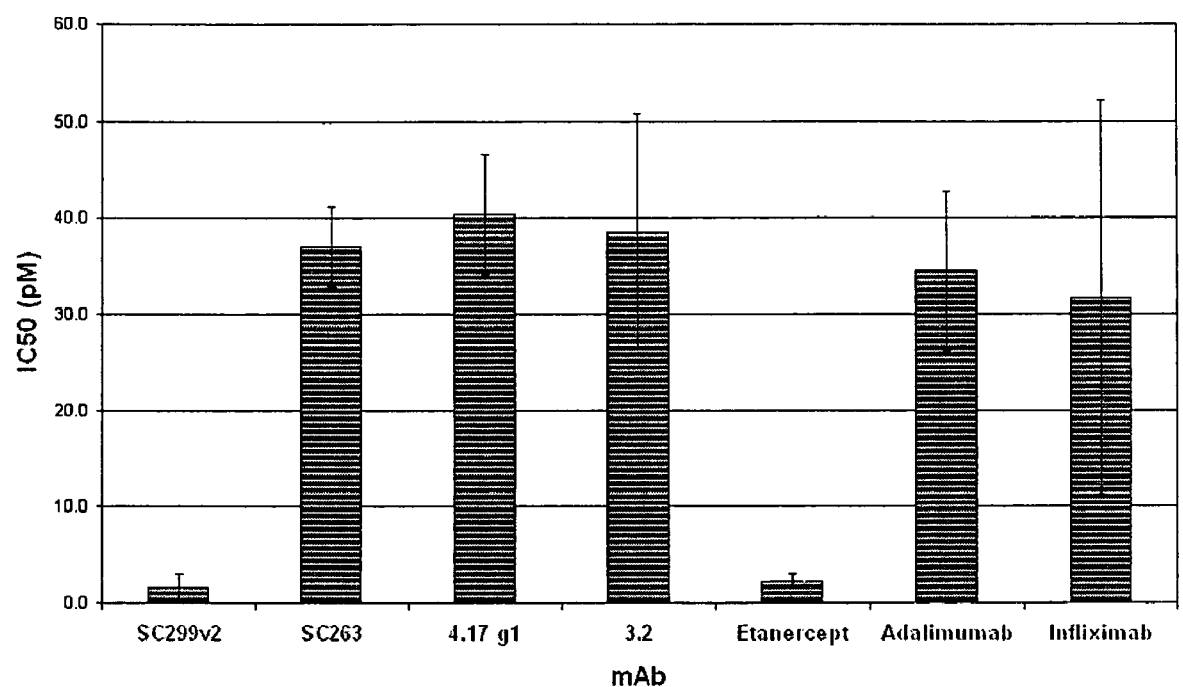
FIG. 9 is a bar graph that shows the average $IC_{50}$ values for anti-TNFα neutralization. Neutralization and $IC_{50}$ calculations were performed as described in the brief description of FIG. 8.

An example of the average $IC_{50}$ values for anti-TNFα neutralization of apoptosis is represented in FIG. 9, a bar graph. As FIG. 9 indicates, all antibodies are potent neutralizers of TNFα induced apoptosis. In particular, antibody 299v2 appears to have a better average potency than Infliximab, Adalimumab or Etanercept.

Table 27 shows the inhibition of TNF induced apoptosis on MCF-7 cells by the rabbit R014 mAb after 1 hour pre-incubation with TNF.

TABLE 27

| Anti-TNFα | Average $IC_{50}$ (pM) | SD (pM) | *n = |
|---|---|---|---|
| RO14 | 14.2 | 4.5 | 12 |

*number of experiments

Inhibition of TNFα Induced Apoptosis on Human WM 266.4 Cells.

Figure 10:
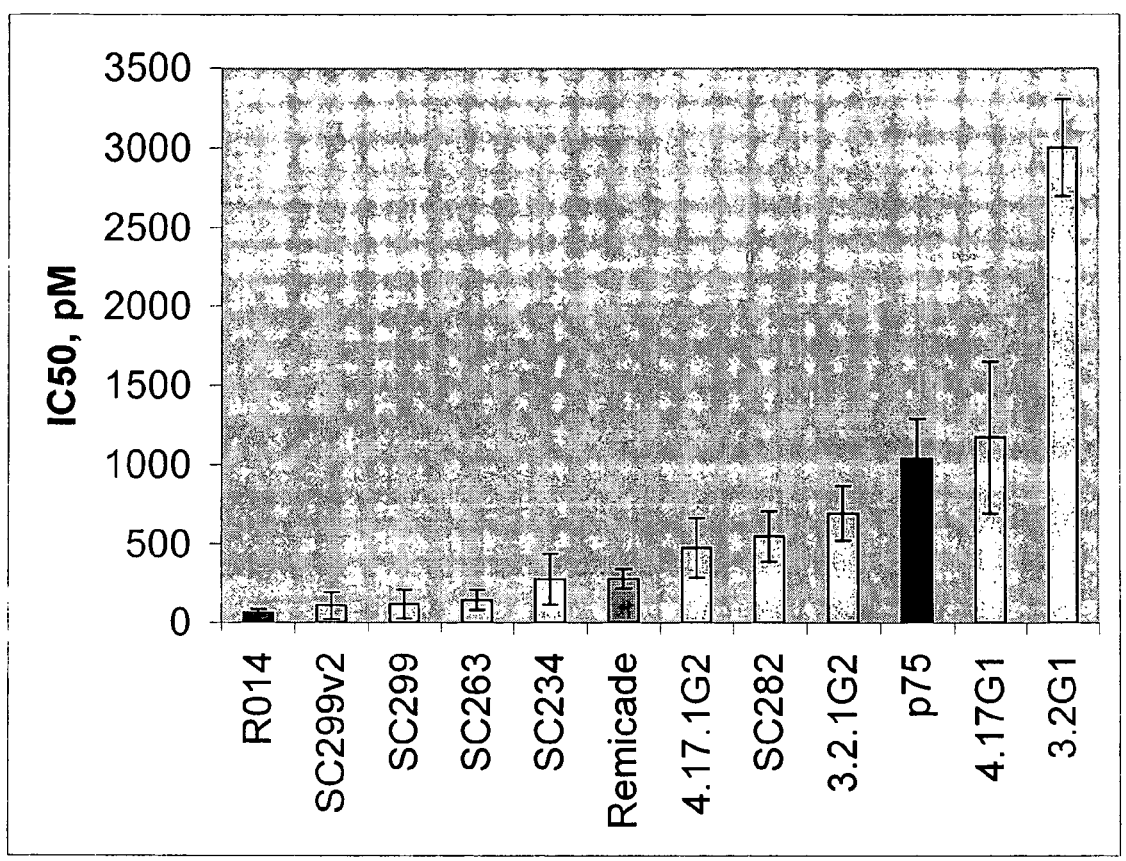
FIG. 10 is a bar graph that shows the average $IC_{50}$ values for anti-TNFα neutralization. Neutralization was performed on human WM266 cells and caspase activity was measured as an indication of TNFα induced apoptosis. Antibody $IC_{50}$ calculations were performed as described in the brief description of FIG. 7.

IgG2 kappa and lambda hybridomas were bulk cultured, purified and quantified as described above. Isotype switched hybridoma and XENOMAX® derived IgG1 recombinant antibodies were expressed, purified and quantitated as above. Antibodies were further assayed for their ability to neutralize the biological effect of TNFα induced apoptosis on human WM 266.4 cells. 20,000 WM266.6 cells were plated in 96-well plates in complete media (RPMI1640/10%FBS/Gln/P/S) and incubated at 37° C./10% $CO_2$ overnight. Media was removed and 50 μL test antibodies plus TNFα (pre-incubated for 30' at room temperature) was added in serum free media (RPMI1640/Gln/P/S). 50 μL cyclohexamide plates were incubated overnight as above final assay conditions: V=100 μL, cyclohexamide=6 μg/mL, TNFα=600 pg/mL=11.4 pM as a trimer. Test antibodies concentrations vary as described. 100 μL Caspase buffer and 0.3 μL Caspase substrate (APO-ONE, Promega) were added per well. Caspase activity was determined on the Victor Wallac; excitation wavelength @ 485 nm; emission wavelength @ 530 nm. An example of the antibodies ability to neutralize apoptosis by is shown in FIG. 10. FIG. 10 is a bar graph that shows the average $IC_{50}$ values for anti-TNFα neutralization. Neutralization was performed on human WM266 cells and caspase activity was measured as an indication of TNFα induced apoptosis. Antibody $IC_{50}$ calculations were performed as described in the brief description of FIG. 7.

A control shows induction of apoptosis by TNFα and cyclohexamide alone. Other controls included Rabbit 014 Ab as well Infliximab and p75-hFc (R&D), as an Etanercept surrogate. The graph shows caspase activity as a measure of TNFα induced apoptosis. As can be seen in FIG. 10, SC299V1 and SC299V2 antibodies are consistently similar to each other and in addition to R014, 263 and perhaps 234 are more potent than Infliximab and p75-hFc. 4.17 IgG2, SC282 and 3.2 IgG2 were more potent than p75-hFc. As also indicated by FIG. 10, all antibodies are potent neutralizers of TNFα induced apoptosis.

Inhibition of TNFα-induced IL-8 Production in Human Whole Blood.

Cultures of human whole blood reproduce naturally occurring conditions of clinical relevance that may not be present in cell cultures or in experimental animals. Whole blood cultures were used to assess the efficacy of anti-TNFα antibodies to neutralize TNFα-induced IL-8 production. Whole blood was obtained from normal donors by venopuncture, collected in EDTA tubes, and plated into 96-well plates. Anti-TNFα antibodies were diluted in RPMI medium and mixed with the whole blood. An irrelevant human IgG1 antibody was used as a control. This was followed by the addition of TNFα (final concentration 100 pg/ml, corresponding to 1.9 pM considering TNFα as a trimer). Plates were then incubated for 6 hours at 37° C.

Figure 11:
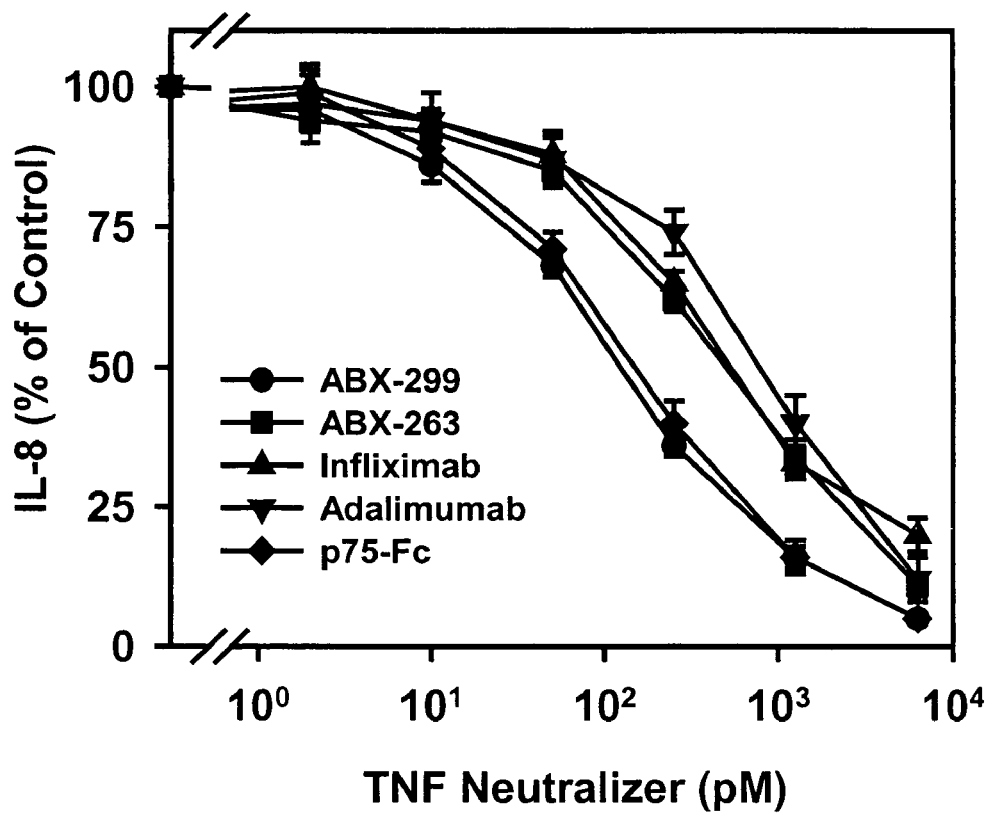
FIG. 11 is a line graph representing a whole blood assay for the inhibition of IL-8 induction by TNF, measured by ELISA. Titration curves were used to generate $IC_{50}$ values.

After incubation, Triton X-100 was added to the cultures at a final concentration of 0.5% v/v to cause cell lysis. IL-8 production was measured in the by ELISA. To express results, IL-8 induced by TNFα in the presence of the IgG1 control was set as 100%. Table 28 reports the IC50s for the anti-TNFα antibodies calculated using inhibition curves (FIG. 11). 299v2 and the Etanercept surrogate demonstrate the lowest IC50s and highest potencies.

TABLE 28

|  | Whole Blood IC50 (pM) |
|---|---|
| 299v2 | 131 ± 9 |
| 263 | 524 ± 60 |
| Infliximab | 546 ± 65 |
| Adalimumab | 896 ± 159 |
| p75-hFc* | 166 ± 32* |

*A p75-hFc construct (R&D Systems) similar to etanercept (Enbrel) was used in these studies. When etanercept was used similar results were obtained (data not shown).

Antibody-dependent Cell-mediated Cytotoxicity

Anti-TNFα antibodies were assayed to determine their ability to support the killing of TNFα-transfected CHO cells mediated by PBMCs, mainly NK cells. Briefly, human PBMCs were obtained from a normal donor and resuspended at a concentration calibrated so that, added to the effector cells, would yield 1:100 effector/target cell ratios. At the same time, TNFα-transfected CHO cells, that stably express membrane-bound TNFα, were labeled with the membrane dye PKH-26. CHO cells were then seeded into 96-well dishes in triplicate with or without 5 μg/ml antibody. After a 30 min incubation, effector cells were added, and the ADCC reaction was allowed to occur overnight at 37° C. At this point, triplicate samples were pooled, stained with the dye TOPO-3 per manufacturer's instruction, and analyzed by FACS. Ratios of the number of PKH-26 and TOPO-3 double-positive cells (dead target cells) versus PKH-26 single-positive cells (live target cells) were calculated and used to express results as percentages. The results indicate that the monoclonal antibodies have the ability to support ADCC at remarkable variance with p75-hFc, that was used as etanercept surrogate (Table 29).

Complement-dependent Cytotoxicity

Anti-TNFα antibodies were also assayed for the ability to fix complement and thus mediate the killing of TNFα-transfected CHO cells. Briefly, CHO cells were seeded at 125000/well in 96-well plates and added with 5 μg/ml antibody in duplicate. After 3 hours of incubation on ice, rabbit complement was added to a final concentration of 10%, and the CDC reaction was allowed to occur for 30 min at room temperature. At this point, cells were stained with 0.5 μg/ml of PI and 2.5 μg/ml of Heochst 33342 for 1 hour and counted using Autoscope. Experiments were conducted in triplicate. Results were calculated and expressed as described above for the TNFα-induced apoptosis assay. As in the case of ADCC, the results indicate that the monoclonal antibodies have ability to incite CDC at variance with p75-hFc, that was used as etanercept surrogate (Table 29).

TABLE 29

|  | ADCC (%) | CDC (%) |
|---|---|---|
| IGg1 Ctrl | 2 ± 2 | 2 ± 0 |
| 299v2 | 16 ± 5 | 9 ± 1 |
| 263 | 10 ± 5 | 17 ± 0 |
| Infliximab | 15 ± 5 | 12 ± 2 |
| Adalimumab | 8 ± 4 | 12 ± 1 |
| p75-hFc * | 2 ± 1 | 2 ± 2 |

* A p75-hFc construct (R&D Systems) similar to etanercept (Enbrel) was used in these studies.

Example 9

In Vivo Anti-HTNFα Antibodies Characterization

Inhibition of TNFα-induced Hepatic Injury in Mice

To test whether anti-human TNFα antibodies neutralize human TNFα in vivo, the ability of anti-human TNFα antibodies to protect against the hepatic injury induced by human TNFα and D-galactosamine (D-GalN) administration in mice was studied (Lehmann V et al., *J. Exp. Med.*, 1987 165(3): 657-63). Administration of TNFα with D-GalN induces fulminant liver injury that resembles the liver injury induced by LPS and D-GalN, characterized by widespread apoptotic death of hepatocytes, ultimately resulting in shock and lethality. D-GalN treatment renders mice 100-1000 more sensitive to the lethal effects of lipopolysaccharide (LPS) as well as murine TNFα (Lehmann V, et al., *J. Exp. Med.*, 1987 165(3): 657-63). The apoptotic liver injury induced by LPS and D-GalN has been shown to be dependent on endogenously produced TNFα (Leist M, et al., *Am. J Pathol.*, 1995, 146(5): 1220-34.). It has also been demonstrated that this liver injury is dependent exclusively on secreted TNFα signaling through the p55 receptor (Nowak M, et al., *Am. J Physiol.* 2000, 278(5): R1202-9), suggesting that D-GalN also sensitizes to the lethal effects of human TNFα, which in mice binds only p55 TNFα receptor. Liver injury induced by hTNFα and D-GalN was assessed by measuring serum enzyme activity of alanine aminotransferase (ALT).

Figure 12:
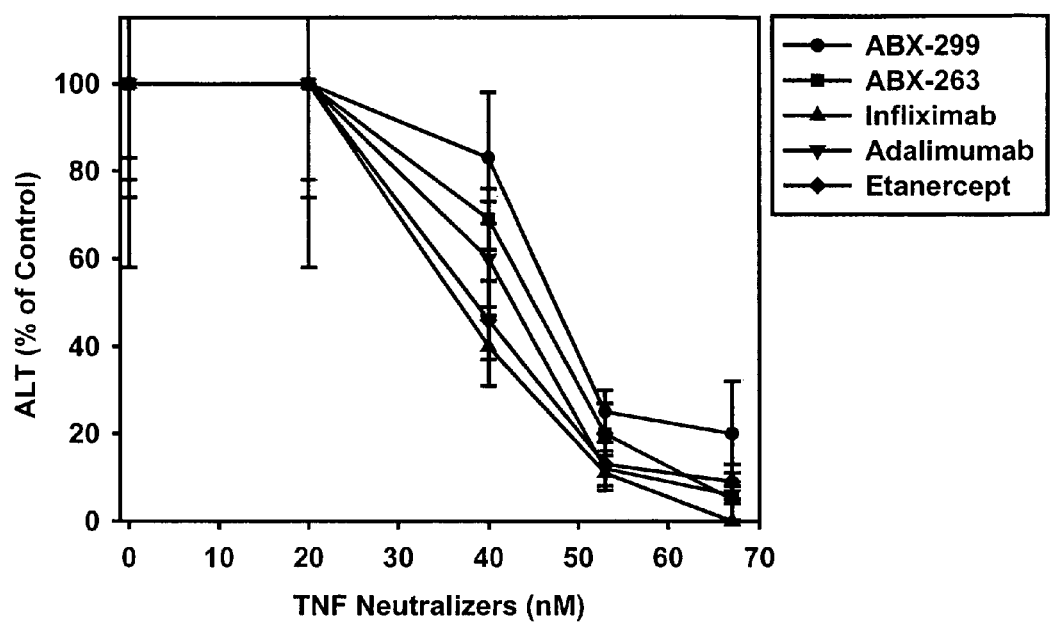
FIG. 12 is a representative line graph of the in-vivo inhibition of TNFα induced hepatic failure using anti-TNF reagents. Liver injury induced by TNFα and D-GalN was assessed by measuring serum enzyme activities of alanine aminotransferase (ALT). Titration curves were used to generate $IC_{50}$ values.

The experiments were performed as described. 8 to 10 weeks old Balb/c female mice, weighing approximately 20 g, were obtained from Charles River Laboratories. 8-10 mice per group were used. The dose and route of administration as well as the time for measuring the ALT levels in the serum were defined in preliminary experiments. Mice were injected with D-GalN (Sigma) (900 mg/kg, ip) 90 min before human TNF (R&D System) (1 μg/mouse, iv). The intravenous administration of 1 μg/mouse of TNF resulted in circulating levels of TNF of 19 nM (considering TNF as a trimer). Hepatocyte damage was assessed 6 hours after TNF/GalN administration by measuring ALT using a commercial diagnostic kit (Sigma). To compare the ability of 299v2, 263, Etanercept, Adalimumab and infliximab to inhibit TNFα in vivo, dose-response experiments were performed by injecting anti-TNF reagents (1-10 i.v. μg/mouse) 90 min before TNF (1 μg/mouse, iv). Control mice received saline before TNF. Data were expressed as % of control and neutralization curves were generated (FIG. 12). IC50s were calculated using a four parameter fit curve. Table 30 shows the IC50s for the different anti-TNF reagents averaged from different experiments.

Inhibition of TNFα-induced IL-6 Production in Mice

Figure 13:
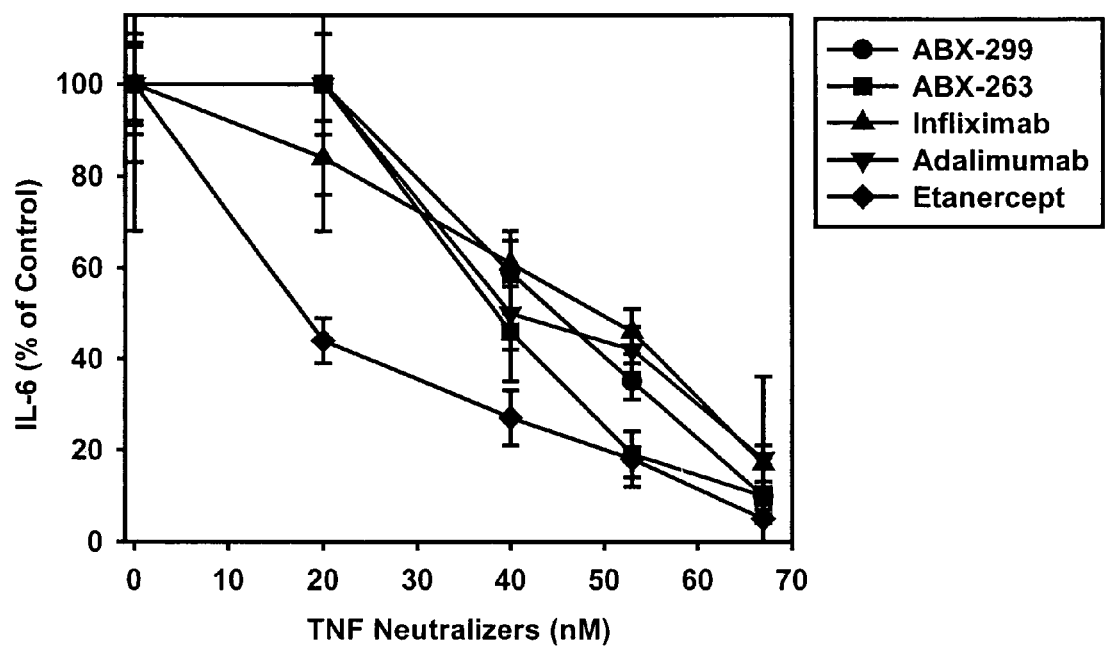
FIG. 13 is a representative line graph of the in-vivo inhibition of TNFα induced IL-6 using anti-TNF reagents and measured by ELISA. Titration curves were used to generate $IC_{50}$ values.

As another approach to testing the ability of anti-TNFα antibodies to inhibit TNFα in vivo, anti-TNFα antibodies were used to block the production of IL-6 induced in mice by human. TNFα engenders many acute biological actions, including the induction of IL-6 (Benigni et al., J. Immunol. 157:5563, 1996). 8-10 mice per group were used. As initially established in time-course experiments, injection of human TNFα into mice causes a rapid rise in serum IL-6 levels that peak at 2 hours after injection. Based on the results of other preliminary experiments aimed to define the dose and the route of administration of TNFα, mice were injected intravenously with 1 µg/mouse of human TNFα. IL-6 levels were measured 2 hours after TNFα administration using a commercial ELISA kit (R&D System). Dose-response experiments were performed by injecting anti-TNFα antibodies (1-10 i.v. µg/mouse) 90 min before TNFα (1 µg/mouse, iv). Control mice received saline before TNFα. Data were expressed as a percentage of control and neutralization curves were generated (FIG. 13). IC50s were calculated using a four parameter fit curve. Table 30 shows the IC50s for the different anti-TNFα antibodies averaged from different experiments.

TABLE 30

| | In vivo Potency (nM) | |
|---|---|---|
| | ALT | IL-6 |
| 299v2 | 50 ± 4 | 43 ± 1 |
| 263 | 48 ± 6 | 35 ± 5 |
| Infliximab | 41 ± 10 | 43 ± 21 |

TABLE 30-continued

| | In vivo Potency (nM) | |
|---|---|---|
| | ALT | IL-6 |
| Adalimumab | 40 ± 1 | 36 ± 5 |
| Etanercept | 27 ± 16 | 27 ± 14 |

Example 10

Structural Analysi of ANTI-TNFα Antibodies

The variable heavy chains and the variable light chains for the antibodies shown in Table 1 above were sequenced to determine their DNA sequences. The complete sequence information for all anti-TNFα antibodies are shown in the sequence listing submitted herewith, including nucleotide and amino acid sequences.

Table 31 is a table comparing various XENOMAX® derived antibody heavy chain regions to a particular germ line heavy chain region. Table 32 is a table comparing various XENOMAX® derived antibody light chain regions to a particular germ line light chain region. Table 33 is a table comparing various hybridoma derived antibody heavy chain regions to a particular germ line heavy chain region. Table 34 is a table comparing various hybridoma derived antibody light chain regions to a particular germ line light chain region.

TABLE 31

Xenomax Heavy Chain Analysis

| SEQ ID NO: | Single Cell | V Heavy/D/J | FR1 | CDR1 | FR2 |
|---|---|---|---|---|---|
| 267 | — | Germline | QVQLVESGGGVVQPGRSLRLSCAASGFTFS | SYGMH | WVRQAPGKGLEWVA |
| 74 | 299 v. 2 | VH3-33/D5—5/JH6b | QVQLVESGGGVVQPGRSLPLSCAASGFTFS | SYDMH | WVRQAPGKGLEWVA |
| 70 | 299 v. 1 | VH3-33/D5—5/JH6b | QVQLVESGGGVVQPGRSLRLSCAASGFTFS | SYDMH | WVRQAPGKGLEWVA |
| 38 | 148 | VH3-33/D5—5/JH6b | QVQLVESGGGVVQPGRSLRLSCAASGFTFS | NYDMH | WVRQAPGKGLEWVA |
| 78 | 313 | VH3-33/D5-24/JH6b | QVQLVESGGGVVQPGRSLRLSCAASGFTFS | NHDIH | WVRQAPGKGLEWVA |
| 6 | 15 | VH3-33/D6—6/JH6b | QVQLVESGGGVVQPGRSLRLSCAASGFTFS | SYDIH | WVRQAPGKGLEWVA |
| 22 | 95 | VH3-33/D6-19/JH6b | QVQLVESGGGVVQPGRSLRLSCAASGFTFS | NYDMH | WVRQAPGKGLEWVA |
| 268 | — | Germline | EVQLVESGGGLIQPGGSLRLSCAASGFTVS | SNYMS | WVRQAPGKGLEWVS |
| 46 | 250 | VH3-53/D3-16/JH4b | EVQLVESGGGLIQPGGSLRLSCAASGFTVS | SNYMS | WVRQAPGKGLEWVS |
| 50 | 263 | VH3-53/D3-16/JH4b | EVQLVESGGGLIQPGGSLRLSCAASGFTVS | RNYMS | WVRQAPGKGLEWVS |
| 54 | 269 | VH3-53/D3-16/JH4b | EVQLVESGGGLIQPGGSLRLSCAASEFTVS | RNYMS | WVRQAPGKGLEWVS |
| 269 | — | Germline | QVQLVESGGGVVQPGRSLRLSCAASGFTFS | SYGMH | WVRQAPGKGLEWVA |
| 58 | 280 | VH3-33/D4-17/JH6b | QVQLVESGGGVVQPGRSLRLSCAASGFTVS | SYGMH | WVRQAPGKGLEWVA |
| 62 | 282 | VH3-33/D4-17/JH6b | QVQLVESGGGVVQPGRSLRLSCAASGFTVS | SYGMH | WVRQAPGKGLEWVA |

TABLE 31-continued

Xenomax Heavy Chain Analysis

| SEQ ID NO: | Single Cell | V Heavy/D/J | FR1 | CDR1 | FR2 |
|---|---|---|---|---|---|
| 66 | 291 | VH3-33/D1-26/JH6b | QVQLVESGGSVVQPGRSLRLSCAASGFTFS | NYGIH | WVRQAPGKGLEWVA |
| 270 | — | Germline | QVQLVESGGGVVQPGRSLRLSCAASGFTFS | SYGMH | WVRQAPGKGLEWVA |
| 42 | 234 | VH3-30/D1-26/JH6b | QVQLVESGGGVVQPGRSLRLSCAASGFTFS | SYDMH | WVRQAPGKGLEWVA |
| 34 | 140 | VH3-30/D1-20/JH6b | QVQLVESGGGVVQPGRSLRLSCAASGFTFS | SYGMH | WVRQAPGKGLEWVA |
| 14 | 28 | VH3-30/D3-3/JH6b | QVQLVESGGGVVQPGRSLRLSCAASGFTFS | NYGMH | WVRQAPGKGLEWVT |
| 271 | — | Germline | QVQLQESGPGLVKPSETLSLTCTVSGGSIS | SYYWS | WIRQPAGKGLEWIG |
| 18 | 69 | VH4-4/D2-2/JH2 | QVQLQESGPGLVKPSETLSLTCTVSGGSIN | HYYWS | WIRQPAGKGLEWIG |
| 272 | — | Germline | QVQLQESGPGLVKPSQTLSLTCTVSGGSIS | SGGYYWS | WIRQHPGKGLEWIG |
| 2 | 2 | VH4-31/D1-20/JH6b | QVQLQESGPGLVKPSQTLSLTCTVSGGSIS | SGGYYWS | WIRQHPGKGLEWIG |
| 10 | 25 | VH4-31/D1-20/JH6b | QVQLQESGPGLVKPSQTLSLTCTVSGGSIS | SGGYYWS | WIRQHPGKGLEWIG |
| 30 | 131 | VH4-31/D1-20/JH6b | QVQLQESGPGLVKPSQTLSLTCTVSGGSIS | SGGYYWS | WIRQHPGKGLEWIG |
| 26 | 123 | VH4-31/D1-20/JH6b | QVQLQESGPGLVKPSQTLSLTCTVSGGSIS | SGGYYWS | WIRQHPGKGLEWIG |
| 267 | — | | VIWYDGSNKYYADSVKG | RFTISRDNSKNTLYLQMNSLRAEDTAVYYCAR | WGQGTTVTVSS |
| 74 | 299 v. 2 | | VIWSDGSIKYYADSVKG | RFTISRDNSKNTLYLQMNSLRAEDTAVYYCAR EVESAMGGFYYNGMDV | WGQGTTVTVSS |
| 70 | 299 v. 1 | | VIWSDGSIKYYADSVKG | RFTISRDNSKNTLYLQMNSLRAEDTAVYYCAR EVESAMGGFYYNGMDV | WGQGATVTVSS |
| 38 | 148 | | VIWYDGSIKYYADSVKG | RFTISRDNSKNTLYLQMNSLRAEDTAVYFCAR ETAILRGYYYYDMDV | WGQGTTVTVSS |
| 78 | 313 | | VIWSDGSNKYYADSVKG | RFTISRDNSKNTLYLQMNSLRAEDTAVYYCAR EKMATIKGYYYYGMDV | WGQGTTVTVSS |
| 6 | 15 | | VIWYDGSIKYYADSVKG | RFTISRDNSKNTLYLQMNSLRAEDTAVYYCAR EEQLVRGGYYYYGMDV | WGQGTTVTVSS |
| 22 | 95 | | VIWYDGSIKYYADSVKG | RFTISRDNSKNTLHLQMNSLRAEDTAVYYCAR EIAVAGGYYYGLDV | WGQGTTVTVSS |
| 268 | — | | VIYSGGSTYYADSVKG | RFTISRDNSKNTLYLQMNSLRAEDTAVYYCAR | WGQGTLVTVSS |
| 46 | 250 | | VIYSGDRTYYADSVKG | RFTISRDNSKNTLYLQMNSLRAEDTAVYYCAR GEGGFDY | WGQGTLVTVSS |
| 50 | 263 | | VIYSGDRTYYADSVKG | RFTISRDNSKNTLYLQMNSLRAEDTAVYYCAR GEGGFDY | WGQGTLVTVSS |
| 54 | 269 | | VIYSGDRTYYADSVKG | RFTISRDNSKNTLYLQMNSLRAEDTAVYYCAR GEGGFDY | WGQGTLVTVSS |
| 269 | — | | VIWYDGSNKYYADSVKG | RFTISRDNSKNTLYLQMNSLRAEDTAVYYCAR | WGQGTTVTVSS |
| 58 | 280 | | VIWSNGSNKYYADSVKG | RETISRDNSKNTLYLQMNSLRAEDTAVYYCAR DNGVYVGYAYYYGMDV | WGQGTTVTVSS |
| 62 | 282 | | VIWSNGSNKYYADSVKG | RFTISRDNSKNTLYLQMNSLRAEDTAVYYCAR DNGVYVGYAYYYGMDV | WGQGTTVTVSS |
| 66 | 291 | | VIWSDGSNKYYADSVKG | RFTISRDNSKNTLYLQMNSLRAEDTAVYYCAR ELPNSGSYSGYYYYYGMDV | WGQGTTVTVSS |
| 270 | — | | VISYDGSNKYYADSVKG | RFTISRDNSKNTLYLQMNSLRAEDTAVYYCAR | WGQGTTVTVSS |
| 42 | 234 | | VISYDGSIKYYADSVKG | RFTISRDNSKNTLYLQVNSLRAEDTAVYYCAR EVRSGSYYYYSMDV | WGQGTTVTVSS |
| 34 | 140 | | VISYDGSNKYYADSVKG | RFTISRDNSKNTLYLQMNSLRAEDTAVYYCAR DQDNWNYYYGMDV | WGQGTTVTVSS |
| 14 | 28 | | IISYDGSNKYYADSVKG | RFTISRDNSKNTLYLQMNSLRAEDTAVYYCVT YYDFWSGYLPGMDV WGQGTTVTVSS | |
| 271 | — | | RIYTSGSTNYNPSLKS | RVTMSVDTSKNQFSLKLSSVTAADTAVYYCAR | WGRGTLVTVSS |
| 18 | 69 | | RIYPTGSTNYNPSLKS | RVTMSVDTSKNQFSLKLSSVTAADTAVYYCAG GWSYWYFDL | WGRGTLVTVSS |
| 272 | — | | YIYYSGSTYYNPSLKS | RVTISVDTSKNQFSLKLSSVTAADTAVYYCAR | WGQGTTVTVSS |
| 2 | 2 | | NIYYSGSTYYNPSLKS | RVTISVDTSKNQFSLKLSSVTAADTAVYYCAR DSNQYNWNDEVYDYGLDV | WGQGTTVTVSS |

TABLE 31-continued

Xenomax Heavy Chain Analysis

| SEQ ID NO: | Single Cell | V Heavy/D/J | FR1 | CDR1 | FR2 |
|---|---|---|---|---|---|
| 10 | 25 | NIYYSGSTYYNPSLKS | RVTISVDTSKNQFSLKLSSVTAADTAVYYCAR | DSNQYNWNDEVYDYGLDV | WGQGTTVTVSS |
| 30 | 131 | NIYYSGSTYYNPSLKS | RVTISVDTSKNQFSLKLSSVTAADTAVYYCAR | DSNQYNWNDEVYDYGLDV | WGQGTTVTVSS |
| 26 | 123 | NIYYSGSTYYTPSLKS | RVTISVDTSKNQFSLKLSSVTAADTAVYYCAR | DSNQYNWNDEVYDYGLDV | WGQGTTVTVSS |

TABLE 32

Xenomax Light Chain Analysis

| SEQ ID NO: | Single Cell | V Kappa/J | FR1 | CDR1 | FR2 |
|---|---|---|---|---|---|
| 273 | — | Germline | DIQMTQSPSSLSASVGDRVTITC | RASQGIRNDLG | WYQQKPGKAPKRLIY |
| 72 | 299 | A30VK1/JK4 | DIQMTQSPSSLSASVGDRVTITC | RASQGIRIDLG | WYQQKPGKAPKRLIY |
| 80 | 313 | A30VK1/JK4 | DIQMTQSPSSLSASVGDRVTITC | RASQGIRNDLG | WYQQKPGKAPKPLIY |
| 68 | 291 | A30VK1/JK4 | DIQMTQSPSSLSASVGDRVTITC | RASQGIRNDLG | WYQQKPGKAPKRLIY |
| 44 | 234 | A30VK1/JK4 | DIQMTQSPSSLSASVGDRVTITC | RASQDIRNDLG | WYQQKPGKAPKRLIY |
| 4 | 2 | A30VK1/JK4 | DIQMTQSPSSLSASVGDRVTITC | RASQGIRNDLG | WYQQKPGKAPKRLIY |
| 12 | 25 | A30VK1/JK4 | DIQMTQSPSSLSASVRDRVTITC | RASQGIRNDLG | WYQQKPGKAPKRLIY |
| 32 | 131 | A30VK1/JK4 | DIQMTQSPSALSASVGDRVTITC | RASQGIRNDLG | WYQQKPGKAPKRLIY |
| 8 | 15 | A30VK1/JK4 | DIQMTQSPSSLSASIGDRVTITC | RASQGIRNDLG | WYQQKPGKAPKRLIY |
| 24 | 95 | A30VK1/JK4 | DIQMTQSPSSLSASVGDRVTITC | RASQGIRNDLG | WYQQKPGKAPKRLIY |
| 40 | 148 | A30VK1/JK4 | DIQMTQSPSSLSASVGDRVTITC | RASQGIRNDLG | WYQQKPGKAPKRLIS |
| 28 | 123 | A30VK1/JK4 | DIQMTQSPSSLSASVGDRVTITC | RASQGIRNDLG | WYQQKPGKAPKRLIY |
| 274 | — | Germline | DIQMTQSPSSLSASVGDRVTITC | RASQGIRNDLG | WYQQKPGKAPKRLIY |
| 60 | 280 | A30VK1/JK1 | DIQMTQSPSSLSASVGDRVTITC | RASQGIRNDLG | WYQQKPGKAPKPLIY |
| 64 | 282 | A30VK1/JK1 | DIQMTQSPSSLSASVGDRVTITC | RASQGIRNDLG | WYQQKPGKAPKRLIY |
| 16 | 28 | A30VK1/JK1 | DIQMTQSPSSLSASVGDRVTITC | RASQGIRNDLT | WYQQKPGKAPKRLIY |
| 275 | — | Germline | DVVMTQSPLSLPVTLGQPASISC | RSSQSLVYSDGNTYLN | WFQQRPGQSPRRLIY |
| 20 | 70 | A1VK2/JK4 | DVVMTQSPLSLPVTLGQPASISC | RSSQSLVYSDGSTYLN | WFQQRPGQSPRRLIY |
| 276 | — | Germline | DIVMTQSPLSLPVTPGEPASISC | RSSQSLLHSNGYNYLD | WYLQKPGQSPQLLIY |
| 36 | 145 | A19VK2/JK1 | DIVMTQSPLSLPVTPGEPASISC | RSSQSLLHSNGYNYLD | WYLQKPGQSPQLLIF |
| 277 | — | Germline | EIVMTQSPATLSVSPGERATLSC | RASQSVSSNLA | WYQQKPGQAPRLLIY |
| 48 | 250 | L2VK3/JK1 | EIVMTQSPATLSVSPGERATLSC | RASQSVTSNLA | WYQQKPGQAPRLLIH |
| 52 | 263 | L2VK3/JK1 | EIVMTQSPATLSVSPGERATLSC | RASQSVSSNLA | WYQQKPGQAPRLLIH |
| 56 | 269 | L2VK3/JK1 | EIVMTQSPATLSVSPGERATLSC | RASQSVSSNLA | WYQQKPGQAPRLLIH |
| 273 | — | AASSLQS | GVPSRFSGSGSGTEFTLTISSLQPEDFATYYC | LQHNSYPLT | FGGGTKVEIK |
| 72 | 299 | AASTLQS | GVPSRFSGSGSGTEFIFTISSLQPEDFASYYC | LQHKSYPLT | FGGGTKVEIK |
| 80 | 313 | AASSLES | GVPSRFSGSGSGPEFTLTISSLQPEDFATYYC | LQHNSYPLT | FGGGTKVEIQ |
| 68 | 291 | AASSLQS | GVPSRFSGSGSGTEFTLTISSLQPEDFATYYC | LQHCCYPLT | FGGGTKVEIK |
| 44 | 234 | AASSLQS | GVPSRFSGSGSGPEFTLTISSLQPEDFATYYC | LQHNSYPLT | FGGGTKVEIK |

TABLE 32-continued

Xenomax Light Chain Analysis

| SEQ ID NO: | Single Cell | V Kappa/J | FR1 | CDR1 | FR2 |
|---|---|---|---|---|---|
| 4 | 2 | AASSLQS | GVPSRFSGSGSGTEFTLTISSLQPEDFATYYC | LQHNNYPLT | FGGGTKVEIK |
| 12 | 25 | AASSLQS | GVPSRFSGSGSGTEFTLTISSLQPEDFATYYC | LQHNSYPLT | FGGGTKVEIK |
| 32 | 131 | AASSLQS | GVPSRFSGSGSGTEFTLTISSLQPEDFATYYC | LQHKSYPLT | FGGGTKVEIK |
| 8 | 15 | AASSLQS | GVPSRFSGSGSGPEFTLTISSLQPEDFATYYC | LQHNSYPLT | FGGGTKVEIK |
| 24 | 95 | AASSLQS | GVPSRFSGSGSGTEFTLTVSSLQPEDFATYYC | LQHHSYPLT | FGGGTKVQIN |
| 40 | 148 | AASSLQG | GVPSRFSGSGSGTEFTLTISSLQPEDFATYYC | LQHNSYPLT | FGGGTKVEIK |
| 28 | 123 | AASSLQS | GVPSRFSGSGSGTEFTLTISSLQPEDFATYYC | LQHNNYPLT | FGGGTKVEIK |
| 274 | — | AASSLQS | GVPSRFSGSGSGTEFTLTISSLQPEDFATYYC | LQHNSYPWT | FGQGTKVEIK |
| 60 | 280 | AASSLQS | GVPSRFSGSGSGTEFTLTISSLQPEDFATYYC | LQHNSYPRT | FGQGTKVEIK |
| 64 | 282 | AASSLHS | GVPSRFSGSGSGTEFTLTISSLQPEDFATYYC | LQHNSYPWT | FGQGTKVEIK |
| 16 | 28 | AASSLQS | GVPSRFSGSGSGTEFTLTISSLQPEDFATYYC | LQHNSFPWT | FGQGTKVEIK |
| 275 | — | KVWNWDS | GVPDRFSGSGSGTDFTLKISRVEAEDVGVYYC | MQGTHWP##LT | FGGGTKVEIK |
| 20 | 70 | KVWNWDS | GVPDRFSGSGSGTDFTLKISRVEAEDVGVYYC | MQGSHWPREFT | FGGGTKVEIK |
| 276 | — | LGSNRAS | GVPDRFSGSGSGTDFTLKISRVEAEDVGVYYC | MQALQTWT | FGQGTKVEIK |
| 36 | 145 | LGSYRAS | GVPDRFSGSGSGTDFTLKISRVEAEDVGVYYC | MQALQTWT | FGQGTKVEIK |
| 277 | — | GASTRAT | GIPARFSGSGSGTEFTLTISSLQSEDFAVYYC | QQYNNWWT | FGQGTKVEIK |
| 48 | 250 | GASIRAT | GLPARFSGSGSGTEFTLTISSLQSEDFAVYYC | QQYNYWWT | FGQGTKVEIK |
| 52 | 263 | GASIRAT | GLPARFSGSGSGTEFTLTISSLQSEDFAVYYC | QQYNYWWT | FGQGTKVEIK |
| 56 | 269 | GASIRAT | GLPARFSGSGSGTEFTLTISSLQSEDFAVYYC | QQYNYWWT | FGQGTKVEIK |

TABLE 33

Hybridoma Heavy Chain Analysis AB-TNFα-XG2

| CHAIN NAME | SEQ ID NO: | | FR1 | CDR1 | FR2 | CDR2 | FR3 | CDR3 | FR4 |
|---|---|---|---|---|---|---|---|---|---|
| | 278 | Germline | QVQLVESGGGVVQ PGRSLRLSCAAS | GFTFSSYGMH | WVRQAPGKGLE WVA | VIWYDGSNKYY ADSVKG | RFTISRDNSKN TLYLQMNSLRA EDTAVYYCAR | | WGQGTTVTVSS |
| 2.14 | 132 | VH3-33/D6-19/JH6b | QVQLVESGGGVVQ PGRSLRLSCAAS | GLIFSSYGMH | WVRQAPGKGLE WVA | VIWYDGSNKYY ADSVKG | RFTISRDNSKN TLYLQMNSLRA EDTAVYYCAR | ERDSSGWYYYG MDV | WGQGTTVTVSS |
| 2.13 | 128 | VH3-33/D6-19/JH6b | QVQLVESGGGVVQ PGRSLRLSCAAS | GLIFSNYGMH | WVRQAPGKGLE WVA | VIWYDGSNKYY ADSVKG | RFTISRDNSKN TLYLQMNSLRA EDTAVYYCAR | EGIAVAGPPYY YYGMDV | WGQGTTVTVSS |
| 2.10 | 124 | VH3-33/D6-19/JH6b | QVQLVESGGGVVQ PGRSLRLSCAAS | GFTFSSYGMH | WVRQAPGKGLE WVA | VIWYDGSIKYY ADSVKG | RFTISRDNSKN TLYLQMNSLRA EDTAVYYCAR | ERDSSGWYYYG MDV | WGQGTTVTVSS |
| | 279 | Germline | EVQLLESGGGLVQ PGGSLRLSCAAS | GFTFSSYAMS | WVRQAPGKGLE WVS | AISGSGGSTYY ADSVKG | RFTISRDNSKN TLYLQMNSLRA EDTAVYYCAK | | WGQGTLVTVSS |
| 4.23 | 262 | VH3-23/D3-22/JH4b | EVQLLESGGGLVQ PGGSLRLSCAAS | GFTFSSYAMS | WVRQAPGKGLE WVS | AISGSGGSTYY ADSVKG | RFTISRDNSKN TLYLQMNSLRA EDTAVYYCAK | DYYDSSGYHPF DY | WGQGTLVTVSS |

TABLE 33-continued

Hybridoma Heavy Chain Analysis AB-TNFα-XG2

| CHAIN NAME | SEQ ID NO: | | FR1 | CDR1 | FR2 | CDR2 | FR3 | CDR3 | FR4 |
|---|---|---|---|---|---|---|---|---|---|
| | 280 | Germline | EVQLVESGGGLVK PGGSLRLSCAAS | GFTFSSYSMN | WVRQAPGKGLE WVS | SISSSSSYIYY ADSVKG | RFTISRDNAKN SLYLQMNSLRA EDTAVYYCAR | | WGQGTTVTVSS |
| 2.21 | 158 | VH3-21/D1-20/JH6b | EVQLVESGGGLVK PGGSLRLSCAAS | GFTFSSYSMN | WVRQAPGKGLE WVS | SISSSSSYIYY ADSVKG | RFTISRDNAKN SLYLQMNSLRA EDTAVYYCAR | GGITGTTNYYG MDV | WGQGTTVTVSS |
| | 281 | Germline | QVQLVESGGGVVQ PGRSLRLSCAAS | GFTFSSYGMH | WVRQAPGKGLE WVA | VIWYDGSNKYY ADSVKG | RFTISRDNSKN TLYLQMNSLRA EDTAVYYCAR | | WGQGTLVTVSS |
| 4.7 | 198 | VH3-33/D6-19/JH4b | QVQLVESGGGVVQ PGPSLRLSCAAS | GFTFSSYGMN | WVRQAPGKGLE WVA | IIWYDGSNEYY GDSVKG | RFTISRDNSKN TLFLQMNSLRA EDTAVYYCAR | DPLRIVVAGDF DY | WGQGTLVTVSS |
| 4.11 | 214 | VH3-33/D6-19/JH4b | QVQLVESGGGVVQ PGRSLRLSCAAS | GFTFSSYGMN | WVRQAPGKGLE WVA | IIWYDGSNEYY GDSVKG | RFTISRDNSKN TLFLQMNSLRA EDTAVYYCAR | DPLRIVVAGDF DY | WGQGTLVTVSS |
| | 282 | Germline | EVQLVESGGGLIQ PGGSLRLSCAAS | GFTVSSNYMS | WVRQAPGKGLE WVS | VIYSGGSTYYA DSVKG | RFTISRDNSKN TLYLQMNSLRA EDTAVYYCAR | | WGQGTMVTVSS |
| 3.9 | 186 | VH3-53/--/JH3b | EVQLVESGGGLIQ PGGSLRLSCAAS | GFTVSSNYMS | WVRQAPGKGLE WVS | VIYSGGSTYYA DSVKG | RFTISRDNSKN TLYLQMNSLRA EDTAVYYCAR | GPGAFDI | WGQGTMVTVSS |
| 3.8 | 182 | VH3-53/--/JH3b | EVQLVESGGGLIQ PGGSLRLSCAAS | GFTVSNNYMH | WVRQAPGKGLE WYS | VIYSGGNTYYA DSVKG | RFTISRDNSKN TLFLQMNSLKT EDTAVYYCAR | GPGAFDI | WGQGTMVTVSS |
| | 283 | Germline | EVQLVQSGAEVKK PGESLKISCKGS | GYSFTSYWIG | WVRQMPGKGLE WMG | IIYPGDSDTRY SPSFQG | QVTISADKSIS TAYLQWSSLKA SDTANYYCAR | | WGQGTTVTVSS |
| 2.4 | 100 | VH5-51/D3-3/JH6b | EVQLVQSGAEVKK PGESLKISCKGS | GYSFTSDWIG | WVRQMPGKGLE WMG | IIYPGDSDTRY SPSFQG | QVTISADKSIT TAYLQWSSLKA SDTANYYCAR | SGYGMDV | WGQGTTVTVSS |
| | 284 | Germline | QVQLVQSGAEVKK PGASVKVSCHAS | GYTFTSYCIS | WVRQAPGQGLE WMG | WISAYNGNTNY AQKLQG | RVTMTTDTSTS TAYMELRSLRS DDTAVYYCAR | | WGQGTLVTVSS |
| 3.4 | 170 | VH1-18/D6-19/JH4b | QVQLVQSGAEVKK PGASVKVSCHAS | GYTFTFYSIT | WVRQAPGQGLE WMG | WISAYNDNTNY AQKLQG | RVTMTTDTSTS TAYMELRSLRS DDTAVYYCAR | TFTSGFDY | WGQGTLVTVSS |
| | 285 | Germline | QVQLVESGGGVVQ PGRSLRLSCAAS | GFTFSSYGMH | WVRQAPGKGLE WVA | VIWYDGSNKYY ADSVKG | RFTISRDNSKN TLYLQMNSLRA EDTAVYYCAR | | WGQGTLVTVSS |
| 2.3 | 96 | VH3-33/D4-23/JH4b | QVQLVESGGGVVQ PGRSLRLSCAAS | GFTFSSYGMN | WVRQAPGKGLE WVA | VIWYDGSNKYY GDSVKG | RFTISRDNSKN TLYVQMNSLRA EDTAVYYCAR | ESDYGGNPYFD Y | WGQGTLVTVSS |
| 4.8 | 202 | VH3-33/D4-23/JH4b | QVHLVESGGGVVQ PGRSLRLSCAAS | GFTFSSYGMH | WVRQAPGKGLE WVA | VIWHDGSNKYY ADSVKG | RFTISRDNSKN TLYLQMNSLRA EDTAVYYCTR | ESDYGGYPYFD Y | WGQGILATVSS |
| 4.4 | 194 | VH3-33/D4-23/JH4b | QVHLVESGGGVVQ PGRSLRLSCAAS | GFTFSSYGMH | WVRQAPGKGLE WVA | VIWHDGSNKYY ADSVKG | RFTISRDNSKN TLYLQMNSLRA EDTAVYYCTR | ESDYGGYPYFD Y | WGQGILATVSS |
| 4.3 | 190 | VH3-33/D4-23/JH4b | QVQLVESGGGVVQ PGRSLRLSCAAS | GFTFSSYGMH | WVRQAPGKGLE WVA | VIWYDGSNKYY ADSVKG | RFTISRDNSKN TLYLQMNSLRA EDTAVYYCAR | ESDYGGNPYFD Y | WGQGTLAAVSS |
| | 286 | Germline | EVQLVESGGGLIQ PGRSLRLSCAAS | GFTVSSNYMS | WVRQAPGKGLE WVS | VIYSGGSTYYA DSVKG | RFTISRDNSRN TLYLQMNSLRA EDTAVYYCAR | | WGQGTLVTVSS |

TABLE 33-continued

Hybridoma Heavy Chain Analysis AB-TNFα-XG2

| CHAIN NAME | SEQ ID NO: | | FR1 | CDR1 | FR2 | CDR2 | FR3 | CDR3 | FR4 |
|---|---|---|---|---|---|---|---|---|---|
| 2.17 | 144 | VH3-53/D7-27/JH4b | EVQLVESGGGLIQ PGGSLRLSCAAS | GFTVSSNYVN | WVRQAPGKGLE WVS | VIYNAGSAYYA DSVKG | RFTISRDNSKN TLFLQMNSLRA EDTAVYYCAR | GTGAFDY | WGQGTLVTVSS |
| | 287 | Germline | QVQLVESGGGVVQ PCRSLRLSCAAS | GFTFSSYGMH | WVRQAPGKGLE WVA | VISYDGSNKYY ADSVKG | RFTISRDNSKN TLYLQMNSLRA EDTAVYYCAR | | WGQGTTVTVSS |
| 4.13 | 222 | VH3-30/D4-17/JH6b | QVQLVESGGGVVQ PGRSLRLSCAAS | GFTFSSYDMH | WVRQAPGKGLE WVA | IISYDGSIKYY ADSVKG | RFTISRDNSKN TLYLQMNSLRA EDTAVYYCAR | ENAVTYGGYYH YGMDV | WGQGTTVTVSS |
| | 288 | Germline | QVQLVESGGGLVK PGGSLRLSCAAS | GFTFSDYYMS | WIRQAPGKGLE WVS | YISSSGSTIYY ADSVKG | RFTISRDNAKN SLYLQMNSLRA EDTAVYYCAR | | WGQGTTVTVSS |
| 1.1 | 84 | VH3-11/--/JH6b | QVQLVESGGGLVK PGGSLRLSCAAS | GFTFSDYYMS | WIRQAPGKGLE WVS | YISRSGSTIYY ADSVKG | RFTISRDNAKN SLYLQMNSLRA EDTAVYYCAR | SLGGMDV | WGQGTTVTVSS |
| 2.16 | 140 | VH3-11/--/JH6b | QVQLVESGGGLVK PGGSLRLSCAAS | GFTFSDYYMS | WIRQAPGKGLE WVS | YISRSGSTIYY ADSVKG | RFTISRDNAKN SLYLQMNSLRA EDTAVYYCAR | SLGGMDV | WGQGTTVTVSS |
| 2.18 | 148 | VH3-11/--/JH6b | QVQLVESGGGLVK PGGSLRLSCAAS | GFTFSDYYMS | WIRQAPGKGLE WVS | YISRSGSTIYY ADSVKG | RFTISRDNAKN SLYLQMNSLRA EDTAVYYCAR | SLGGMDV | WGQGTTVTVSS |
| | 289 | Germline | QVQLVESGGGVVQ PGRSLRLSCAAS | GFTFSSYGMH | WVRQAPGKGLE WVA | VIWYDGSNKYY ADSVKG | RFTISRDNSKN TLYLQMNSLRA EDTAVYYCAR | | WGQGTTVTVSS |
| 4.12 | 218 | VH3-33/D4-17/JH6b | QVQLVESGGGVVQ PGRSLRLSCAAS | GFTFSSYGMH | WVRQAPGKGLE WVA | VIWYDGSNKYY ADSVKG | RFTISRDNSKN TLYLQMNSLRA EDTAVYYCAR | ETTVTKEGYYY YGMDV | WGQGTTVTVSS |
| 4.9 | 206 | VH3-33/D4-17/JH6b | QVQLVESGGGVVQ PGRSLRLSCAAS | GFTFSSYGMH | WVRQAPGKGLE WVA | VIWYDGSNKYY ADSVKG | RFTISRDNSKN TLYLQMNSLRA EDTAVYYCAR | ETTVTKEGYYY YGMDV | WGQGTTVTVSS |
| | 290 | Germline | QVQLVQSGAEVKK PGASVKVSCKAS | GYTFTSYGIS | WVRQAPGQGLE WMG | WISAYNGNTNY AQKLQG | RVTMTTDTSTS TAYMELRSLRS DDTAVYYCAR | | WGQGTLVTVSS |
| 2.6 | 108 | VH1-18/D1-7/JH4b | QVQLVQSGAEVKK PGASVKVSCKAS | GYTFTSYGIS | WVRQAPGQGLE WMG | WISAYNVNTNY AQKLQG | RVTMTTDTSTN TAYMELRSLRS DDTAVYYCAR | DPITETMEDYF DY | WGQGTLVTVSS |
| | 291 | Germline | EVQLVQSGAEVKK PGESLKISCKGS | GYSFTSYWIG | WVRQMPGKGLE WMG | IIYPGDSDTRY SPSFQG | QVTISADKSIS TAYLQWSSLKA SDTAMYYCAR | | WGQGTLVTVSS |
| 3.2 | 166 | VH5-51/D7-27/JH4b | EVQLVQSGAEVKK PGESLKISCKTS | GYSFTSYWIG | WVRQMPGKGLE WMG | IIYLGDSDTRY SPSFQG | QVTISADKSIS TAYLQWSSLKA SDTAMYYCAR | SNWGLDY | WGQGTLVTVSS |
| | 292 | Germline | QVQLVESGGGVVQ PGRSLRLSCAAS | GFTFSSYGMH | WVRQAPGKGLE WVA | VIWYDGSNKYY ADSVKG | RFTISRDNSKN TLYLQMNSLRA EDTAVYYCAR | | WGQGTTVTVSS |
| 4.16 | 234 | VN3-33/D2-21/JH6b | QVQLVESGGGVVQ PGRSLRLSCTTS | GFTFSNYGMH | WVRQAPGKGLE WVA | VIWYDGSIKYY VDSVKG | RFTISRDNSKN TLYLQMNSLRA EDTAVYYCAR | EKCGGGDCYSH YGMDV | WGQGTTVTVSS |
| 4.15 | 230 | VN3-33/D2-21/JH6b | QVQLVESGGGVVQ PGRSLRLSCTTS | GFTFSNYGMH | WVRQAPGKGLE WVA | VIWYDGSIKYY VDSVKG | RFTISRDNSKN TLYLQMNSLRA EDTAVYYCAR | EKDCGGDCYSH YGMDV | WGQGTTVTVSS |
| 4.14 | 226 | VN3-33/D2-21/JH6b | QVQLVESGGGVVQ PGRSLRLSCTTS | GFTFSNYGMH | WVRQAPGKGLE WVA | VIWYDGSIKYY VDSVKG | RFTISRDNSKN TLYLQMNSLRA EDTAVYYCAR | EKDCGGDCYSH YGMDV | WGQGTTVTVSS |

TABLE 33-continued

Hybridoma Heavy Chain Analysis AB-TNFα-XG2

| CHAIN NAME | SEQ ID NO: | | FR1 | CDR1 | FR2 | CDR2 | FR3 | CDR3 | FR4 |
|---|---|---|---|---|---|---|---|---|---|
| 4.17 | 238 | VN3-33/D2-21/JH6b | QVQLVESGGGVVQ PGRSLRLSCTTS | GFTFSNYGMH | WVRQAPGKGLE WVA | VIWYDGSIKYY VDSVKG | RFTISRDNSKN TLYLQMNSLRA EDTAVYYCAR | EKDCGGDCYSH YGMDV | WGQGTTVTVSS |
| | 293 | Germline | QVQLVESGGGVVQ PGRSLRLSCAAS | GFTFSSYGMH | WVRQAPGKGLE WVA | VIWYDGSNKYY ADSVKG | RFTISRDNSKN TLYLQMNSLRA EDTAVYYCAR | | WGQGTTVTVSS |
| 2.1 | 88 | VH3-33/--/JH6b | QVQLVESGGDVVQ PGRSLRLSCAAS | GFTFSSSGMH | WVRQAPGKGLE WVA | VIWYDGSNKYY ADSVKG | RFTISRDNSKN TLYLQMNSLRA EDTAVYYCAR | DDYYYGMDV | WGQGTTVTVSS |
| | 294 | Germline | QVQLVESGGGVVQ PGRSLRLSCAAS | GFTFSSYGMH | WVRQAPGKGLE WVA | VIWYDGSNKYY ADSVKG | RFTISRDNSKN TLYLQMNSLRA EDTAVYYCAR | | WGQGTLVTVSS |
| 2.2 | 92 | VH3-33/D4-23/JH4a | QVQLVESGGGVVQ PGRSLRLSCAAS | GFTFSSYGMH | WVRQAPGKGLE WVA | VIWYDGNNKYY ADSVKG | RFTISRDNSKN TLYLQMNSLRA EDTAVYYCAR | ESDYGGNPYFD Y | WGQGTTVTVSS |
| | 295 | Germline | QVQLQESGPGLVK PSETLSLTCTVS | GGSISSYYWS | WIRQPPGKGLE WIG | YIYYSGSTNYN PSLKS | RVTISVDTSKN QFSLKLSSVTA ADTAVYYCAR | | WGQGTLVTVSS |
| 3.6 | 178 | VH4-59/D6-19/JH4b | QVQLQESGPGLVK PSETLSLTCTVS | GGSISSYYWS | WIRQPPGKGLE WIG | YFYYSGSTNYN PSLKS | RVTISVDTSKN QFSLKLRSVTA ADTAVYYCAR | DRFTSGWFDY | WGQGTLVTVSS |
| | 296 | Germline | EVQLVESGGGLVQ PGGSLRLSCAAS | GFTFSSYSMN | WVRQAPGKGLE WVS | YISSSSSTIYY ADSVKG | RFTISRDNAKN SLYLQMNSLRD EDTAVYYCAR | | WGQGTLVTVSS |
| 4.22 | 258 | VH3-48/D1-14/JH4b | EVQLVESGGGLVQ PGGSLRLSCAAS | GPTFSNYGMN | WVRQAPGKGLE WVS | YISNSITSKYY ADSVKG | RFTISRDNAKN SLYLQMNSLRD VDTAVYYCAR | GPGGFDY | WGQGTLVTVSS |
| | 297 | Germline | EVQLVESGGGLIQ PGGSLRLSCAAS | GFTVSSNYMS | WVRQAPGKGLE WVS | VIYSGGSTYYA DSVKG | RFTISRDNSKN TLYLQMNSLRA EDTAVYYCAR | | WGQGTLVTVSS |
| 2.9 | 120 | VH3-53/--/JH4b | EVQLVESGGGLIQ PGGSLRLSCAAS | GFTVSSNYMS | WVRQAPGKGLE WVS | VIYSGGGTYYA DSVKG | RFTISRDNSKN TLYLQMNSLRA EDTAVYYCAR | GPGSFDY | WGQGTLVTVSS |
| | 298 | Germline | QVQLVQSGAEVKK PGASVKVSCKAS | GYTFTGYYMH | WVRQAPGQGLE WMG | WINPNSGGTNY AQKFQG | RVTMTRDTSIS TAYMELSRLRS DDTAVYYCAR | | WGQGTTVTVSS |
| 3.1 | 162 | VH1-2/D6-19/JH6b | QVQLVQSGAEVKK PGASVKVSCKAS | GYTFTGYYMH | WVRQAPGQGLE WMG | WINPNSGGTNY AQKFQG | RVTMTRDTSIS TAYWELSRLRS DDTAVYYCAR | APLWTVRSWYY YGMDV | WGQGTTVTVSS |
| | 299 | Germline | QVQLVESGGGVVQ PGRSLRLSCAAS | GFTFSSYGMH | WVRQAPGKGLE WVA | VIWYDGSNKYY ADSVKG | RFTISRDNSKN TLYLQMNSLRA EDTAVYYCAR | | WGQGTTVTVSS |
| 4.19 | 246 | VH3-33/D3-9/JH6b | QVQLVESGGGVVQ PGRSLRLSCAAS | GFTFSSYGMH | WVRQAPGKGLE WVA | VIWYDGRNKYN ADSVKG | RFTISRDNSKN TLNLQMNSLRA EDTAVYYCAR | DLTYYDILGGM DV | WGQGTTVTVSS |
| 4.18 | 242 | VH3-33/D3-9/JH6b | QVQLVESGGGVVQ PGRSLRLSCAAS | GFTFSSYGMH | WVRQAPGKGLE WVA | VIWYDGRNKYN ADSVKG | RFTISRDNSKN TLNLQMNSLRA EDTAVYYCAR | DLTYYDILGGM DV | WGQGTTVTVSS |
| 2.8 | 116 | VH3-33/D3-9/JH6b | QVQLVESGGGVVQ PGRSLRLSCAAS | GFTFSSYGMH | WVRQAPGKGLE WVA | VIWYDGRNKYN ADSVKG | RFTISRDNSKN TLNLQMNSLRA EDTAVYYCAR | DLTYYDILGGM DV | WGQGTTVTVSS |
| 4.20 | 250 | VH3-33/D3-9/JH6b | QVQLVESGGGVVQ PGRSLRLSCAAS | GFTFSSYGMH | WVRQAPGKGLE WVA | VIWYDGRNKYN ADSVKG | RFTISRDNSKN TLNLQMNSLRA EDTAVYYCAR | DLTYYDILGGM DV | WGQGTTVTVSS |

TABLE 33-continued

Hybridoma Heavy Chain Analysis AB-TNFα-XG2

| CHAIN NAME | SEQ ID NO: | | FR1 | CDR1 | FR2 | CDR2 | FR3 | CDR3 | FR4 |
|---|---|---|---|---|---|---|---|---|---|
| 2.7 | 112 | VH3-33/D3-9/JH6b | QVQLVESGGGVVQ PGRSLRLSCAAS | GFTFSSYGMH | WVRQAPGKGLE WVA | VIWYDGRNKYN ADSVKG | RFTISRDNSKN TLNLQMNSLRA EDTAVYYCAR | DLTYYDILGGM DV | WGQGTTVTVSS |
| | 300 | Germline | EVQLVESGGGLIQ PGGSLRLSCAAS | GFTVSSNYMS | WVRQAPGKGLE WVS | VIYSGGSTYYA DSVKG | RFTISRDNSKN TLYLQMNSLRA EDTAVYYCAR | | WGQGTTVTVSS |
| 2.19 | 152 | VH3-53/--/JH6b | EVQLVESGGGLIQ PGGSLRLSCAAS | GFTVSSNYMS | WVRQAPGKGLE WVS | VIYSGGSTYYA DSVKG | RFTISRDNSKN TLYLQMNSLRA EDTAVYYCAR | GEGGMDV | WGQGTTVTVSS |
| 2.15 | 136 | VH3-53/--/JH6b | EVQLVESGGGLIQ PGGSLRLSCAAS | GFTVSSNYMS | WVRQAPGKGLE WVS | VIYSGGSTYYA DSVKG | RFTISRDNSKN TLYLQMNSLRA EDTAVYYCAR | GEGGMDV | WGQGTTVTVSS |
| | 301 | Germline | QVQLVESGGGVVQ PGRSLRLSCAAS | GFTFSSYGMH | WVRQAPGKGLE WVA | VIWYDGSNKYY ADSVKG | RFTISRDNSKN TLYLQMNSLRA EDTAVYYCAR | | WGQGTTVTVSS |
| 2.5 | 104 | VH3-33/D3-10/JH6b | QVQLVESGGGVVQ PGRSLRLSCAAS | GFTFSSYDMH | WVRQAPGKGLE WVA | VIWYDGSNKYH ADSVKG | RFTISRDNSKN TLYLQMNSLRA EDTAVYYCAR | ENTMVRGGDYY YGMDV | WGQGTTVTVSS |
| 3.5 | 174 | VH3-33/D3-10/JH6b | QVQLVESGGGVVQ PGRSLRLSCAAS | GFTFSSYDMH | WVRQAPGKGLE WVA | VIWYDGSNKYN ADSVKG | RFTISRDNSKN TLYLQMNSLRA EDTAVYYCAR | ENTMVRGGDYY YGMDV | WGQGTTVTVSS |
| | 302 | Germline | QVQLVESGGGVVQ PGRSLRLSCAAS | GFTFSSYGMH | WVRQAPGKGLE WVA | VIWYDGSNKYY ADSVKG | RFTISRDNSKN TLYLQMNSLRA EDTAVYYCAR | | WGQGTLVTVSS |
| 4.10 | 210 | VH3-33/D4-17/JH5b | QVQLVESGGGVVQ PGRSLRLSCAAS | GFTFSSYGMH | WVRQAPGKGLE WVA | VIWYDGSNKYY ADSVKG | RFTISRDNSKN TLYLQMNSLRA EDTAVYYCAR | SRYGDWGWFDP | WGQGTLVTVSS |
| | 303 | Germline | QVQLVESGGGVVQ PGRSLRLSCAAS | GFTFSSYGMH | WVRQAPGKGLE WVA | VIWYDGSNKYY ADSVKG | RFTISRDNSKN TLYLQMNSLRA EDTAVYYCAR | | WGQGTTVTVSS |
| 4.21 | 254 | VH3-33/D6-19-D7-27/JH6b | QVQLVESGGGVVQ PGRSLRLSCAAS | GFTFSSYGMH | WVRQAPGKGLE WVA | VIWYDGSNKYY ADSVKG | RFTISRDNSKN TLYLQMNSLRA EDTAVYYCAR | GNRVVVAGTRV TPANWGYYYYG MDV | WGQGTTVTVSS |

TABLE 34

Hybridoma Light Chain Analysis AB-TNFα-XG2K

| CHAIN NAME | SEQ ID NO: | | FR1 | CDR1 | FR2 | CDR2 | FR3 | CDR3 | FR4 |
|---|---|---|---|---|---|---|---|---|---|
| | 304 | Germline | QSVLTQPPSVSGAP GQRVTISC | TGSSSNIGAY DVH | WYQQLPGTAPK LLIY | GNSNRPS | GVPDRFSGSKSGTS ASLAITGLQAEDEA DYYC | QSYDSSLSGSV | FGGGTKLTVL |
| 2.4 | 102 | V1-13/JL2 | QSLLTQPPSVSGAP GQRVTISC | TGSSSNIGAY DVH | WYQQFPGTAPK LLIY | GNSNRPS | GVPDRFSGSKSGTS ASLAITGLQAEDEA DYYC | QSYDSSLSGSV | FGGGTKLTVL |
| 4.7 | 200 | V1-13/JL2 | QSVLTQPPSVSGAP GLRVTISC | TGNSSNIGAY DVH | WYQQLPGTAPK LLIY | GNSNRPS | GVPDRFSGSKSGTS ASLAITGLQAEDT DYYC | QSYDSSLSGSV | FGGGTKLTVL |
| | 305 | Germline | DIQMTQSPSSLSAS VGDRVTITC | RASQGIRNDLG | WYQQKPGKAPK RLIY | AASSLQS | GVPSRFSGSGSGTE FTLTISSLQPEDFA TYYC | LQHNSYPLT | FGGGTKVEIK |

TABLE 34-continued

Hybridoma Light Chain Analysis AB-TNFα-XG2K

| CHAIN NAME | SEQ ID NO: | FR1 | CDR1 | FR2 | CDR2 | FR3 | CDR3 | FR4 |
|---|---|---|---|---|---|---|---|---|
| 4.9 | 208 A30/JK4 | DIQMTQSPSSLSAS VGDRVTITC | RASQGIRNDLG | WYQQKPGKAPK RLIY | AASSLQS | GVPSRFSGSGSGTE FTLTISSLQPEDFA TYYC | LQHNSYPLT | FGGGTKVEIK |
| 4.21 | 256 A30/JK4 | DIQMTQSPSSLSAS VGDRVTITC | RASQGIRNDLG | WYQQKPGKAPK CLIY | VASSLQS | GVPSRFSGSGSGTE FTLTISSLQPEDFA TYYC | LQHNSYPLT | FGGGTKVEIK |
| 4.20 | 252 A30/JK4 | DIQMTQSPSSLSAS VGDRVTITC | RASQGIRHDLG | WYQQKPGKAPE RLIY | GASSLQS | GVPSRFSGSGSGTE FTLTISSLQPEDFA TYYC | LQHNSYPLT | FGGGTKVEIK |
| 4.17 | 240 A30/JK4 | DIQMTQSPSSLSAS VGDRVTITC | RASQGIRNDLG | WYQQKPGKAPK RLIY | AASSLQS | GVPSRFSGSGSGTE FTLTISSLQPEDFA TYYC | LQHMSLPLT | FGGGTKVEIK |
| 4.16 | 236 A30/JK4 | DIQMTQSPSSLSAS VGDRVTITC | RASQGIRNDLG | WYQQKPGKAPK RLIY | AASSLQS | GVPSRFSGSGSGTE FTLTISSLQPEDFA TYYC | LQHMSLPLT | FGGGTKVEIK |
| 2.14 | 134 A30/JK4 | DIQMTQSPSSLSAS VGDRVTITC | RASQAIRNDLG | WYQQKPGKAPK RLIY | AASSLQS | GVPSRFSGSRSGTE FTLTISSLQPEDFA SYYC | LQHRSYPLT | FGGGTKVEIK |
| 4.15 | 232 A30/JK4 | DIQMTQSPSSLSAS VGDRVTITC | RASQGIRNDLG | WYQQKPGKAPK RLIY | AASSLQS | GVPSRFSGSGSGTE FTLTISSLQPEDFA TYYC | LQHMSLPLT | FGGGTKVEIK |
| 3.9 | 188 A30/JK4 | DIQMTQSPSSLSAS VGDRVTITC | RASQGIRNDLG | WFQQKPGKAPK RLIY | AASNFLS | GVPSRFSGSGSGTE FTLTISSLQPEDFT TYYC | LQHNPYPPRLT | FGGGTKVEIK |
| 4.14 | 228 A30/JK4 | DIQMTQSPSSLSAS VGDRVTITC | RASQGIRNDLG | WYQQKPGKAPK RLIY | AASSLQS | GVPSRFSGSGSGTE FTLTISSLQPEDFA TYYC | LQHMSLPLT | FGGGTKVEIK |
| 4.13 | 224 A30/JK4 | DIQMTQSPSSLSTS VGDRVTITC | RASQGIRNDLG | WYQQKPGKAPK RLIY | AASSLQS | GVPSRFSGSGSGTE FTLTISSLQPEDFA TYYC | LQHNSYPLT | FGGGTKVEIK |
| 4.12 | 220 A30/JK4 | DIQMTQSPSSLSAS VGDRVTITC | RASQGIRNDLG | WYQQKPGKAPK RLIY | AASSLQS | GVPSRFSGSGSGTE FTLTISSLQPEDFA TYYC | LQHNSYPLT | FGGGTKVEIK |
| 2.10 | 126 A30/JK4 | DIQMTQSPSSLSAS VGDRVTITC | RASQGIRNDLG | WYQQKPGKAPK RLIY | AASSLQS | GVPSRFSGSGSGTE FTLTVSSLQPEDFA TYYC | LQHNSLPLT | FGGGTKVEIK |
| 3.6 | 180 A30/JK4 | DIQMTQSPSSLSAS VGDRVTITC | RASQGIRNDLG | WYQQKPRKAPK RLIF | AASSLQS | GVPSRFSGSGSGPE FTLTISSLQPEDFA TYYC | LQHNSYPLT | FGGGTKVEIK |
| 3.5 | 176 A30/JK4 | DIQMTQSPSSLSAS VGDRVTITC | RASQGIRNDLG | WYQQKPRKAPK RLIF | AASSLQS | GVPSRFSGSGSGPE FTLTISSLQPEDFA TYYC | LQHNSYPLT | FGGGTKVEIK |
|  | 306 Germline | DIQMTQSPSSLSAS VGDRVTITC | RASQGISNYLA | WYQQKPGKVPK LLIY | AASTLQS | GVPSRF-SGSGSGTD FTLTISSLQPEDVA TYYC | QKYNSAPFT | FGPGTKVDIK |
| 4.23 | 264 A20/JK3 | DIQMTQSPSSLSAS VGDRVTITC | RASQGISNYLA | WYQQKPGKVPK FLIY | AASTLQS | GVPSRFSGSGSGTD FTLTVSSLQPEDVA TYYC | QMYNSVPFT | FGPGTKVDIK |
|  | 307 Germline | DIQMTQSPSSLSAS VGDRVTITC | RASQGIRNDLG | WYQQKPGKAPK RLIY | AASSLQS | GVPSRFSGSGSGTE FTLTISSLQPEDFA TYYC | LQHNSYPWT | FGQGTKVEIK |
| 4.22 | 260 A30/JK1 | DIQMTQSPSSLSAS VCDRVTITC | RASQGIRNDLG | WYQQKPGKAPK CLIY | VASSLQS | GVPSRFSGSGSGTE FTLTISSLQPEDFA TYYC | LQHNSYPWT | FGQGTKVEIK |

TABLE 34-continued

Hybridoma Light Chain Analysis AB-TNFα-XG2K

| CHAIN NAME | SEQ ID NO: | FR1 | CDR1 | FR2 | CDR2 | FR3 | CDR3 | FR4 |
|---|---|---|---|---|---|---|---|---|
| | 308 Germline | DIQMTQSPSSLSAS VGDRVTITC | RASQSISSYLN | WYQQKPGKAPK LLIY | AASSLQS | GVPSRFSGSGSGTD FTLTISSLQPEDFA TYYC | QQSYSTPIT | FGQGTRLEIK |
| 2.16 | 142 O12/JK5 | DIQMTQSPSSLSAS VGDRVAITC | RTSQSISSYLN | WYQQKPGKAPE LLIY | AASNLQS | GVPSRFSGSGSGTD FTLTISSLQPEDFA TYYC | QQSSSTLIT | FGQGTRLEIK |
| 2.19 | 156 O12/JK5 | DIQMTQSPSSLSAS VGDRVTITC | RTSQSISSYLN | WYQQKPGKAPE VLIY | AASNLQR | GVPSRFSGSGSGTD FTLTISSLQPEDFA TYYC | QQSSSTLIT | FGQGTRLEIK |
| 2.18 | 150 O12/JK5 | DIQMTQSPSSLSAS VGDRVTITC | RTSQSISSYLN | WYNQKPGKAPE LLIY | AAFNLQS | GVPSRFSGSGSGTD FTLTISSLQPEDFA TYYC | QQSSSTLIT | FGQGTRLEIK |
| 2.21 | 160 O12/JK5 | DIQMTQSPSSLSAS VGDRVTITC | RTSQSISSYLN | WYQQKPGKAPE LLIY | AAFNLQS | GVPSRISGSGSGTD FTLTISSLHPEDFA TYYC | QQSSSTLIT | FGQGTRLEIK |
| | 309 Germline | QSVLTQPPSVSAAP GQKVTISC | SGSSSNIGNNY VS | WYQQLPGTAPK LLIY | DNNKRPS | GIPDRFSGSKSGTS ATLGITGLQTGDEA DYYC | GTWDSSLSAGV | FGGGTKLTVL |
| 3.1 | 164 V1-19/JL3 | QSVLTQPPSMSAAP GQKVTISC | SGSSSNIGNNY VS | WYQQLPGIAPK LLIY | DNNKRPS | GIPDRFSGSKSGTS ATLGITGLQTGDEA DYYC | GTWDSSLSAGV | FGGGTKLTVL |
| 1.1 | 86 V1-19/JL3 | QSVLTQPPSVSAAP GQKVTISC | SGSSSNIGNNY VS | WYQQFPGTAPK LLIY | DNNSRPS | GIPDRFSGSKSGTS ATLGITGLQTGDEA DYYC | GTWDSSLSAGV | FGGGTKLTVL |
| | 310 Germline | EIVMTQSPATLSVS PGERATLSC | RASQSVSSNLA | WYQQKPGQAPR LLIY | GASTRAT | GIPARFSGSGSGTE FTLTISSLQSEDFA VYYC | QQYNNWPIT | FGQGTRLEIK |
| 3.8 | 184 L2/JK5 | EIVMTQSPATLSVS PGERVTLSC | RASQSATSNLA | WYQQKPGQAPR LLIY | GASTRAT | GIPARFSGSGSGTE FTLTISSLQSEDFA VYYC | QQYNNWPFT | FGQGTRLEIK |
| | 311 Germline | QSVLTQPPSVSAAP GQKVTISC | SGSSSNIGNNY VS | WYQQLPGTAPK LLIY | DNNKRPS | GIPDRFSGSKSGTS ATLGITGLQTGDEA DYYC | GTWDSSLSAGV | FGGGTKLTVL |
| 2.1 | 90 V1-19/JL2 | QSALTQPPSVSAAP GQKVTISC | SGSSSNIGSNY VS | WCQQLPRTAPK LLIY | DNNKRPS | GIPDRFSGSKSGTS ATLVITGLQTGDEA DYYC | GAWDSSLSAGV | FGGGTKLTVL |
| | 312 Germline | DIQMTQSPSSVSAS VGDRVTITC | RASQGISSWLA | WYQQKPGKAPK LLIY | AASSLQS | GVPSRFSGSGSGTD FTLTISSLQPEDFA TYYC | QQANSFPWT | FGQGTKVEIK |
| 2.9 | 122 L5/JK1 | DIQMTQSPSSVSAS VGDRVTITC | RASQGISSWLA | WYQQKPGKAPK LLIY | AASSLQS | GVPSRFSGSGSGTD FTLTISSLQPEDFA SYYC | QQANSFPWT | FGQGTKVEIK |
| | 313 Germline | EIVMTQSPATLSVS PGERATLSC | RASQSVSSNLA | WYQQKPGQAPR LLIY | GASTRAT | GIPARFSGSGSGTE FTLTISSLQSEDFA VYYC | QQYNNWPLT | FGGGTKVEIK |
| 4.11 | 216 L2/JK4 | EIVMTQSPATLSVS PGERATLSC | RASQSVISNLA | WYQQQPGQAPR LLIY | GASTRAT | GFPARFSGSGSGTE FTLTISSLQSEDFA VYYC | QQYNNWPLT | FGGGTKVEIK |
| 2.17 | 146 L2/JK4 | EIVMTQSPATLSVS PGERATLSC | RASQSVSSNLA | WYQQKPGQAPR LLIY | GASTRAT | GIPARFSGSRTGTE FTLTISSLQSEDFA VYYC | QQYNNWPLT | FGGGTKVEIK |
| | 314 Germline | EIVMTQSPATLSVS PGERATLSC | RASQSVSSNLA | WYQQKPGQAPR LLIY | GASTRAT | GIPARFSGSGSGTE FTLTISSLQSEDFA VYYC | QQYNNWPFT | FGPGTKVDIK |

TABLE 34-continued

Hybridoma Light Chain Analysis AB-TNFα-XG2K

| CHAIN NAME | SEQ ID NO: | FR1 | CDR1 | FR2 | CDR2 | FR3 | CDR3 | FR4 |
|---|---|---|---|---|---|---|---|---|
| 4.18 | 244 | L2/JK3 EIVMTQSPATLSVS PGERATLSC | RASQSVTSNLA | WYQQKPGQAPR LLIY | GASTRAT | GIPARFSGSGSTE FTLTISSLPSEDFA VYYC | QQYHTWPFT | FGPGTKVDIK |
| 2.15 | 138 | L2/JK3 EIVMTQSPSTLSVS PGERATLSC | RASQSVSSNLA | WYQQKPGQAPR LLIY | GASIRAT | GIPARFSGSGSTE YTLTISSLQSEDFA VYYC | QQYNNWPFT | FGPGTKVDIK |
| 4.19 | 248 | L2/JK3 EIVMTQSPSTLSVS PGERATLSC | RASQSVTSNLA | WYQQKPGQAPR LLIY | GASTRAT | GIPARFSGSGSTE FTLTISSLPSEDFA VYYC | QQYHTWPFT | FGPGTKVDIK |
|  | 315 | Germline QSVLTQPPSASGTP GQRVTISC | SGSSSNIGSNT VN | WYQQLPGTAPK LLIY | SNNQRPS | GVPDRFSGSKSGTS ASLAISGLQSEDEA DYYC | AAWDDSLNGPV | FGGGTKLTVL |
| 4.10 | 212 | V1-16/JL3 QSVLTQPPSASGTP GQRVTISC | SGSSSNIGSNT VN | WYQQLPGTAPK LLIY | SNNQRPS | GVPDRFSGSKSGTS ASLAISGLQSEDEA DYYC | AAWDDSLNGPV | FGGGTKLTVL |
|  | 316 | Germline SSELTQDPAVSVAL GQTVRITC | QGDSLRSYYAS | WYQQKPGQAPV LVIY | GKNNRPS | GIPDRFSGSSSGNT ASLTITGAQAEDEA DYYC | NSRDSSGNHLV | FGGGTKLTVL |
| 2.5 | 106 | V2-13/JL3 SSELTQDPAVSVAL GQTVRITC | QGDSLRRYYAS | WYQQKPGQAPI LVIY | GKNNRPS | GIPDRFSGSSSGNT ASLTITGAQAEDEA DYYC | NSRDSSGNHLV | FGGGTKLTVL |
| 3.4 | 172 | V2-13/JL3 SSELTQDPAVSVAL GQTVRITC | QGDSLRRYYAS | WYQQKPGQAPI LVIY | GKNNRPS | GIPDRFSGSSSGNT ASLTITGAQAEDEA DYYC | NSRDSSGNHLV | FGGGTKLTVL |
|  | 317 | Germline SYELTQPPSVSVSP GQTARITC | SGDALPKKYAY | WYQQKSGQAPV LVIY | EDSKRPS | GIPERFSGSSSGTM ATLTISGAQVEDEA DYYC | YSTDSSGNHVV | FGGGTKLTVL |
| 2.19 | 154 | V2-7/JL2 SYELTQPPSVSVSP GQTARITC | SGDALPKKYVY | WYQQKSGQAPV LVIY | EDSKRPS | GIPERFSGSSSGTM ATLTINGAQVEDEA DYYC | YSTDSSGNHVV | FGGGTKLTVL |
|  | 318 | Germline DIQMTQSPSSLSAS VGDRVTITC | QASQDISNYLN | WYQQKPGKAPK LLIY | DASNLET | GVPSRFSGSGSGTD FTFTISSLQPEDIA TYYC | QQYDNLPIT | FGQGTRLEIK |
| 2.13 | 130 | O18/JK5 DIQMTQSPSSLSAS VGDRVTITC | QASQDISNYLN | WYQQKPGKAPK LLIY | DASNLET | GVPSRFSGSGSGTD FTFTISSLQPEDIA TYYC | HQCDNLPH | FGQGTRLEIK |
|  | 319 | Germline SSELTQDPAVSVAL GQTVRITC | QGDSLRSYYAS | WYQQKPGQAPV LVIY | GKNNRPS | GIPDRFSGSSSGNT ASLTITGAQAEDEA DYYC | NSRDSSGNHVV | FGGGTKLTVL |
| 2.3 | 98 | V2-13/JL2 SSELTQDPAVSVAL GQTVRITC | QGDSLRIYYAS | WYQQKPGQAPV LVIY | GKNNRPS | GIPDRFSGSSSGNT ASLTVTGAQAEDEA DYYC | KSRDSSFNHVT | FGGGTKLTVL |
| 2.6 | 110 | V2-13/JL2 SSELTQDPAVSVAL GQTVRITC | QGDSLRNYYAS | WYQQKPGQAPI LVIY | GKNNRPS | GIPDRFSGSSSGNT ASLTITGAQAEDEA DYYC | NSRDSSGNHVT | FGGGTKLTVL |
| 4.3 | 192 | V2-13/JL2 SSELTQDPAVSVAL GQTVRITC | QGDSLRSYYAS | WYQQKPGQAPV LVIY | GKNNRPS | GIPDRFSGSSSENT ASLTITGAQAEDEA DYYC | KSRDSSFNHVT | FGGGTKLTVL |
| 4.8 | 204 | V2-13/JL2 SSELTQDPAVSVAL GQTVRITC | QGDILRSYYAS | WYQQKPGQAPI LVIY | GKNNRPS | GIPDRFSGSSSGNT ASLTITGAQAEDEA DYYC | KSRDSSYNHVT | FGGGTKLTVL |
| 2.8 | 118 | V2-13/JL2 SSELTQDPAVSVAL GQTVRITC | QGDSLRRYYAS | WYQQKPGQAPI VVIY | GKKNRPS | GIPDRFSGSSSGNT ASLTITGAQAEDEA DYYC | KSRDSSGNHVT | FGGGTKLTVL |

TABLE 34-continued

Hybridoma Light Chain Analysis AB-TNFα-XG2K

| CHAIN NAME | SEQ ID NO: | | FR1 | CDR1 | FR2 | CDR2 | FR3 | CDR3 | FR4 |
|---|---|---|---|---|---|---|---|---|---|
| 2.2 | 94 | V2-13/JL2 | SSELTQDPAVSVAL GQTVRITC | QGDSLRSYYAS | WYQQRPGQAPV LVIY | GRNNRPS | GIPDRFSGSSSGLT ASLTVTGAQAEDEA DYYC | NSRDSSYNHVA | FGGGTKLTVL |
| 4.4 | 196 | V2-13/JL2 | SSELTQDPAVSVAL GQTVRITC | QGDILRSYYAS | WYQQKPGQAPV LVIY | GKNNRPS | GIPDRFSGSSSGNT ASLTITGAQAEDEA DYYC | KSRDSSYNHVT | FGGGTKLTVL |
|  | 320 | Germline | QSVLTQPPSVSGAP GQRVTISC | TGSSSNIGAGY DVH | WYQQLPGTAPK LLIY | GNSNRPS | GVPDRFSGSKSGTS ASLAITGLQAEDEA DYYC | QSYDSSLSGSV | FGGGTKLTVL |
| 3.2 | 168 | V1-13/JL3 | QSVLTQPPSVSGAP GQRVTISC | TGSSSNIGAGY DVH | WYQQFPGTAPK LLIQ | GNSNRPS | GVPDRFSGSKSGTS ASLAITGLQAEDEA DYYC | QSYDSSLSGSV | FGGGTKLTVL |
| 2.7 | 114 | V1-13/JL3 | QSVLTQSPSVSGAP GQRVTISC | TGSSSNIGAGY DVH | WYQQLPGTAPR LLIY | GNNNRPS | GVPDRFSGSKSGTS ASLAITGLQAEDEA DYYC | QSYDSSLSGSV | FGGGTKLTVL |

Example 11

Detemination of Canonical Classes of Antibodies

Chothia, et al have described antibody structure in terms of "canonical classes" for the hypervariable regions of each immunoglobulin chain (J Mol Biol. 1987 August 20;196(4): 901-17). The atomic structures of the Fab and VL fragments of a variety of immunoglobulins were analyzed to determine the relationship between their amino acid sequences and the three-dimensional structures of their antigen binding sites. Chothia, et al. found that there were relatively few residues that, through their packing, hydrogen bonding or the ability to assume unusual phi, psi or omega conformations, were primarily responsible for the main-chain conformations of the hypervariable regions. These residues were found to occur at sites within the hypervariable regions and in the conserved beta-sheet framework. By examining sequences of immunoglobulins having unknown structure, Chothia, et al show that many immunoglobuins have hypervariable regions that are similar in size to one of the known structures and additionally contained identical residues at the sites responsible for the observed conformation.

Their discovery implied that these hypervariable regions have conformations close to those in the known structures. For five of the hypervariable regions, the repertoire of conformations appeared to be limited to a relatively small number of discrete structural classes. These commonly occurring main-chain conformations of the hypervariable regions were termed "canonical structures". Further work by Chothia, et al. (Nature. 1989 Dec 21-28;342(6252):877-83) and others (Martin, et al. J. Mol Biol. 1996 Nov 15;263(5): 800-15) confirmed that that there is a small repertoire of main-chain conformations for at least five of the six hypervariable regions of antibodies.

Each of the antibodies described above was analyzed to determine the canonical class for each of the antibody's complementarity determining regions (CDRs). As is known, canonical classes have only been assigned for CDR1 and CDR2 of the antibody heavy chain, along with CDR1, CDR2 and CDR3 of the antibody light chain. The tables below (35 and 36) summarize the results of the analysis. The Canonical Class data is in the form of *HCDR1-HCDR2-LCDR1-LCDR2-LCDR3, wherein "HCDR" refers to the heavy chain CDR and "LCDR" refers to the light chain CDR. Thus, for example, a canonical class of 1-3-2-1-5 refers to an antibody that has a HCDR1 that falls into canonical class 1, a HCDR2 that falls into canonical class 3, a LCDR1 that falls into canonical class 2, a LCDR2 that falls into canonical class 1, and a LCDR3 that falls into canonical class 5.

Assignments were made to a particular canonical class where there was 70% or greater identity of the amino acids in the antibody with the amino acids defined for each canonical class. Where there was less than 70% identity, the canonical class assignment is marked with an asterisk ("*") to indicate that the best estimate of the proper canonical class was made, based on the length of each CDR and the totality of the data. The amino acids defined for each antibody can be found, for example, in the articles by Chothia, et al. referred to above.

TABLE 35

| Antibody | Canonical Class |
|---|---|
| 3.6 | 1-1*-2-1-1 |
| 2.19 | 1-1-2*-1-5 |
| 3.9 | 1-1-2-1-* |
| 2.15 | 1-1-2-1-1 |
| 2.17 | 1-1-2-1-1 |
| 2.9 | 1-1-2-1-1 |
| 3.8 | 1-1-2-1-1 |
| 250 | 1-1-2-1-3 |
| 263 | 1-1-2-1-3 |
| 269 | 1-1-2-1-3 |
| 69 | 1-1*-4-1-1 |
| 3.4 | 1-3*-1*-1-5* |
| 2.6 | 1-3*-2*-1-5* |
| 4.22 | 1-3*-2-1-1 |
| 2.4 | 1-3*-6-1-5 |
| 3.2 | 1-3*-6-1-5 |
| 2.2 | 1-3-2*-1-5* |
| 2.3 | 1-3-2*-1-5* |
| 2.5 | 1-3-2*-1-5* |

TABLE 35-continued

| Antibody | Canonical Class |
|---|---|
| 2.8 | 1-3-2*-1-5* |
| 4.3 | 1-3-2*-1-5* |
| 4.4 | 1-3-2*-1-5* |
| 4.8 | 1-3-2*-1-5* |
| 15 | 1-3-2-1-1 |
| 28 | 1-3-2-1-1 |
| 95 | 1-3-2-1-1 |
| 148 | 1-3-2-1-1 |
| 2.10 | 1-3-2-1-1 |
| 2.13 | 1-3-2-1-1 |
| 2.14 | 1-3-2-1-1 |
| 2.16 | 1-3-2-1-1 |
| 2.18 | 1-3-2-1-1 |
| 2.21 | 1-3-2-1-1 |
| 234 | 1-3-2-1-1 |
| 280 | 1-3-2-1-1 |
| 282 | 1-3-2-1-1 |
| 291 | 1-3-2-1-1 |
| 299v1 | 1-3-2-1-1 |
| 299v2 | 1-3-2-1-1 |
| 3.5 | 1-3-2-1-1 |
| 313 | 1-3-2-1-1 |
| 4.11 | 1-3-2-1-1 |
| 4.12 | 1-3-2-1-1 |
| 4.13 | 1-3-2-1-1 |
| 4.14 | 1-3-2-1-1 |
| 4.15 | 1-3-2-1-1 |
| 4.16 | 1-3-2-1-1 |
| 4.17 | 1-3-2-1-1 |
| 4.18 | 1-3-2-1-1 |
| 4.19 | 1-3-2-1-1 |
| 4.20 | 1-3-2-1-1 |
| 4.21 | 1-3-2-1-1 |
| 4.23 | 1-3-2-1-1 |
| 4.9 | 1-3-2-1-1 |
| 140 | 1-3-4-1-* |
| 1.1 | 1-3-5-1-5 |
| 2.1 | 1-3-5-1-5 |
| 3.1 | 1-3-5-1-5 |
| 4.10 | 1-3-5-1-5 |
| 2.7 | 1-3-6-1-5 |
| 4.7 | 1-3-6-1-5 |
| 2 | 3-1-2-1-1 |
| 25 | 3-1-2-1-1 |
| 123 | 3-1-2-1-1 |
| 131 | 3-1-2-1-1 |

Example 12

Domain Analysis of ANTI-TNF-α Antibodies Through Expression and Binding Assays to TNF-α Epitopes Sequencing/Binning Results The variable (V) regions of immunoglobulin chains are encoded by multiple germ line DNA segments, which are joined into functional variable regions ($V_H DJ_H$ or $V_K J_K$) during B-cell ontogeny. The Molecular and genetic diversity of the antibody response to TNF-α was studied in detail. These assays revealed several points specific to anti TNF-α. Analysis of 65 individual antibodies specific to TNF-a yielded 13 germline $V_H$ genes, 54 of them from the VH3 family, with 34 of them using the VH3-33 gene segment. The most frequent gene, VH3-33 germline gene was expressed in 34 of the 65 antibodies analyzed, and was limited to 2 different bins with clear linkage to the type of the light chain involved in the binding (Kappa A30 versus L2 or lambda). Selection of functional antibodies and binning showed that antibodies in specific bin expressed the same Ig $V_H$ and in some cases the same $V_H DJ_H$ rearrangements. Furthermore, it was also discovered that pairs of H and L chain were conserved within the bin. These findings suggest that, for any given epitope, only a few members of the germ line repertoire are used to form the corresponding paratope, and for each antigenic epitope a limited number of L- and H -chain genes can pair to form a specific paratope.

The location of biologically relevant epitopes on human TNF-α was evaluated by expression and binding assay of mAbs specific for human TNF-α to a set of chimeric human/mouse TNF-α molecules. The antibodies described above fall into 4 major binning groups, all linked to several sites crucial for hTNF-α biological activity. The N-terminal domain of TNF-α was found to be involved in receptor binding.

In the first group antibodies, which neutralize TNF-α activity through direct binding to TNF-α receptor binding domain, all recognized sequences in the first 36 residues of the secreted TNF-α molecule. The results showed that both receptors bind to the same N-terminal region. Van Ostade et al, ((1993) nature, 361:266-269) reported that the P75 Receptor binding domain was localized in loops at the base of the molecule, and that single amino substitutions at position 29 and 32 reduced binding activities with the p75 receptor. Antibodies in group I (VH3-33/JH6b coupled with kappa chain A30/JK4) all have canonical class 1-3-2-1-1. All tested antibodies exhibit binding to the first 36 residues, with Lys11 and Arg31 present. Antibodies expressing VH3-33/Jh6b coupled with lambda as a light chain showed different specificity.

Van Ostade et al ((1991) EMBO 10:827-836) demonstrated that by means of random and site directed mutagenesis, the integrity of four regions amino-acid 32-34, 84-91, 117-119 and 143-148 is important for maintaining the biological activity. Antibodies using the VH3-33/JH4b coupled with L2 kappa chain were shown to recognize different discontinuous domains of the TNF-α molecule. These antibodies were highly specific for human TNF-α, and their epitope is a constellation of residues located in different, noncontiguous positions of the TNF Polypeptide.

The third group of antibodies includes antibodies utilizing VH3-33 coupled to lambda light chain as mAb 3.2. The binding site of this group lies between residues 1-91. Although replacement of Gln27 and arg31 did not affect the binding to human TNF-α, the N-terminus appeared important for their binding activity. The results are provided below in Table 36.

TABLE 36

| TNF Epitope | mAb | VH | DH | JH | VK | JK | VL | JL | Canonical Class |
|---|---|---|---|---|---|---|---|---|---|
|  | 3.1 | VH1-2 | D6-19 | JH6b |  |  | V1-19 | JL3 | 1-3-5-1-5 |
| 1–91 | 2.6 | VH1-18 | D1-7 | JH4b |  |  | V2-13 | JL2 | 1-3*-2*-1-5* |
| 1–125 | 3.4 | VH1-18 | D6-19 | JH4b |  |  | V2-13 | JL3 | 1-3*-1*-1-5* |
|  | 1.1 | VH3-11 | D3-16 | JH6b |  |  | V1-19 | JL3 | 1-3-5-1-5 |

TABLE 36-continued

| TNF Epitope | mAb | VH | DH | JH | VK | JK | VL | JL | Canonical Class |
|---|---|---|---|---|---|---|---|---|---|
|  | 2.16 | VH3-11 | D3-16 | JH6b | O12 | JK5 |  |  | 1-3-2-1-1 |
|  | 2.18 | VH3-11 | D3-16 | JH6b | O12 | JK5 |  |  | 1-3-2-1-1 |
| 1–125 | 2.21 | VH3-21 | D1-20 | JH6b | O12 | JK5 |  |  | 1-3-2-1-1 |
|  | 4.23 | VH3-23 | D3-22 | JH4b | A20 | JK3 |  |  | 1-3-2-1-1 |
|  | 4.13 | VH3-30 | D4-17 | JH6b | A30 | JK4 |  |  | 1-3-2-1-1 |
|  | SC234 | VH3-30 | D1-26 | JH6b | A30 | JK4 |  |  | 1-3-2-1-1 |
|  | SC140 | VH3-30 | D1-20 | JH6b | A19 | JK1 |  |  | 1-3-4-1-* |
|  | SC28 | VH3-30 | D3-3 | JH6b | A30 | JK1 |  |  | 1-3-2-1-1 |
| 1–157 | 4.11 | VH3-33 | D6-19 | JH4b | L2 | JK4 |  |  | 1-3-2-1-1 |
|  | 4.19 | VH3-33 | D3-9 | JH6b | L2 | JK3 |  |  | 1-3-2-1-1 |
| 1–157 | 4.18 | VH3-33 | D3-9 | JH6b | L2 | JK3 |  |  | 1-3-2-1-1 |
|  | 4.7 | VH3-33 | D6-19 | JH4b |  |  | V1-13 | JL2 | 1-3-6-1-5 |
|  | 2.8 | VH3-33 | D3-9 | JH6b |  |  | V2-13 | JL2 | 1-3-2*-1-5* |
| 36–91 | 2.7 | VH3-33 | D3-9 | JH6b |  |  | V1-13 | JL3 | 1-3-6-1-5 |
|  | 2.1 | VH3-33 |  | JH6 |  |  | V1-19 | JL2 | 1-3-5-1-5 |
|  | 2.2 | VH3-33 | D4-23 | JH4a |  |  | V2-13 | JL2 | 1-3-2*-1-5* |
|  | 2.5 | VH3-33 | D3-10 | JH6b |  |  | V2-13 | JL3 | 1-3-2*-1-5* |
|  | 4.4 | VH3-33 | D4-23 | JH4b |  |  | V2-13 | JL2 | 1-3-2*-1-5* |
| 1–157 | 4.3 | VH3-33 | D4-23 | JH4b |  |  | V2-13 | JL2 | 1-3-2*-1-5* |
|  | 4.10 | VH3-33 | D4-17 | JH5b |  |  | V1-16 | JL3 | 1-3-5-1-5 |
|  | 2.3 | VH3-33 | D4-23 | JH4b |  |  | V2-13 | JL2 | 1-3-2*-1-5* |
|  | 4.8 | VH3-33 | D4-23 | JH4b |  |  | V2-13 | JL2 | 1-3-2*-1-5* |
|  | 2.13 | VH3-33 | D6-19 | JH6b | O18 | JK5 |  |  | 1-3-2-1-1 |
|  | 4.20 | VH3-33 | D3-9 | JH6b | A30 | JK4 |  |  | 1-3-2-1-1 |
|  | 4.21 | VH3-33 |  | JH6b | A30 | JK4 |  |  | 1-3-2-1-1 |
|  | 2.14 | VH3-33 | D6-19 | JH6b | A30 | JK4 |  |  | 1-3-2-1-1 |
| 1–36 | 2.10 | VH3-33 | D6-19 | JH6b | A30 | JK4 |  |  | 1-3-2-1-1 |
|  | 3.5 | VH3-33 | D3-10 | JH6b | A30 | JK4 |  |  | 1-3-2-1-1 |
|  | 4.12 | VH3-33 | D4-17 | JH6b | A30 | JK4 |  |  | 1-3-2-1-1 |
|  | 4.9 | VH3-33 | D4-17 | JH6b | A30 | JK4 |  |  | 1-3-2-1-1 |
|  | SC280 | VH3-33 | D4-17 | JH6b | A30 | JK1 |  |  | 1-3-2-1-1 |
|  | SC282 | VH3-33 | D4-17 | JH6b | A30 | JK1 |  |  | 1-3-2-1-1 |
|  | SC291 | VH3-33 | D1-26 | JH6b | A30 | JK4 |  |  | 1-3-2-1-1 |
|  | 4.16 | VH3-33 | D2-21 | JH6b | A30 | JK4 |  |  | 1-3-2-1-1 |
| 1–36 | 4.17 | VH3-33 | D2-21 | JH6b | A30 | JK4 |  |  | 1-3-2-1-1 |
|  | 4.14 | VH3-33 | D2-21 | JH6b | A30 | JK4 |  |  | 1-3-2-1-1 |
|  | 4.15 | VH3-33 | D2-21 | JH6b | A30 | JK4 |  |  | 1-3-2-1-1 |
| 1–36 | SC299 | VH3-33 | D5-5 | JH6b | A30 | JK4 |  |  | 1-3-2-1-1 |
|  | SC313 | VH3-33 | D5-24 | JH6b | A30 | JK4 |  |  | 1-3-2-1-1 |
|  | SC148 | VH3-33 | D5-5 | JH6b | A30 | JK4 |  |  | 1-3-2-1-1 |
|  | SC15 | VH3-33 | D6-6 | JH6b | A30 | JK4 |  |  | 1-3-2-1-1 |
|  | SC95 | VH3-33 | D6-19 | JH6b | A30 | JK4 |  |  | 1-3-2-1-1 |
|  | 4.22 | VH3-48 | D1-14 | JH4b | A30 | JK1 |  |  | 1-3*-2-1-1 |
|  | 3.7 | VH3-53 | D3-1 | JH3 | L2 | JK4 |  |  |  |
|  | 2.17 | VH3-53 | D7-27 | JH4b | L2 | JK4 |  |  | 1-1-2-1-1 |
| 1–157 | 2.9 | VH3-53 | D7-27 | JH4b | L5 | JK1 |  |  | 1-1-2-1-1 |
| 1–125 | 2.19 | VH3-53 | D1-1 | JH6 | O12 | JK5 |  |  | 1-1-2*-1-5 |
|  | 2.15 | VH3-53 | D1-1 | JH6 | L2 | JK3 | V2-7 | JL2 | 1-1-2-1-1 |
|  | 3.8 | VH3-53 | D1-14 | JH3b | L2 | JK5 |  |  | 1-1-2-1-1 |
| 1–157 | 3.9 | VH3-53 | D1-14 | JH3b | A30 | JK4 |  |  | 1-1-2-1-* |
|  | SC250 | VH3-53 | D3-16 | JH4b | L2 | JK1 |  |  | 1-1-2-1-3 |
| 1–157 | SC263 | VH3-53 | D3-16 | JH4b | L2 | JK1 |  |  | 1-1-2-1-3 |
|  | SC269 | VH3-53 | D3-16 | JH4b | L2 | JK1 |  |  | 1-1-2-1-3 |
|  | SC69 | VH4-4 | D2-2 | JH2 | A1 | JK4 |  |  | 1-1*-4-1-1 |
|  | SC2 | VH4-31 | D1-20 | JH6b | A30 | JK4 |  |  | 3-1-2-1-1 |
|  | SC25 | VH4-31 | D1-20 | JH6b | A30 | JK4 |  |  | 3-1-2-1-1 |
|  | SC131 | VH4-31 | D1-20 | JH6b | A30 | JK4 |  |  | 3-1-2-1-1 |
|  | SC123 | VH4-31 | D1-20 | JH6b | A30 | JK4 |  |  | 3-1-2-1-1 |
| 1–157 | 3.6 | VH4-59 | D6-19 | JH4b | A30 | JK4 |  |  | 1-1*-2-1-1 |
| 1–91 | 3.2 | VH5-51 | D7-27 | JH4b |  |  | V1-13 | JL3 | 1-3*-6-1-5 |
| 36–91 | 2.4 | VH5-51 | D3-3 | JH6b |  |  | V1-13 | JL2 | 1-3*-6-1-5 |

Example 13

Uses of ANTI-TNFα Antibodies and Antibody Conjugates for Arthritis Treatment To determine the in vivo effects of anti-TNFα antibody treatment in human patients with arthritis, such human patients are injected over a certain amount of time with an effective amount of anti-TNFα antibody. At periodic times during the treatment, the human patients are monitored to determine whether their arthritis is being treated.

An arthritic patient treated with anti-TNFα antibodies has a lower level of arthritic symptoms, including inflammation, as compared to arthritic patients treated with control antibodies. Control antibodies that may be used include antibodies of the same isotype as the anti-TNFα antibodies tested and further, may not have the ability to bind to TNFα antigen.

Example 14

Use of ANTI-TNFα Antibodies as a Diagnostic Agent

Detection of TNFα Antigen in a Sample

An Enzyme-Linked Immunosorbent Assay (ELISA) for the detection of TNFα antigen in a sample may be developed. In the assay, wells of a microtiter plate, such as a 96-well microtiter plate or a 384-well microtiter plate, are adsorbed for several hours with a first fully human monoclonal antibody directed against the antigen. The immobilized antibody serves as a capture antibody for any of the antigen that may be present in a test sample. The wells are rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample may be, for example, a serum sample from a subject suspected of having levels of circulating antigen considered to be diagnostic of a pathology.

After rinsing away the test sample or standard, the wells are treated with a second fully human monoclonal anti-TNFα antibody that is labeled by conjugation with biotin. The labeled anti-TNFα antibody serves as a detecting antibody. After rinsing away excess second antibody, the wells are treated with avidin-conjugated horseradish peroxidase (HRP) and a suitable chromogenic substrate. The concentration of the antigen in the test samples is determined by comparison with a standard curve developed from the standard samples.

This ELISA assay provides a highly specific and very sensitive assay for the detection of the TNFα antigen in a test sample.

Determination of TNFα Antigen Concentration in Patients

A sandwich ELISA is developed to quantify TNFα levels in human serum. The 2 fully human monoclonal anti-TNFα antibodies from the sandwich ELISA, recognizes different epitopes on the TNFα molecule. The ELISA is performed as follows: 50 µL of capture anti-TNFα antibody in coating buffer (0.1 M NaHCO$_3$, pH 9.6) at a concentration of 2 µg/mL is coated on ELISA plates (Fisher). After incubation at 4° C. overnight, the plates are treated with 200 µL of blocking buffer (0.5% BSA, 0.1% Tween 20, 0.01% Thimerosal in PBS) for 1 hour at 25° C. The plates are washed (3×) using 0.05% Tween 20 in PBS (washing buffer, WB). Normal or patient sera (Clinomics, Bioreclaimation) are diluted in blocking buffer containing 50% human serum. The plates are incubated with serum samples overnight at 4° C., washed with WB, and then incubated with 100 µL/well of biotinylated detection anti-TNFα antibody for 1 hour at 25° C. After washing, the plates are incubated with HRP-Streptavidin for 15 min, washed as before, and then treated with 100 µL/well of o-phenylenediamine in H$_2$O$_2$ (Sigma developing solution) for color generation. The reaction is stopped with 50 µL/well of H$_2$SO$_4$ (2M) and analyzed using an ELISA plate reader at 492 nm. Concentration of TNFα antigen in serum samples is calculated by comparison to dilutions of purified TNFα antigen using a four parameter curve fitting program.

Incorporation by Reference

All references cited herein, including patents, patent applications, papers, text books, and the like, and the references cited therein, to the extent that they are not already, are hereby incorporated herein by reference in their entirety.

Equivalents

The foregoing written specification is considered to be sufficient to enable one skilled in the art to practice the invention. The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

SEQUENCE LISTING

```
<160> NUMBER OF SEQ ID NOS: 320

<210> SEQ ID NO 1
<211> LENGTH: 384
<212> TYPE: DNA
<213> ORGANISM: Homo sapiens

<400> SEQUENCE: 1
caggtgcagt tgcaggagtc gggcccagga ctggtgaagc cttcacagac cctgtccctc       60
```

```
acctgcactg tctctggtgg ctccatcagc agtggtggtt actactggag ctggatccgc    120
cagcacccag ggaagggcct ggagtggatt gggaacatct attacagtgg gagcacctac    180
tacaacccgt ccctcaagag tcgagttacc atatcagtag acacgtctaa gaaccagttc    240
tccctgaagc tgagctctgt gactgccgcg gacacggccg tgtattactg tgcgagagat    300
agtaaccaat ataactggaa cgacgaggtc tacgactacg gtttggacgt ctggggccaa    360
gggaccacgg tcaccgtgtc ctca                                          384
```

<210> SEQ ID NO 2
<211> LENGTH: 128
<212> TYPE: PRT
<213> ORGANISM: Homo sapiens

<400> SEQUENCE: 2

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Asn Gln Tyr Asn Trp Asn Asp Glu Val Tyr Asp
            100                 105                 110

Tyr Gly Leu Asp Val Trp Gly Gln Gly Thr Thr Val Thr Val Ser Ser
        115                 120                 125

<210> SEQ ID NO 3
<211> LENGTH: 321
<212> TYPE: DNA
<213> ORGANISM: Homo sapiens

<400> SEQUENCE: 3

```
gacatccaga tgacccagtc tccatcctcc ctgtctgcat ctgtaggaga cagagtcacc     60
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacaa cataataatt accctctcac tttcggcgga    300
gggaccaagg tggagatcaa a                                              321
```

<210> SEQ ID NO 4
<211> LENGTH: 107
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile

```
                35                  40                  45
Tyr Ala Ala Ser Ser Leu Gln Ser Gly Val Pro Ser Arg Phe Ser Gly
             50                  55                  60
Ser Gly Ser Gly Thr Glu Phe Thr Leu Thr Ile Ser Ser Leu Gln Pro
 65                  70                  75                  80
Glu Asp Phe Ala Thr Tyr Tyr Cys Leu Gln His Asn Asn Tyr Pro Leu
                 85                  90                  95
Thr Phe Gly Gly Gly Thr Lys Val Glu Ile Lys
                100                 105

<210> SEQ ID NO 5
<211> LENGTH: 375
<212> TYPE: DNA
<213> ORGANISM: Homo sapiens

<400> SEQUENCE: 5
caggtgcagc tggtggagtc tgggggaggc gtggtccagc ctggggaggtc cctgagactc    60 tcctgtgcag cgtctggatt caccttcagt agctatgaca ttcactgggt ccgccaggct   120
ccaggcaagg ggctggagtg ggtggcagtt atatggtatg atggaagtat taaatactat   180
gcagactccg tgaagggccg attcaccatc tccagagaca attccaagaa cacgctgtat   240
ctacaaatga acagcctgag agccgaggac acggctgtgt attactgtgc gagagaggag   300
cagctcgtcc ggggagggta ctactactac ggtatggacg tctggggcca agggaccacg   360
gtcaccgtct cctca                                                   375

<210> SEQ ID NO 6
<211> LENGTH: 125
<212> TYPE: PRT
<213> ORGANISM: Homo sapiens

<400> SEQUENCE: 6

Gln Val Gln Leu Val Glu Ser Gly Gly Gly Val Val Gln Pro Gly Arg
  1               5                  10                  15
Ser Leu Arg Leu Ser Cys Ala Ala Ser Gly Phe Thr Phe Ser Ser Tyr
             20                  25                  30
Asp Ile His Trp Val Arg Gln Ala Pro Gly Lys Gly Leu Glu Trp Val
         35                  40                  45
Ala Val Ile Trp Tyr Asp Gly Ser Ile Lys Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Glu Glu Gln Leu Val Arg Gly Gly Tyr Tyr Tyr Gly Met
                100                 105                 110
Asp Val Trp Gly Gln Gly Thr Thr Val Thr Val Ser Ser
            115                 120                 125

<210> SEQ ID NO 7
<211> LENGTH: 321
<212> TYPE: DNA
<213> ORGANISM: Homo sapiens

<400> SEQUENCE: 7
gacatccaga tgacccagtc tccatcctcc ctgtctgcat ctataggaga cagagtcacc    60
atcacttgcc gggcaagtca gggcattaga aatgatttag gctggtatca gcagaaacca   120
```

```
gggaaagccc ctaagcgcct gatctatgct gcatccagtt tgcaaagtgg ggtcccgtca      180
aggttcagcg gcagtggatc tgggccagaa ttcactctca caatcagcag cctgcagcct      240
gaagattttg caacttatta ctgtctacag cataatagtt acccgctcac tttcggcgga      300
gggaccaagg tggagatcaa a                                                321
```

<210> SEQ ID NO 8
<211> LENGTH: 107
<212> TYPE: PRT
<213> ORGANISM: Homo sapiens

<400> SEQUENCE: 8

```
Asp Ile Gln Met Thr Gln Ser Pro Ser Ser Leu Ser Ala Ser Ile Gly
 1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
 50                  55                  60

Ser Gly Ser Gly Pro Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                 85                  90                  95

Thr Phe Gly Gly Gly Thr Lys Val Glu Ile Lys
            100                 105
```

<210> SEQ ID NO 9
<211> LENGTH: 384
<212> TYPE: DNA
<213> ORGANISM: Homo sapiens

<400> SEQUENCE: 9

```
caggtgcagc tgcaggagtc gggcccagga ctggtgaagc cttcacagac cctgtccctc      60
acctgcactg tctctggtgg ctccatcagc agtggtggtt actactggag ctggatccgc      120
cagcacccag ggaagggcct ggagtggatt gggaacatct attacagtgg gagcacctac      180
tacaacccgt ccctcaagag tcgagttacc atatcagtag acacgtctaa gaaccagttc      240
tccctgaagc tgagctctgt gactgccgcg gacacggccg tgtattactg tgcgagagat      300
agtaaccaat ataactggaa cgacgaggtc tacgactacg gtttggacgt ctggggccaa      360
gggaccacgg tcaccgtgtc ctca                                             384
```

<210> SEQ ID NO 10
<211> LENGTH: 128
<212> TYPE: PRT
<213> ORGANISM: Homo sapiens

<400> SEQUENCE: 10

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Gly Tyr Tyr Trp Ser Trp Ile Arg Gln His Pro Gly Lys Gly Leu Glu
         35                  40                  45

Trp Ile Gly Asn Ile Tyr Tyr Ser Gly Ser Thr Tyr Tyr Asn Pro Ser
 50                  55                  60
```

```
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Asp Ser Asn Gln Tyr Asn Trp Asn Asp Glu Val Tyr Asp
            100                 105                 110

Tyr Gly Leu Asp Val Trp Gly Gln Gly Thr Thr Val Thr Val Ser Ser
        115                 120                 125
```

<210> SEQ ID NO 11
<211> LENGTH: 321
<212> TYPE: DNA
<213> ORGANISM: Homo sapiens

<400> SEQUENCE: 11

```
gacatccaga tgacccagtc tccatcctcc ctgtctgcat ctgtaagaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt accctctcac tttcggcgga   300
gggaccaagg tggagatcaa a                                             321
```

<210> SEQ ID NO 12
<211> LENGTH: 107
<212> TYPE: PRT
<213> ORGANISM: Homo sapiens

<400> SEQUENCE: 12

```
Asp Ile Gln Met Thr Gln Ser Pro Ser Ser Leu Ser Ala Ser Val Arg
  1               5                  10                  15

Asp Arg Val Thr Ile Thr Cys Arg Ala Ser Gln Gly Ile Arg Asn Asp
             20                  25                  30

Leu Gly Trp Tyr Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Leu
                 85                  90                  95

Thr Phe Gly Gly Gly Thr Lys Val Glu Ile Lys
            100                 105
```

<210> SEQ ID NO 13
<211> LENGTH: 369
<212> TYPE: DNA
<213> ORGANISM: Homo sapiens

<400> SEQUENCE: 13

```
caggtgcagc tggtggagtc tgggggaggc gtggtccagc ctgggaggtc cctgagactc    60
tcctgtgcag cctctggatt caccttcagt aactatggca tgcactgggt ccgccaggct   120
ccaggcaagg ggctggagtg ggtgacaatt atatcatatg atggaagtaa taaatactat   180
gcagactccg tgaagggccg attcaccatc tccagagaca attccaagaa cacgctgtat   240
ctgcaaatga acagcctgag agctgaggac acggctgtgt attactgtgt gacgtattac   300
```

```
gattttttgga gtggttatct cccaggtatg gacgtctggg gccaagggac cacggtcacc    360
gtctcctca                                                              369
```

<210> SEQ ID NO 14
<211> LENGTH: 123
<212> TYPE: PRT
<213> ORGANISM: Homo sapiens

<400> SEQUENCE: 14

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Asn Tyr
                20                  25                  30

Gly Met His Trp Val Arg Gln Ala Pro Gly Lys Gly Leu Glu Trp Val
            35                  40                  45

Thr Ile Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Thr Tyr Tyr Asp Phe Trp Ser Gly Tyr Leu Pro Gly Met Asp Val
               100                 105                 110

Trp Gly Gln Gly Thr Thr Val Thr Val Ser Ser
           115                 120
```

<210> SEQ ID NO 15
<211> LENGTH: 321
<212> TYPE: DNA
<213> ORGANISM: Homo sapiens

<400> SEQUENCE: 15

```
gacatccaga tgacccagtc tccatcctcc ctgtctgcat ctgtaggaga cagagtcacc    60
atcacttgcc gggcaagtca gggcattaga aatgatttaa cctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt tcccgtggac gttcggccaa   300
gggaccaagg tggaaatcaa a                                             321
```

<210> SEQ ID NO 16
<211> LENGTH: 107
<212> TYPE: PRT
<213> ORGANISM: Homo sapiens

<400> SEQUENCE: 16

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                20                  25                  30

Leu Thr Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80
```

Glu Asp Phe Ala Thr Tyr Tyr Cys Leu Gln His Asn Ser Phe Pro Trp
            85                  90                  95

Thr Phe Gly Gln Gly Thr Lys Val Glu Ile Lys
            100                 105

<210> SEQ ID NO 17
<211> LENGTH: 351
<212> TYPE: DNA
<213> ORGANISM: Homo sapiens

<400> SEQUENCE: 17
caggtgcagc tgcaggagtc gggcccagga ctggtgaagc cttcggagac cctgtccctc    60
acctgcactg tctctggtgg ctccatcaat cattactact ggagctggat ccggcagccc   120
gccgggaagg gcctggaatg gattgggcgt atctatccca ctgggagcac caactacaac   180
ccctccctca agagtcgagt caccatgtca gtagacacgt ccaagaacca gttctccctg   240
aagctgagct ctgtgaccgc cgcggacacg gccgtatatt actgtgcggg cggctggtcg   300
tactggtact cgatctctg gggccgtggc accctggtca ctgtctcctc a             351

<210> SEQ ID NO 18
<211> LENGTH: 117
<212> TYPE: PRT
<213> ORGANISM: Homo sapiens

<400> SEQUENCE: 18

Gln Val Gln Leu Gln Glu Ser Gly Pro Gly Leu Val Lys Pro Ser Glu
 1               5                   10                  15

Thr Leu Ser Leu Thr Cys Thr Val Ser Gly Gly Ser Ile Asn His Tyr
            20                  25                  30

Tyr Trp Ser Trp Ile Arg Gln Pro Ala Gly Lys Gly Leu Glu Trp Ile
            35                  40                  45

Gly Arg Ile Tyr Pro Thr Gly Ser Thr Asn Tyr Asn Pro Ser Leu Lys
        50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Gly Gly Trp Ser Tyr Trp Tyr Phe Asp Leu Trp Gly Arg Gly Thr Leu
            100                 105                 110

Val Thr Val Ser Ser
        115

<210> SEQ ID NO 19
<211> LENGTH: 342
<212> TYPE: DNA
<213> ORGANISM: Homo sapiens

<400> SEQUENCE: 19
gatgttgtga tgactcagtc tcctctctcc ctgcccgtca cccttggaca gccggcctcc    60
atctcctgca ggtctagtca agcctcgta tacagtgatg gaagcaccta cttgaattgg   120
tttcagcaga ggccaggcca atctccaagg cgcctaattt ataaggtttc taactgggac   180
tctggggtcc cagacagatt cagcggcagt gggtcaggca ctgatttcac actgaaaatc   240
agcagggtgg aggctgaaga tgttgggtt tattactgca tgcaaggttc acactggcct   300
cgggagttca ctttcggcgg agggaccaag gtggagatca aa                     342

<210> SEQ ID NO 20
<211> LENGTH: 114
<212> TYPE: PRT
<213> ORGANISM: Homo sapiens

<400> SEQUENCE: 20

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
            20                  25                  30

Asp Gly Ser Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ser His Trp Pro Arg Glu Phe Thr Phe Gly Gly Gly Thr Lys Val Glu
            100                 105                 110

Ile Lys
```

<210> SEQ ID NO 21
<211> LENGTH: 369
<212> TYPE: DNA
<213> ORGANISM: Homo sapiens

<400> SEQUENCE: 21

```
caggtgcagc tggtggagtc tgggggaggc gtggtccagc ctggagggtc cctgagactc      60
tcctgtgcag cgtctggatt caccttcagt aactatgaca tgcactgggt ccgccaggct     120
ccaggcaagg ggctggagtg ggtggcagtt atatggtatg atggaagtat taaatactat     180
gcagactccg tgaagggccg attcaccatc tccagagaca attccaagaa cacgctgcat     240
ctgcaaatga acagcctgag agccgaggac acggctgtgt attactgtgc gagagagata     300
gcagtggctg gaggttacta ctacggtttg gacgtctggg gccaagggac cacggtcacc     360
gtctcctca                                                            369
```

<210> SEQ ID NO 22
<211> LENGTH: 123
<212> TYPE: PRT
<213> ORGANISM: Homo sapiens

<400> SEQUENCE: 22

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
            20                  25                  30

Asp Met His Trp Val Arg Gln Ala Pro Gly Lys Gly Leu Glu Trp Val
        35                  40                  45

Ala Val Ile Trp Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu His
65                  70                  75                  80

Leu Gln Met Asn Ser Leu Arg Ala Glu Asp Thr Ala Val Tyr Tyr Cys
                85                  90                  95
```

```
Ala Arg Glu Ile Ala Val Ala Gly Gly Tyr Tyr Tyr Gly Leu Asp Val
            100                 105                 110

Trp Gly Gln Gly Thr Thr Val Thr Val Ser Ser
        115                 120
```

<210> SEQ ID NO 23
<211> LENGTH: 321
<212> TYPE: DNA
<213> ORGANISM: Homo sapiens

<400> SEQUENCE: 23

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca cagtcagcag cctgcagcct   240
gaagattttg caacttatta ctgtctacag catcatagtt acccgctcac tttcggcgga   300
gggaccaagg tacagatcaa t                                             321
```

<210> SEQ ID NO 24
<211> LENGTH: 107
<212> TYPE: PRT
<213> ORGANISM: Homo sapiens

<400> SEQUENCE: 24

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Val Ser Ser Leu Gln Pro
65                  70                  75                  80

Glu Asp Phe Ala Thr Tyr Tyr Cys Leu Gln His His Ser Tyr Pro Leu
                85                  90                  95

Thr Phe Gly Gly Gly Thr Lys Val Gln Ile Asn
            100                 105
```

<210> SEQ ID NO 25
<211> LENGTH: 384
<212> TYPE: DNA
<213> ORGANISM: Homo sapiens

<400> SEQUENCE: 25

```
caggtgcagc tgcaggagtc gggcccagga ctggtgaagc cttcacagac cctgtccctc    60
acctgcactg tctctggtgg ctccatcagc agtggtggtt actactggag ctggatccgc   120
cagcacccag ggaagggcct ggagtggatt gggaacatct attacagtgg gagcacctac   180
tacaccccgt ccctcaagag tcgagttacc atatcagtag acacgtctaa gaaccagttc   240
tccctgaagc tgagctctgt gactgccgcg gacacggccg tgtattactg tgcgagagat   300
agtaaccaat ataactggaa cgacgaggtc tacgactacg gtttggacgt ctggggccaa   360
gggaccacgg tcaccgtgtc ctca                                          384
```

<210> SEQ ID NO 26

<211> LENGTH: 128
<212> TYPE: PRT
<213> ORGANISM: Homo sapiens

<400> SEQUENCE: 26

Gln Val Gln Leu Gln Glu Ser Gly Pro Gly Leu Val Lys Pro Ser Gln
 1               5                  10                  15
Thr Leu Ser Leu Thr Cys Thr Val Ser Gly Gly Ser Ile Ser Ser Gly
            20                  25                  30
Gly Tyr Tyr Trp Ser Trp Ile Arg Gln His Pro Gly Lys Gly Leu Glu
        35                  40                  45
Trp Ile Gly Asn Ile Tyr Tyr Ser Gly Ser Thr Tyr Tyr Thr Pro Ser
    50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Arg Asp Ser Asn Gln Tyr Asn Trp Asn Asp Glu Val Tyr Asp
            100                 105                 110
Tyr Gly Leu Asp Val Trp Gly Gln Gly Thr Thr Val Thr Val Ser Ser
        115                 120                 125

<210> SEQ ID NO 27
<211> LENGTH: 321
<212> TYPE: DNA
<213> ORGANISM: Homo sapiens

<400> SEQUENCE: 27
gacatccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataataatt accctctcac tttcggcgga     300
gggaccaagg tggagatcaa a                                               321

<210> SEQ ID NO 28
<211> LENGTH: 107
<212> TYPE: PRT
<213> ORGANISM: Homo sapiens

<400> SEQUENCE: 28

Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Arg Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Asn Tyr Pro Leu
                85                  90                  95
Thr Phe Gly Gly Gly Thr Lys Val Glu Ile Lys
            100                 105

<210> SEQ ID NO 29
<211> LENGTH: 384
<212> TYPE: DNA
<213> ORGANISM: Homo sapiens

<400> SEQUENCE: 29

```
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatt gggaacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagagat     300
agtaaccagt ataactggaa cgacgaggtc tacgactacg gtttggacgt ctggggccaa     360
gggaccacgg tcaccgtctc ctca                                            384
```

<210> SEQ ID NO 30
<211> LENGTH: 128
<212> TYPE: PRT
<213> ORGANISM: Homo sapiens

<400> SEQUENCE: 30

```
Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Ser Ser Gly
             20                  25                  30

Gly Tyr Tyr Trp Ser Trp Ile Arg Gln His Pro Gly Lys Gly Leu Glu
         35                  40                  45

Trp Ile Gly Asn Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
             85                  90                  95

Cys Ala Arg Asp Ser Asn Gln Tyr Asn Trp Asn Asp Glu Val Tyr Asp
            100                 105                 110

Tyr Gly Leu Asp Val Trp Gly Gln Gly Thr Thr Val Thr Val Ser Ser
        115                 120                 125
```

<210> SEQ ID NO 31
<211> LENGTH: 321
<212> TYPE: DNA
<213> ORGANISM: Homo sapiens

<400> SEQUENCE: 31

```
gacatccaaa tgacccagtc tccatccgcc ctgtctgcat ctgtaggaga cagagtcacc      60
atcacttgcc gggcaagtca gggcattaga aatgatttag gctggtatca gcagaaacca     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtcttcag cataaaagtt accctctcac tttcggcgga     300
gggaccaagg tggagatcaa a                                                321
```

<210> SEQ ID NO 32
<211> LENGTH: 107
<212> TYPE: PRT
<213> ORGANISM: Homo sapiens

<400> SEQUENCE: 32

Asp Ile Gln Met Thr Gln Ser Pro Ser Ala Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Lys Ser Tyr Pro Leu
                85                  90                  95

Thr Phe Gly Gly Gly Thr Lys Val Glu Ile Lys
            100                 105

<210> SEQ ID NO 33
<211> LENGTH: 366
<212> TYPE: DNA
<213> ORGANISM: Homo sapiens

<400> SEQUENCE: 33
caggtgcagc tggtggagtc tgggggaggt gtggtccagc ctggaggtc cctgagactc      60 tcctgtgcag cctctggatt caccttcagt agctatggca tgcactgggt ccgccaggct    120
ccaggcaagg ggctggagtg gtggcagtt atatcatatg atggaagtaa taaatactat    180
gcagactccg tgaagggccg attcaccatc tccagacaca attccaagaa cacgctgtat    240
ctgcaaatga acagcctgag agctgaggac acggctgtgt attactgtgc gagagatcag    300
gataactgga actactacta cggtatggac gtctggggcc aagggaccac ggtcaccgtc    360
tcctca                                                                366

<210> SEQ ID NO 34
<211> LENGTH: 122
<212> TYPE: PRT
<213> ORGANISM: Homo sapiens

<400> SEQUENCE: 34

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Asp Asn Trp Asn Tyr Tyr Tyr Gly Met Asp Val Trp
            100                 105                 110

Gly Gln Gly Thr Thr Val Thr Val Ser Ser
        115                 120

<210> SEQ ID NO 35
<211> LENGTH: 333
<212> TYPE: DNA
<213> ORGANISM: Homo sapiens

<400> SEQUENCE: 35

```
gatattgtga tgactcagtc tccactctcc ctgcccgtca cccctggaga gccggcctcc      60
atctcctgca ggtctagtca gagcctcctt catagtaatg gatacaacta tttggattgg     120
tacctgcaga agccagggca gtctccacag ctcctgatct ttttgggttc ttatcgggcc     180
tccggggtcc ctgacaggtt cagtggcagt ggatcaggca cagattttac actgaaaatc     240
agcagagtgg aggctgagga tgttggggtt tattactgca tgcaagctct acaaacttgg     300
acgttcggcc aagggaccaa ggtggaaatc aaa                                  333
```

<210> SEQ ID NO 36
<211> LENGTH: 111
<212> TYPE: PRT
<213> ORGANISM: Homo sapiens

<400> SEQUENCE: 36

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Phe Leu Gly Ser Tyr Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Trp Thr Phe Gly Gln Gly Thr Lys Val Glu Ile Lys
            100                 105                 110
```

<210> SEQ ID NO 37
<211> LENGTH: 372
<212> TYPE: DNA
<213> ORGANISM: Homo sapiens

<400> SEQUENCE: 37

```
caggtgcagc tggtggagtc tgggggaggc gtggtccagc ctggagggtc cctgagactc      60
tcctgtgcag cgtctggatt caccttcagt aactatgaca tgcactgggt ccgccaggct     120
ccaggcaagg ggctggagtg ggtggcagtt atatggtatg atggaagtat taaatactat     180
gcagactccg tgaagggccg attcaccatc tccagagaca attccaagaa cacgctgtat     240
ctgcaaatga acagcctgag agccgaggac acggctgtgt atttctgtgc gagagagaca     300
gctatcctta gggctactac tactacgat atggacgtct ggggccaagg gaccacggtc     360
accgtctcct ca                                                          372
```

<210> SEQ ID NO 38
<211> LENGTH: 124
<212> TYPE: PRT
<213> ORGANISM: Homo sapiens

<400> SEQUENCE: 38

```
Gln Val Gln Leu Val Glu Ser Gly Gly Gly Val Val Gln Pro Gly Arg
```

```
                1               5                  10                 15
Ser Leu Arg Leu Ser Cys Ala Ala Ser Gly Phe Thr Phe Ser Asn Tyr
                    20                  25                  30

Asp Met His Trp Val Arg Gln Ala Pro Gly Lys Gly Leu Glu Trp Val
            35                  40                  45

Ala Val Ile Trp Tyr Asp Gly Ser Ile Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Phe Cys
                85                  90                  95

Ala Arg Glu Thr Ala Ile Leu Arg Gly Tyr Tyr Tyr Tyr Asp Met Asp
                    100                 105                 110

Val Trp Gly Gln Gly Thr Thr Val Thr Val Ser Ser
                115                 120
```

<210> SEQ ID NO 39
<211> LENGTH: 321
<212> TYPE: DNA
<213> ORGANISM: Homo sapiens

<400> SEQUENCE: 39

```
gacatccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct gatctctgct gcatccagtt tgcaaggtgg ggtcccatca     180
aggttcagcg gcagtggatc tgggacagaa ttcactctca caatcagcag cctgcagcct     240
gaagattttg caacttatta ctgtctacag cataatagtt accctctcac tttcggcgga     300
gggaccaagg tggagatcaa a                                                321
```

<210> SEQ ID NO 40
<211> LENGTH: 107
<212> TYPE: PRT
<213> ORGANISM: Homo sapiens

<400> SEQUENCE: 40

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Ser Ala Ala Ser Ser Leu Gln Gly Gly Val Pro Ser Arg Phe Ser Gly
    50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
                100                 105
```

<210> SEQ ID NO 41
<211> LENGTH: 372
<212> TYPE: DNA
<213> ORGANISM: Homo sapiens

<400> SEQUENCE: 41

```
caggtgcagt tggtggagtc tgggggaggc gtggtccagc ctgggaggtc cctgagactc    60
tcctgtgcag cctctggatt caccttcagt agctatgaca tgcactgggt ccgccaggct   120
ccaggcaagg gctggagtg gtggcagtt atatcatatg atggaagtat taaatactat   180
gcagactccg tgaagggccg attcaccatc tccagagaca attccaagaa cacgctgtat   240
ctgcaagtga acagcctgag agctgaggac acggctgtgt attactgtgc gagagaggtc   300
cgtagtggga gctactacta ttactacagt atggacgtct ggggccaagg gaccacggtc   360
accgtctcct ca                                                      372
```

<210> SEQ ID NO 42
<211> LENGTH: 124
<212> TYPE: PRT
<213> ORGANISM: Homo sapiens

<400> SEQUENCE: 42

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Asp Met His Trp Val Arg Gln Ala Pro Gly Lys Gly Leu Glu Trp Val
         35                  40                  45

Ala Val Ile Ser Tyr Asp Gly Ser Ile Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Val Asn Ser Leu Arg Ala Glu Asp Thr Ala Val Tyr Tyr Cys
                 85                  90                  95

Ala Arg Glu Val Arg Ser Gly Ser Tyr Tyr Tyr Tyr Ser Met Asp
            100                 105                 110

Val Trp Gly Gln Gly Thr Thr Val Thr Val Ser Ser
        115                 120
```

<210> SEQ ID NO 43
<211> LENGTH: 321
<212> TYPE: DNA
<213> ORGANISM: Homo sapiens

<400> SEQUENCE: 43

```
gacatccaga tgacccagtc tccatcctcc ctgtctgcat ctgtaggaga cagagtcacc    60
atcacttgcc gggcaagtca ggacatcaga aatgatttag gctggtatca gcagaaacca   120
gggaaagccc ctaagcgcct gatctatgct gcgtccagtt tgcaaagtgg ggtcccatca   180
aggttcagcg gcagtggatc tgggccagaa ttcactctca caatcagcag cctgcagcct   240
gaagattttg caacttatta ctgtctacaa cataatagtt atccgctcac tttcggcgga   300
gggaccaagg tggagatcaa a                                             321
```

<210> SEQ ID NO 44
<211> LENGTH: 107
<212> TYPE: PRT
<213> ORGANISM: Homo sapiens

<400> SEQUENCE: 44

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Arg Asn Asp
```

```
            20                  25                  30
Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Pro Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105
```

<210> SEQ ID NO 45
<211> LENGTH: 345
<212> TYPE: DNA
<213> ORGANISM: Homo sapiens

<400> SEQUENCE: 45

```
gaggtgcagc tggtggagtc tggaggaggc ttgatccagc ctggggggtc cctgagactc    60
tcctgtgcag cctctgggtt caccgtcagt agcaactaca tgagctgggt ccgccaggct   120
ccagggaagg ggctggaatg ggtctcagtt atttatagcg gtgataggac atactacgca   180
gactccgtga agggccgatt caccatctcc agagacaatt ccaagaacac gctgtatctt   240
caaatgaaca gcctgagagc cgaggacacg gccgtgtatt actgtgcgcg aggggagggg   300
ggatttgact actggggcca gggaaccctg gtcaccgtct cctca                  345
```

<210> SEQ ID NO 46
<211> LENGTH: 115
<212> TYPE: PRT
<213> ORGANISM: Homo sapiens

<400> SEQUENCE: 46

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Asp Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Glu Gly Gly Phe Asp Tyr Trp Gly Gln Gly Thr Leu Val Thr
            100                 105                 110

Val Ser Ser
        115
```

<210> SEQ ID NO 47
<211> LENGTH: 318
<212> TYPE: DNA
<213> ORGANISM: Homo sapiens

<400> SEQUENCE: 47

```
gaaatagtga tgacgcagtc tccagccacc ctgtctgtgt ctccagggga aagagccacc    60
```

```
ctctcctgca gggccagtca gagtgttacc agcaacttag cctggtacca gcagaaacct      120
ggccaggctc ccagactcct catccatggt gcatccatta gggccactgg tctcccagcc      180
aggttcagtg gcagtgggtc tgggacagag ttcactctca ccatcagtag cctgcagtct      240
gaagattttg cagtctatta ctgtcagcag tataattatt ggtggacgtt cggccaaggg      300
accaaggtgg aaatcaaa                                                    318
```

<210> SEQ ID NO 48
<211> LENGTH: 106
<212> TYPE: PRT
<213> ORGANISM: Homo sapiens

<400> SEQUENCE: 48

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Thr Ser Asn
            20                  25                  30

Leu Ala Trp Tyr Gln Gln Lys Pro Gly Gln Ala Pro Arg Leu Leu Ile
        35                  40                  45

His Gly Ala Ser Ile Arg Ala Thr Gly Leu Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Tyr Trp Trp Thr
                85                  90                  95

Phe Gly Gln Gly Thr Lys Val Glu Ile Lys
            100                 105
```

<210> SEQ ID NO 49
<211> LENGTH: 345
<212> TYPE: DNA
<213> ORGANISM: Homo sapiens

<400> SEQUENCE: 49

```
gaggtgcagc tggtggagtc tggaggaggc ttgatccagc ctggggggtc cctgagactc      60
tcctgtgcag cctctgggtt caccgtcagt aggaactaca tgagctgggt ccgccaggct      120
ccagggaagg gctggaatg gtctcagtt atttatagcg gtgataggac atactacgca       180
gactccgtga agggccgatt caccatctcc agagacaatt ccaagaacac gctgtatctt      240
caaatgaaca gcctgagagc cgaggacacg gccgtgtatt actgtgcgcg aggggagggg      300
ggatttgact actggggcca gggaaccctg gtcaccgtct cctca                     345
```

<210> SEQ ID NO 50
<211> LENGTH: 115
<212> TYPE: PRT
<213> ORGANISM: Homo sapiens

<400> SEQUENCE: 50

```
Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Val Ser Arg Asn
            20                  25                  30

Tyr Met Ser Trp Val Arg Gln Ala Pro Gly Lys Gly Leu Glu Trp Val
        35                  40                  45

Ser Val Ile Tyr Ser Gly Asp Arg Thr Tyr Tyr Ala Asp Ser Val Lys
    50                  55                  60
```

```
Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Glu Gly Gly Phe Asp Tyr Trp Gly Gln Gly Thr Leu Val Thr
            100                 105                 110

Val Ser Ser
        115

<210> SEQ ID NO 51
<211> LENGTH: 318
<212> TYPE: DNA
<213> ORGANISM: Homo sapiens

<400> SEQUENCE: 51
gaaatagtga tgacgcagtc tccagccacc ctgtctgtgt ctccagggga aagagccacc      60
ctctcctgca gggccagtca gagtgttagc agcaacttag cctggtacca gcagaaacct    120
ggccaggctc ccagactcct catccatggt gcatccatta gggccactgg tctcccagcc    180
aggttcagtg gcagtgggtc tgggacagag ttcactctca ccatcagtag cctccagtct    240
gaagattttg cagtctatta ctgtcagcag tataattatt ggtggacgtt cggccaaggg    300
accaaggtgg aaatcaaa                                                  318

<210> SEQ ID NO 52
<211> LENGTH: 106
<212> TYPE: PRT
<213> ORGANISM: Homo sapiens

<400> SEQUENCE: 52

Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Ser Ser Asn
                 20                  25                  30

Leu Ala Trp Tyr Gln Gln Lys Pro Gly Gln Ala Pro Arg Leu Leu Ile
             35                  40                  45

His Gly Ala Ser Ile Arg Ala Thr Gly Leu Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Tyr Trp Trp Thr
                 85                  90                  95

Phe Gly Gln Gly Thr Lys Val Glu Ile Lys
            100                 105

<210> SEQ ID NO 53
<211> LENGTH: 345
<212> TYPE: DNA
<213> ORGANISM: Homo sapiens

<400> SEQUENCE: 53
gaggtgcagc tggtggagtc tggaggaggc ttgatccagc ctgggggtc cctgagactc       60 tcctgtgcag cctctgagtt caccgtcagt aggaactaca tgagctgggt ccgccaggct    120
ccagggaagg gactggaatg ggtctcagtt atttatagcg gtgataggac atactacgca    180
gactccgtga aggccgatt caccatctc agagacaatt ccaagaacac gctgtatctt     240
caaatgaaca gcctgagagc cgaggacacg gccgtgtatt actgtgcgcg aggggagggg    300
```

```
ggatttgact actggggcca gggaaccctg gtcaccgtct cctca            345
```

<210> SEQ ID NO 54
<211> LENGTH: 115
<212> TYPE: PRT
<213> ORGANISM: Homo sapiens

<400> SEQUENCE: 54

```
Glu Val Gln Leu Val Glu Ser Gly Gly Leu Ile Gln Pro Gly Gly
 1               5                  10                  15

Ser Leu Arg Leu Ser Cys Ala Ala Ser Glu Phe Thr Val Ser Arg Asn
            20                  25                  30

Tyr Met Ser Trp Val Arg Gln Ala Pro Gly Lys Gly Leu Glu Trp Val
        35                  40                  45

Ser Val Ile Tyr Ser Gly Asp Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Glu Gly Gly Phe Asp Tyr Trp Gly Gln Gly Thr Leu Val Thr
            100                 105                 110

Val Ser Ser
        115
```

<210> SEQ ID NO 55
<211> LENGTH: 318
<212> TYPE: DNA
<213> ORGANISM: Homo sapiens

<400> SEQUENCE: 55

```
gaaatagtga tgacgcagtc tccagccacc ctgtctgtgt ctccagggga aagagccacc     60
ctctcctgca gggccagtca gagtgttagc agcaacttag cctggtacca gcagaaacct   120
ggccaggctc ccagactcct catccatggt gcatccatta gggccactgg tctcccagcc   180
aggttcagtg gcagtgggtc tgggacagag ttcactctca ccatcagtag cctgcagtct   240
gaagattttg cagtctatta ctgtcagcag tataattatt ggtggacgtt cggccaaggg   300
accaaggtgg aaatcaaa                                                  318
```

<210> SEQ ID NO 56
<211> LENGTH: 106
<212> TYPE: PRT
<213> ORGANISM: Homo sapiens

<400> SEQUENCE: 56

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

His Gly Ala Ser Ile Arg Ala Thr Gly Leu Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Tyr Trp Trp Thr
                85                  90                  95
```

```
Phe Gly Gln Gly Thr Lys Val Glu Ile Lys
            100                 105
```

<210> SEQ ID NO 57
<211> LENGTH: 375
<212> TYPE: DNA
<213> ORGANISM: Homo sapiens

<400> SEQUENCE: 57

| | | | | | |
|---|---|---|---|---|---|
| caggtgcaac | tggtggagtc | tgggggaggc | gtggtccagc | ctgggaggtc | cctgagactc | 60 |
| tcctgtgcag | cgtctggatt | caccgtcagt | agctatggca | tgcactgggt | ccgccaggct | 120 |
| ccaggcaagg | ggctggagtg | ggtggcagtt | atatggtcta | atggaagtaa | taagtactat | 180 |
| gcagactccg | tgaagggccg | attcaccatc | tccagagaca | attccaagaa | cacgctgtat | 240 |
| ctgcaaatga | acagcctgag | agccgaggac | acggctgtgt | attactgtgc | gagagataac | 300 |
| ggtgtctacg | tgggatacgc | ctactattac | ggtatggacg | tctggggcca | agggaccacg | 360 |
| gtcaccgtct | cctca | | | | | 375 |

<210> SEQ ID NO 58
<211> LENGTH: 125
<212> TYPE: PRT
<213> ORGANISM: Homo sapiens

<400> SEQUENCE: 58

```
Gln Val Gln Leu Val Glu Ser Gly Gly Val Val Gln Pro Gly Arg
 1               5                   10                  15
Ser Leu Arg Leu Ser Cys Ala Ala Ser Gly Phe Thr Val Ser Ser Tyr
             20                  25                  30
Gly Met His Trp Val Arg Gln Ala Pro Gly Lys Gly Leu Glu Trp Val
         35                  40                  45
Ala Val Ile Trp Ser Asn Gly Ser Asn Lys Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Asp Asn Gly Val Tyr Val Gly Tyr Ala Tyr Tyr Tyr Gly Met
            100                 105                 110
Asp Val Trp Gly Gln Gly Thr Thr Val Thr Val Ser Ser
        115                 120                 125
```

<210> SEQ ID NO 59
<211> LENGTH: 321
<212> TYPE: DNA
<213> ORGANISM: Homo sapiens

<400> SEQUENCE: 59

| | | | | | |
|---|---|---|---|---|---|
| gacatccaga | tgacccagtc | tccatcctcc | ctgtctgcat | ctgtaggaga | cagagtcacc | 60 |
| atcacttgcc | gggcaagtca | gggcattaga | aatgatttag | ctggtatca | gcagaaacca | 120 |
| gggaaagccc | ctaagcgcct | gatctatgct | gcatccagtt | tgcaaagtgg | ggtcccatca | 180 |
| aggttcagcg | gcagtggatc | tgggacagaa | ttcactctca | caatcagcag | cctgcagcct | 240 |
| gaagattttg | caacttatta | ctgtctacag | cataatagtt | accctcggac | gttcggccaa | 300 |
| gggaccaagg | tggaaatcaa | a | | | | 321 |

<210> SEQ ID NO 60
<211> LENGTH: 107
<212> TYPE: PRT
<213> ORGANISM: Homo sapiens

<400> SEQUENCE: 60

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Lys
            100                 105
```

<210> SEQ ID NO 61
<211> LENGTH: 375
<212> TYPE: DNA
<213> ORGANISM: Homo sapiens

<400> SEQUENCE: 61

```
caggtgcaac tggtggagtc tgggggaggc gtggtccagc ctgggaggtc cctgagactc     60
tcctgtgcag cgtctggatt caccgtcagt agctatggca tgcactgggt ccgccaggct    120
ccaggcaagg ggctggagtg ggtggcagtt atatggtcta atggaagtaa taagtactat    180
gcagactccg tgaagggccg attcaccatc tccagagaca attccaagaa cacgctgtat    240
ctgcaaatga acagcctgag agccgaggac acggctgtgt attactgtgc gagagataac    300
ggtgtctacg tgggatacgc ctactattac ggtatggacg tctggggcca agggaccacg    360
gtcaccgtct cctca                                                    375
```

<210> SEQ ID NO 62
<211> LENGTH: 125
<212> TYPE: PRT
<213> ORGANISM: Homo sapiens

<400> SEQUENCE: 62

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Val Ser Ser Tyr
            20                  25                  30

Gly Met His Trp Val Arg Gln Ala Pro Gly Lys Gly Leu Glu Trp Val
        35                  40                  45

Ala Val Ile Trp Ser Asn Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Gly Val Tyr Val Gly Tyr Ala Tyr Tyr Tyr Gly Met
            100                 105                 110
```

-continued

Asp Val Trp Gly Gln Gly Thr Thr Val Thr Val Ser Ser
        115                 120                 125

<210> SEQ ID NO 63
<211> LENGTH: 321
<212> TYPE: DNA
<213> ORGANISM: Homo sapiens

<400> SEQUENCE: 63
gacatccaga tgacccagtc tccatcctcc ctgtctgcat ctgtaggaga cagagtcacc      60
atcacttgcc gggcaagtca gggcattaga aatgatttag ctggtatca gcaaaaacca     120
gggaaagccc ctaagcgcct gatctatgct gcatccagtt tgcacagtgg ggtcccatca    180
aggttcagcg gcagtggatc tgggacagaa ttcactctca caatcagcag cctgcagcct    240
gaagattttg caacttatta ctgtctacaa cataatagtt acccgtggac gttcggccaa    300
gggaccaagg tggaaatcaa a                                              321

<210> SEQ ID NO 64
<211> LENGTH: 107
<212> TYPE: PRT
<213> ORGANISM: Homo sapiens

<400> SEQUENCE: 64

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu His Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys
            100                 105

<210> SEQ ID NO 65
<211> LENGTH: 384
<212> TYPE: DNA
<213> ORGANISM: Homo sapiens

<400> SEQUENCE: 65
caggtgcagc tggtggagtc tgggggaagc gtggtccagc ctgggaggtc cctgagactc      60
tcctgtgcag cgtctggatt caccttcagt aactatggca tacactgggt ccgccaggct    120
ccaggcaagg ggctggagtg gtggcagtt atatggtctg atggaagtaa taatactat      180
gcagactccg tgaagggccg attcaccatc tccagagaca attccaagaa cacgctgtat    240
ctgcaaatga acagcctgag agccgaggac acggctgtgt attactgtgc gagagagctc    300
ccgaatagtg ggagctactc cggttactac tactactacg gtatggacgt ctggggccaa    360
gggaccacgg tcaccgtctc ctca                                            384

<210> SEQ ID NO 66
<211> LENGTH: 128
<212> TYPE: PRT
<213> ORGANISM: Homo sapiens

<400> SEQUENCE: 66

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Ala Val Ile Trp Ser Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Pro Asn Ser Gly Ser Tyr Ser Gly Tyr Tyr Tyr Tyr
            100                 105                 110

Tyr Gly Met Asp Val Trp Gly Gln Gly Thr Thr Val Thr Val Ser Ser
        115                 120                 125

<210> SEQ ID NO 67
<211> LENGTH: 321
<212> TYPE: DNA
<213> ORGANISM: Homo sapiens

<400> SEQUENCE: 67
gacatccaga tgacccagtc tccatcctcc ctgtctgcat ctgtaggaga cagagtcacc    60
atcacttgcc gggcaagtca gggcattaga aatgatttag ctggtatca gcagaaacca   120 gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cattgttgtt accctctcac tttcggcgga   300
gggaccaagg tggaaatcaa a                                             321

<210> SEQ ID NO 68
<211> LENGTH: 107
<212> TYPE: PRT
<213> ORGANISM: Homo sapiens

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Cys Cys Tyr Pro Leu
                85                  90                  95

Thr Phe Gly Gly Gly Thr Lys Val Glu Ile Lys
            100                 105

<210> SEQ ID NO 69
<211> LENGTH: 375

-continued

<212> TYPE: DNA
<213> ORGANISM: Homo sapiens

<400> SEQUENCE: 69

```
caggtgcagc tggtggagtc tgggggaggc gtggtccagc ctgggaggtc cctgagactc      60
tcctgtgcag cgtctggatt caccttcagt agctatgaca tgcactgggt ccgccaggct     120
ccaggcaagg gctggagtg gtggcagtt atatggtctg atggaagtat aaatactat         180
gcagactccg tgaagggccg attcaccatc tccagagaca attccaagaa cacgctgtat     240
ctgcaaatga acagcctgag agccgaggac acggctgtgt attactgtgc gagagaagtg     300
gaatcagcta tgggagggtt ctactacaac ggtatggacg tctggggcca agggccacg      360
gtcaccgtct cctca                                                      375
```

<210> SEQ ID NO 70
<211> LENGTH: 125
<212> TYPE: PRT
<213> ORGANISM: Homo sapiens

<400> SEQUENCE: 70

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Asp Met His Trp Val Arg Gln Ala Pro Gly Lys Gly Leu Glu Trp Val
         35                  40                  45

Ala Val Ile Trp Ser Asp Gly Ser Ile Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Val Glu Ser Ala Met Gly Gly Phe Tyr Tyr Asn Gly Met
            100                 105                 110

Asp Val Trp Gly Gln Gly Ala Thr Val Thr Val Ser Ser
        115                 120                 125
```

<210> SEQ ID NO 71
<211> LENGTH: 321
<212> TYPE: DNA
<213> ORGANISM: Homo sapiens

<400> SEQUENCE: 71

```
gacatccaga tgacccagtc tccatcctcc ctgtctgcat ctgtagggga cagagtcacc      60
atcacttgcc gggcaagtca gggcattaga attgatttag ctggtatca gcagaaacca     120
gggaaagccc ctaagcgcct gatctatgct gcatccactt tgcaaagtgg ggtcccatca     180
aggttcagcg gcagtggatc gggacagaa ttcattttca caatcagcag cctgcagcct     240
gaagattttg caagttatta ctgtctacag cataaaagtt accctctcac tttcggcgga     300
gggaccaagg tggagatcaa a                                               321
```

<210> SEQ ID NO 72
<211> LENGTH: 107
<212> TYPE: PRT
<213> ORGANISM: Homo sapiens

<400> SEQUENCE: 72

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Ile Asp
            20                  25                  30

Leu Gly Trp Tyr Gln Gln Lys Pro Gly Lys Ala Pro Lys Arg Leu Ile
        35                  40                  45

Tyr Ala Ala Ser Thr Leu Gln Ser Gly Val Pro Ser Arg Phe Ser Gly
 50                  55                  60

Ser Gly Ser Gly Thr Glu Phe Ile Phe Thr Ile Ser Ser Leu Gln Pro
65                  70                  75                  80

Glu Asp Phe Ala Ser Tyr Tyr Cys Leu Gln His Lys Ser Tyr Pro Leu
                85                  90                  95

Thr Phe Gly Gly Gly Thr Lys Val Glu Ile Lys
                100                 105
```

<210> SEQ ID NO 73
<211> LENGTH: 375
<212> TYPE: DNA
<213> ORGANISM: Homo sapiens

<400> SEQUENCE: 73

```
caggtgcagc tggtggagtc tgggggaggc gtggtccagc ctggggaggtc cctgagactc    60
tcctgtgcag cgtctggatt caccttcagt agctatgaca tgcactgggt ccgccaggct   120
ccaggcaagg gctggagtg gtggcagtt atatggtctg atggaagtat taaatactat   180
gcagactccg tgaagggccg attcaccatc tccagagaca attccaagaa cacgctgtat   240
ctgcaaatga acagcctgag agccgaggac acggctgtgt attactgtgc gagagaagtg   300
gaatcagcta tgggagggtt ctactacaac ggtatggacg tctggggcca agggaccacg   360
gtcaccgtct cctca                                                    375
```

<210> SEQ ID NO 74
<211> LENGTH: 125
<212> TYPE: PRT
<213> ORGANISM: Homo sapiens

<400> SEQUENCE: 74

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Trp Ser Asp Gly Ser Ile Lys Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Val Glu Ser Ala Met Gly Gly Phe Tyr Tyr Asn Gly Met
                100                 105                 110

Asp Val Trp Gly Gln Gly Thr Thr Val Thr Val Ser Ser
            115                 120                 125
```

<210> SEQ ID NO 75
<211> LENGTH: 375
<212> TYPE: DNA

<213> ORGANISM: Homo sapiens

<400> SEQUENCE: 75

```
caggtgcagc tggtggagtc tgggggaggc gtggtccagc ctgggaggtc cctgagactc    60
tcctgtgcag cgtctggatt caccttcagt aaccatgaca tacactgggt ccgccaggct   120
ccaggcaagg gctggagtg gtggcagtt atatggtctg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagagagaag   300
atggctacaa ttaaggggta ctactactac ggtatggacg tctggggcca agggaccacg   360
gtcaccgtct cctca                                                    375
```

<210> SEQ ID NO 76
<211> LENGTH: 125
<212> TYPE: PRT
<213> ORGANISM: Homo sapiens

<400> SEQUENCE: 76

```
Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Ser Asn His
            20                  25                  30
Asp Ile His Trp Val Arg Gln Ala Pro Gly Lys Gly Leu Glu Trp Val
        35                  40                  45
Ala Val Ile Trp Ser Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Lys Met Ala Thr Ile Lys Gly Tyr Tyr Tyr Tyr Gly Met
            100                 105                 110
Asp Val Trp Gly Gln Gly Thr Thr Val Thr Val Ser Ser
        115                 120                 125
```

<210> SEQ ID NO 77
<211> LENGTH: 321
<212> TYPE: DNA
<213> ORGANISM: Homo sapiens

<400> SEQUENCE: 77

```
gacatccaga tgacccagtc tccatcctcc ctgtctgcat ctgtaggaga cagagtcacc    60
atcacttgcc gggcaagtca gggcattaga aatgatttag ctggtatca gcagaaacca   120
gggaaagccc ctaagcgcct gatctatgct gcatccagtt tggaaagtgg ggtcccatca   180
aggttcagcg gcagtggatc tgggccagaa ttcactctca caatcagcag cctgcagcct   240
gaagattttg caacttatta ctgtctacag cataatagtt acccgctcac tttcggcgga   300
gggaccaagg tggagatcca a                                              321
```

<210> SEQ ID NO 78
<211> LENGTH: 107
<212> TYPE: PRT
<213> ORGANISM: Homo sapiens

<400> SEQUENCE: 78

```
Asp Ile Gln Met Thr Gln Ser Pro Ser Ser Leu Ser Ala Ser Val Gly
```

```
                 1               5                  10                 15
Asp Arg Val Thr Ile Thr Cys Arg Ala Ser Gln Gly Ile Arg Asn Asp
                20                  25                 30

Leu Gly Trp Tyr Gln Gln Lys Pro Gly Lys Ala Pro Lys Arg Leu Ile
            35                  40                  45

Tyr Ala Ala Ser Ser Leu Glu Ser Gly Val Pro Ser Arg Phe Ser Gly
        50                  55                  60

Ser Gly Ser Gly Pro Glu Phe Thr Leu Thr Ile Ser Ser Leu Gln Pro
 65                 70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Gln
            100                 105
```

<210> SEQ ID NO 79
<211> LENGTH: 336
<212> TYPE: DNA
<213> ORGANISM: Oryctolagus cuniculus

<400> SEQUENCE: 79

```
cagtcactgg aggagtccgg gggtcgcctg gtcacgcctg ggacacccct gacactcacc    60
tgcacagtct ctggaatcga cctcagtagc aatacaatgg gctggttccg ccgggctcca   120
gggaaggggc tggagtggat cggaatcatt attagtagtg gtaccacata ctacgcgagc   180
tgggtaaaag gccgattcac catctccaaa acctcgacca cggtggatct gaaaatcacc   240
cgtccgacaa ccgaggacac ggccacatat ttctgtgcca gaggctggta cgagtttaac   300
ttgtggggcc aggcaccct ggtcaccgtc tcctca                              336
```

<210> SEQ ID NO 80
<211> LENGTH: 112
<212> TYPE: PRT
<213> ORGANISM: Oryctolagus cuniculus

<400> SEQUENCE: 80

```
Gln Ser Leu Glu Glu Ser Gly Gly Arg Leu Val Thr Pro Gly Thr Pro
 1               5                  10                 15

Leu Thr Leu Thr Cys Thr Val Ser Gly Ile Asp Leu Ser Ser Asn Thr
                20                  25                 30

Met Gly Trp Phe Arg Arg Ala Pro Gly Lys Gly Leu Glu Trp Ile Gly
            35                  40                  45

Ile Ile Ile Ser Ser Gly Thr Thr Tyr Tyr Ala Ser Trp Val Lys Gly
        50                  55                  60

Arg Phe Thr Ile Ser Lys Thr Ser Thr Thr Val Asp Leu Lys Ile Thr
 65                 70                  75                  80

Arg Pro Thr Thr Glu Asp Thr Ala Thr Tyr Phe Cys Ala Arg Gly Trp
                85                  90                  95

Tyr Glu Phe Asn Leu Trp Gly Pro Gly Thr Leu Val Thr Val Ser Ser
            100                 105                 110
```

<210> SEQ ID NO 81
<211> LENGTH: 339
<212> TYPE: DNA
<213> ORGANISM: Oryctolagus cuniculus

<400> SEQUENCE: 81

```
gatgttgtga tgacccagac tccagcctcc gtggaggcag ctgtgggagg cacagtcacc    60
```

```
atcaagtgcc aggccagtga gaacattgat atcttattgg cctggtatca gcagaaagta      120
gggcagcctc ccaagctcct gatctatagg gcatccaaac tggcctctgg ggccccatcg      180
cggttcagcg gcagtggatc tgggacagag ttcactctca ccatcagcga cctggagtgt      240
ggcgatgctg ccacttacta ctgtcaaagc aatgttggta gtactgctag aagtagttat      300
ggtaatgctt tcggcggagg gaccgaggtg gtggtcaaa                             339
```

<210> SEQ ID NO 82
<211> LENGTH: 113
<212> TYPE: PRT
<213> ORGANISM: Oryctolagus cuniculus

<400> SEQUENCE: 82

Asp Val Val Met Thr Gln Thr Pro Ala Ser Val Glu Ala Ala Val Gly
1               5                   10                  15

Gly Thr Val Thr Ile Lys Cys Gln Ala Ser Glu Asn Ile Asp Ile Leu
            20                  25                  30

Leu Ala Trp Tyr Gln Gln Lys Val Gly Gln Pro Pro Lys Leu Leu Ile
        35                  40                  45

Tyr Arg Ala Ser Lys Leu Ala Ser Gly Ala Pro Ser Arg Phe Ser Gly
    50                  55                  60

Ser Gly Ser Gly Thr Glu Phe Thr Leu Thr Ile Ser Asp Leu Glu Cys
65                  70                  75                  80

Gly Asp Ala Ala Thr Tyr Tyr Cys Gln Ser Asn Val Gly Ser Thr Ala
                85                  90                  95

Arg Ser Ser Tyr Gly Asn Ala Phe Gly Gly Thr Glu Val Val Val
            100                 105                 110

Lys

<210> SEQ ID NO 83
<211> LENGTH: 348
<212> TYPE: DNA
<213> ORGANISM: Homo sapiens

<400> SEQUENCE: 83

```
caggtgcagc tggtggagtc tgggggaggc ttggtcaagc ctggagggtc cctgagactc      60
tcctgtgcag cctctggatt caccttcagt gactactaca tgagctggat ccgccaggct      120
ccagggaagg gctggagtg gtttcatac attagtagaa gtggtagtac catatactac      180
gcagactctg tgaagggccg attcaccatc tccagggaca cgccaagaa ctcactgtat      240 ctgcaaatga acagcctgag agccgaggac acggccgtgt attactgtgc gagatcttta      300
ggcggtatgg acgtctgggg ccaagggacc acggtcaccg tctcctca                  348
```

<210> SEQ ID NO 84
<211> LENGTH: 116
<212> TYPE: PRT
<213> ORGANISM: Homo sapiens

<400> SEQUENCE: 84

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Arg Ser Gly Ser Thr Ile Tyr Tyr Ala Asp Ser Val

```
            50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Leu Gly Gly Met Asp Val Trp Gly Gln Gly Thr Thr Val
                100                 105                 110

Thr Val Ser Ser
        115

<210> SEQ ID NO 85
<211> LENGTH: 330
<212> TYPE: DNA
<213> ORGANISM: Homo sapiens

<400> SEQUENCE: 85
cagtctgtgt tgacgcagcc gccctcagtg tctgcggccc caggacagaa ggtcaccatc      60
tcctgctctg gaagcagctc caacattggg aataattatg tatcctggta ccagcagttc     120
ccaggaacag cccccaaact cctcatttat gacaataata gccgaccctc agggattcct     180
gaccgattct ctggctccaa gtctggcacg tcagccaccc tgggcatcac cggactccag     240
actggggacg aggccgatta ttactgcgga acatgggata gcagcctgag tgctggggtg     300
ttcggcggag ggaccaagct gaccgtccta                                       330

<210> SEQ ID NO 86
<211> LENGTH: 110
<212> TYPE: PRT
<213> ORGANISM: Homo sapiens

<400> SEQUENCE: 86

Gln Ser Val Leu Thr Gln Pro Pro Ser Val Ser Ala Ala Pro Gly Gln
  1               5                  10                  15

Lys Val Thr Ile Ser Cys Ser Gly Ser Ser Ser Asn Ile Gly Asn Asn
                 20                  25                  30

Tyr Val Ser Trp Tyr Gln Gln Phe Pro Gly Thr Ala Pro Lys Leu Leu
             35                  40                  45

Ile Tyr Asp Asn Asn Ser Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Gly Val Phe Gly Gly Gly Thr Lys Leu Thr Val Leu
                100                 105                 110

<210> SEQ ID NO 87
<211> LENGTH: 354
<212> TYPE: DNA
<213> ORGANISM: Homo sapiens

<400> SEQUENCE: 87
caggtgcagc tggtggagtc tgggggagac gtggtccagc ctggggaggtc cctgagactc      60 tcctgtgcag cgtctggatt caccttcagt agctctggca tgcactgggt ccgccaggct     120
ccaggcaagg ggctggagtg ggtggcaatt atatggtatg atggaagtaa taaatactat     180
gcagactccg tgaagggccg attcaccatc tccagagaca attccaagaa cacgctgtat     240
```

```
ctgcaaatga acagcctgag agccgaggac acggctgtgt attactgtgc gagagatgac      300
tactactacg gtatggacgt ctggggccaa gggaccacgg tcaccgtctc ctca            354
```

<210> SEQ ID NO 88
<211> LENGTH: 118
<212> TYPE: PRT
<213> ORGANISM: Homo sapiens

<400> SEQUENCE: 88

Gln Val Gln Leu Val Glu Ser Gly Gly Asp Val Val Gln Pro Gly Arg
 1               5                  10                  15

Ser Leu Arg Leu Ser Cys Ala Ala Ser Gly Phe Thr Phe Ser Ser Ser
             20                  25                  30

Gly Met His Trp Val Arg Gln Ala Pro Gly Lys Gly Leu Glu Trp Val
         35                  40                  45

Ala Ile Ile Trp Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                 85                  90                  95

Ala Arg Asp Asp Tyr Tyr Tyr Gly Met Asp Val Trp Gly Gln Gly Thr
            100                 105                 110

Thr Val Thr Val Ser Ser
        115

<210> SEQ ID NO 89
<211> LENGTH: 330
<212> TYPE: DNA
<213> ORGANISM: Homo sapiens

<400> SEQUENCE: 89

```
cagtctgcgt tgacgcagcc gccctcagtg tctgcggccc caggacagaa ggtcaccatc       60
tcctgctctg gaagcagctc caacattggg agtaattatg tatcctggtg ccagcagctc      120
ccaagaacag ccccccaaact cctcatttat gacaataata agcgaccctc agggattcct     180
gaccgattct ctggctccaa gtctggcacg tcagccaccc tggtcatcac cggactccag      240
actggggacg aggccgatta ttactgcgga gcatgggata gcagcctgag tgctgggggta     300 ttcggcggag ggaccaagct gaccgtccta                                       330
```

<210> SEQ ID NO 90
<211> LENGTH: 110
<212> TYPE: PRT
<213> ORGANISM: Homo sapiens

<400> SEQUENCE: 90

Gln Ser Ala Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Ser Asn
             20                  25                  30

Tyr Val Ser Trp Cys Gln Gln Leu Pro Arg Thr Ala Pro Lys Leu Leu
         35                  40                  45

Ile Tyr Asp Asn Asn Lys Arg Pro Ser Gly Ile Pro Asp Arg Phe Ser
     50                  55                  60

Gly Ser Lys Ser Gly Thr Ser Ala Thr Leu Val Ile Thr Gly Leu Gln
 65                 70                  75                  80

```
Thr Gly Asp Glu Ala Asp Tyr Tyr Cys Gly Ala Trp Asp Ser Ser Leu
                85                  90                  95
Ser Ala Gly Val Phe Gly Gly Thr Lys Leu Thr Val Leu
            100                 105                 110

<210> SEQ ID NO 91
<211> LENGTH: 363
<212> TYPE: DNA
<213> ORGANISM: Homo sapiens

<400> SEQUENCE: 91
caggtgcagc tggtggagtc tgggggaggc gtggtccagc ctggagggtc cctgagactc      60
tcctgtgcag cgtctggatt caccttcagt agctatggca tgcactgggt ccgccaggct     120
ccaggcaagg ggctggagtg ggtggcagtt atatggtatg atggaaataa taaatactat     180
gcagactccg tgaagggccg attcaccatc tccagagaca attccaagaa cacgctatat     240
ctgcaaatga acagcctgag agccgaggac acggctgtgt attactgtgc gagagagagc     300
gactacggtg gtaacccta ctttgactac tggggccaag ggaccctggt caccgtctcc     360
tca                                                                  363

<210> SEQ ID NO 92
<211> LENGTH: 121
<212> TYPE: PRT
<213> ORGANISM: Homo sapiens

<400> SEQUENCE: 92

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Asp Tyr Gly Gly Asn Pro Tyr Phe Asp Tyr Trp Gly
            100                 105                 110

Gln Gly Thr Leu Val Thr Val Ser Ser
        115                 120

<210> SEQ ID NO 93
<211> LENGTH: 324
<212> TYPE: DNA
<213> ORGANISM: Homo sapiens

<400> SEQUENCE: 93
tcttctgagc tgactcagga cctgctgtg tctgtggcct tgggacagac agtcaggatc       60
acatgccaag agacagcct cagaagctat tatgcaagct ggtaccagca gaggccagga     120
caggcccctg tacttgtcat ctatggtaga aacaaccggc cctcagggat cccagaccga     180
ttctctggct ccagctcagg actcacagct tccttgaccg tcactggggc tcaggcggaa     240
gatgaggctg actattactg taactcccgg gacagcagtt ataaccatgt ggcattcggc     300
ggagggacca agctgaccgt ccta                                           324
```

<210> SEQ ID NO 94
<211> LENGTH: 108
<212> TYPE: PRT
<213> ORGANISM: Homo sapiens

<400> SEQUENCE: 94

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Arg Pro Gly Gln Ala Pro Val Leu Val Ile Tyr
        35                  40                  45

Gly Arg Asn Asn Arg Pro Ser Gly Ile Pro Asp Arg Phe Ser Gly Ser
    50                  55                  60

Ser Ser Gly Leu Thr Ala Ser Leu Thr Val Thr Gly Ala Gln Ala Glu
65                  70                  75                  80

Asp Glu Ala Asp Tyr Tyr Cys Asn Ser Arg Asp Ser Ser Tyr Asn His
                85                  90                  95

Val Ala Phe Gly Gly Gly Thr Lys Leu Thr Val Leu
            100                 105

<210> SEQ ID NO 95
<211> LENGTH: 363
<212> TYPE: DNA
<213> ORGANISM: Homo sapiens

<400> SEQUENCE: 95
caggtgcagc tggtggagtc tgggggaggc gtggtccagc ctgggaggtc cctgagactc      60
tcctgtgcag cgtctggatt caccttcagt agctatggca tgaactgggt ccgccaggct    120
ccaggcaagg ggctggagtg ggtggcagtt atatggtatg atggaagtaa taaatactat    180
ggagactccg tgaagggccg attcaccatc tccagagaca attccaagaa cacgctgtat    240
gtgcaaatga acagcctgag agccgaggac acggctgtgt attactgtgc gagagagagc    300
gactacggtg gtaaccctta ctttgactac tggggccagg gaaccctggt caccgtctcc    360
tca                                                                  363

<210> SEQ ID NO 96
<211> LENGTH: 121
<212> TYPE: PRT
<213> ORGANISM: Homo sapiens

<400> SEQUENCE: 96

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Asn Trp Val Arg Gln Ala Pro Gly Lys Gly Leu Glu Trp Val
        35                  40                  45

Ala Val Ile Trp Tyr Asp Gly Ser Asn Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Val Gln Met Asn Ser Leu Arg Ala Glu Asp Thr Ala Val Tyr Tyr Cys
                85                  90                  95

Ala Arg Glu Ser Asp Tyr Gly Gly Asn Pro Tyr Phe Asp Tyr Trp Gly 100                 105                 110
Gln Gly Thr Leu Val Thr Val Ser Ser
        115                 120

<210> SEQ ID NO 97
<211> LENGTH: 324
<212> TYPE: DNA
<213> ORGANISM: Homo sapiens

<400> SEQUENCE: 97
tcttctgagc tgactcagga ccctgctgtg tctgtggcct tgggacagac agtcaggatc      60
acatgccaag agacagcct cagaatctat atgcaagct ggtaccagca gaagccagga     120
caggcccctg tacttgtcat ctatggtaaa acaaccggc cctcagggat cccagaccga     180
ttctctggct ccagctcagg aaacacagct tccttgaccg tcactggggc tcaggcggaa     240
gatgaggctg actattactg taagtcccgg gacagcagtt ttaaccatgt gacattcggc     300
ggagggacca agctgaccgt ccta                                            324

<210> SEQ ID NO 98
<211> LENGTH: 108
<212> TYPE: PRT
<213> ORGANISM: Homo sapiens

<400> SEQUENCE: 98

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ile Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Val Thr Gly Ala Gln Ala Glu
65                  70                  75                  80

Asp Glu Ala Asp Tyr Tyr Cys Lys Ser Arg Asp Ser Ser Phe Asn His
                85                  90                  95

Val Thr Phe Gly Gly Gly Thr Lys Leu Thr Val Leu
            100                 105

<210> SEQ ID NO 99
<211> LENGTH: 348
<212> TYPE: DNA
<213> ORGANISM: Homo sapiens

<400> SEQUENCE: 99
gaggtgcagc tggtgcagtc tggagcagag gtgaaaaagc ccggggagtc tctgaagatc      60
tcctgtaagg gttctggata cagctttacc agtgactgga tcggctgggt gcgccagatg     120
cccgggaaag gcctggagtg gatggggatc atctatcctg gtgactctga taccagatac     180
agcccgtcct tccaaggcca ggtcaccatc tcagccgaca gtccatcac caccgcctac     240 ctgcagtgga gcagcctgaa ggcctcggac accgccatgt attactgtgc gaggagtggt     300
tacggtatgg acgtctgggg ccaagggacc acggtcaccg tctcctca                 348

<210> SEQ ID NO 100
<211> LENGTH: 116
<212> TYPE: PRT
<213> ORGANISM: Homo sapiens

<400> SEQUENCE: 100

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Asp
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Gly Met Asp Val Trp Gly Gln Gly Thr Thr Val
            100                 105                 110

Thr Val Ser Ser
        115

<210> SEQ ID NO 101
<211> LENGTH: 334
<212> TYPE: DNA
<213> ORGANISM: Homo sapiens

<400> SEQUENCE: 101
cagtctctgc tgacgcagcc gccctcagtg tctggggccc cagggcagag ggtcaccatc      60
tcctgcactg ggagcagctc caacatcggg gcaggttatg atgtacactg gtaccagcag     120
tttccaggaa cagcccccaa actcctcatc tatggtaaca gcaatcggcc ctcaggggtc     180
cctgaccgat tctctggctc caagtctggc acctcagcct ccctggccat cactgggctc     240
caggctgagg atgaggctga ttattactgc cagtcctatg acagcagcct gagtggttcg     300
gtattcggcg gagggaccaa gctgaccgtc ctag                                 334

<210> SEQ ID NO 102
<211> LENGTH: 111
<212> TYPE: PRT
<213> ORGANISM: Homo sapiens

<400> SEQUENCE: 102

Gln Ser Leu Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Phe Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu
            100                 105                 110

<210> SEQ ID NO 103
<211> LENGTH: 375

```
<212> TYPE: DNA
<213> ORGANISM: Homo sapiens

<400> SEQUENCE: 103
caggtgcagc tggtggagtc tgggggaggc gtggtccagc ctgggaggtc cctgagactc    60
tcctgtgcag cgtctggatt taccttcagt agttatgaca tgcactgggt ccgccaggct   120
ccaggcaagg gctggagtg gtggcagtt atatggtatg atggaagtaa taaataccat    180
gcagactccg tgaagggccg attcaccatc tccagagaca attccaagaa cacgctgtat   240
ctgcaaatga acagcctgag agccgaggac acggctgtgt attactgtgc gagagagaat   300
actatggttc gggggggga ctactactac ggtatggacg tctggggcca agggaccacg    360
gtcaccgtct cctca                                                    375

<210> SEQ ID NO 104
<211> LENGTH: 125
<212> TYPE: PRT
<213> ORGANISM: Homo sapiens

<400> SEQUENCE: 104

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Trp Tyr Asp Gly Ser Asn Lys Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Thr Met Val Arg Gly Gly Asp Tyr Tyr Tyr Gly Met
            100                 105                 110

Asp Val Trp Gly Gln Gly Thr Thr Val Thr Val Ser Ser
        115                 120                 125

<210> SEQ ID NO 105
<211> LENGTH: 324
<212> TYPE: DNA
<213> ORGANISM: Homo sapiens

<400> SEQUENCE: 105
tcttctgagc tgactcagga ccctgctgtg tctgtggcct tgggacagac agtcaggatc    60
acatgccaag agacagcct cagaaggtat tatgcaagct ggtaccagca gaagccagga   120
caggccccta tacttgtcat ctatggtaaa acaaccggc cctcaggat cccagaccga    180 ttctctggct ccagctcagg aaacacagct tccttgacca tcactgggc tcaggcggaa   240 gatgaggctg actattactg taactcccgg gacagcagtg gtaaccatct ggtgttcggc   300
ggagggacca agctgaccgt ccta                                          324

<210> SEQ ID NO 106
<211> LENGTH: 108
<212> TYPE: PRT
<213> ORGANISM: Homo sapiens

<400> SEQUENCE: 106
```

```
Ser Ser Glu Leu Thr Gln Asp Pro Ala Val Ser Val Ala Leu Gly Gln
  1               5                  10                 15

Thr Val Arg Ile Thr Cys Gln Gly Asp Ser Leu Arg Arg Tyr Tyr Ala
             20                  25                  30

Ser Trp Tyr Gln Gln Lys Pro Gly Gln Ala Pro Ile Leu Val Ile Tyr
             35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
65                   70                  75                  80

Asp Glu Ala Asp Tyr Tyr Cys Asn Ser Arg Asp Ser Ser Gly Asn His
             85                  90                  95

Leu Val Phe Gly Gly Gly Thr Lys Leu Thr Val Leu
            100                 105
```

<210> SEQ ID NO 107
<211> LENGTH: 366
<212> TYPE: DNA
<213> ORGANISM: Homo sapiens

<400> SEQUENCE: 107

```
caggttcagc tggtgcagtc tggagctgag gtgaagaagc ctggggcctc agtgaaggtc    60
tcctgcaagg cttctggtta cacctttacc agctatggta tcagctgggt gcgacaggcc   120
cctggacaag gcttgagtg gatgggatgg atcagcgctt acaatgttaa cacaaactat   180
gcacagaagc tccagggcag agtcaccatg accacagaca catccacgaa cacagcctac   240
atggaactga ggagcctgag atctgacgac acggccgtgt attactgtgc gagagatcct   300
ataactgaaa ctatggagga ctactttgac tactggggcc agggaaccct ggtcaccgtc   360
tcctca                                                              366
```

<210> SEQ ID NO 108
<211> LENGTH: 122
<212> TYPE: PRT
<213> ORGANISM: Homo sapiens

<400> SEQUENCE: 108

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Gly Ile Ser Trp Val Arg Gln Ala Pro Gly Gln Gly Leu Glu Trp Met
             35                  40                  45

Gly Trp Ile Ser Ala Tyr Asn Val Asn Thr Asn Tyr Ala Gln Lys Leu
 50                  55                  60

Gln Gly Arg Val Thr Met Thr Thr Asp Thr Ser Thr Asn Thr Ala Tyr
65                   70                  75                  80

Met Glu Leu Arg Ser Leu Arg Ser Asp Asp Thr Ala Val Tyr Tyr Cys
             85                  90                  95

Ala Arg Asp Pro Ile Thr Glu Thr Met Glu Asp Tyr Phe Asp Tyr Trp
            100                 105                 110

Gly Gln Gly Thr Leu Val Thr Val Ser Ser
            115                 120
```

<210> SEQ ID NO 109
<211> LENGTH: 324
<212> TYPE: DNA

<213> ORGANISM: Homo sapiens

<400> SEQUENCE: 109

| | | | | | |
|---|---|---|---|---|---|
| tcttctgagc | tgactcagga | ccctgctgtg | tctgtggcct | tgggacagac | agtcaggatc | 60 |
| acatgccaag | gagacagcct | cagaaactat | tatgcaagtt | ggtaccagca | gaagccagga | 120 |
| caggccccta | tacttgtcat | ctatggtaaa | aacaaccggc | cctcagggat | cccagaccga | 180 |
| ttctctggct | ccagctcagg | aaacacagct | tccttgacca | tcactggggc | tcaggcggaa | 240 |
| gatgaggctg | actattactg | taactcccgg | gacagcagtg | gtaatcatct | ggtattcggc | 300 |
| ggagggacca | agttgaccgt | ccta | | | | 324 |

<210> SEQ ID NO 110
<211> LENGTH: 107
<212> TYPE: PRT
<213> ORGANISM: Homo sapiens

<400> SEQUENCE: 110

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Asn Tyr Tyr Ala
            20                  25                  30

Ser Trp Tyr Gln Gln Lys Pro Gly Gln Ala Pro Ile Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Val Phe Gly Gly Gly Thr Lys Leu Thr Val
            100                 105

<210> SEQ ID NO 111
<211> LENGTH: 366
<212> TYPE: DNA
<213> ORGANISM: Homo sapiens

<400> SEQUENCE: 111

| | | | | | |
|---|---|---|---|---|---|
| caggtgcagc | tggtggagtc | tgggggaggc | gtggtccagc | ctggaggtc | cctgagactc | 60 |
| tcctgtgcag | cgtctggatt | caccttcagc | agctatggca | tgcactgggt | ccgccaggct | 120 |
| ccaggcaagg | ggctggagtg | ggtggcagtt | atatggtatg | atggaagaaa | taaatacaat | 180 |
| gcagactccg | tgaagggccg | attcaccatc | tccagagaca | attccaagaa | cacgctgaat | 240 |
| ctgcaaatga | acagcctgag | agccgaggac | acggctgtgt | attactgtgc | gagagattta | 300 |
| acgtattacg | atatttttggg | cggtatggac | gtctggggcc | aagggaccac | ggtcaccgtc | 360 |
| tcctca | | | | | | 366 |

<210> SEQ ID NO 112
<211> LENGTH: 122
<212> TYPE: PRT
<213> ORGANISM: Homo sapiens

<400> SEQUENCE: 112

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr

```
                    20                  25                  30
Gly Met His Trp Val Arg Gln Ala Pro Gly Lys Gly Leu Glu Trp Val
             35                  40                  45

Ala Val Ile Trp Tyr Asp Gly Arg Asn Lys Tyr Asn Ala Asp Ser Val
 50                  55                  60

Lys Gly Arg Phe Thr Ile Ser Arg Asp Asn Ser Lys Asn Thr Leu Asn
 65                  70                  75                  80

Leu Gln Met Asn Ser Leu Arg Ala Glu Asp Thr Ala Val Tyr Tyr Cys
                 85                  90                  95

Ala Arg Asp Leu Thr Tyr Tyr Asp Ile Leu Gly Gly Met Asp Val Trp
             100                 105                 110

Gly Gln Gly Thr Thr Val Thr Val Ser Ser
             115                 120
```

<210> SEQ ID NO 113
<211> LENGTH: 333
<212> TYPE: DNA
<213> ORGANISM: Homo sapiens

<400> SEQUENCE: 113

```
cagtctgtgc tgacgcagtc gccctcagtg tctggggccc cagggcagag ggtcaccatc    60
tcctgcactg ggagcagctc caacatcggg gcaggttatg atgtacactg gtaccagcag   120
cttccaggaa cagcccccag actcctcatc tatggtaaca acaatcgtcc ctcagggguc   180
cctgaccgat tctctggctc caagtctggc acctcagcct ccctggccat cactgggctc   240
caggctgagg atgaggctga ttattactgc cagtcctatg acagcagcct gagtggttcg   300
gtgttcggcg gagggaccaa gctgaccgtc cta                                333
```

<210> SEQ ID NO 114
<211> LENGTH: 111
<212> TYPE: PRT
<213> ORGANISM: Homo sapiens

<400> SEQUENCE: 114

```
Gln Ser Val Leu Thr Gln Ser Pro Ser Val Ser Gly Ala Pro Gly Gln
 1               5                  10                  15

Arg Val Thr Ile Ser Cys Thr Gly Ser Ser Ser Asn Ile Gly Ala Gly
             20                  25                  30

Tyr Asp Val His Trp Tyr Gln Gln Leu Pro Gly Thr Ala Pro Arg Leu
             35                  40                  45

Leu Ile Tyr Gly Asn Asn Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Ser Val Phe Gly Gly Gly Thr Lys Leu Thr Val Leu
             100                 105                 110
```

<210> SEQ ID NO 115
<211> LENGTH: 366
<212> TYPE: DNA
<213> ORGANISM: Homo sapiens

<400> SEQUENCE: 115

```
caggtgcagc tggtggagtc tgggggaggc gtggtccagc ctgggaggtc cctgagactc    60
```

```
tcctgtgcag cgtctggatt caccttcagc agctatggca tgcactgggt ccgccaggct    120
ccaggcaagg ggctggagtg ggtggcagtt atatggtatg atggaagaaa taaatacaat    180
gcagactccg tgaagggccg attcaccatc tccagagaca attccaagaa cacgctgaat    240
ctgcaaatga acagcctgag agccgaggac acggctgtgt attactgtgc gagagattta    300
acgtattacg atattttggg cggtatggac gtctggggcc aagggaccac ggtcaccgtc    360
tcctca                                                               366
```

<210> SEQ ID NO 116
<211> LENGTH: 122
<212> TYPE: PRT
<213> ORGANISM: Homo sapiens

<400> SEQUENCE: 116

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Arg Asn Lys Tyr Asn Ala Asp Ser Val
     50                  55                  60

Lys Gly Arg Phe Thr Ile Ser Arg Asp Asn Ser Lys Asn Thr Leu Asn
 65                  70                  75                  80

Leu Gln Met Asn Ser Leu Arg Ala Glu Asp Thr Ala Val Tyr Tyr Cys
                 85                  90                  95

Ala Arg Asp Leu Thr Tyr Tyr Asp Ile Leu Gly Gly Met Asp Val Trp
            100                 105                 110

Gly Gln Gly Thr Thr Val Thr Val Ser Ser
        115                 120
```

<210> SEQ ID NO 117
<211> LENGTH: 324
<212> TYPE: DNA
<213> ORGANISM: Homo sapiens

<400> SEQUENCE: 117

```
tcttctgagc tgactcagga ccctgctgtg tctgtggcct tgggacagac agtcaggatc     60
acatgccaag agacagcct cagaagatat tatgcaagct ggtaccagca gaagccagga    120
caggccccta tagttgtcat ctatggtaaa aaaaaccggc cctcagggat cccagaccga    180
ttctctggct ccagctcagg aaacacagct tccttgacca tcactggggc tcaggcggaa    240
gatgaggctg actattactg taagtcccgg gacagcagtg taaccatct ggtattcggc    300 ggagggacca agctgaccgt ccta                                           324
```

<210> SEQ ID NO 118
<211> LENGTH: 108
<212> TYPE: PRT
<213> ORGANISM: Homo sapiens

<400> SEQUENCE: 118

```
Ser Ser Glu Leu Thr Gln Asp Pro Ala Val Ser Val Ala Leu Gly Gln
  1               5                  10                  15

Thr Val Arg Ile Thr Cys Gln Gly Asp Ser Leu Arg Arg Tyr Tyr Ala
             20                  25                  30

Ser Trp Tyr Gln Gln Lys Pro Gly Gln Ala Pro Ile Val Val Ile Tyr
```

```
                35                  40                  45
Gly Lys Lys Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Lys Ser Arg Asp Ser Ser Gly Asn His
                 85                  90                  95

Leu Val Phe Gly Gly Gly Thr Lys Leu Thr Val Leu
            100                 105
```

<210> SEQ ID NO 119
<211> LENGTH: 345
<212> TYPE: DNA
<213> ORGANISM: Homo sapiens

<400> SEQUENCE: 119

| | | |
|---|---|---|
| gaggtgcagc tggtggagtc tggaggaggc ttgatccagc ctgggggtc cctgagactc | 60 |
| tcctgtgcag cctctgggtt caccgtcagt agcaactaca tgagctgggt ccgccaggct | 120 |
| ccagggaagg gtctggagtg gtctcagtt atttatagcg gtggtggcac atactacgca | 180 |
| gactccgtga aggccgatt caccatctcc agagacaatt ccaagaacac gctgtatctt | 240 |
| caaatgaaca gcctgagagc cgaggacacg gccgtgtatt actgtgcgag aggaccgggg | 300 |
| tcctttgact actggggcca gggaaccctg gtcaccgtct cctca | 345 |

<210> SEQ ID NO 120
<211> LENGTH: 115
<212> TYPE: PRT
<213> ORGANISM: Homo sapiens

<400> SEQUENCE: 120

```
Glu Val Gln Leu Val Glu Ser Gly Gly Gly Leu Ile Gln Pro Gly Gly
  1               5                  10                  15

Ser Leu Arg Leu Ser Cys Ala Ala Ser Gly Phe Thr Val Ser Ser Asn
             20                  25                  30

Tyr Met Ser Trp Val Arg Gln Ala Pro Gly Lys Gly Leu Glu Trp Val
         35                  40                  45

Ser Val Ile Tyr Ser Gly Gly Gly Thr Tyr Tyr Ala Asp Ser Val Lys
    50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Pro Gly Ser Phe Asp Tyr Trp Gly Gln Gly Thr Leu Val Thr
            100                 105                 110

Val Ser Ser
        115
```

<210> SEQ ID NO 121
<211> LENGTH: 321
<212> TYPE: DNA
<213> ORGANISM: Homo sapiens

<400> SEQUENCE: 121

| | | |
|---|---|---|
| gacatccaga tgacccagtc tccatcttcc gtgtctgcat ctgtaggaga cagagtcacc | 60 |
| atcacttgtc gggcgagtca gggtattagc agctggttag cctggtatca gcagaaacca | 120 |
| gggaaagccc ctaagctcct gatctatgct gcatccagtt tgcaaagtgg ggtcccatca | 180 |

```
aggttcagcg gcagtggatc tgggacagat tttactctca ccatcagcag cctgcagcct      240
gaagattttg caagttacta ttgtcaacag gctaacagtt tcccgtggac gttcggccaa      300
gggaccaagg tggaaatcaa a                                                321
```

<210> SEQ ID NO 122
<211> LENGTH: 107
<212> TYPE: PRT
<213> ORGANISM: Homo sapiens

<400> SEQUENCE: 122

```
Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Ser Tyr Tyr Cys Gln Gln Ala Asn Ser Phe Pro Trp
                 85                  90                  95

Thr Phe Gly Gln Gly Thr Lys Val Glu Ile Lys
            100                 105
```

<210> SEQ ID NO 123
<211> LENGTH: 369
<212> TYPE: DNA
<213> ORGANISM: Homo sapiens

<400> SEQUENCE: 123

```
caggtgcagc tggtggagtc tgggggaggc gtggtccagc ctggggaggtc cctgagactc       60 tcctgtgcag cgtctggatt caccttcagt agctatggca tgcactgggt ccgccaggct      120
ccaggcaagg ggctggagtg gtggcagtt atatggtatg atggaagtat taaatactat      180
gcagactccg tgaagggccg attcaccatc tccagagaca attccaagaa cacgctgtat      240
ctgcaaatga acagcctgag agccgaggac acggctgtgt attactgtgc gagagagcgg      300
gatagcagtg gctggtacta ctacggtatg gacgtctggg gccaagggac cacggtcacc      360
gtctcctca                                                               369
```

<210> SEQ ID NO 124
<211> LENGTH: 123
<212> TYPE: PRT
<213> ORGANISM: Homo sapiens

<400> SEQUENCE: 124

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Ile Lys Tyr Tyr Ala Asp Ser Val
     50                  55                  60

Lys Gly Arg Phe Thr Ile Ser Arg Asp Asn Ser Lys Asn Thr Leu Tyr
```

```
            65                  70                  75                  80
Leu Gln Met Asn Ser Leu Arg Ala Glu Asp Thr Ala Val Tyr Tyr Cys
                    85                  90                  95

Ala Arg Glu Arg Asp Ser Ser Gly Trp Tyr Tyr Tyr Gly Met Asp Val
                100                 105                 110

Trp Gly Gln Gly Thr Thr Val Thr Val Ser Ser
        115                 120
```

<210> SEQ ID NO 125
<211> LENGTH: 321
<212> TYPE: DNA
<213> ORGANISM: Homo sapiens

<400> SEQUENCE: 125

```
gacatccaga tgacccagtc tccatcctcc ctgtctgcat ctgtaggaga cagagtcacc    60
atcacttgcc gggcaagtca gggcattaga aatgatttag␣ctggtatca gcagaaacca   120
gggaaagccc␣ctaagcgcct gatctatgct gcatccagtt␣tgcaaagtgg ggtcccatca   180
aggttcagcg gcagtggatc tgggacagaa ttcactctca cagtcagcag cctgcagcct   240
gaagattttg caacttatta ctgtctacag cataatagtc tcccgctcac tttcggcgga   300
gggaccaagg ttgagatcaa a                                             321
```

<210> SEQ ID NO 126
<211> LENGTH: 107
<212> TYPE: PRT
<213> ORGANISM: Homo sapiens

<400> SEQUENCE: 126

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
                 20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Val Ser Ser Leu Gln Pro
 65                 70                  75                  80

Glu Asp Phe Ala Thr Tyr Tyr Cys Leu Gln His Asn Ser Leu Pro Leu
                85                  90                  95

Thr Phe Gly Gly Gly Thr Lys Val Glu Ile Lys
            100                 105
```

<210> SEQ ID NO 127
<211> LENGTH: 378
<212> TYPE: DNA
<213> ORGANISM: Homo sapiens

<400> SEQUENCE: 127

```
caggtgcagc tggtggagtc tgggggaggc gtggtccagc ctgggaggtc cctgagactc    60
tcctgtgcag cgtctggatt caccttcagt aactatggca tgcactgggt ccgccaggct   120
ccaggcaagg␣ggctggagtg␣ggtggcagtt␣atatggtatg␣atggaagtaa␣taaatactat   180
gcagactccg tgaagggccg attcaccatc tccagagaca attccaagaa cacgctgtat   240
ctgcaaatga acagcctgag agccgaggac acggctgtgt attactgtgc gagagagggg   300
atagcagtgg␣ctggtcctcc␣ttactactac␣tacggtatgg␣acgtctgggg␣ccaagggacc   360
```
acggtcaccg tctcctca     378

<210> SEQ ID NO 128
<211> LENGTH: 126
<212> TYPE: PRT
<213> ORGANISM: Homo sapiens

<400> SEQUENCE: 128

```
Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Ser Asn Tyr
            20                  25                  30
Gly Met His Trp Val Arg Gln Ala Pro Gly Lys Gly Leu Glu Trp Val
        35                  40                  45
Ala Val Ile Trp Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Gly Ile Ala Val Ala Gly Pro Pro Tyr Tyr Tyr Tyr Gly
            100                 105                 110
Met Asp Val Trp Gly Gln Gly Thr Thr Val Thr Val Ser Ser
        115                 120                 125
```

<210> SEQ ID NO 129
<211> LENGTH: 318
<212> TYPE: DNA
<213> ORGANISM: Homo sapiens

<400> SEQUENCE: 129
gacatccaga tgacccagtc tccatcctcc ctgtctgcat ctgtaggaga cagagtcacc     60
atcacttgcc aggcgagtca ggacattagc aactatttaa attggtatca gcagaaacca    120
gggaaagccc ctaagctcct gatctacgat gcatccaatt tggaaacagg ggtcccatca    180
aggttcagtg gaagtggatc tgggacagat tttactttca ccatcagcag cctgcagcct    240
gaagatattg caacatatta ctgtcaccag tgtgataatc tccctcactt cggccaaggg    300
acacgactgg agattaaa    318

<210> SEQ ID NO 130
<211> LENGTH: 106
<212> TYPE: PRT
<213> ORGANISM: Homo sapiens

<400> SEQUENCE: 130

```
Asp Ile Gln Met Thr Gln Ser Pro Ser Ser Leu Ser Ala Ser Val Gly
 1               5                  10                  15
Asp Arg Val Thr Ile Thr Cys Gln Ala Ser Gln Asp Ile Ser Asn Tyr
            20                  25                  30
Leu Asn Trp Tyr Gln Gln Lys Pro Gly Lys Ala Pro Lys Leu Leu Ile
        35                  40                  45
Tyr Asp Ala Ser Asn Leu Glu Thr Gly Val Pro Ser Arg Phe Ser Gly
    50                  55                  60
Ser Gly Ser Gly Thr Asp Phe Thr Phe Thr Ile Ser Ser Leu Gln Pro
65                  70                  75                  80
Glu Asp Ile Ala Thr Tyr Tyr Cys His Gln Cys Asp Asn Leu Pro His
```

```
                    85                  90                  95
Phe Gly Gln Gly Thr Arg Leu Glu Ile Lys
            100                 105

<210> SEQ ID NO 131
<211> LENGTH: 369
<212> TYPE: DNA
<213> ORGANISM: Homo sapiens

<400> SEQUENCE: 131
caggtgcagc tggtggagtc tgggggaggc gtggtccagc ctggagggtc cctgagactc      60
tcctgtgcag cgtctggatt aatcttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagagcgg     300
gatagcagtg gctggtacta ctacggtatg gacgtctggg gccaagggac cacggtcacc     360
gtctcctca                                                             369

<210> SEQ ID NO 132
<211> LENGTH: 123
<212> TYPE: PRT
<213> ORGANISM: Homo sapiens

<400> SEQUENCE: 132

Gln Val Gln Leu Val Glu Ser Gly Gly Gly Val Val Gln Pro Gly Arg
1               5                   10                  15

Ser Leu Arg Leu Ser Cys Ala Ala Ser Gly Leu Ile Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Asp Ser Ser Gly Trp Tyr Tyr Tyr Gly Met Asp Val
            100                 105                 110

Trp Gly Gln Gly Thr Thr Val Thr Val Ser Ser
        115                 120

<210> SEQ ID NO 133
<211> LENGTH: 321
<212> TYPE: DNA
<213> ORGANISM: Homo sapiens

<400> SEQUENCE: 133
gacatccaga tgacccagtc tccatcctcc ctgtctgcat ctgtaggaga cagagtcacc      60
atcacttgcc gggcaagtca ggccattaga aatgatttag gctggtatca gcagaaacca     120
gggaaagccc ctaagcgcct gatctatgct gcctccagtt tgcaaagtgg ggtcccatca     180
aggttcagcg gcagtcgatc tgggacagaa ttcaccctca caatcagcag cctgcagcct     240
gaagattttg caagttatta ctgtctacag cataggagtt acccgctcac tttcggcgga     300
gggaccaagg tggagatcaa a                                               321
```

<210> SEQ ID NO 134
<211> LENGTH: 107
<212> TYPE: PRT
<213> ORGANISM: Homo sapiens

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Glu Asp Phe Ala Ser Tyr Tyr Cys Leu Gln His Arg Ser Tyr Pro Leu
                85                  90                  95

Thr Phe Gly Gly Gly Thr Lys Val Glu Ile Lys
            100                 105

<210> SEQ ID NO 135
<211> LENGTH: 345
<212> TYPE: DNA
<213> ORGANISM: Homo sapiens

<400> SEQUENCE: 135
gaggtgcagc tggtggagtc tggaggaggc ttgatccagc ctggggggtc cctgagactc      60
tcctgtgcag cctctgggtt caccgtcagt agcaactaca tgagctgggt ccgccaggct     120
ccagggaagg gctggagtg gtctcagtt atttatagcg gtggtagcac atactacgca      180
gactccgtga aggccgatt caccatctcc agagacaatt ccaagaacac gctgtatctt     240
caaatgaaca gcctgagagc cgaggacacg gccgtgtatt actgtgcgag aggcgaagga     300
ggtatggacg tctggggcca agggaccacg gtcaccgtct cctca                    345

<210> SEQ ID NO 136
<211> LENGTH: 115
<212> TYPE: PRT
<213> ORGANISM: Homo sapiens

<400> SEQUENCE: 136

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Glu Gly Gly Met Asp Val Trp Gly Gln Gly Thr Thr Val Thr
            100                 105                 110

Val Ser Ser

<210> SEQ ID NO 137
<211> LENGTH: 321
<212> TYPE: DNA
<213> ORGANISM: Homo sapiens

<400> SEQUENCE: 137

```
gaaatagtga tgacgcagtc tccatccacc ctgtctgtgt ctccagggga aagagccacc      60
ctctcctgca gggccagtca gagtgttagc agcaacttag cctggtacca gcagaaacct     120
ggccaggctc ccaggctcct catctatggt gcatccatca gggccactgg tatcccagcc     180
aggttcagtg gcagtgggtc tgggacagag tacactctca ccatcagcag cctgcagtct     240
gaagattttg cagtttatta ctgtcaacag tataataact ggccattcac tttcggccct     300
gggaccaaag tggatatcaa a                                               321
```

<210> SEQ ID NO 138
<211> LENGTH: 107
<212> TYPE: PRT
<213> ORGANISM: Homo sapiens

<400> SEQUENCE: 138

Glu Ile Val Met Thr Gln Ser Pro Ser Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Ile Arg Ala Thr Gly Ile Pro Ala Arg Phe Ser Gly
    50                  55                  60

Ser Gly Ser Gly Thr Glu Tyr Thr Leu Thr Ile Ser Ser Leu Gln Ser
65                  70                  75                  80

Glu Asp Phe Ala Val Tyr Tyr Cys Gln Gln Tyr Asn Asn Trp Pro Phe
                85                  90                  95

Thr Phe Gly Pro Gly Thr Lys Val Asp Ile Lys
            100                 105

<210> SEQ ID NO 139
<211> LENGTH: 348
<212> TYPE: DNA
<213> ORGANISM: Homo sapiens

<400> SEQUENCE: 139

```
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtagaa gtggtagtac catatactac     180
gcagactctg tgaagggccg attcaccatc tccagggaca acgccaagaa ctcactgtat     240
ctgcaaatga acagcctgag agccgaggac acggccgtgt attactgtgc gagatcttta     300
ggcggtatgg acgtctgggg ccaagggacc acggtcaccg tctcctca                  348
```

<210> SEQ ID NO 140
<211> LENGTH: 116
<212> TYPE: PRT
<213> ORGANISM: Homo sapiens

<400> SEQUENCE: 140

```
Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
             20                  25                  30

Tyr Met Ser Trp Ile Arg Gln Ala Pro Gly Lys Gly Leu Glu Trp Val
         35                  40                  45

Ser Tyr Ile Ser Arg Ser Gly Ser Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Leu Gly Gly Met Asp Val Trp Gly Gln Gly Thr Thr Val
            100                 105                 110

Thr Val Ser Ser
        115
```

<210> SEQ ID NO 141
<211> LENGTH: 321
<212> TYPE: DNA
<213> ORGANISM: Homo sapiens

<400> SEQUENCE: 141

```
gacatccaga tgacccagtc tccatcctcc ctgtctgcat ctgtaggaga cagagtcgcc    60
atcacttgcc ggacaagtca gagcattagc agttatttaa attggtatca gcagaaacca   120
gggaaagccc ctgagctcct gatctatgct gcatccaatt tgcaaagtgg ggtcccatca   180
aggttcagtg gcagtggatc tgggacagat tcactctca ccatcagcag tctgcaacct   240
gaagattttg caacttacta ctgtcaacag agttccagta ccctcatcac cttcggccaa   300
gggacacgac tggagattaa a                                             321
```

<210> SEQ ID NO 142
<211> LENGTH: 107
<212> TYPE: PRT
<213> ORGANISM: Homo sapiens

<400> SEQUENCE: 142

```
Asp Ile Gln Met Thr Gln Ser Pro Ser Ser Leu Ser Ala Ser Val Gly
  1               5                  10                  15

Asp Arg Val Ala Ile Thr Cys Arg Thr Ser Gln Ser Ile Ser Ser Tyr
             20                  25                  30

Leu Asn Trp Tyr Gln Gln Lys Pro Gly Lys Ala Pro Glu Leu Leu Ile
         35                  40                  45

Tyr Ala Ala Ser Asn Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Ser Ser Thr Leu Ile
                 85                  90                  95

Thr Phe Gly Gln Gly Thr Arg Leu Glu Ile Lys
            100                 105
```

<210> SEQ ID NO 143
<211> LENGTH: 345
<212> TYPE: DNA
<213> ORGANISM: Homo sapiens

<400> SEQUENCE: 143

```
gaggtgcagc tggtggagtc tggaggaggc ttgatccagc ctggggggtc cctgagactc        60
tcctgtgcag cctctgggtt caccgtcagt agcaactacg tgaactgggt ccgccaggct       120
ccagggaagg gctggagtg gtctcagtt atttataacg ctggtagcgc gtactacgca        180
gactccgtga agggccgatt caccatctcc agagacaatt ccaagaacac gctgtttctt       240
caaatgaaca gcctgagagc cgaggacacg gccgtgtatt actgtgcgag aggaactggg       300
gcctttgact actggggcca gggaaccctg gtcaccgtct cctca                      345
```

<210> SEQ ID NO 144
<211> LENGTH: 115
<212> TYPE: PRT
<213> ORGANISM: Homo sapiens

<400> SEQUENCE: 144

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Val Asn Trp Val Arg Gln Ala Pro Gly Lys Gly Leu Glu Trp Val
        35                  40                  45

Ser Val Ile Tyr Asn Ala Gly Ser Ala Tyr Tyr Ala Asp Ser Val Lys
    50                  55                  60

Gly Arg Phe Thr Ile Ser Arg Asp Asn Ser Lys Asn Thr Leu Phe Leu
65                  70                  75                  80

Gln Met Asn Ser Leu Arg Ala Glu Asp Thr Ala Val Tyr Tyr Cys Ala
                85                  90                  95

Arg Gly Thr Gly Ala Phe Asp Tyr Trp Gly Gln Gly Thr Leu Val Thr
            100                 105                 110

Val Ser Ser
        115

<210> SEQ ID NO 145
<211> LENGTH: 321
<212> TYPE: DNA
<213> ORGANISM: Homo sapiens

<400> SEQUENCE: 145

```
gaaatagtga tgacgcagtc tccagccacc ctgtctgtgt ctccagggga aagagccacc        60
ctctcctgca gggccagtca gagtgttagc agcaacttag cctggtacca gcagaaacct       120
ggccaggctc ccagactcct catctatggt gcatccacca gggccactgg tatcccagcc       180
aggttcagtg gcagtaggac tgggacagag ttcactctca ccatcagcag cctgcagtct       240
gaagattttg cagtttatta ctgtcagcag tataataact ggcctctcac tttcggcgga       300
gggaccaagg tggagatcaa a                                                  321
```

<210> SEQ ID NO 146
<211> LENGTH: 107
<212> TYPE: PRT
<213> ORGANISM: Homo sapiens

<400> SEQUENCE: 146

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

```
Leu Ala Trp Tyr Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Gly
         50                  55                  60

Ser Arg Thr Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Leu
                 85                  90                  95

Thr Phe Gly Gly Gly Thr Lys Val Glu Ile Lys
                100                 105
```

<210> SEQ ID NO 147
<211> LENGTH: 348
<212> TYPE: DNA
<213> ORGANISM: Homo sapiens

<400> SEQUENCE: 147

```
caggtgcagc tggtggagtc tgggggaggc ttggtcaagc ctggagggtc cctgagactc     60
tcctgtgcag cctctggatt caccttcagt gactactaca tgagctggat ccgccaggct    120
ccagggaagg gctggagtg  gtttcatac  attagtagaa gtggtagtac catatactac    180
gcagactctg tgaagggccg attcaccatc tccaggaca  acgccaagaa ctcactgtat    240
ctgcaaatga acagcctgag agccgaggac acggccgtgt attactgtgc gagatcttta    300
ggcggtatgg acgtctgggg ccaagggacc acggtcaccg tctcctca                 348
```

<210> SEQ ID NO 148
<211> LENGTH: 116
<212> TYPE: PRT
<213> ORGANISM: Homo sapiens

<400> SEQUENCE: 148

```
Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
             20                  25                  30

Tyr Met Ser Trp Ile Arg Gln Ala Pro Gly Lys Gly Leu Glu Trp Val
         35                  40                  45

Ser Tyr Ile Ser Arg Ser Gly Ser Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Leu Gly Gly Met Asp Val Trp Gly Gln Gly Thr Thr Val
                100                 105                 110

Thr Val Ser Ser
        115
```

<210> SEQ ID NO 149
<211> LENGTH: 321
<212> TYPE: DNA
<213> ORGANISM: Homo sapiens

<400> SEQUENCE: 149

```
gacatccaga tgacccagtc tccatcctcc ctgtctgcat ctgtaggaga cagagtcacc     60
atcacttgcc ggacaagtca gagcattagc agctatttaa actggtatca ccagaaacca    120
```

-continued

```
gggaaagccc ctgagctcct gatctatgct gcattcaatt tacaaagtgg ggtcccatca      180
aggttcagtg gcagtggatc tgggacagat tcactctca ccatcagcag tctgcaacct       240
gaagattttg caacttacta ctgtcaacag agttccagta ccctcatcac cttcggccaa      300
gggacacgac tggagattaa a                                                321
```

<210> SEQ ID NO 150
<211> LENGTH: 107
<212> TYPE: PRT
<213> ORGANISM: Homo sapiens

<400> SEQUENCE: 150

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Ser Tyr
            20                  25                  30

Leu Asn Trp Tyr His Gln Lys Pro Gly Lys Ala Pro Glu Leu Leu Ile
        35                  40                  45

Tyr Ala Ala Phe Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ser Thr Leu Ile
                85                  90                  95

Thr Phe Gly Gln Gly Thr Arg Leu Glu Ile Lys
            100                 105

<210> SEQ ID NO 151
<211> LENGTH: 345
<212> TYPE: DNA
<213> ORGANISM: Homo sapiens

<400> SEQUENCE: 151

```
gaggtgcagc tggtggagtc tggaggaggc ttgatccagc ctgggggtc cctgagactc       60 tcctgtgcag cctctgggtt caccgtcagt agcaactaca tgagctgggt ccgccaggct     120
ccagggaagg ggctggagtg ggtctcagtt atttatagcg gtggtagcac atactacgca     180
gactccgtga agggccgatt caccatctcc agagacaatt ccaagaacac gctgtatctt     240
caaatgaaca gcctgagagc cgaggacacg gccgtgtatt actgtgcgag aggcgaagga     300 ggtatgacg tctggggcca agggaccacg gtcaccgtct cctca                      345
```

<210> SEQ ID NO 152
<211> LENGTH: 115
<212> TYPE: PRT
<213> ORGANISM: Homo sapiens

<400> SEQUENCE: 152

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu

```
                65                  70                  75                  80
            Gln Met Asn Leu Arg Ala Glu Asp Thr Ala Val Tyr Tyr Cys Ala
                            85                  90                  95
            Arg Gly Glu Gly Gly Met Asp Val Trp Gly Gln Gly Thr Thr Val Thr
                            100                 105                 110
            Val Ser Ser
                    115

<210> SEQ ID NO 153
<211> LENGTH: 324
<212> TYPE: DNA
<213> ORGANISM: Homo sapiens

<400> SEQUENCE: 153
tcctatgagc tgacacagcc accctcggtg tcagtgtccc caggacaaac ggccaggatc       60
acctgctctg gagatgcatt gccaaaaaaa tatgtttatt ggtaccagca gaagtcaggc      120
caggcccctg tgctggtcat ctatgaggac agcaaacgac cctccgggat ccctgagaga      180
ttctctggct ccagctcagg gacaatggcc accttgacta tcaatgggrc ccaggtggag      240
gatgaagctg actactactg ttactcaacg gacagcagtg gtaatcatgt ggtattcggc      300
ggagggacca agctgaccgt ccta                                             324

<210> SEQ ID NO 154
<211> LENGTH: 108
<212> TYPE: PRT
<213> ORGANISM: Homo sapiens

<400> SEQUENCE: 154

Ser Tyr Glu Leu Thr Gln Pro Pro Ser Val Ser Val Ser Pro Gly Gln
 1               5                   10                  15

Thr Ala Arg Ile Thr Cys Ser Gly Asp Ala Leu Pro Lys Lys Tyr Val
                20                  25                  30

Tyr Trp Tyr Gln Gln Lys Ser Gly Gln Ala Pro Val Leu Val Ile Tyr
            35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Asn Gly Ala Gln Val Glu
65                  70                  75                  80

Asp Glu Ala Asp Tyr Tyr Cys Tyr Ser Thr Asp Ser Ser Gly Asn His
                85                  90                  95

Val Val Phe Gly Gly Gly Thr Lys Leu Thr Val Leu
            100                 105

<210> SEQ ID NO 155
<211> LENGTH: 321
<212> TYPE: DNA
<213> ORGANISM: Homo sapiens

<400> SEQUENCE: 155
gacatccaga tgacccagtc tccatcctcc ctgtctgcat ctgtaggaga cagagtcacc       60
atcacttgcc ggacaagtca gagcattagc agctatttaa attggtatca gcagaaacca      120
gggaaagccc ctgaggtcct gatctatgct gcatccaatt tgcaacgtgg ggtcccatca      180
aggttcagtg gcagtggatc tgggacagat ttcactctca ccatcagcag tctgcaacct      240
gaagattttg caacttacta ctgtcaacag agttccagta ccctcatcac cttcggccaa      300
gggacacgac tggagattaa a                                                321
```

<210> SEQ ID NO 156
<211> LENGTH: 107
<212> TYPE: PRT
<213> ORGANISM: Homo sapiens

<400> SEQUENCE: 156

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Ser Tyr
            20                  25                  30

Leu Asn Trp Tyr Gln Gln Lys Pro Gly Lys Ala Pro Glu Val Leu Ile
        35                  40                  45

Tyr Ala Ala Ser Asn Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ser Thr Leu Ile
                85                  90                  95

Thr Phe Gly Gln Gly Thr Arg Leu Glu Ile Lys
            100                 105

<210> SEQ ID NO 157
<211> LENGTH: 369
<212> TYPE: DNA
<213> ORGANISM: Homo sapiens

<400> SEQUENCE: 157
gaggtgcagc tggtggagtc tgggggaggc ctggtcaagc ctggggggtc cctgagactc      60
tcctgtgcag cctctggatt caccttcagt agctatagca tgaactgggt ccgccaggct     120
ccagggaagg ggctggagtg gtctcatct attagtagta gtagtagtta catatactac     180
gcagactcag tgaagggccg attcaccatc tccagagaca acgccaagaa ctcactgtat     240
ctgcaaatga acagcctgag agccgaggac acggctgtgt attactgtgc gagggggggt     300
ataactggaa ctacgaacta ctacggtatg gacgtctggg gccaagggac cacggtcacc     360
gtctcctca                                                             369

<210> SEQ ID NO 158
<211> LENGTH: 123
<212> TYPE: PRT
<213> ORGANISM: Homo sapiens

<400> SEQUENCE: 158

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ile Thr Gly Thr Thr Asn Tyr Tyr Gly Met Asp Val

-continued

```
                    100                 105                 110

Trp Gly Gln Gly Thr Thr Val Thr Val Ser Ser
        115                 120

<210> SEQ ID NO 159
<211> LENGTH: 321
<212> TYPE: DNA
<213> ORGANISM: Homo sapiens

<400> SEQUENCE: 159
gacatccaga tgacccagtc tccatcctcc ctgtctgcat ctgtaggaga cagagtcacc    60
atcacttgcc ggacaagtca gagcattagc agctatttaa attggtatca gcagaaacca   120
gggaaagccc ctgaactcct gatctatgct gcatttaatt tgcaaagtgg ggtcccatca   180
aggatcagtg gcagtggatc tgggacagat ttcactctca ccatcagcag tctgcaccct   240
gaagattttg caacttacta ctgtcaacag agttccagta ccctcatcac cttcggccaa   300
gggacacgac tggagattaa a                                             321

<210> SEQ ID NO 160
<211> LENGTH: 107
<212> TYPE: PRT
<213> ORGANISM: Homo sapiens

<400> SEQUENCE: 160

Asp Ile Gln Met Thr Gln Ser Pro Ser Ser Leu Ser Ala Ser Val Gly
 1               5                  10                  15

Asp Arg Val Thr Ile Thr Cys Arg Thr Ser Gln Ser Ile Ser Ser Tyr
            20                  25                  30

Leu Asn Trp Tyr Gln Gln Lys Pro Gly Lys Ala Pro Glu Leu Leu Ile
        35                  40                  45

Tyr Ala Ala Phe Asn Leu Gln Ser Gly Val Pro Ser Arg Ile Ser Gly
    50                  55                  60

Ser Gly Ser Gly Thr Asp Phe Thr Leu Thr Ile Ser Ser Leu His Pro
65                  70                  75                  80

Glu Asp Phe Ala Thr Tyr Tyr Cys Gln Gln Ser Ser Ser Thr Leu Ile
                85                  90                  95

Thr Phe Gly Gln Gly Thr Arg Leu Glu Ile Lys
            100                 105

<210> SEQ ID NO 161
<211> LENGTH: 375
<212> TYPE: DNA
<213> ORGANISM: Homo sapiens

<400> SEQUENCE: 161
caggtgcagc tggtgcagtc tggggctgag gtgaagaagc ctggggcctc agtgaaggtc    60
tcctgcaagg cttctggata caccttcacc ggctactata tgcactgggt gcgacaggcc   120
cctggacaag gcttgagtg gatgggatgg atcaacccta acagtggtgg cacaaactat   180
gcacagaagt ttcagggcag ggtcaccatg accagggaca cgtccatcag cacagcctac   240
atggagctga gcaggctgag atctgacgac acggccgtgt attactgtgc gagagcccct   300
ctctggacgg tacgtagctg gtactactac ggtatggacg tctggggcca agggaccacg   360
gtcaccgtct cctca                                                    375

<210> SEQ ID NO 162
<211> LENGTH: 125
```

<212> TYPE: PRT
<213> ORGANISM: Homo sapiens

<400> SEQUENCE: 162

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ala Pro Leu Trp Thr Val Arg Ser Trp Tyr Tyr Gly Met
            100                 105                 110

Asp Val Trp Gly Gln Gly Thr Thr Val Thr Val Ser Ser
        115                 120                 125
```

<210> SEQ ID NO 163
<211> LENGTH: 330
<212> TYPE: DNA
<213> ORGANISM: Homo sapiens

<400> SEQUENCE: 163

| | | | | | |
|---|---|---|---|---|---|
| cagtctgtat | tgacgcagcc | gccctcaatg | tctgcggccc | caggacagaa ggtcaccatc | 60 |
| tcctgctctg | gaagcagctc | caacattggg | aataattatg | tatcctggta ccagcagctc | 120 |
| ccaggaatag | cccccaaact | cctcatttat | gacaataata | agcgaccctc agggattcct | 180 |
| gaccgattct | ctggctccaa | gtctggcacg | tcagccaccc | tgggcatcac cggactccag | 240 |
| actggggacg | aggccgatta | ttactgcgga | acatgggata | gcagcctgag tgctggggtg | 300 |
| ttcggcggag | ggaccaagct | gaccgtccta | | | 330 |

<210> SEQ ID NO 164
<211> LENGTH: 110
<212> TYPE: PRT
<213> ORGANISM: Homo sapiens

<400> SEQUENCE: 164

```
Gln Ser Val Leu Thr Gln Pro Pro Ser Met Ser Ala Ala Pro Gly Gln
 1               5                  10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Ile Ala Pro Lys Leu Leu
        35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Gly Gly Thr Lys Leu Thr Val Leu
            100                 105                 110
```

<210> SEQ ID NO 165
<211> LENGTH: 348
<212> TYPE: DNA
<213> ORGANISM: Homo sapiens

<400> SEQUENCE: 165

```
gaggtgcagc tggtgcagtc tggagcagag gtgaaaaagc ccggggagtc tctgaagatc      60
tcctgtaaga cttctgaata cagctttacc agctactgga tcggctgggt gcgccagatg     120
cccgggaaag gcctggagtg gatggggatc atctatcttg gtgactcaga taccagatac     180
agcccgtcct ccaaggcca ggtcaccatc tcagccgaca gtccatcag taccgcctac      240
ctgcagtgga gcagcctgaa ggcctcggac accgccatgt attactgtgc gagaagtaac     300
tggggtcttg actactgggg ccagggaacc ctggtcaccg tctcctca                  348
```

<210> SEQ ID NO 166
<211> LENGTH: 116
<212> TYPE: PRT
<213> ORGANISM: Homo sapiens

<400> SEQUENCE: 166

```
Glu Val Gln Leu Val Gln Ser Gly Ala Glu Val Lys Lys Pro Gly Glu
  1               5                  10                  15
Ser Leu Lys Ile Ser Cys Lys Thr Ser Glu Tyr Ser Phe Thr Ser Tyr
             20                  25                  30
Trp Ile Gly Trp Val Arg Gln Met Pro Gly Lys Gly Leu Glu Trp Met
         35                  40                  45
Gly Ile Ile Tyr Leu Gly Asp Ser Asp Thr Arg Tyr Ser Pro Ser Phe
     50                  55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Ser Asn Trp Gly Leu Asp Tyr Trp Gly Gln Gly Thr Leu Val
            100                 105                 110
Thr Val Ser Ser
        115
```

<210> SEQ ID NO 167
<211> LENGTH: 333
<212> TYPE: DNA
<213> ORGANISM: Homo sapiens

<400> SEQUENCE: 167

```
cagtctgtgc tgacgcagcc gccctcagtg tctggggccc cagggcagag ggtcaccatc      60
tcctgcactg ggagcagttc aacatcgggg caggttatg atgtacactg gtaccagcag     120
tttccaggaa cagcccccaa actcctcatc caagtaaca gcaatcggcc ctcaggggtc      180
cctgaccgat tctctggctc caagtctggc acctcagcct ccctggccat cactgggctc     240
caggctgagg atgaggctga ttattactgc cagtcctatg acagcagcct gagtggttcg     300
gtgttcggcg gagggaccaa gctgaccgtc ctt                                  333
```

<210> SEQ ID NO 168
<211> LENGTH: 111
<212> TYPE: PRT
<213> ORGANISM: Homo sapiens

<400> SEQUENCE: 168

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Phe Pro Gly Thr Ala Pro Lys Leu
            35                  40                  45

Leu Ile Gln Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu
            100                 105                 110

<210> SEQ ID NO 169
<211> LENGTH: 351
<212> TYPE: DNA
<213> ORGANISM: Homo sapiens

<400> SEQUENCE: 169
caggttcagc tggtgcagtc tggagctgag gtgaagaagc ctggggcctc agtgaaggtc     60
tcctgcaagg cttctggtta cacctttacg ttctatagta tcacctgggt gcgacaggcc    120
cctggacaag gcttgagtg gatgggatgg atcagcgctt acaatgataa cacaaactat    180
gcacagaagc tccagggcag agtcaccatg accacagaca catccacgag cacagcctac    240
atggaactga ggagcctgag atctgacgac acggccgtgt attactgtgc gagaacgttt    300
accagtggct ttgactactg gggccaggga accctggtca ccgtctcctc a             351

<210> SEQ ID NO 170
<211> LENGTH: 117
<212> TYPE: PRT
<213> ORGANISM: Homo sapiens

<400> SEQUENCE: 170

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Phe Tyr
            20                  25                  30

Ser Ile Thr Trp Val Arg Gln Ala Pro Gly Gln Gly Leu Glu Trp Met
            35                  40                  45

Gly Trp Ile Ser Ala Tyr Asn Asp Asn Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Thr Phe Thr Ser Gly Phe Asp Tyr Trp Gly Gln Gly Thr Leu
            100                 105                 110

Val Thr Val Ser Ser
        115

<210> SEQ ID NO 171
<211> LENGTH: 324
<212> TYPE: DNA
<213> ORGANISM: Homo sapiens -continued

<400> SEQUENCE: 171

```
tcttctgagc tgactcagga ccctgctgtg tctgtggcct tgggacagac agtcaggatc    60
acatgccaag agacagcct cagaaggtat tatgcaagct ggtaccagca gaagccagga   120
caggccccta tacttgtcat ctatggtaaa acaaccggc cctcaggat cccagaccga    180
ttctctggct ccagctcagg aaacacagct tccttgacca tcactgggc tcaggcggaa   240
gatgaggctg actattactg taactcccgg gacagcagtg gtaaccatct ggtgttcggc   300
ggagggacca agctgaccgt ccta                                         324
```

<210> SEQ ID NO 172
<211> LENGTH: 108
<212> TYPE: PRT
<213> ORGANISM: Homo sapiens

<400> SEQUENCE: 172

```
Ser Ser Glu Leu Thr Gln Asp Pro Ala Val Ser Val Ala Leu Gly Gln
  1               5                  10                  15

Thr Val Arg Ile Thr Cys Gln Gly Asp Ser Leu Arg Arg Tyr Tyr Ala
             20                  25                  30

Ser Trp Tyr Gln Gln Lys Pro Gly Gln Ala Pro Ile Leu Val Ile Tyr
         35                  40                  45

Gly Lys Asn Asn Arg Pro Ser Gly Ile Pro Asp Arg Phe Ser Gly Ser
     50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95

Leu Val Phe Gly Gly Gly Thr Lys Leu Thr Val Leu
                100                 105
```

<210> SEQ ID NO 173
<211> LENGTH: 375
<212> TYPE: DNA
<213> ORGANISM: Homo sapiens

<400> SEQUENCE: 173

```
caggtgcagc tggtggagtc tggggaggc gtggtccagc ctgggaggtc cctgagactc    60
tcctgtgcag cgtctggatt taccttcagt agttatgaca tgcactgggt ccgccaggct   120
ccaggcaagg ggctggagtg gtggcagtt atatggtatg atggaagtaa taaataccat   180
gcagactccg tgaagggccg attcaccatc tccagagaca attccaagaa cacgctgtat   240
ctgcaaatga acagcctgag agccgaggac acggctgtgt attactgtgc gagagagaat   300
actatggttc gggggggggga ctactactac ggtatggacg tctggggcca agggaccacg   360
gtcaccgtct cctca                                                  375
```

<210> SEQ ID NO 174
<211> LENGTH: 125
<212> TYPE: PRT
<213> ORGANISM: Homo sapiens

<400> SEQUENCE: 174

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30
```

Asp Met His Trp Val Arg Gln Ala Pro Gly Lys Gly Leu Glu Trp Val
            35                  40                  45

Ala Val Ile Trp Tyr Asp Gly Ser Asn Lys Tyr His Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Asn Thr Met Val Arg Gly Gly Asp Tyr Tyr Tyr Gly Met
            100                 105                 110

Asp Val Trp Gly Gln Gly Thr Thr Val Thr Val Ser Ser
            115                 120                 125

<210> SEQ ID NO 175
<211> LENGTH: 321
<212> TYPE: DNA
<213> ORGANISM: Homo sapiens

<400> SEQUENCE: 175
gacatccaga tgacccagtc tccatcctcc ctgtctgcat ctgtaggaga cagagtcacc     60
atcacttgcc gggcaagtca gggcattaga aatgatttag gctggtatca gcagaaacca    120
aggaaagccc ctaagcgcct gatctttgct gcgtccagtt tgcaaagtgg ggtcccatca    180
aggttcagcg gcagtggatc tgggccagaa ttcactctca caatcagcag cctgcagcct    240
gaagattttg caacttatta ctgtctacag cataatagtt acccgctcac tttcggcgga    300
gggaccaagg tggagatcaa a                                              321

<210> SEQ ID NO 176
<211> LENGTH: 107
<212> TYPE: PRT
<213> ORGANISM: Homo sapiens

<400> SEQUENCE: 176

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Arg Lys Ala Pro Lys Arg Leu Ile
         35                  40                  45

Phe Ala Ala Ser Ser Leu Gln Ser Gly Val Pro Ser Arg Phe Ser Gly
     50                  55                  60

Ser Gly Ser Gly Pro Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Leu
                 85                  90                  95

Thr Phe Gly Gly Gly Thr Lys Val Glu Ile Lys
            100                 105

<210> SEQ ID NO 177
<211> LENGTH: 354
<212> TYPE: DNA
<213> ORGANISM: Homo sapiens

<400> SEQUENCE: 177
caggtgcagc tgcaggagtc gggcccagga ctggtgaagc cttcggagac cctgtccctc     60
acctgcactg tctctggtgg ctccatcagt agttactact ggagctggat ccggcagccc    120

```
ccagggaagg gactggagtg gattgggtat ttctattaca gtgggagcac caactacaac    180
ccctccctca agagtcgagt caccatatca gtagacacgt ccaagaacca gttctccctg    240
aagctgaggt ctgtgaccgc tgcggacacg gccgtgtatt actgtgcgag agataggttt    300
accagtggct ggtttgacta ctggggccag ggaaccctgg tcaccgtctc ctca          354
```

<210> SEQ ID NO 178
<211> LENGTH: 118
<212> TYPE: PRT
<213> ORGANISM: Homo sapiens

<400> SEQUENCE: 178

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Phe Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Arg Asp Arg Phe Thr Ser Gly Trp Phe Asp Tyr Trp Gly Gln Gly Thr
            100                 105                 110

Leu Val Thr Val Ser Ser
        115
```

<210> SEQ ID NO 179
<211> LENGTH: 321
<212> TYPE: DNA
<213> ORGANISM: Homo sapiens

<400> SEQUENCE: 179

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
aggaaagccc ctaagcgcct gatctttgct gcgtccagtt tgcaaagtgg ggtcccatca   180
aggttcagcg gcagtggatc tgggccagaa ttcactctca caatcagcag cctgcagcct   240
gaagattttg caacttatta ctgtctacag cataatagtt acccgctcac tttcggcgga   300
gggaccaagg tggagatcaa a                                             321
```

<210> SEQ ID NO 180
<211> LENGTH: 107
<212> TYPE: PRT
<213> ORGANISM: Homo sapiens

<400> SEQUENCE: 180

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Arg Lys Ala Pro Lys Arg Leu Ile
        35                  40                  45

Phe Ala Ala Ser Ser Leu Gln Ser Gly Val Pro Ser Arg Phe Ser Gly
    50                  55                  60
```

Ser Gly Ser Gly Pro Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 181
<211> LENGTH: 345
<212> TYPE: DNA
<213> ORGANISM: Homo sapiens

<400> SEQUENCE: 181
gaggtgcagc tggtggagtc tggaggaggc ttgatccagc ctgggggtc cctgagactc      60 tcctgtgcag cctctgggtt caccgtcagt aacaactaca tgcactgggt ccgccaggct     120
ccagggaagg gctggagtg gtctcagtt atttatagcg gtggtaacac atactacgca      180
gactccgtga agggccgatt caccatctcc agagacaatt ccaagaacac gctatttctt     240
caaatgaaca gcctgaaaac cgaggacacg gccgtgtatt actgtgcgag aggtcccggg    300
gcttttgata tctggggcca aggacaatg gtcaccgtct cttca                       345

<210> SEQ ID NO 182
<211> LENGTH: 115
<212> TYPE: PRT
<213> ORGANISM: Homo sapiens

<400> SEQUENCE: 182

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Asn Asn
            20                  25                  30

Tyr Met His Trp Val Arg Gln Ala Pro Gly Lys Gly Leu Glu Trp Val
        35                  40                  45

Ser Val Ile Tyr Ser Gly Gly Asn Thr Tyr Tyr Ala Asp Ser Val Lys
    50                  55                  60

Gly Arg Phe Thr Ile Ser Arg Asp Asn Ser Lys Asn Thr Leu Phe Leu
65                  70                  75                  80

Gln Met Asn Ser Leu Lys Thr Glu Asp Thr Ala Val Tyr Tyr Cys Ala
                85                  90                  95

Arg Gly Pro Gly Ala Phe Asp Ile Trp Gly Gln Gly Thr Met Val Thr
            100                 105                 110

Val Ser Ser
        115

<210> SEQ ID NO 183
<211> LENGTH: 321
<212> TYPE: DNA
<213> ORGANISM: Homo sapiens

<400> SEQUENCE: 183
gaaatagtga tgacgcagtc tccagccacc ctgtctgtgt ctccagggga aagagtcacc      60
ctctcctgca gggccagtca gagtgctacc agcaacttag cctggtacca gcagaaacct    120
ggccaggctc ccaggctcct catctatggt gcatccacca gggccactgg tatcccagcc    180
agattcagtg gcagtgggtc tgggacagag ttcactctca ccatcagcag cctgcagtct    240
gaagattttg cagtttatta ctgtcagcag tataataact ggcctttcac cttcggccaa    300
gggacacgac tggagattaa a                                           321

<210> SEQ ID NO 184
<211> LENGTH: 107
<212> TYPE: PRT
<213> ORGANISM: Homo sapiens

<400> SEQUENCE: 184

Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Ala Thr Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Phe
                85                  90                  95

Thr Phe Gly Gln Gly Thr Arg Leu Glu Ile Lys
            100                 105

<210> SEQ ID NO 185
<211> LENGTH: 345
<212> TYPE: DNA
<213> ORGANISM: Homo sapiens

<400> SEQUENCE: 185
gaggtgcagc tggtggagtc tggaggaggc ttgatccagc ctggggggtc cctgagactc     60
tcctgtgcag cctctgggtt caccgtcagt agcaactaca tgagttgggt ccgccaggct    120
ccagggaagg ggctggagtg ggtctcagtt atttatagcg gtggtagcac atactacgca    180
gactccgtga aggccgatt caccatctcc agagacaatt ccaagaacac gctgtatctt    240
caaatgaaca gcctgagagc cgaggacacg gccgtgtatt actgtgcgag aggtcccggg    300
gcttttgata tctggggcca agggacaatg gtcaccgtct cttca                   345

<210> SEQ ID NO 186
<211> LENGTH: 115
<212> TYPE: PRT
<213> ORGANISM: Homo sapiens

<400> SEQUENCE: 186

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Pro Gly Ala Phe Asp Ile Trp Gly Gln Gly Thr Met Val Thr

Val Ser Ser
        115

<210> SEQ ID NO 187
<211> LENGTH: 327
<212> TYPE: DNA
<213> ORGANISM: Homo sapiens

<400> SEQUENCE: 187
gacatccaga tgacccagtc tccatcctcc ctgtctgcat ctgtaggaga cagagtcacc       60
atcacttgcc gggcaagtca gggcattaga aatgatttag gctggtttca gcagaaacca     120
gggaaagccc ctaagcgcct gatctatgct gcatccaatt ttctaagtgg ggtcccatca     180
aggttcagcg gcagtggctc tgggacagaa ttcactctca caatcagcag cctgcagcct     240
gaagatttta caacttatta ctgtctacag cataatcctt accctccgag gctcactttc     300
ggcggaggga ccaaggtaga gatcaaa                                         327

<210> SEQ ID NO 188
<211> LENGTH: 109
<212> TYPE: PRT
<213> ORGANISM: Homo sapiens

<400> SEQUENCE: 188

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Phe Gln Gln Lys Pro Gly Lys Ala Pro Lys Arg Leu Ile
        35                  40                  45

Tyr Ala Ala Ser Asn Phe Leu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Thr Thr Tyr Tyr Cys Leu Gln His Asn Pro Tyr Pro Pro
                85                  90                  95

Arg Leu Thr Phe Gly Gly Gly Thr Lys Val Glu Ile Lys
            100                 105

<210> SEQ ID NO 189
<211> LENGTH: 363
<212> TYPE: DNA
<213> ORGANISM: Homo sapiens

<400> SEQUENCE: 189
caggtgcagc tggtggagtc tgggggaggc gtggtccagc ctgggaggtc cctgagactc       60
tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagagggg     300
gactacggtg gtaaccctta ctttgactac tggggccagg gaaccctggt caccgtctcc     360
tca                                                                   363

<210> SEQ ID NO 190
<211> LENGTH: 121

```
<212> TYPE: PRT
<213> ORGANISM: Homo sapiens

<400> SEQUENCE: 190

Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Asp Tyr Gly Gly Asn Pro Tyr Phe Asp Tyr Trp Gly
            100                 105                 110

Gln Gly Thr Leu Val Thr Val Ser Ser
        115                 120

<210> SEQ ID NO 191
<211> LENGTH: 324
<212> TYPE: DNA
<213> ORGANISM: Homo sapiens

<400> SEQUENCE: 191
tcttctgagc tgactcagga ccctgctgtg tctgtggcct tgggacagac agtcaggatc      60
acatgccaag agacagcct cagaagctat tatgcaagct ggtaccagca aaagccagga     120 caggccctg tacttgtcat ctatggtaaa acaaccggc cctcagggat cccagaccga     180
ttctctggct ccagctcaga aaacacagct tccttgacca tcactgggc tcaggcggaa     240 gatgaggctg actattactg taagtcccgg gacagcagtt ttaaccatct ggtattcggc     300
ggagggacca gttgaccgt ccta                                             324

<210> SEQ ID NO 192
<211> LENGTH: 108
<212> TYPE: PRT
<213> ORGANISM: Homo sapiens

<400> SEQUENCE: 192

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
             20                  25                  30

Ser Trp Tyr Gln Gln Lys Pro Gly Gln Ala Pro Val Leu Val Ile Tyr
         35                  40                  45

Gly Lys Asn Asn Arg Pro Ser Gly Ile Pro Asp Arg Phe Ser Gly Ser
     50                  55                  60

Ser Ser Glu Asn Thr Ala Ser Leu Thr Ile Thr Gly Ala Gln Ala Glu
 65                  70                  75                  80

Asp Glu Ala Asp Tyr Tyr Cys Lys Ser Arg Asp Ser Ser Phe Asn His
                 85                  90                  95

Leu Val Phe Gly Gly Gly Thr Lys Leu Thr Val Leu
            100                 105
```

<210> SEQ ID NO 193
<211> LENGTH: 363
<212> TYPE: DNA
<213> ORGANISM: Homo sapiens

<400> SEQUENCE: 193

```
caggtgcacc tggtggagtc tgggggaggc gtggtccagc ctgggaggtc cctgagactc        60
tcctgtgcag cgtctggatt caccttcagt agctatggca tgcactgggt ccgccaggct       120
ccaggcaagg ggctggagtg ggtggcagtt atatggcatg atggaagtaa taaatactat       180
gcagactccg tgaagggccg attcaccatc tccagagaca attccaagaa cacgctgtat       240
ctgcaaatga acagcctgag agccgaggac acggctgtgt attactgtac aagagagggg       300
gactacggtg gttacccttt ctttgactac tggggccagg gaaccctggt caccgtctcc       360
tca                                                                     363
```

<210> SEQ ID NO 194
<211> LENGTH: 121
<212> TYPE: PRT
<213> ORGANISM: Homo sapiens

<400> SEQUENCE: 194

Gln Val His Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Trp His Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Thr Arg Glu Gly Asp Tyr Gly Gly Tyr Pro Tyr Phe Asp Tyr Trp Gly
            100                 105                 110
Gln Gly Thr Leu Val Thr Val Ser Ser
        115                 120

<210> SEQ ID NO 195
<211> LENGTH: 324
<212> TYPE: DNA
<213> ORGANISM: Homo sapiens

<400> SEQUENCE: 195

```
tcttctgagc tgactcagga ccctgctgtg tctgtggcct tgggacagac agtcaggatc        60
acatgccaag agacatcct cagaagctat tatgcaagct ggtaccagca gaagccagga       120
caggcccctg tacttgtcat ctatggtaaa acaaccggc cctcagggat cccagaccga       180
ttctctggct ccagctcagg aaacacagct tccttgacca tcactgggc tcaggcggaa       240
gatgaggctg actattactg taagtcccgg gacagcagtt ataaccatct ggtattcggc       300
ggagggacca aactgaccgt ccta                                              324
```

<210> SEQ ID NO 196
<211> LENGTH: 108
<212> TYPE: PRT
<213> ORGANISM: Homo sapiens

<400> SEQUENCE: 196

| Ser | Ser | Glu | Leu | Thr | Gln | Asp | Pro | Ala | Val | Ser | Val | Ala | Leu | Gly | Gln |
|---|---|---|---|---|---|---|---|---|---|---|---|---|---|---|---|
| 1 | | | | 5 | | | | | 10 | | | | | 15 | |

| Thr | Val | Arg | Ile | Thr | Cys | Gln | Gly | Asp | Ile | Leu | Arg | Ser | Tyr | Tyr | Ala |
|---|---|---|---|---|---|---|---|---|---|---|---|---|---|---|---|
| | | | 20 | | | | | 25 | | | | | 30 | | |

| Ser | Trp | Tyr | Gln | Gln | Lys | Pro | Gly | Gln | Ala | Pro | Val | Leu | Val | Ile | Tyr |
|---|---|---|---|---|---|---|---|---|---|---|---|---|---|---|---|
| | | 35 | | | | | 40 | | | | | 45 | | | |

| Gly | Lys | Asn | Asn | Arg | Pro | Ser | Gly | Ile | Pro | Asp | Arg | Phe | Ser | Gly | Ser |
|---|---|---|---|---|---|---|---|---|---|---|---|---|---|---|---|
| | 50 | | | | | 55 | | | | | 60 | | | | |

| Ser | Ser | Gly | Asn | Thr | Ala | Ser | Leu | Thr | Ile | Thr | Gly | Ala | Gln | Ala | Glu |
|---|---|---|---|---|---|---|---|---|---|---|---|---|---|---|---|
| 65 | | | | 70 | | | | | 75 | | | | | 80 | |

| Asp | Glu | Ala | Asp | Tyr | Tyr | Cys | Lys | Ser | Arg | Asp | Ser | Ser | Tyr | Asn | His |
|---|---|---|---|---|---|---|---|---|---|---|---|---|---|---|---|
| | | | 85 | | | | | 90 | | | | | 95 | | |

| Leu | Val | Phe | Gly | Gly | Gly | Thr | Lys | Leu | Thr | Val | Leu |
|---|---|---|---|---|---|---|---|---|---|---|---|
| | | | 100 | | | | | 105 | | | |

<210> SEQ ID NO 197
<211> LENGTH: 366
<212> TYPE: DNA
<213> ORGANISM: Homo sapiens

<400> SEQUENCE: 197

```
caggtgcagc tggtggagtc tgggggaggc gtggtccagc ctggaggtc cctgagactc        60
tcctgtgcag cgtctggatt caccttcagt agctatggca tgcactgggt ccgccaggct      120
ccaggcaagg ggctggagtg ggtggcaatt atatggtatg atggaagtaa tgaatactat      180
ggagactccg tgaagggccg attcaccatc tccagagaca attccaagaa cacgctgttt      240
ctgcaaatga acagcctgag agccgaggac acggctgtgt attactgtgc gagagatccc      300
ctccgtatag tagtggctgg ggactttgac tactggggcc agggaaccct ggtcaccgtc      360
tcctca                                                                 366
```

<210> SEQ ID NO 198
<211> LENGTH: 122
<212> TYPE: PRT
<213> ORGANISM: Homo sapiens

<400> SEQUENCE: 198

| Gln | Val | Gln | Leu | Val | Glu | Ser | Gly | Gly | Val | Val | Gln | Pro | Gly | Arg |
|---|---|---|---|---|---|---|---|---|---|---|---|---|---|---|
| 1 | | | | 5 | | | | | 10 | | | | | 15 |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Gly | Met | His | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Ile | Ile | Trp | Tyr | Asp | Gly | Ser | Asn | Glu | Tyr | Tyr | Gly | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Phe |
|---|---|---|---|---|---|---|---|---|---|---|---|---|---|---|---|
| 65 | | | | 70 | | | | | 75 | | | | | 80 | |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | 85 | | | | | 90 | | | | | 95 | | |

| Ala | Arg | Asp | Pro | Leu | Arg | Ile | Val | Val | Ala | Gly | Asp | Phe | Asp | Tyr | Trp |
|---|---|---|---|---|---|---|---|---|---|---|---|---|---|---|---|
| | | | 100 | | | | | 105 | | | | | 110 | | |

| Gly | Gln | Gly | Thr | Leu | Val | Thr | Val | Ser | Ser |
|---|---|---|---|---|---|---|---|---|---|
| | | | 115 | | | | | 120 | |

<210> SEQ ID NO 199

<211> LENGTH: 333
<212> TYPE: DNA
<213> ORGANISM: Homo sapiens

<400> SEQUENCE: 199

```
cagtctgtgc tgacgcagcc gccctcagtg tctggggccc cagggctgag ggtcaccatc    60
tcctgcactg gaaacagctc caacatcggg gcaggttatg atgtacactg gtaccagcag   120
cttccaggaa cagcccccaa actcctcatc tatggtaaca gcaatcggcc ctcagggggtc  180
cctgaccgat tctctggctc caagtctggc acctcagcct ccctggccat cactgggctc   240
caggctgagg atgagactga ttattactgc cagtcctatg acagcagcct gagtggttcg   300
gtattcggcg gagggaccaa gctgaccgtc cta                                333
```

<210> SEQ ID NO 200
<211> LENGTH: 111
<212> TYPE: PRT
<213> ORGANISM: Homo sapiens

<400> SEQUENCE: 200

```
Gln Ser Val Leu Thr Gln Pro Pro Ser Val Ser Gly Ala Pro Gly Leu
 1               5                  10                  15

Arg Val Thr Ile Ser Cys Thr Gly Asn Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Thr Asp Tyr Tyr Cys Gln Ser Tyr Asp Ser Ser
                85                  90                  95

Leu Ser Gly Ser Val Phe Gly Gly Gly Thr Lys Leu Thr Val Leu
            100                 105                 110
```

<210> SEQ ID NO 201
<211> LENGTH: 363
<212> TYPE: DNA
<213> ORGANISM: Homo sapiens

<400> SEQUENCE: 201

```
caggtgcacc tggtggagtc tgggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtt atatggcatg atggaagtaa taaatactat   180
gcagactccg tgaagggccg attcaccatc tccagagaca attccaagaa cacgctgtat   240
ctgcaaatga acagcctgag agccgaggac acggctgtgt attactgtac aagagagggg   300
gactacggtg gttacccta ctttgactac tggggccagg gaaccctggt caccgtctcc   360
tca                                                                 363
```

<210> SEQ ID NO 202
<211> LENGTH: 121
<212> TYPE: PRT
<213> ORGANISM: Homo sapiens

<400> SEQUENCE: 202

```
Gln Val His Leu Val Glu Ser Gly Gly Gly Val Val Gln Pro Gly Arg
 1               5                  10                  15
```

```
Ser Leu Arg Leu Ser Cys Ala Ala Ser Gly Phe Thr Phe Ser Ser Tyr
         20                  25                  30

Gly Met His Trp Val Arg Gln Ala Pro Gly Lys Gly Leu Glu Trp Val
         35                  40                  45

Ala Val Ile Trp His Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
             85                  90                  95

Thr Arg Glu Gly Asp Tyr Gly Tyr Pro Tyr Phe Asp Tyr Trp Gly
             100                 105                 110

Gln Gly Thr Leu Val Thr Val Ser Ser
         115                 120
```

<210> SEQ ID NO 203
<211> LENGTH: 324
<212> TYPE: DNA
<213> ORGANISM: Homo sapiens

<400> SEQUENCE: 203

```
tcttctgagc tgactcagga ccctgctgtg tctgtggcct tgggacagac agtcaggatc    60
acatgccaag agacatcct cagaagctat atgcaagct ggtaccagca gaagccagga    120
caggccccta acttgtcat ctatggtaaa acaaccggc cctcaggat cccagaccga    180
ttctctggct ccagctcagg aaacacagct tccttgacca tcactggggc tcaggcggaa    240
gatgaggctg actattactg taagtcccgg gacagcagtt ataaccatct ggtattcggc    300
ggagggacca aactgaccgt ccta                                          324
```

<210> SEQ ID NO 204
<211> LENGTH: 108
<212> TYPE: PRT
<213> ORGANISM: Homo sapiens

<400> SEQUENCE: 204

```
Ser Ser Glu Leu Thr Gln Asp Pro Ala Val Ser Val Ala Leu Gly Gln
1               5                   10                  15

Thr Val Arg Ile Thr Cys Gln Gly Asp Ile Leu Arg Ser Tyr Tyr Ala
             20                  25                  30

Ser Trp Tyr Gln Gln Lys Pro Gly Gln Ala Pro Ile Leu Val Ile Tyr
         35                  40                  45

Gly Lys Asn Asn Arg Pro Ser Gly Ile Pro Asp Arg Phe Ser Gly Ser
     50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Ser Ser Tyr Asn His
             85                  90                  95

Leu Val Phe Gly Gly Thr Lys Leu Thr Val Leu
             100                 105
```

<210> SEQ ID NO 205
<211> LENGTH: 375
<212> TYPE: DNA
<213> ORGANISM: Homo sapiens

<400> SEQUENCE: 205

```
caggtgcagc tggtggagtc tgggggaggc gtggtccagc ctggagggtc cctgagactc        60
tcctgtgcag cgtctggatt caccttcagt agctatggca tgcactgggt ccgccaggct       120
ccaggcaagg gctggagtg gtggcagtt atatggtatg atggaagtaa taaatactat        180
gcagactccg tgaagggccg attcaccatc tccagagaca attccaagaa cacgctgtat       240
ctgcaaatga acagcctgag agccgaggac acggctgtgt attactgtgc gagagagact       300
acggtgacta aggagggcta ctactactac ggtatggacg tctggggcca agggaccacg       360
gtcaccgtct cctca                                                       375
```

```
<210> SEQ ID NO 206
<211> LENGTH: 125
<212> TYPE: PRT
<213> ORGANISM: Homo sapiens

<400> SEQUENCE: 206
```

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Glu Thr Thr Val Thr Lys Glu Gly Tyr Tyr Tyr Tyr Gly Met
            100                 105                 110

Asp Val Trp Gly Gln Gly Thr Thr Val Thr Val Ser Ser
            115                 120                 125
```

```
<210> SEQ ID NO 207
<211> LENGTH: 321
<212> TYPE: DNA
<213> ORGANISM: Homo sapiens

<400> SEQUENCE: 207
```

```
gacatccaga tgacccagtc tccatcttcc ctgtctgcat ctgtaggaga cagagtcacc        60
atcacttgcc gggcaagtca gggcattaga aatgatttag gctggtatca gcagaaacca       120
gggaaagccc ctaagcgcct gatctatgct gcatccagtt tgcaaagtgg ggtcccatca       180
aggttcagcg gcagtggatc tgggacagaa ttcactctca caatcagcag cctgcagcct       240
gaagattttg caacttatta ctgtctacag cataatagtt accgctcac tttcggcgga       300 gggaccaagg tggagatcaa a                                                 321
```

```
<210> SEQ ID NO 208
<211> LENGTH: 107
<212> TYPE: PRT
<213> ORGANISM: Homo sapiens

<400> SEQUENCE: 208
```

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30
```

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Leu
                 85                  90                  95

Thr Phe Gly Gly Gly Thr Lys Val Glu Ile Lys
                100                 105

<210> SEQ ID NO 209
<211> LENGTH: 360
<212> TYPE: DNA
<213> ORGANISM: Homo sapiens

<400> SEQUENCE: 209
caggtgcagc tggtggagtc tgggggaggc gtggtccagc ctggagggtc cctgagactc    60
tcctgtgcag cgtctggatt caccttcagt acctatggca tgcactgggt ccgccaggct   120
ccaggcaagg ggctggagtg gtggcagtt atatggtatg atggaagtaa taaatactat   180
gcagactccg tgaagggccg attcaccatc tccagagaca attccaagaa cacgctatat   240
ctgcaaatga acagcctgag agccgaggac acggctgtgt attactgtgc gagatcccgc   300
tacggtgact gggggtggtt cgaccctgg ggccagggaa ccctggtcac cgtctcctca   360

<210> SEQ ID NO 210
<211> LENGTH: 120
<212> TYPE: PRT
<213> ORGANISM: Homo sapiens

<400> SEQUENCE: 210

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Thr Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Arg Tyr Gly Asp Trp Gly Trp Phe Asp Pro Trp Gly Gln
                100                 105                 110

Gly Thr Leu Val Thr Val Ser Ser
            115                 120

<210> SEQ ID NO 211
<211> LENGTH: 330
<212> TYPE: DNA
<213> ORGANISM: Homo sapiens

<400> SEQUENCE: 211
cagtctgtgc tgactcagcc accctcagcg tctgggaccc ccgggcagag ggtcaccatc    60
tcttgttctg gaagcagctc caacatcgga agtaatactg taaactggta ccagcagctc   120

```
ccaggaacgg cccccaaact cctcatctat agtaataatc agcggccctc agggtccct      180 gaccgattct ctggctccaa gtctggcacc tcagcctccc tggccatcag tgggctccag      240
tctgaggatg aggctgatta ttactgtgca gcatgggatg acagcctgaa tggtccggtg      300
ttcggcggag ggaccaagct gaccgtccta                                       330
```

<210> SEQ ID NO 212
<211> LENGTH: 110
<212> TYPE: PRT
<213> ORGANISM: Homo sapiens

<400> SEQUENCE: 212

```
Gln Ser Val Leu Thr Gln Pro Pro Ser Ala Ser Gly Thr Pro Gly Gln
  1               5                  10                  15

Arg Val Thr Ile Ser Cys Ser Gly Ser Ser Asn Ile Gly Ser Asn
             20                  25                  30

Thr Val Asn Trp Tyr Gln Gln Leu Pro Gly Thr Ala Pro Lys Leu Leu
         35                  40                  45

Ile Tyr Ser Asn Asn Gln Arg Pro Ser Gly Val Pro Asp Arg Phe Ser
     50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Pro Val Phe Gly Gly Gly Thr Lys Leu Thr Val Leu
            100                 105                 110
```

<210> SEQ ID NO 213
<211> LENGTH: 366
<212> TYPE: DNA
<213> ORGANISM: Homo sapiens

<400> SEQUENCE: 213

```
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcaatt atatggtatg atggaagtaa tgaatactat     180
ggagactccg tgaagggccg attcaccatc tccagagaca attccaagaa cacgctgttt     240
ctgcaaatga acagcctgag agccgaggac acggctgtgt attactgtgc gagagatccc     300
ctccgtatag tagtggctgg gactttgac tactggggcc agggaaccct ggtcaccgtc     360
tcctca                                                                 366
```

<210> SEQ ID NO 214
<211> LENGTH: 122
<212> TYPE: PRT
<213> ORGANISM: Homo sapiens

<400> SEQUENCE: 214

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Ile Ile Trp Tyr Asp Gly Ser Asn Glu Tyr Tyr Gly Asp Ser Val
     50                  55                  60
```

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
            85                  90                  95

Ala Arg Asp Pro Leu Arg Ile Val Val Ala Gly Asp Phe Asp Tyr Trp
            100                 105                 110

Gly Gln Gly Thr Leu Val Thr Val Ser Ser
            115                 120

<210> SEQ ID NO 215
<211> LENGTH: 321
<212> TYPE: DNA
<213> ORGANISM: Homo sapiens

<400> SEQUENCE: 215
gaaatagtga tgacgcagtc tccagccacc ctgtctgtgt ctccagggga aagagccacc      60
ctctcctgca gggccagtca gagtgttatc agcaacttag cctggtacca gcagcaacct     120
ggccaggctc ccaggctcct catctatggt gcatccacca gggccactgg tttcccagcc     180
aggttcagtg gcagtgggtc tgggacagag ttcactctca ccatcagcag cctgcagtct     240
gaagattttg cagtttatta ctgtcagcag tataataact ggccgctcac tttcggcgga     300
gggaccaagg tggagatcaa a                                                321

<210> SEQ ID NO 216
<211> LENGTH: 107
<212> TYPE: PRT
<213> ORGANISM: Homo sapiens

<400> SEQUENCE: 216

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ile Ser Asn
            20                  25                  30

Leu Ala Trp Tyr Gln Gln Pro Gly Gln Ala Pro Arg Leu Leu Ile
        35                  40                  45

Tyr Gly Ala Ser Thr Arg Ala Thr Gly Phe Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
            85                  90                  95

Thr Phe Gly Gly Gly Thr Lys Val Glu Ile Lys
            100                 105

<210> SEQ ID NO 217
<211> LENGTH: 375
<212> TYPE: DNA
<213> ORGANISM: Homo sapiens

<400> SEQUENCE: 217
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagagact     300
acggtgacta aggagggcta ctactactac ggtatggacg tctggggcca agggaccacg    360
gtcaccgtct cctca                                                     375

<210> SEQ ID NO 218
<211> LENGTH: 125
<212> TYPE: PRT
<213> ORGANISM: Homo sapiens

<400> SEQUENCE: 218

Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Thr Val Thr Lys Glu Gly Tyr Tyr Tyr Gly Met
            100                 105                 110

Asp Val Trp Gly Gln Gly Thr Thr Val Thr Val Ser Ser
        115                 120                 125

<210> SEQ ID NO 219
<211> LENGTH: 321
<212> TYPE: DNA
<213> ORGANISM: Homo sapiens

<400> SEQUENCE: 219
gacatccaga tgacccagtc tccatcttcc ctgtctgcat ctgtaggaga cagagtcacc     60
atcacttgcc gggcaagtca gggcattaga aatgatttag ctggtatca gcagaaacca    120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccgctcac tttcggcgga    300
gggaccaagg tggagatcaa a                                              321

<210> SEQ ID NO 220
<211> LENGTH: 107
<212> TYPE: PRT
<213> ORGANISM: Homo sapiens

<400> SEQUENCE: 220

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

-continued

Glu Asp Phe Ala Thr Tyr Tyr Cys Leu Gln His Asn Ser Tyr Pro Leu
                85                  90                  95
Thr Phe Gly Gly Gly Thr Lys Val Glu Ile Lys
            100                 105

<210> SEQ ID NO 221
<211> LENGTH: 375
<212> TYPE: DNA
<213> ORGANISM: Homo sapiens

<400> SEQUENCE: 221
caggtgcagc tggtggagtc tgggggaggc gtggtccagc ctggagggtc cctgagactc     60
tcctgtgcag cctctggatt caccttcagt agctatgaca tgcactgggt ccgccaggct    120
ccaggcaagg ggctggagtg ggtggcaatt atatcatatg atggaagtat aaatactat    180 gcagactccg tgaagggccg attcaccatc tccagagaca attccaagaa cacgctgtat    240
ctgcaaatga acagcctgag agctgaggac acggctgtgt attactgtgc gagagagaat    300
gcggtgactt acggggggcta ctaccactac ggtatggacg tctggggcca agggaccacg    360
gtcaccgtct cctca                                                     375

<210> SEQ ID NO 222
<211> LENGTH: 125
<212> TYPE: PRT
<213> ORGANISM: Homo sapiens

<400> SEQUENCE: 222

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Asp Met His Trp Val Arg Gln Ala Pro Gly Lys Gly Leu Glu Trp Val
        35                  40                  45
Ala Ile Ile Ser Tyr Asp Gly Ser Ile Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Asn Ala Val Thr Tyr Gly Gly Tyr Tyr His Tyr Gly Met
            100                 105                 110
Asp Val Trp Gly Gln Gly Thr Thr Val Thr Val Ser Ser
        115                 120                 125

<210> SEQ ID NO 223
<211> LENGTH: 321
<212> TYPE: DNA
<213> ORGANISM: Homo sapiens

<400> SEQUENCE: 223
gacatccaga tgacccagtc tccatcctcc ctgtctacat ctgtaggaga cagagtcacc     60
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccgctcac tttcggcgga    300

-continued gggaccaagg tggagatcaa a    321

<210> SEQ ID NO 224
<211> LENGTH: 107
<212> TYPE: PRT
<213> ORGANISM: Homo sapiens

<400> SEQUENCE: 224

Asp Ile Gln Met Thr Gln Ser Pro Ser Ser Leu Ser Thr Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 225
<211> LENGTH: 375
<212> TYPE: DNA
<213> ORGANISM: Homo sapiens

<400> SEQUENCE: 225
caggtgcagc tggtggagtc tgggggaggc gtggtccagc ctggggaggtc cctgagactc    60 tcctgtacaa catctggatt caccttcagt aactatggca tgcactgggt ccgccaggct   120
ccaggcaagg ggctggagtg gtggcagtt atctggtatg atggaagtat taaatactat   180
gtagactccg tgaagggccg attcaccatc tccagagaca attccaagaa cacgctgtat   240
ctgcaaatga acagcctgag agccgaggac acggctgtgt attactgtgc gagagagaag   300
gattgtggtg gtgactgtta cagccactac ggtatggacg tctggggcca aggaccacg    360 gtcaccgtct cctca    375

<210> SEQ ID NO 226
<211> LENGTH: 125
<212> TYPE: PRT
<213> ORGANISM: Homo sapiens

<400> SEQUENCE: 226

Gln Val Gln Leu Val Glu Ser Gly Gly Gly Val Val Gln Pro Gly Arg
1               5                   10                  15

Ser Leu Arg Leu Ser Cys Thr Thr Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Ile Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Arg Glu Lys Asp Cys Gly Gly Asp Cys Tyr Ser His Tyr Gly Met
        100                 105                 110

Asp Val Trp Gly Gln Gly Thr Thr Val Thr Val Ser Ser
        115                 120                 125
```

<210> SEQ ID NO 227
<211> LENGTH: 321
<212> TYPE: DNA
<213> ORGANISM: Homo sapiens

<400> SEQUENCE: 227

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacgtatta ctgtctacag catatgagtc tcccgctcac tttcggcgga   300
gggaccaagg tggagatcaa a                                             321
```

<210> SEQ ID NO 228
<211> LENGTH: 107
<212> TYPE: PRT
<213> ORGANISM: Homo sapiens

<400> SEQUENCE: 228

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Met Ser Leu Pro Leu
                85                  90                  95

Thr Phe Gly Gly Gly Thr Lys Val Glu Ile Lys
            100                 105
```

<210> SEQ ID NO 229
<211> LENGTH: 375
<212> TYPE: DNA
<213> ORGANISM: Homo sapiens

<400> SEQUENCE: 229

```
caggtgcagc tggtggagtc tgggggaggc gtggtccagc ctgggaggtc cctgagactc    60
tcctgtacaa catctggatt caccttcagt aactatggca tgcactgggt ccgccaggct   120
ccaggcaagg ggctggagtg ggtggcagtt atctggtatg atggaagtat taaatactat   180
gtagactccg tgaagggccg attcaccatc tccagagaca attccaagaa cacgctgtat   240
ctgcaaatga acagcctgag agccgaggac acggctgtgt attactgtgc gagagagaag   300
gattgtggtg gtgactgtta cagccactac ggtatggacg tctggggcca agggaccacg   360
gtcaccgtct cctca                                                    375
```

<210> SEQ ID NO 230

<211> LENGTH: 125
<212> TYPE: PRT
<213> ORGANISM: Homo sapiens

<400> SEQUENCE: 230

```
Gln Val Gln Leu Val Glu Ser Gly Gly Val Val Gln Pro Gly Arg
1               5                   10                  15

Ser Leu Arg Leu Ser Cys Thr Thr Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Ile Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Lys Asp Cys Gly Gly Asp Cys Tyr Ser His Tyr Gly Met
            100                 105                 110

Asp Val Trp Gly Gln Gly Thr Thr Val Thr Val Ser Ser
        115                 120                 125
```

<210> SEQ ID NO 231
<211> LENGTH: 321
<212> TYPE: DNA
<213> ORGANISM: Homo sapiens

<400> SEQUENCE: 231

```
gacatccaga tgacccagtc tccatcctcc ctgtctgcat ctgtaggaga cagagtcacc      60
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacgtatta ctgtctacag catatgagtc tcccgctcac tttcggcgga    300
gggaccaagg tggagatcaa a                                             321
```

<210> SEQ ID NO 232
<211> LENGTH: 107
<212> TYPE: PRT
<213> ORGANISM: Homo sapiens

<400> SEQUENCE: 232

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Met Ser Leu Pro Leu
                85                  90                  95

Thr Phe Gly Gly Gly Thr Lys Val Glu Ile Lys
            100                 105
```

<210> SEQ ID NO 233
<211> LENGTH: 375
<212> TYPE: DNA
<213> ORGANISM: Homo sapiens

<400> SEQUENCE: 233

```
caggtgcagc tggtggagtc tgggggaggc gtggtccagc ctggagggtc cctgagactc    60
tcctgtacaa catctggatt caccttcagt aactatggca tgcactgggt ccgccaggct   120
ccaggcaagg ggctggagtg ggtggcagtt atctggtatg atggaagtat taaatactat   180
gtagactccg tgaagggccg attcaccatc tccagagaca attccaagaa cacgctgtat   240
ctgcaaatga acagcctgag agccgaggac acggctgtgt attactgtgc gagagagaag   300
gattgtggtg gtgactgtta cagccactac ggtatggacg tctggggcca agggaccacg   360
gtcaccgtct cctca                                                    375
```

<210> SEQ ID NO 234
<211> LENGTH: 125
<212> TYPE: PRT
<213> ORGANISM: Homo sapiens

<400> SEQUENCE: 234

```
Gln Val Gln Leu Val Glu Ser Gly Gly Gly Val Val Gln Pro Gly Arg
 1               5                  10                  15

Ser Leu Arg Leu Ser Cys Thr Thr Ser Gly Phe Thr Phe Ser Asn Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Ile Lys Tyr Tyr Val Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Lys Asp Cys Gly Gly Asp Cys Tyr Ser His Tyr Gly Met
            100                 105                 110

Asp Val Trp Gly Gln Gly Thr Thr Val Thr Val Ser Ser
        115                 120                 125
```

<210> SEQ ID NO 235
<211> LENGTH: 321
<212> TYPE: DNA
<213> ORGANISM: Homo sapiens

<400> SEQUENCE: 235

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacgtatta ctgtctacag catatgagtc tcccgctcac tttcggcgga   300
gggaccaagg tggagatcaa a                                             321
```

<210> SEQ ID NO 236
<211> LENGTH: 107
<212> TYPE: PRT
<213> ORGANISM: Homo sapiens

<400> SEQUENCE: 236

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Met Ser Leu Pro Leu
                85                  90                  95

Thr Phe Gly Gly Gly Thr Lys Val Glu Ile Lys
            100                 105

<210> SEQ ID NO 237
<211> LENGTH: 375
<212> TYPE: DNA
<213> ORGANISM: Homo sapiens

<400> SEQUENCE: 237
caggtgcagc tggtggagtc tgggggaggc gtggtccagc ctggggaggtc cctgagactc    60
tcctgtacaa catctggatt caccttcagt aactatggca tgcactgggt ccgccaggct   120
ccaggcaagg ggctggagtg gtggcagtt atctggtatg atggaagtat taaatactat   180
gtagactccg tgaagggccg attcaccatc tccagagaca attccaagaa cacgctgtat   240
ctgcaaatga acagcctgag agccgaggac acggctgtgt attactgtgc gagagagaag   300
gattgtggtg gtgactgtta cagccactac ggtatggacg tctggggcca agggaccacg   360
gtcaccgtct cctca                                                    375

<210> SEQ ID NO 238
<211> LENGTH: 125
<212> TYPE: PRT
<213> ORGANISM: Homo sapiens

<400> SEQUENCE: 238

Gln Val Gln Leu Val Glu Ser Gly Gly Gly Val Val Gln Pro Gly Arg
1               5                   10                  15

Ser Leu Arg Leu Ser Cys Thr Thr Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Ile Lys Tyr Tyr Val Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Lys Asp Cys Gly Asp Cys Tyr Ser His Tyr Gly Met
            100                 105                 110

Asp Val Trp Gly Gln Gly Thr Thr Val Thr Val Ser Ser
        115                 120                 125

<210> SEQ ID NO 239
<211> LENGTH: 321
<212> TYPE: DNA
<213> ORGANISM: Homo sapiens

<400> SEQUENCE: 239

```
gacatccaga tgacccagtc tccatcctcc ctgtctgcat ctgtaggaga cagagtcacc      60
atcacttgcc gggcaagtca gggcattaga aatgatttag ctggtatca gcagaaacca     120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacgtatta ctgtctacag catatgagtc tcccgctcac tttcggcgga    300
gggaccaagg tggagatcaa a                                              321
```

<210> SEQ ID NO 240
<211> LENGTH: 107
<212> TYPE: PRT
<213> ORGANISM: Homo sapiens

<400> SEQUENCE: 240

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Arg Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Met Ser Leu Pro Leu
                85                  90                  95
Thr Phe Gly Gly Gly Thr Lys Val Glu Ile Lys
            100                 105

<210> SEQ ID NO 241
<211> LENGTH: 366
<212> TYPE: DNA
<213> ORGANISM: Homo sapiens

<400> SEQUENCE: 241

```
caggtgcagc tggtggagtc tgggggaggc gtggtccagc ctgggaggtc cctgagactc      60
tcctgtgcag cgtctggatt caccttcagc agctatggca tgcactgggt ccgccaggct    120
ccaggcaagg ggctggagtg ggtggcagtt atatggtatg atggaagaaa taaatacaat    180
gcagactccg tgaagggccg attcaccatc tccagagaca attccaagaa cacgctgaat    240
ctgcaaatga acagcctgag agccgaggac acggctgtgt attactgtgc gagagattta    300
acgtattacg atattttggg cggtatggac gtctggggcc aagggaccac ggtcaccgtc    360
tcctca                                                               366
```

<210> SEQ ID NO 242
<211> LENGTH: 122
<212> TYPE: PRT
<213> ORGANISM: Homo sapiens

<400> SEQUENCE: 242

Gln Val Gln Leu Val Glu Ser Gly Gly Gly Val Val Gln Pro Gly Arg

```
                1               5                  10                 15
Ser Leu Arg Leu Ser Cys Ala Ala Ser Gly Phe Thr Phe Ser Ser Tyr
                    20                  25                  30

Gly Met His Trp Val Arg Gln Ala Pro Gly Lys Gly Leu Glu Trp Val
            35                  40                  45

Ala Val Ile Trp Tyr Asp Gly Arg Asn Lys Tyr Asn Ala Asp Ser Val
        50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Arg Asp Leu Thr Tyr Tyr Asp Ile Leu Gly Gly Met Asp Val Trp
            100                 105                 110

Gly Gln Gly Thr Thr Val Thr Val Ser Ser
                115                 120
```

<210> SEQ ID NO 243
<211> LENGTH: 321
<212> TYPE: DNA
<213> ORGANISM: Homo sapiens

<400> SEQUENCE: 243

```
gaaatagtga tgacgcagtc tccagccacc ctgtctgtgt ctccggggga aagagccacc    60
ctctcctgca gggccagtca gagtgttacc agcaacttag cctggtacca gcagaaacct   120
ggccaggctc ccaggctcct catctatggt gcatccacca gggccactgg tatcccagcc   180
aggttcagtg gcagtgggtc tgggacagaa ttcactctca ccatcagcag cctgccgtct   240
gaagattttg cagtttatta ctgtcagcag tatcatacct ggccattcac tttcggccct   300
gggaccaaag tggatatcaa a                                             321
```

<210> SEQ ID NO 244
<211> LENGTH: 107
<212> TYPE: PRT
<213> ORGANISM: Homo sapiens

<400> SEQUENCE: 244

```
Glu Ile Val Met Thr Gln Ser Pro Ala Thr Leu Ser Val Ser Pro Gly
1               5                  10                  15

Glu Arg Ala Thr Leu Ser Cys Arg Ala Ser Gln Ser Val Thr Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Pro Ser
65                  70                  75                  80

Glu Asp Phe Ala Val Tyr Tyr Cys Gln Gln Tyr His Thr Trp Pro Phe
                85                  90                  95

Thr Phe Gly Pro Gly Thr Lys Val Asp Ile Lys
            100                 105
```

<210> SEQ ID NO 245
<211> LENGTH: 366
<212> TYPE: DNA
<213> ORGANISM: Homo sapiens

<400> SEQUENCE: 245

```
caggtgcagc tggtggagtc tggggggaggc gtggtccagc ctgggaggtc cctgagactc    60
tcctgtgcag cgtctggatt caccttcagc agctatggca tgcactgggt ccgccaggct   120
ccaggcaagg gctggagtg gtggcagtt atatggtatg atggaagaaa taaatacaat    180
gcagactccg tgaagggccg attcaccatc tccagagaca attccaagaa cacgctgaat   240
ctgcaaatga acagcctgag agccgaggac acggctgtgt attactgtgc gagagattta   300
acgtattacg atatttttggg cggtatggac gtctggggcc aagggaccac ggtcaccgtc   360
tcctca                                                                366
```

<210> SEQ ID NO 246
<211> LENGTH: 122
<212> TYPE: PRT
<213> ORGANISM: Homo sapiens

<400> SEQUENCE: 246

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Arg Asn Lys Tyr Asn Ala Asp Ser Val
         50                  55                  60

Lys Gly Arg Phe Thr Ile Ser Arg Asp Asn Ser Lys Asn Thr Leu Asn
 65                  70                  75                  80

Leu Gln Met Asn Ser Leu Arg Ala Glu Asp Thr Ala Val Tyr Tyr Cys
                 85                  90                  95

Ala Arg Asp Leu Thr Tyr Tyr Asp Ile Leu Gly Gly Met Asp Val Trp
                100                 105                 110

Gly Gln Gly Thr Thr Val Thr Val Ser Ser
            115                 120
```

<210> SEQ ID NO 247
<211> LENGTH: 321
<212> TYPE: DNA
<213> ORGANISM: Homo sapiens

<400> SEQUENCE: 247

```
gaaatagtga tgacgcagtc tccatccacc ctgtctgtgt ctccggggga aagagccacc    60
ctctcctgca gggccagtca gagtgttacc agcaacttag cctggtacca gcagaaacct   120
ggccaggctc ccaggctcct catctatggt gcatccacca gggccactgg tatcccagcc   180
aggttcagtg gcagtgggtc tgggacagaa ttcactctca ccatcagcag cctgccgtct   240
gaagattttg cagtttatta ctgtcagcag tatcatacct ggccattcac tttcggccct   300
gggaccaaag tggatatcaa a                                              321
```

<210> SEQ ID NO 248
<211> LENGTH: 107
<212> TYPE: PRT
<213> ORGANISM: Homo sapiens

<400> SEQUENCE: 248

```
Glu Ile Val Met Thr Gln Ser Pro Ser Thr Leu Ser Val Ser Pro Gly
  1               5                  10                  15

Glu Arg Ala Thr Leu Ser Cys Arg Ala Ser Gln Ser Val Thr Ser Asn
```

```
            20                  25                  30
Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Pro Ser
 65                  70                  75                  80

Glu Asp Phe Ala Val Tyr Tyr Cys Gln Gln Tyr His Thr Trp Pro Phe
                 85                  90                  95

Thr Phe Gly Pro Gly Thr Lys Val Asp Ile Lys
            100                 105

<210> SEQ ID NO 249
<211> LENGTH: 366
<212> TYPE: DNA
<213> ORGANISM: Homo sapiens

<400> SEQUENCE: 249
caggtgcagc tggtggagtc tgggggaggc gtggtccagc ctggggaggtc cctgagactc      60 tcctgtgcag cgtctggatt caccttcagc agctatggca tgcactgggt ccgccaggct     120
ccaggcaagg ggctggagtg ggtggcagtt atatggtatg atggaagaaa taaataacaat     180 gcagactccg tgaagggccg attcaccatc tccagagaca attccaagaa cacgctgaat     240
ctgcaaatga acagcctgag agccgaggac acggctgtgt attactgtgc gagagattta     300
acgtattacg atatttttggg cggtatggac gtctggggcc aagggaccac ggtcaccgtc     360
tcctca                                                                 366

<210> SEQ ID NO 250
<211> LENGTH: 122
<212> TYPE: PRT
<213> ORGANISM: Homo sapiens

<400> SEQUENCE: 250

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
         35                  40                  45

Ala Val Ile Trp Tyr Asp Gly Arg Asn Lys Tyr Asn Ala Asp Ser Val
 50                  55                  60

Lys Gly Arg Phe Thr Ile Ser Arg Asp Asn Ser Lys Asn Thr Leu Asn
 65                  70                  75                  80

Leu Gln Met Asn Ser Leu Arg Ala Glu Asp Thr Ala Val Tyr Tyr Cys
                 85                  90                  95

Ala Arg Asp Leu Thr Tyr Tyr Asp Ile Leu Gly Gly Met Asp Val Trp
            100                 105                 110

Gly Gln Gly Thr Thr Val Thr Val Ser Ser
         115                 120

<210> SEQ ID NO 251
<211> LENGTH: 321
<212> TYPE: DNA
<213> ORGANISM: Homo sapiens

<400> SEQUENCE: 251
```

```
gacatccaga tgacccagtc tccatcctcc ctgtctgcat ctgtaggaga cagagtcacc      60
atcacttgcc gggcaagtca gggcattaga catgatttag gctggtatca gcagaaacca     120
gggaaagccc ctgagcgcct gatctatggt gcatccagtt tgcaaagtgg ggtcccatca     180
aggttcagcg gcagtggatc tgggacagaa ttcactctca caatcagcag cctgcagcct     240
gaagattttg caacttatta ctgtctacag cataatagtt acccgctcac tttcggcgga     300
gggaccaagg tggagatcaa a                                               321
```

<210> SEQ ID NO 252
<211> LENGTH: 107
<212> TYPE: PRT
<213> ORGANISM: Homo sapiens

<400> SEQUENCE: 252

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg His Asp
             20                  25                  30

Leu Gly Trp Tyr Gln Gln Lys Pro Gly Lys Ala Pro Glu Arg Leu Ile
         35                  40                  45

Tyr Gly Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Leu
                 85                  90                  95

Thr Phe Gly Gly Gly Thr Lys Val Glu Ile Lys
            100                 105

<210> SEQ ID NO 253
<211> LENGTH: 402
<212> TYPE: DNA
<213> ORGANISM: Homo sapiens

<400> SEQUENCE: 253

```
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtg atatggtatg atggaagtaa taatactat      180 gcagactccg tgaagggccg attcaccatc tccagagaca attccaagaa cacgctgtat     240
ctgcaaatga acagcctgag agccgaggac acggctgtgt attactgtgc gagaggtaat     300
cgcgtagtag tggctggtac gagggtaact cccgctaact ggggatacta ctattacgga     360
atggacgtct ggggccaagg gaccacggtc accgtctcct ca                        402
```

<210> SEQ ID NO 254
<211> LENGTH: 134
<212> TYPE: PRT
<213> ORGANISM: Homo sapiens

<400> SEQUENCE: 254

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
                50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Asn Arg Val Val Val Ala Gly Thr Arg Val Thr Pro Ala
                100                 105                 110

Asn Trp Gly Tyr Tyr Tyr Gly Met Asp Val Trp Gly Gln Gly Thr
            115                 120                 125

Thr Val Thr Val Ser Ser
    130

<210> SEQ ID NO 255
<211> LENGTH: 321
<212> TYPE: DNA
<213> ORGANISM: Homo sapiens

<400> SEQUENCE: 255
gacatccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagtgcct gatctatgtt gcatccagtt tgcaaagtgg ggtcccatca     180
aggttcagcg gcagtggatc tgggacagaa ttcactctca caatcagcag cctgcagcct     240
gaagattttg caacttatta ctgtctacag cataatagtt acccgctcac tttcggcgga     300
gggaccaagg tggagatcaa a                                               321

<210> SEQ ID NO 256
<211> LENGTH: 107
<212> TYPE: PRT
<213> ORGANISM: Homo sapiens

<400> SEQUENCE: 256

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Cys Leu Ile
            35                  40                  45

Tyr Val Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Leu
                 85                  90                  95

Thr Phe Gly Gly Gly Thr Lys Val Glu Ile Lys
            100                 105

<210> SEQ ID NO 257
<211> LENGTH: 348
<212> TYPE: DNA
<213> ORGANISM: Homo sapiens

<400> SEQUENCE: 257
gaggtgcaac tggtggagtc tgggggaggc ttggtacagc ctggggggtc cctgagactc      60
tcctgtgcag cctctggatt caccttcagt aattatggca tgaactgggt ccgccaggct     120

```
ccagggaagg ggctggagtg ggtttcatac ataagtaata gtattacttc caaatactac    180
gctgactctg tgaagggccg attcaccatc tccagagaca atgccaagaa ttcactgtat    240
ctgcaaatga acagcctgag agacgtggac acggctgtgt atcactgtgc gagaggaccg    300
ggcgggtttg actactgggg ccagggaacc ctggtcaccg tctcctca                 348
```

<210> SEQ ID NO 258
<211> LENGTH: 116
<212> TYPE: PRT
<213> ORGANISM: Homo sapiens

<400> SEQUENCE: 258

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Gly Met Asn Trp Val Arg Gln Ala Pro Gly Lys Gly Leu Glu Trp Val
        35                  40                  45

Ser Tyr Ile Ser Asn Ser Ile Thr Ser Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Val Asp Thr Ala Val Tyr His Cys
                85                  90                  95

Ala Arg Gly Pro Gly Gly Phe Asp Tyr Trp Gly Gln Gly Thr Leu Val
            100                 105                 110

Thr Val Ser Ser
        115
```

<210> SEQ ID NO 259
<211> LENGTH: 321
<212> TYPE: DNA
<213> ORGANISM: Homo sapiens

<400> SEQUENCE: 259

```
gacatccaga tgacccagtc tccatcctcc ctgtctgcat ctgtaggaga cagagtcacc     60
atcacttgcc gggcaagtca gggcattaga aatgatttag gctggtatca gcagaaacca    120
gggaaagccc cgaagtgcct gatctatgtt gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccgtggac gttcggccaa    300
gggaccaagg tggaaatcaa a                                              321
```

<210> SEQ ID NO 260
<211> LENGTH: 107
<212> TYPE: PRT
<213> ORGANISM: Homo sapiens

<400> SEQUENCE: 260

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Cys Leu Ile
        35                  40                  45

Tyr Val Ala Ser Ser Leu Gln Ser Gly Val Pro Ser Arg Phe Ser Gly
```

```
            50                  55                  60
Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys
            100                 105

<210> SEQ ID NO 261
<211> LENGTH: 366
<212> TYPE: DNA
<213> ORGANISM: Homo sapiens

<400> SEQUENCE: 261
gaggtgcagc tgttggagtc tgggggaggc ttggtacagc cggggggtc cctgagactc      60 tcctgtgcag cctctggatt cacctttagc agctatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acggccgtat attactgtgc gaaagattac    300
tatgatagta gtggttatca tcctttgac tactggggcc agggaaccct ggtcaccgtc     360
tcctca                                                               366

<210> SEQ ID NO 262
<211> LENGTH: 122
<212> TYPE: PRT
<213> ORGANISM: Homo sapiens

<400> SEQUENCE: 262

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Tyr Tyr Asp Ser Ser Gly Tyr His Pro Phe Asp Tyr Trp
            100                 105                 110

Gly Gln Gly Thr Leu Val Thr Val Ser Ser
        115                 120

<210> SEQ ID NO 263
<211> LENGTH: 321
<212> TYPE: DNA
<213> ORGANISM: Homo sapiens

<400> SEQUENCE: 263
gacatccaga tgacccagtc tccatcctcc ctgtctgcat ctgtaggaga cagagtcacc      60
atcacttgcc gggcgagtca gggcattagc aattatttag cctggtatca acagaaacca    120
gggaaagttc ctaagttcct gatctatgct gcatccactt tgcaatcagg ggtcccatct    180
```

```
cggttcagtg gcagtggatc tgggacagat ttcactctca ccgtcagcag cctgcagcct      240
gaagatgttg caacttatta ctgtcaaatg tataacagtg tcccattcac tttcggccct      300
gggaccaaag tggatatcaa a                                                321
```

<210> SEQ ID NO 264
<211> LENGTH: 107
<212> TYPE: PRT
<213> ORGANISM: Homo sapiens

<400> SEQUENCE: 264

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Phe Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Val Ser Ser Leu Gln Pro
65                  70                  75                  80

Glu Asp Val Ala Thr Tyr Tyr Cys Gln Met Tyr Asn Ser Val Pro Phe
                85                  90                  95

Thr Phe Gly Pro Gly Thr Lys Val Asp Ile Lys
            100                 105

<210> SEQ ID NO 265
<211> LENGTH: 157
<212> TYPE: PRT
<213> ORGANISM: homo sapiens

<400> SEQUENCE: 265

Val Arg Ser Ser Arg Thr Pro Ser Asp Lys Pro Val Ala His Val
 1               5                  10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 266
<211> LENGTH: 156
<212> TYPE: PRT
<213> ORGANISM: Mus musculus

```
<400> SEQUENCE: 266

Leu Arg Ser Ser Ser Gln Asn Ser Ser Asp Lys Pro Val Ala His Val
1               5                   10                  15

Val Ala Asn His Gln Val Glu Glu Gln Leu Glu Trp Leu Ser Gln Arg
            20                  25                  30

Ala Asn Ala Leu Leu Ala Asn Gly Met Asp Leu Lys Asp Asn Gln Leu
        35                  40                  45

Val Val Pro Ala Asp Gly Leu Tyr Leu Val Tyr Ser Gln Val Leu Phe
    50                  55                  60

Lys Gly Gln Gly Cys Pro Asp Tyr Val Leu Leu Thr His Thr Val Ser
65                  70                  75                  80

Arg Phe Ala Ile Ser Tyr Gln Glu Lys Val Asn Leu Leu Ser Ala Val
                85                  90                  95

Lys Ser Pro Cys Pro Lys Asp Thr Pro Glu Gly Ala Glu Leu Lys Pro
            100                 105                 110

Trp Tyr Glu Pro Ile Tyr Leu Gly Gly Val Phe Gln Leu Glu Lys Gly
        115                 120                 125

Asp Gln Leu Ser Ala Glu Val Asn Leu Pro Lys Tyr Leu Asp Phe Ala
130                 135                 140

Glu Ser Gly Gln Val Tyr Phe Gly Val Ile Ala Leu
145                 150                 155

<210> SEQ ID NO 267
<211> LENGTH: 109
<212> TYPE: PRT
<213> ORGANISM: Homo sapiens

<400> SEQUENCE: 267

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Thr Val Thr Val Ser Ser
            100                 105

<210> SEQ ID NO 268
<211> LENGTH: 108
<212> TYPE: PRT
<213> ORGANISM: Homo sapiens

<400> SEQUENCE: 268

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
```

```
                        50                  55                  60
Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Trp Gly Gln Gly Thr Leu Val Thr Val Ser Ser
            100                 105
```

<210> SEQ ID NO 269
<211> LENGTH: 109
<212> TYPE: PRT
<213> ORGANISM: Homo sapiens

<400> SEQUENCE: 269

```
Gln Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Gln Gly Thr Thr Val Thr Val Ser Ser
             100                 105
```

<210> SEQ ID NO 270
<211> LENGTH: 109
<212> TYPE: PRT
<213> ORGANISM: Homo sapiens

<400> SEQUENCE: 270

```
Gln Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Gln Gly Thr Thr Val Thr Val Ser Ser
             100                 105
```

<210> SEQ ID NO 271
<211> LENGTH: 108
<212> TYPE: PRT
<213> ORGANISM: Homo sapiens

<400> SEQUENCE: 271

```
Gln Val Gln Leu Gln Glu Ser Gly Pro Gly Leu Val Lys Pro Ser Glu
  1               5                  10                  15
```

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Trp Gly Arg Gly Thr Leu Val Thr Val Ser Ser
            100                 105

<210> SEQ ID NO 272
<211> LENGTH: 110
<212> TYPE: PRT
<213> ORGANISM: Homo sapiens

<400> SEQUENCE: 272

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Trp Gly Gln Gly Thr Thr Val Thr Val Ser Ser
            100                 105                 110

<210> SEQ ID NO 273
<211> LENGTH: 107
<212> TYPE: PRT
<213> ORGANISM: Homo sapiens

<400> SEQUENCE: 273

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 274

```
<211> LENGTH: 107
<212> TYPE: PRT
<213> ORGANISM: Homo sapiens

<400> SEQUENCE: 274

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
             85                  90                  95

Thr Phe Gly Gln Gly Thr Lys Val Glu Ile Lys
            100                 105

<210> SEQ ID NO 275
<211> LENGTH: 114
<212> TYPE: PRT
<213> ORGANISM: Homo sapiens
<220> FEATURE:
<221> NAME/KEY: VARIANT
<222> LOCATION: 101, 102
<223> OTHER INFORMATION: Xaa = Any Amino Acid

<400> SEQUENCE: 275

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
             20                  25                  30

Asp Gly Asn Thr Tyr Leu Asn Trp Phe Gln Gln Arg Pro Gly Gln Ser
         35                  40                  45

Pro Arg Arg Leu Ile Tyr Lys Val Trp Asn Trp Asp Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
             85                  90                  95

Thr His Trp Pro Xaa Xaa Leu Thr Phe Gly Gly Gly Thr Lys Val Glu
            100                 105                 110

Ile Lys

<210> SEQ ID NO 276
<211> LENGTH: 111
<212> TYPE: PRT
<213> ORGANISM: Homo sapiens

<400> SEQUENCE: 276

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45
```

```
Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Trp Thr Phe Gly Gln Gly Thr Lys Val Glu Ile Lys
            100                 105                 110

<210> SEQ ID NO 277
<211> LENGTH: 106
<212> TYPE: PRT
<213> ORGANISM: Homo sapiens

<400> SEQUENCE: 277

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Trp Thr
                85                  90                  95

Phe Gly Gln Gly Thr Lys Val Glu Ile Lys
            100                 105

<210> SEQ ID NO 278
<211> LENGTH: 109
<212> TYPE: PRT
<213> ORGANISM: Homo sapiens

<400> SEQUENCE: 278

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Thr Val Thr Val Ser Ser
            100                 105

<210> SEQ ID NO 279
<211> LENGTH: 109
<212> TYPE: PRT
<213> ORGANISM: Homo sapiens

<400> SEQUENCE: 279

Glu Val Gln Leu Leu Glu Ser Gly Gly Gly Leu Val Gln Pro Gly Gly
```

```
             1               5                  10                 15
Ser Leu Arg Leu Ser Cys Ala Ala Ser Gly Phe Thr Phe Ser Ser Tyr
            20                  25                 30

Ala Met Ser Trp Val Arg Gln Ala Pro Gly Lys Gly Leu Glu Trp Val
            35                  40                 45

Ser Ala Ile Ser Gly Ser Gly Gly Ser Thr Tyr Tyr Ala Asp Ser Val
            50                  55                 60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                    85                  90                  95

Ala Lys Trp Gly Gln Gly Thr Leu Val Thr Val Ser Ser
                100                 105
```

<210> SEQ ID NO 280
<211> LENGTH: 109
<212> TYPE: PRT
<213> ORGANISM: Homo sapiens
<220> FEATURE:
<221> NAME/KEY: VARIANT
<222> LOCATION: 98
<223> OTHER INFORMATION: Xaa = Any Amino Acid

<400> SEQUENCE: 280

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
            50                  55                  60

Lys Gly Arg Phe Thr Ile Ser Arg Asp Asn Ala Lys Asn Ser Leu Tyr
65                      70                  75                  80

Leu Gln Met Asn Ser Leu Arg Ala Glu Asp Thr Ala Val Tyr Tyr Cys
                    85                  90                  95

Ala Xaa Trp Gly Gln Gly Thr Thr Val Thr Val Ser Ser
                100                 105
```

<210> SEQ ID NO 281
<211> LENGTH: 109
<212> TYPE: PRT
<213> ORGANISM: Homo sapiens

<400> SEQUENCE: 281

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                    85                  90                  95
```

-continued

```
Ala Arg Trp Gly Gln Gly Thr Leu Val Thr Val Ser Ser
            100                 105

<210> SEQ ID NO 282
<211> LENGTH: 108
<212> TYPE: PRT
<213> ORGANISM: Homo sapiens

<400> SEQUENCE: 282

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Trp Gly Gln Gly Thr Met Val Thr Val Ser Ser
            100                 105

<210> SEQ ID NO 283
<211> LENGTH: 109
<212> TYPE: PRT
<213> ORGANISM: Homo sapiens

<400> SEQUENCE: 283

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Gly Gln Gly Thr Thr Val Thr Val Ser Ser
            100                 105

<210> SEQ ID NO 284
<211> LENGTH: 109
<212> TYPE: PRT
<213> ORGANISM: Homo sapiens

<400> SEQUENCE: 284

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
```

```
                50                  55                  60
Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Trp Gly Gln Gly Thr Leu Val Thr Val Ser Ser
                100                 105

<210> SEQ ID NO 285
<211> LENGTH: 109
<212> TYPE: PRT
<213> ORGANISM: Homo sapiens

<400> SEQUENCE: 285

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Gln Gly Thr Leu Val Thr Val Ser Ser
                100                 105

<210> SEQ ID NO 286
<211> LENGTH: 108
<212> TYPE: PRT
<213> ORGANISM: Homo sapiens

<400> SEQUENCE: 286

Glu Val Gln Leu Val Glu Ser Gly Gly Gly Leu Ile Gln Pro Gly Gly
  1               5                  10                  15

Ser Leu Arg Leu Ser Cys Ala Ala Ser Gly Phe Thr Val Ser Ser Asn
                 20                  25                  30

Tyr Met Ser Trp Val Arg Gln Ala Pro Gly Lys Gly Leu Glu Trp Val
             35                  40                  45

Ser Val Ile Tyr Ser Gly Gly Ser Thr Tyr Tyr Ala Asp Ser Val Lys
         50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Trp Gly Gln Gly Thr Leu Val Thr Val Ser Ser
                100                 105

<210> SEQ ID NO 287
<211> LENGTH: 109
<212> TYPE: PRT
<213> ORGANISM: Homo sapiens

<400> SEQUENCE: 287

Gln Val Gln Leu Val Glu Ser Gly Gly Gly Val Val Gln Pro Gly Arg
  1               5                  10                  15
```

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Thr Val Thr Val Ser Ser
            100                 105
```

<210> SEQ ID NO 288
<211> LENGTH: 109
<212> TYPE: PRT
<213> ORGANISM: Homo sapiens

<400> SEQUENCE: 288

```
Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Thr Val Thr Val Ser Ser
            100                 105
```

<210> SEQ ID NO 289
<211> LENGTH: 109
<212> TYPE: PRT
<213> ORGANISM: Homo sapiens

<400> SEQUENCE: 289

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Thr Val Thr Val Ser Ser
            100                 105
```

<210> SEQ ID NO 290

```
<211> LENGTH: 109
<212> TYPE: PRT
<213> ORGANISM: Homo sapiens

<400> SEQUENCE: 290

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Gly Gln Gly Thr Leu Val Thr Val Ser Ser
            100                 105

<210> SEQ ID NO 291
<211> LENGTH: 109
<212> TYPE: PRT
<213> ORGANISM: Homo sapiens

<400> SEQUENCE: 291

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Gly Gln Gly Thr Leu Val Thr Val Ser Ser
            100                 105

<210> SEQ ID NO 292
<211> LENGTH: 109
<212> TYPE: PRT
<213> ORGANISM: Homo sapiens

<400> SEQUENCE: 292

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Arg Trp Gly Gln Gly Thr Thr Val Thr Val Ser Ser
            100                 105
```

<210> SEQ ID NO 293
<211> LENGTH: 109
<212> TYPE: PRT
<213> ORGANISM: Homo sapiens

<400> SEQUENCE: 293

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Thr Val Thr Val Ser Ser
            100                 105
```

<210> SEQ ID NO 294
<211> LENGTH: 109
<212> TYPE: PRT
<213> ORGANISM: Homo sapiens

<400> SEQUENCE: 294

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Leu Val Thr Val Ser Ser
            100                 105
```

<210> SEQ ID NO 295
<211> LENGTH: 108
<212> TYPE: PRT
<213> ORGANISM: Homo sapiens

<400> SEQUENCE: 295

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
```

```
                35                  40                  45
Gly Tyr Ile Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Trp Gly Gln Gly Thr Leu Val Thr Val Ser Ser
                100                 105
```

<210> SEQ ID NO 296
<211> LENGTH: 109
<212> TYPE: PRT
<213> ORGANISM: Homo sapiens

<400> SEQUENCE: 296

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ser Met Asn Trp Val Arg Gln Ala Pro Gly Lys Gly Leu Glu Trp Val
                 35                  40                  45

Ser Tyr Ile Ser Ser Ser Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg Trp Gly Gln Gly Thr Leu Val Thr Val Ser Ser
                100                 105
```

<210> SEQ ID NO 297
<211> LENGTH: 108
<212> TYPE: PRT
<213> ORGANISM: Homo sapiens

<400> SEQUENCE: 297

```
Glu Val Gln Leu Val Glu Ser Gly Gly Gly Leu Ile Gln Pro Gly Gly
  1               5                  10                  15

Ser Leu Arg Leu Ser Cys Ala Ala Ser Gly Phe Thr Val Ser Ser Asn
                 20                  25                  30

Tyr Met Ser Trp Val Arg Gln Ala Pro Gly Lys Gly Leu Glu Trp Val
                 35                  40                  45

Ser Val Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Trp Gly Gln Gly Thr Leu Val Thr Val Ser Ser
                100                 105
```

<210> SEQ ID NO 298
<211> LENGTH: 109
<212> TYPE: PRT
<213> ORGANISM: Homo sapiens

<400> SEQUENCE: 298

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Gly Gln Gly Thr Thr Val Thr Val Ser Ser
            100                 105

<210> SEQ ID NO 299
<211> LENGTH: 109
<212> TYPE: PRT
<213> ORGANISM: Homo sapiens

<400> SEQUENCE: 299

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Thr Val Thr Val Ser Ser
            100                 105

<210> SEQ ID NO 300
<211> LENGTH: 108
<212> TYPE: PRT
<213> ORGANISM: Homo sapiens

<400> SEQUENCE: 300

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Trp Gly Gln Gly Thr Thr Val Thr Val Ser Ser
            100                 105

<210> SEQ ID NO 301
<211> LENGTH: 109
<212> TYPE: PRT
<213> ORGANISM: Homo sapiens

<400> SEQUENCE: 301

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Thr Val Thr Val Ser Ser
            100                 105

<210> SEQ ID NO 302
<211> LENGTH: 109
<212> TYPE: PRT
<213> ORGANISM: Homo sapiens

<400> SEQUENCE: 302

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Leu Val Thr Val Ser Ser
            100                 105

<210> SEQ ID NO 303
<211> LENGTH: 109
<212> TYPE: PRT
<213> ORGANISM: Homo sapiens

<400> SEQUENCE: 303

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Gln Gly Thr Thr Val Thr Val Ser Ser
            100                 105

<210> SEQ ID NO 304
<211> LENGTH: 111
<212> TYPE: PRT
<213> ORGANISM: Homo sapiens

<400> SEQUENCE: 304

Gln Ser Val Leu Thr Gln Pro Pro Ser Val Ser Gly Ala Pro Gly Gln
  1               5                  10                  15

Arg Val Thr Ile Ser Cys Thr Gly Ser Ser Asn Ile Gly Ala Gly
             20                  25                  30

Tyr Asp Val His Trp Tyr Gln Gln Leu Pro Gly Thr Ala Pro Lys Leu
             35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Ser Val Phe Gly Gly Gly Thr Lys Leu Thr Val Leu
            100                 105                 110

<210> SEQ ID NO 305
<211> LENGTH: 107
<212> TYPE: PRT
<213> ORGANISM: Homo sapiens

<400> SEQUENCE: 305

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Leu
                 85                  90                  95

Thr Phe Gly Gly Gly Thr Lys Val Glu Ile Lys
            100                 105

<210> SEQ ID NO 306
<211> LENGTH: 107
<212> TYPE: PRT
<213> ORGANISM: Homo sapiens

<400> SEQUENCE: 306

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Asn Tyr
```

```
                20                  25                  30
Leu Ala Trp Tyr Gln Gln Lys Pro Gly Lys Val Pro Lys Leu Leu Ile
            35                  40                  45
Tyr Ala Ala Ser Thr Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Val Ala Thr Tyr Tyr Cys Gln Lys Tyr Asn Ser Ala Pro Phe
                85                  90                  95
Thr Phe Gly Pro Gly Thr Lys Val Asp Ile Lys
                100                 105
```

<210> SEQ ID NO 307
<211> LENGTH: 107
<212> TYPE: PRT
<213> ORGANISM: Homo sapiens

<400> SEQUENCE: 307

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Arg Leu Ile
            35                  40                  45
Tyr Ala Ala Ser Ser Leu Gln Ser Gly Val Pro Ser Arg Phe Ser Gly
        50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Ser Tyr Pro Trp
                85                  90                  95
Thr Phe Gly Gln Gly Thr Lys Val Glu Ile Lys
                100                 105
```

<210> SEQ ID NO 308
<211> LENGTH: 107
<212> TYPE: PRT
<213> ORGANISM: Homo sapiens

<400> SEQUENCE: 308

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
            35                  40                  45
Tyr Ala Ala Ser Ser Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Ile
                85                  90                  95
Thr Phe Gly Gln Gly Thr Arg Leu Glu Ile Lys
                100                 105
```

<210> SEQ ID NO 309
<211> LENGTH: 110
<212> TYPE: PRT

<213> ORGANISM: Homo sapiens

<400> SEQUENCE: 309

```
Gln Ser Val Leu Thr Gln Pro Pro Ser Val Ala Ala Pro Gly Gln
 1               5                  10                  15
Lys Val Thr Ile Ser Cys Ser Gly Ser Ser Asn Ile Gly Asn Asn
             20                  25                  30
Tyr Val Ser Trp Tyr Gln Gln Leu Pro Gly Thr Ala Pro Lys Leu Leu
         35                  40                  45
Ile Tyr Asp Asn Asn Lys Arg Pro Ser Gly Ile Pro Asp Arg Phe Ser
 50                  55                  60
Gly Ser Lys Ser Gly Thr Ser Ala Thr Leu Gly Ile Thr Gly Leu Gln
65                   70                  75                  80
Thr Gly Asp Glu Ala Asp Tyr Tyr Cys Gly Thr Trp Asp Ser Ser Leu
                 85                  90                  95
Ser Ala Gly Val Phe Gly Gly Gly Thr Lys Leu Thr Val Leu
                100                 105                 110
```

<210> SEQ ID NO 310
<211> LENGTH: 107
<212> TYPE: PRT
<213> ORGANISM: Homo sapiens

<400> SEQUENCE: 310

```
Glu Ile Val Met Thr Gln Ser Pro Ala Thr Leu Ser Val Ser Pro Gly
 1               5                  10                  15
Glu Arg Ala Thr Leu Ser Cys Arg Ala Ser Gln Ser Val Ser Ser Asn
             20                  25                  30
Leu Ala Trp Tyr Gln Gln Lys Pro Gly Gln Ala Pro Arg Leu Leu Ile
         35                  40                  45
Tyr Gly Ala Ser Thr Arg Ala Thr Gly Ile Pro Ala Arg Phe Ser Gly
 50                  55                  60
Ser Gly Ser Gly Thr Glu Phe Thr Leu Thr Ile Ser Ser Leu Gln Ser
65                   70                  75                  80
Glu Asp Phe Ala Val Tyr Tyr Cys Gln Gln Tyr Asn Asn Trp Pro Ile
                 85                  90                  95
Thr Phe Gly Gln Gly Thr Arg Leu Glu Ile Lys
                100                 105
```

<210> SEQ ID NO 311
<211> LENGTH: 110
<212> TYPE: PRT
<213> ORGANISM: Homo sapiens

<400> SEQUENCE: 311

```
Gln Ser Val Leu Thr Gln Pro Pro Ser Val Ala Ala Pro Gly Gln
 1               5                  10                  15
Lys Val Thr Ile Ser Cys Ser Gly Ser Ser Asn Ile Gly Asn Asn
             20                  25                  30
Tyr Val Ser Trp Tyr Gln Gln Leu Pro Gly Thr Ala Pro Lys Leu Leu
         35                  40                  45
Ile Tyr Asp Asn Asn Lys Arg Pro Ser Gly Ile Pro Asp Arg Phe Ser
 50                  55                  60
Gly Ser Lys Ser Gly Thr Ser Ala Thr Leu Gly Ile Thr Gly Leu Gln
65                   70                  75                  80
Thr Gly Asp Glu Ala Asp Tyr Tyr Cys Gly Thr Trp Asp Ser Ser Leu
                 85                  90                  95
```

Ser Ala Gly Val Phe Gly Gly Gly Thr Lys Leu Thr Val Leu
            100                 105                 110

<210> SEQ ID NO 312
<211> LENGTH: 107
<212> TYPE: PRT
<213> ORGANISM: Homo sapiens

<400> SEQUENCE: 312

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys Val Glu Ile Lys
            100                 105

<210> SEQ ID NO 313
<211> LENGTH: 107
<212> TYPE: PRT
<213> ORGANISM: Homo sapiens

<400> SEQUENCE: 313

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 314
<211> LENGTH: 107
<212> TYPE: PRT
<213> ORGANISM: Homo sapiens

<400> SEQUENCE: 314

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

```
Tyr Gly Ala Ser Thr Arg Ala Thr Gly Ile Pro Ala Arg Phe Ser Gly
         50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Phe
                 85                  90                  95

Thr Phe Gly Pro Gly Thr Lys Val Asp Ile Lys
            100                 105
```

<210> SEQ ID NO 315
<211> LENGTH: 110
<212> TYPE: PRT
<213> ORGANISM: Homo sapiens

<400> SEQUENCE: 315

```
Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
             20                  25                  30

Thr Val Asn Trp Tyr Gln Gln Leu Pro Gly Thr Ala Pro Lys Leu Leu
             35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Pro Val Phe Gly Gly Gly Thr Lys Leu Thr Val Leu
            100                 105                 110
```

<210> SEQ ID NO 316
<211> LENGTH: 108
<212> TYPE: PRT
<213> ORGANISM: Homo sapiens

<400> SEQUENCE: 316

```
Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
             20                  25                  30

Ser Trp Tyr Gln Gln Lys Pro Gly Gln Ala Pro Val Leu Val Ile Tyr
             35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95

Leu Val Phe Gly Gly Gly Thr Lys Leu Thr Val Leu
            100                 105
```

<210> SEQ ID NO 317
<211> LENGTH: 108
<212> TYPE: PRT
<213> ORGANISM: Homo sapiens

<400> SEQUENCE: 317

```
Ser Tyr Glu Leu Thr Gln Pro Pro Ser Val Ser Val Ser Pro Gly Gln
```

-continued

```
                  1               5                  10                 15
           Thr Ala Arg Ile Thr Cys Ser Gly Asp Ala Leu Pro Lys Lys Tyr Ala
                           20                  25                  30

Tyr Trp Tyr Gln Gln Lys Ser Gly Gln Ala Pro Val Leu Val Ile Tyr
                           35                  40                  45

Glu Asp Ser Lys Arg Pro Ser Gly Ile Pro Glu Arg Phe Ser Gly Ser
                           50                  55                  60

Ser Ser Gly Thr Met Ala Thr Leu Thr Ile Ser Gly Ala Gln Val Glu
            65                  70                  75                  80

Asp Glu Ala Asp Tyr Tyr Cys Tyr Ser Thr Asp Ser Ser Gly Asn His
                           85                  90                  95

Val Val Phe Gly Gly Gly Thr Lys Leu Thr Val Leu
                          100                 105

<210> SEQ ID NO 318
<211> LENGTH: 107
<212> TYPE: PRT
<213> ORGANISM: Homo sapiens

<400> SEQUENCE: 318

Asp Ile Gln Met Thr Gln Ser Pro Ser Ser Leu Ser Ala Ser Val Gly
            1               5                  10                  15

Asp Arg Val Thr Ile Thr Cys Gln Ala Ser Gln Asp Ile Ser Asn Tyr
                           20                  25                  30

Leu Asn Trp Tyr Gln Gln Lys Pro Gly Lys Ala Pro Lys Leu Leu Ile
                           35                  40                  45

Tyr Asp Ala Ser Asn Leu Glu Thr Gly Val Pro Ser Arg Phe Ser Gly
                           50                  55                  60

Ser Gly Ser Gly Thr Asp Phe Thr Phe Thr Ile Ser Ser Leu Gln Pro
            65                  70                  75                  80

Glu Asp Ile Ala Thr Tyr Tyr Cys Gln Gln Tyr Asp Asn Leu Pro Ile
                           85                  90                  95

Thr Phe Gly Gln Gly Thr Arg Leu Glu Ile Lys
                          100                 105

<210> SEQ ID NO 319
<211> LENGTH: 108
<212> TYPE: PRT
<213> ORGANISM: Homo sapiens

<400> SEQUENCE: 319

Ser Ser Glu Leu Thr Gln Asp Pro Ala Val Ser Val Ala Leu Gly Gln
            1               5                  10                  15

Thr Val Arg Ile Thr Cys Gln Gly Asp Ser Leu Arg Ser Tyr Tyr Ala
                           20                  25                  30

Ser Trp Tyr Gln Gln Lys Pro Gly Gln Ala Pro Val Leu Val Ile Tyr
                           35                  40                  45

Gly Lys Asn Asn Arg Pro Ser Gly Ile Pro Asp Arg Phe Ser Gly Ser
                           50                  55                  60

Ser Ser Gly Asn Thr Ala Ser Leu Thr Ile Thr Gly Ala Gln Ala Glu
            65                  70                  75                  80

Asp Glu Ala Asp Tyr Tyr Cys Asn Ser Arg Asp Ser Ser Gly Asn His
                           85                  90                  95

Val Val Phe Gly Gly Gly Thr Lys Leu Thr Val Leu
                          100                 105
```

```
-continued
<210> SEQ ID NO 320
<211> LENGTH: 111
<212> TYPE: PRT
<213> ORGANISM: Homo sapiens

<400> SEQUENCE: 320

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu
                100                 105                 110
```

What is claimed is:

1. A fully human monoclonal antibody, or binding fragment thereof, comprising a light chain comprising the amino acid sequence of SEQ ID NO: 72 and a heavy chain polypeptide comprising the amino acid sequence of SEQ ID NO: 74 and wherein said antibody or said binding fragment thereof binds to human Tumor Necrosis Factor-α.

2. A composition comprising the antibody; or binding fragment of claim 1 and a pharmaceutically acceptable carrier.

3. A conjugate comprising the antibody or binding fragment of claim 1 and a therapeutic agent.

4. The conjugate of claim 3, wherein the therapeutic agent is a toxin.

5. The conjugate of claim 3, wherein the therapeutic agent is a radioisotope.

6. A fully human monoclonal antibody, or binding fragment thereof, comprising a light chain comprising the amino acid sequence of SEQ ID NO: 72 and a heavy chain polypeptide comprising the amino acid sequence of SEQ ID NO: 70 and wherein said antibody or said binding fragment thereof binds to human Tumor Necrosis Factor-α.

7. A composition comprising the antibody or binding fragment of claim 6, and a pharmaceutically acceptable carrier.

8. A fully human monoclonal antibody, or bindivg fragment thereof comprising a light chain comprising the amino acid sequence of SEQ ID NO: 50 and a heavy chain polypeptide comprising the amino acid sequence of SEQ ID NO: 52 and wherein said antibody or said binding fragment thereof binds to human Tumor Necrosis Factor-α.

9. A composition comprising the antibody or binding fragment of claim 8, and a pharmaceutically acceptable carrier.

10. A conjugate comprising the antibody or binding fragment of claim 8, and a therapeutic agent.

11. The conjugate of claim 10, wherein the therapeutic agent is a toxin.

12. The conjugate of claim 10, wherein the therapeutic agent is a radioisotope.

13. A fully human monoclonal antibody, or binding fragment thereof, comprising a light chain comprising the amino acid sequence of SEQ ID NO: 54 and a heavy chain polypeptide comprising the amino acid sequence of SEQ ID NO: 56 and wherein, said antibody or said binding fragment thereof binds to human Tumor Necrosis Factor-α.

14. A composition comprising the antibody or binding fragment of claim 13, and a pharmaceutically acceptable carrier.

15. A conjugate comprising the antibody or binding fragment of claim 6 and a therapeutic agent.

16. The conjugate of claim 15, wherein the therapeutic agent comprises a toxin.

17. The conjugate of claim 15, wherein the therapeutic agent comprises a radioistope.

18. The fully human monoclonal antibody or binding fragment of claim 6, wherein said binding fragment comprises a Fab, Fab', F(ab')$_2$, or Fv fragment.

19. The fully human monoclonal antibody or binding fragment of claim 6, wherein said antibody has an IgG2 isotype.

20. The fully human monoclonal antibody or binding fragment of claim 1, wherein said binding fragment comprises a Fab, Fab', F(ab')$_2$, or Fv fragment.

21. The fully human monoclonal antibody or binding fragment of claim 1, wherein said antibody has an IgG2 isotype.

22. The fully human monoclonal antibody or binding fragment of claim 8, wherein said binding fragment comprises a Fab, Fab', F(ab')$_2$, or Fv fragment.

23. The fully human monoclonal antibody or binding fragment of claim 8, wherein said antibody has an IgG2 isotype.

24. The fully human monoclonal antibody or binding fragment of claim 13, wherein said binding fragment comprises a Fab, Fab', F(ab')$_2$, or Fv fragment.

25. The fully human monoclonal antibody or binding fragment of claim 13 wherein said antibody has an IgG2 isotype.

26. A fully human monoclonal antibody, or binding fragment thereof, that binds to Tumor Necrosis Factor-α, wherein the antibody, or binding fragment thereof, comprises:
- a heavy chain complementarity determining region 1 (CDR1) comprising the amino acid sequence of "Ser Tyr Asp Met His" (SEQ ID NO: 321);
- a heavy chain complementarity determining region 2 (CDR2) comprising the amino acid sequence of "Val Ile Trp Ser Asp Gly Ser Ile Lys Tyr Tyr Ala Asp Ser Val Lys Gly" (SEQ ID NO: 322);
- a heavy chain complementarity determining region 3 (CDR3) the amino acid sequence of "Glu Val Glu Ser Ala Met Gly Gly Phe Tyr Tyr Asn Gly Met Asp Val" (SEQ ID NO: 323);
- a light chain complementarity determining region 1 (CDR1) comprising the amino acid sequence of "Arg Ala Ser Gln Gly Ile Arg Ile Asp Len Gly" (SEQ ID NO: 324);
- a light chain complementarity determining region 2 (CDR2) comprising the amino acid sequence of "Ala Ala Ser Thr Leu Gln Ser" (SEQ ID NO: 325); and
- a light chain complementarity determining region 3 (CDR3) the amino acid sequence of "Leu Gin His Lys Ser Tyr Pro Leu Thr" (SEQ ID NO: 326).

27. The antibody, or binding fragment thereof of claim 26, wherein the antibody, or binding fragment thereof, comprises a heavy chain polypeptide comprising the amino acid sequence of SEQ ID NO: 70 and a light chain polypeptide comprising the amino acid sequence of SEQ ID NO: 72.

28. The antibody, or binding fragment thereof, of claim 26, wherein the antibody, or binding fragment thereof, comprises a heavy chain polypeptide comprising the amino acid sequence of SEQ ID NO: 74 and a light chain polypeptide comprising the amino acid sequence of SEQ ID NO: 72.

29. The fully human monoclonal antibody or binding fragment of claim 26, wherein said binding fragment comprises a Fab, Fab', F(ab')$_2$, or Fv fragment.

30. The fully human monoclonal antibody or binding fragment of claim 26, wherein said antibody has an IgG2 isotype.

31. A composition comprising the antibody or binding fragment of claim 30, and a pharmaceutically acceptable carrier.

32. A conjugate comprising the antibody or binding fragment of claim 30, and a therapeutic agent.

33. The conjugate of claim 32, wherein the therapeutic agent is a toxin.

34. The conjugate of claim 32, wherein the therapeutic agent is a radioisotope.

35. The conjugate according to claim 3, 10, 15 or 32, admixed with a pharmaceutically acceptable carrier.

* * * * *

UNITED STATES PATENT AND TRADEMARK OFFICE
CERTIFICATE OF CORRECTION

PATENT NO. : 7,285,269 B2  
APPLICATION NO. : 10/727155  
DATED : October 23, 2007  
INVENTOR(S) : Babcook et al.

Page 1 of 17

It is certified that error appears in the above-identified patent and that said Letters Patent is hereby corrected as shown below:

On the (title page), under "Foreign Patent Documents", please insert --EP 0 614 984 A, 09-14-1994, Miles Inc.--.

On page 3 (title page), under "non Patent Literature Documents" please insert:
--Baselga et al. *Journal of clinical Oncology.* 18(4):904-914 (2000).
Glennie et al. *Immunology Today.* 21(8):403-410 (2000).
Kempeni. *Annals of the Rheumatic Diseases.* 58(3):170-172 (1999).
Kempeni. *Annals of the Rheumatic Diseases.* 59(Supp. 1):144-145 (2000).
Mukhtyar et al. *Journal of Forensic Sciences.* 64(Supp. 4):31-36 (2005).
Taylor. *Current Opinion in Rheumatology.* 13(3):164-169 (2001).--.

On page 3, Col. 1, 14th line under the heading "Other Publications", please delete "Characterizaion" and insert --Characterization--, therefor.

On page 3, Col. 1, 25th line under the heading "Other Publications", please delete "Appliation" and insert --Application--, therefor.

On page 3, Col. 1, 31st line under the heading "Other Publications", please delete "Immuniation" and insert --Immunization--, therefor.

On page 3, Col. 1, 46th line under the heading "Other Publications", please delete "Pseudomanas" and insert --Pseudomonas--, therefor.

On page 3, Col. 2 (Other Publications), line 9, please delete "Sciencesl" and insert --Sciences--, therefor.

On page 3, Col. 2 (Other Publications), line 12, please delete "Lipopolysacchardie" and insert --Lipopolysaccharide--, therefor.

On page 3, Col. 2 (Other Publications), line 18, please delete "LPS-induced" and insert --LPS-Induced--, therefor.

Signed and Sealed this  
Twenty-fifth Day of September, 2012

David J. Kappos  
*Director of the United States Patent and Trademark Office*

CERTIFICATE OF CORRECTION (continued)

U.S. Pat. No. 7,285,269 B2

On page 3, Col. 2 (Other Publications), line 44, please delete "libraries," and insert --libraries."--, therefor.

On page 3, Col. 2 (Other Publications), line 65, please delete "7(3)251" and insert --7(3):251--, therefor.

In Col. 2, line 41, before "SEQ" please insert --(--.

In Col. 2, line 44, please delete "lie" and insert --Ile--, therefor.

In Col. 2, line 55, please delete "(CDR 1)" and insert --(CDR1)--, therefor.

In Col. 3, line 14, please delete "lie" and insert --Ile--, therefor.

In Col. 3, line 45, please delete "of"Val" and insert --of "Val--, therefor.

In Col. 3, line 54, please delete "Gin" and insert --Gln--, therefor.

In Col. 3, line 59, please delete "of"Gln" and insert --of "Gln--, therefor.

In Col. 4, line 3, please delete "of"Gly" and insert --of "Gly--, therefor.

In Col. 4, line 14, please delete "of"Gly" and insert --of "Gly--, therefor.

In Col. 7, line 19, please delete "cell'" and insert --cells--, therefor.

In Col. 18, line 21, please delete "understood." and insert --understood--, therefor.

In Col. 20, line 11, please delete "J" and insert --J.--, therefor.

In Col. 26, line 66, please delete "FRI" and insert --FR1,--, therefor.

In Col. 31, line 3, please delete "described,the" and insert --described the--, therefor.

In Col. 35, line 2, please delete "(EDC.," and insert --(EDC,--, therefor.

In Col. 40, line 5, please delete "HA$^1/_2$" and insert --½ HA--, therefor.

In Col. 40, line 12, please delete "NaHCO$_{38.4}$" and insert --NaHCO$_3$ 8.4--, therefor.

In Col. 42, line 12, please delete "Isoptype" and insert --Isotype--, therefor.

In Col. 43, line 34, please delete "0.0" and insert --0.01--, therefor.

In Col. 43, line 45, please delete "5μL" and insert --50μL--, therefor.

In Col. 44, lines 44-45, please delete "Neutralization of - - - - Assay" and insert the same on Line 45 as a Heading of the next paragraph.

In Col. 45, line 15, please delete "poptosis" and insert --Apoptosis--, therefor.

In Col. 60, line 16, please delete "Structual Analysi" and insert --Structural Analysis--, therefor.

In Cols. 59-64 (Table 31), please delete all of Table 31 and insert the attached Table 31 therefor.

In Cols. 63-66 (Table 32), please delete all of Table 32 and insert the attached Table 32 therefor.

In Cols. 65-74 (Table 33), please delete all of Table 33 and insert the attached Table 33 therefor.

CERTIFICATE OF CORRECTION (continued)
U.S. Pat. No. 7,285,269 B2

In Cols. 73-82 (Table 34), please delete all of Table 34 and insert the attached Table 34 therefor.

In Col. 81, line 28, please delete "Detemination" and insert --Determination--, therefor.

In Col. 81, line 46, please delete "immunoglobuins" and insert --immunoglobulins--, therefor.

In Col. 301, please insert:

```
--<210> 321
<211> 5
<212> PRT
<213> Homo sapiens

<400> 321
Ser Tyr Asp Met His
 1               5

<210> 322
<211> 17
<212> PRT
<213> Homo sapiens

<400> 322
Val Ile Trp Ser Asp Gly Ser Ile Lys Tyr Tyr Ala Asp Ser Val Lys
 1               5                  10                  15
Gly

<210> 323
<211> 16
<212> PRT
<213> Homo sapiens

<400> 323
Glu Val Glu Ser Ala Met Gly Gly Phe Tyr Tyr Asn Gly Met Asp Val
 1               5                  10                  15

<210> 324
<211> 11
<212> PRT
<213> Homo sapiens

<400> 324
Arg Ala Ser Gln Gly Ile Arg Ile Asp Leu Gly
 1               5                  10

<210> 325
<211> 7
<212> PRT
<213> Homo sapiens

<400> 325
Ala Ala Ser Thr Leu Gln Ser
 1               5

<210> 326
<211> 9
<212> PRT
```

```
<213> Homo sapiens

<400> 326
Leu Gln His Lys Ser Tyr Pro Leu Thr
 1               5

<210> 327
<211> 5
<212> PRT
<213> Homo sapiens

<400> 327
Arg Asn Tyr Met Ser
 1               5

<210> 328
<211> 16
<212> PRT
<213> Homo sapiens

<400> 328
Val Ile Tyr Ser Gly Asp Arg Thr Tyr Tyr Ala Asp Ser Val Lys Gly
 1               5                  10                  15

<210> 329
<211> 7
<212> PRT
<213> Homo sapiens

<400> 329
Gly Glu Gly Gly Phe Asp Tyr
 1               5

<210> 330
<211> 11
<212> PRT
<213> Homo sapiens

<400> 330
Arg Ala Ser Gln Ser Val Ser Ser Asn Leu Ala
 1               5                  10

<210> 331
<211> 7
<212> PRT
<213> Homo sapiens

<400> 331
Gly Ala Ser Ile Arg Ala Thr
 1               5

<210> 332
<211> 8
<212> PRT
<213> Homo sapiens
```

```
<400> 332
Gln Gln Tyr Asn Tyr Trp Trp Thr
 1               5
```
--.

In Col. 301, line 35, Claim 2, please delete "antibody;" and insert --antibody--, therefor.

In Col. 301, line 36, Claim 2, after "claim 1" insert --,--.

In Col. 301, line 39, Claim 3, after "claim 1" insert --,--.

In Col. 301, line 53, Claim 8, please delete "bindivg" and insert --binding--, therefor.

In Col. 301, line 54, Claim 8, after "thereof", please insert --,--.

In Col. 301, line 54, Claim 8, please delete "light" and insert --heavy--, therefor.

In Col. 301, line 55, Claim 8, please delete "heavy" and insert --light--, therefor.

In Col. 302, line 29, Claim 13, please delete "light" and insert --heavy--, therefor.

In Col. 302, line 30, Claim 13, please delete "heavy" and insert --light--, therefor.

In Col. 302, line 32, Claim 13, please delete "wherein," and insert --wherein--, therefor.

In Col. 302, line 42, Claim 17, please delete "radioistope" and insert --radioisotope--, therefor.

In Col. 302, line 66, Claim 25, after "claim 13" please insert --,--.

In Col. 303, line 13, Claim 26, after "(CDR3)" please insert --comprising--.

In Col. 303, line 18, Claim 26, please delete "Len" and insert --Leu--, therefor.

In Col. 303, line 24, Claim 26, after "(CDR3)" please insert --comprising--.

In Col. 303, line 24, Claim 26, please delete "Gin" and insert --Gln--, therefor.

In Col. 303, line 26, Claim 27, after "thereof", please insert --,--.

Table 31. XENOMAX® Heavy Chain Analysis

| SEQ ID NO: | Single Cell | V Heavy/D/J | FR1 | CDR1 | FR2 |
|---|---|---|---|---|---|
| 267 | - | Germline | QVQLVESGGGVVQPGRSLRLSCAASGFTFS | SYGMH | WVRQAPGKGLEWVA |
| 74 | 299 v. 2 | VH3-33/D5-5/JH6b | QVQLVESGGGVVQPGRSLRLSCAASGFTFS | SYDMH | WVRQAPGKGLEWVA |
| 70 | 299 v. 1 | VH3-33/D5-5/JH6b | QVQLVESGGGVVQPGRSLRLSCAASGFTFS | SYDMH | WVRQAPGKGLEWVA |
| 38 | 148 | VH3-33/D5-5/JH6b | QVQLVESGGGVVQPGRSLRLSCAASGFTFS | NYDMH | WVRQAPGKGLEWVA |
| 78 | 313 | VH3-33/D5-24/JH6b | QVQLVESGGGVVQPGRSLRLSCAASGFTFS | NHDIH | WVRQAPGKGLEWVA |
| 6 | 15 | VH3-33/D6-6/JH6b | QVQLVESGGGVVQPGRSLRLSCAASGFTFS | SYDIH | WVRQAPGKGLEWVA |
| 22 | 95 | VH3-33/D6-19/JH6b | QVQLVESGGGVVQPGRSLRLSCAASGFTFS | NYDMH | WVRQAPGKGLEWVA |
| 268 | - | Germline | EVQLVESGGGLIQPGGSLRLSCAASGFTVS | SNYMS | WVRQAPGKGLEWVS |
| 46 | 250 | VH3-53/D3-16/JH4b | EVQLVESGGGLIQPGGSLRLSCAASGFTVS | SNYMS | WVRQAPGKGLEWVS |
| 50 | 263 | VH3-53/D3-16/JH4b | EVQLVESGGGLIQPGGSLRLSCAASGFTVS | RNYMS | WVRQAPGKGLEWVS |
| 54 | 269 | VH3-53/D3-16/JH4b | EVQLVESGGGLIQPGGSLRLSCAASEFTVS | RNYMS | WVRQAPGKGLEWVA |
| 269 | - | Germline | QVQLVESGGGVVQPGRSLRLSCAASGFTFS | SYGMH | WVRQAPGKGLEWVA |
| 58 | 280 | VH3-33/D4-17/JH6b | QVQLVESGGGVVQPGRSLRLSCAASGFTVS | SYDMH | WVRQAPGKGLEWVA |
| 62 | 282 | VH3-33/D4-17/JH6b | QVQLVESGGGVVQPGRSLRLSCAASGFTFS | SYGMH | WVRQAPGKGLEWVA |
| 66 | 291 | VH3-33/D1-26/JH6b | QVQLVESGGSVVQPGRSLRLSCAASGFTFS | NYGIH | WVRQAPGKGLEWVA |
| 270 | - | Germline | QVQLQESGPGLVKPSETLSLTCTVSGGSIS | SYGMH | WVRQAPGKGLEWVA |
| 42 | 234 | VH3-30/D1-26/JH6b | QVQLQESGPGLVKPSETLSLTCTVSGGSIS | SYDMH | WVRQAPGKGLEWVA |
| 34 | 140 | VH3-30/D1-20/JH6b | QVQLQESGPGLVKPSQTLSLTCTVSGGSIS | SYGMH | WVRQAPGKGLEWVA |
| 14 | 28 | VH3-30/D3-3/JH6b | QVQLQESGPGLVKPSQTLSLTCTVSGGSIS | NYGMH | WVRQAPGKGLEWVT |
| 271 | - | Germline | QVQLQESGPGLVKPSETLSLTCTVSGGSIS | SYYWS | WIRQPAGKGLEWIG |
| 18 | 69 | VH4-4/D2-2/JH2 | QVQLQESGPGLVKPSETLSLTCTVSGGSIN | HYYWS | WIRQPAGKGLEWIG |
| 272 | - | Germline | QVQLQESGPGLVKPSQTLSLTCTVSGGSIS | SGGYYWS | WIRQHPGKGLEWIG |
| 2 | 2 | VH4-31/D1-20/JH6b | QVQLQESGPGLVKPSQTLSLTCTVSGGSIS | SGGYYWS | WIRQHPGKGLEWIG |
| 10 | 25 | VH4-31/D1-20/JH6b | QVQLQESGPGLVKPSQTLSLTCTVSGGSIS | SGGYYWS | WIRQHPGKGLEWIG |
| 30 | 131 | VH4-31/D1-20/JH6b | QVQLQESGPGLVKPSQTLSLTCTVSGGSIS | SGGYYWS | WIRQHPGKGLEWIG |
| 26 | 123 | VH4-31/D1-20/JH6b | QVQLQESGPGLVKPSQTLSLTCTVSGGSIS | SGGYYWS | WIRQHPGKGLEWIG |

Table 31, 1

| SEQ ID NO: | Single Cell | CDR2 | FR3 | CDR3 | FR4 |
|---|---|---|---|---|---|
| 267 | - | VIWYDGSNKYYADSVKG | RFTISRDNSKNTLYLQMNSLRAEDTAVYYCAR | | WGQGTTVTVSS |
| 74 | 299 v. 2 | VIWSDGSIKYYADSVKG | RFTISRDNSKNTLYLQMNSLRAEDTAVYYCAR | EVESAMGGFYYNGMDV | WGQGTTVTVSS |
| 70 | 299 v. 1 | VIWSDGSIKYYADSVKG | RFTISRDNSKNTLYLQMNSLRAEDTAVYYCAR | EVESAMGGFYYNGMDV | WGQGTTVTVSS |
| 38 | 148 | VIWYDGSIKYYADSVKG | RFTISRDNSKNTLYLQMNSLRAEDTAVYFCAR | ETAILRGYYYDMDV | WGQGTTVTVSS |
| 78 | 313 | VIWSDGSNKYYADSVKG | RFTISRDNSKNTLYLQMNSLRAEDTAVYYCAR | EKMATIKGYYYGMDV | WGQGATVTVSS |
| 6 | 15 | VIWYDGSIKYYADSVKG | RFTISRDNSKNTLYLQMNSLRAEDTAVYYCAR | EEQLVRGGYYYGMDV | WGQGTTVTVSS |
| 22 | 95 | VIWYDGSIKYYADSVKG | RFTISRDNSKNTLHLQMNSLRAEDTAVYYCAR | EIAVAGGYYYGLDV | WGQGTLVTVSS |
| 268 | - | VIYSGGSTYYADSVKG | RFTISRDNSKNTLYLQMNSLRAEDTAVYYCAR | | WGQGTLVTVSS |
| 46 | 250 | VIYSGDRTYYADSVKG | RFTISRDNSKNTLYLQMNSLRAEDTAVYYCAR | GEGGFDY | WGQGTLVTVSS |
| 50 | 263 | VIYSGDRTYYADSVKG | RFTISRDNSKNTLYLQMNSLRAEDTAVYYCAR | GEGGFDY | WGQGTLVTVSS |
| 54 | 269 | VIYSGDRTYYADSVKG | RFTISRDNSKNTLYLQMNSLRAEDTAVYYCAR | GEGGFDY | WGQGTLVTVSS |
| 269 | - | VIWYDGSNKYYADSVKG | RFTISRDNSKNTLYLQMNSLRAEDTAVYYCAR | | WGQGTTVTVSS |
| 58 | 280 | VIWSNGSNKYYADSVKG | RFTISRDNSKNTLYLQVNSLRAEDTAVYYCAR | DNGVYVGYAYYYGMDV | WGQGTTVTVSS |
| 62 | 282 | VIWSNGSNKYYADSVKG | RFTISRDNSKNTLYLQMNSLRAEDTAVYYCAR | DNGVYVGYAYYYGMDV | WGQGTTVTVSS |
| 66 | 291 | VIWSDGSNKYYADSVKG | RFTISRDNSKNTLYLQMNSLRAEDTAVYYCAR | ELPNSGSYSGYYYYGMDV | WGQGTTVTVSS |
| 270 | - | VISYDGSNKYYADSVKG | RFTISRDNSKNTLYLQMNSLRAEDTAVYYCAR | | WGQGTTVTVSS |
| 42 | 234 | VISYDGSIKYYADSVKG | RFTISRDNSKNTLYLQMNSLRAEDTAVYYCAR | EVRSGSYYYYYSMDV | WGQGTTVTVSS |
| 34 | 140 | VISYDGSNKYYADSVKG | RFTISRDNSKNTLYLQMNSLRAEDTAVYYCAR | DQDNWNYYYGMDV | WGQGTTVTVSS |
| 14 | 28 | IISYDGSNKYYADSVKG | RFTISRDNSKNTLYLQMNSLRAEDTAVYYCVT | YYDFWSGYLPGMDV | WGQGTTVTVSS |
| 271 | - | RIYTSGSTNYNPSLKS | RVTMSVDTSKNQFSLKLSSVTAADTAVYYCAR | | WGRGTLVTVSS |
| 18 | 69 | RIYTGSTNYNPSLKS | RVTMSVDTSKNQFSLKLSSVTAADTAVYYCAG | GWSYWYFDL | WGRGTLVTVSS |
| 272 | - | YIYYSGSTYYNPSLKS | RVTISVDTSKNQFSLKLSSVTAADTAVYYCAR | | WGQGTTVTVSS |
| 2 | 2 | NIYYSGSTYYNPSLKS | RVTISVDTSKNQFSLKLSSVTAADTAVYYCAR | DSNQYNWNDEVYDYGLDV | WGQGTTVTVSS |
| 10 | 25 | NIYYSGSTYYNPSLKS | RVTISVDTSKNQFSLKLSSVTAADTAVYYCAR | DSNQYNWNDEVYDYGLDV | WGQGTTVTVSS |
| 30 | 131 | NIYYSGSTYYNPSLKS | RVTISVDTSKNQFSLKLSSVTAADTAVYYCAR | DSNQYNWNDEVYDYGLDV | WGQGTTVTVSS |
| 26 | 123 | NIYYSGSTYYTPSLKS | RVTISVDTSKNQFSLKLSSVTAADTAVYYCAR | DSNQYNWNDEVYDYGLDV | WGQGTTVTVSS |

Table 31, 2

Table 32. XENOMAX® Light Chain Analysis

| SEQ ID NO: | Single Cell | V Kappa/J | FR1 | CDR1 | FR2 |
|---|---|---|---|---|---|
| 273 | - | Germline | DIQMTQSPSSLSASVGDRVTITC | RASQGIRNDLG | WYQQKPGKAPKRLIY |
| 72 | 299 | A30VK1/JK4 | DIQMTQSPSSLSASVGDRVTITC | RASQGIRIDLG | WYQQKPGKAPKRLIY |
| 80 | 313 | A30VK1/JK4 | DIQMTQSPSSLSASVGDRVTITC | RASQGIRNDLG | WYQQKPGKAPKRLIY |
| 68 | 291 | A30VK1/JK4 | DIQMTQSPSSLSASVGDRVTITC | RASQGIRNDLG | WYQQKPGKAPKRLIY |
| 44 | 234 | A30VK1/JK4 | DIQMTQSPSSLSASVGDRVTITC | RASQDIRNDLG | WYQQKPGKAPKRLIY |
| 4 | 2 | A30VK1/JK4 | DIQMTQSPSSLSASVGDRVTITC | RASQGIRNDLG | WYQQKPGKAPKRLIY |
| 12 | 25 | A30VK1/JK4 | DIQMTQSPSSLSASVRDRVTITC | RASQGIRNDLG | WYQQKPGKAPKRLIY |
| 32 | 131 | A30VK1/JK4 | DIQMTQSPSALSASVGDRVTITC | RASQGIRNDLG | WYQQKPGKAPKRLIY |
| 8 | 15 | A30VK1/JK4 | DIQMTQSPSSLSASIGDRVTITC | RASQGIRNDLG | WYQQKPGKAPKRLIY |
| 24 | 95 | A30VK1/JK4 | DIQMTQSPSSLSASVGDRVTITC | RASQGIRNDLG | WYQQKPGKAPKRLIY |
| 40 | 148 | A30VK1/JK4 | DIQMTQSPSSLSASVGDRVTITC | RASQGIRNDLG | WYQQKPGKAPKRLIS |
| 28 | 123 | A30VK1/JK4 | DIQMTQSPSSLSASVGDRVTITC | RASQGIRNDLT | WYQQKPGKAPKRLIY |
| 274 | - | Germline | DIQMTQSPSSLSASVGDRVTITC | RASQGIRNDLG | WYQQKPGKAPKRLIY |
| 60 | 280 | A30VK1/JK1 | DIQMTQSPSSLSASVGDRVTITC | RASQGIRNDLG | WYQQKPGKAPKRLIY |
| 64 | 282 | A30VK1/JK1 | DIQMTQSPSSLSASVGDRVTITC | RASQGIRNDLG | WYQQKPGKAPKRLIY |
| 16 | 28 | A30VK1/JK1 | DIQMTQSPSSLSASVGDRVTITC | RASQGIRNDLG | WYQQKPGKAPKRLIY |
| 275 | - | Germline | DVVMTQSPLSLPVTLGQPASISC | RSSQSLVYSDGNTYLN | WFQQRPGQSPRRLIY |
| 20 | 70 | A1VK2/JK4 | DVVMTQSPLSLPVTLGQPASISC | RSSQSLVYSDGSTYLN | WFQQRPGQSPRRLIY |
| 276 | - | Germline | DIVMTQSPLSLPVTPGEPASISC | RSSQSLLHSNGYNYLD | WYLQKPGQSPQLLIY |
| 36 | 145 | A19VK2/JK1 | DIVMTQSPLSLPVTPGEPASISC | RSSQSLLHSNGYNYLD | WYLQKPGQSPQLLIF |
| 277 | - | Germline | EIVMTQSPATLSVSPGERATLSC | RASQSVSSNLA | WYQQKPGQAPRLLIY |
| 48 | 250 | L2VK3/JK1 | EIVMTQSPATLSVSPGERATLSC | RASQSVTSNLA | WYQQKPGQAPRLLIH |
| 52 | 263 | L2VK3/JK1 | EIVMTQSPATLSVSPGERATLSC | RASQSVSSNLA | WYQQKPGQAPRLLIH |
| 56 | 269 | L2VK3/JK1 | EIVMTQSPATLSVSPGERATLSC | RASQSVSSNLA | WYQQKPGQAPRLLIH |

Table 32, 1

| SEQ ID NO: | single Cell | CDR2 | FR3 | CDR3 | FR4 |
|---|---|---|---|---|---|
| 273 | - | AASSLQS | GVPSRFSGSGSGTEFTLTISSLQPEDFATYYC | LQHNSYPLT | FGGGTKVEIK |
| 72 | 299 | AASTLQS | GVPSRFSGSGSGTEFIFTISSLQPEDFASYYC | LQHKSYPLT | FGGGTKVEIK |
| 80 | 313 | AASSLES | GVPSRFSGSGSGGPEFTLTISSLQPEDFATYYC | LQHNSYPLT | FGGGTKVEIQ |
| 68 | 291 | AASSLQS | GVPSRFSGSGSGTEFTLTISSLQPEDFATYYC | LQHCCYPLT | FGGGTKVEIK |
| 44 | 234 | AASSLQS | GVPSRFSGSGSGGPEFTLTISSLQPEDFATYYC | LQHNSYPLT | FGGGTKVEIK |
| 4 | 2 | AASSLQS | GVPSRFSGSGSGTEFTLTISSLQPEDFATYYC | LQHNYPLT | FGGGTKVEIK |
| 12 | 25 | AASSLQS | GVPSRFSGSGSGTEFTLTISSLQPEDFATYYC | LQHKSYPLT | FGGGTKVEIK |
| 32 | 131 | AASSLQS | GVPSRFSGSGSGTEFIFTISSLQPEDFATYYC | LQHKSYPLT | FGGGTKVEIK |
| 8 | 15 | AASSLQS | GVPSRFSGSGSGGPEFTLTISSLQPEDFATYYC | LQHNSYPLT | FGGGTKVEIK |
| 24 | 95 | AASSLQS | GVPSRFSGSGSGTEFTLTVSSLQPEDFATYYC | LQHHSYPLT | FGGGTKVQIN |
| 40 | 148 | AASSLQG | GVPSRFSGSGSGTEFTLTISSLQPEDFATYYC | LQHNSYPLT | FGGGTKVBIK |
| 28 | 123 | AASSLQS | GVPSRFSGSGSGTEFTLTISSLQPEDFATYYC | LQHNYPLT | FGGGTKVBIK |
| 274 | - | AASSLQS | GVPSRFSGSGSGTEFTLTISSLQPEDFATYYC | LQHNSYPWT | FGGGTKVEIK |
| 60 | 280 | AASSLQS | GVPSRFSGSGSGTEFTLTISSLQPEDFATYYC | LQHNSYPRT | FGGGTKVEIK |
| 64 | 282 | AASSLHS | GVPSRFSGSGSGTEFTLTISSLQPEDFATYYC | LQHNSYPWT | FGGGTKVEIK |
| 16 | 28 | AASSLQS | GVPSRFSGSGSGTEFTLTISSLQPEDFATYYC | LQHNSFPWT | FGQGTKVEIK |
| 275 | - | KVWNWDS | GVPDRFSGSGSGTDFTLKISRVEAEDVGVYYC | MQGTHWP##LT | FGQGTKVEIK |
| 20 | 70 | KVWNWDS | GVPDRFSGSGSGTDFTLKISRVEAEDVGVYYC | MQGSHWPREFT | FGQGTKVEIK |
| 276 | - | LGSNRAS | GVPDRFSGSGSGTDFTLKISRVEAEDVGVYYC | MQALQTWT | FGQGTKVEIK |
| 36 | 145 | LGSYRAS | GVPDRFSGSGSGTDFTLKISRVEAEDVGVYYC | MQALQTWT | FGQGTKVEIK |
| 277 | - | GASTRAT | GIPARFSGSGSGTEFTLTISSLQSEDFAVYYC | QQYNNWWT | FGQGTKVEIK |
| 48 | 250 | GASIRAT | GLPARFSGSGSGTEFTLTISSLQSEDFAVYYC | QQYNYWT | FGQGTKVEIK |
| 52 | 263 | GASIRAT | GLPARFSGSGSGTEFTLTISSLQSEDFAVYYC | QQYNYWT | FGQGTKVEIK |
| 56 | 269 | GASIRAT | GLPARFSGSGSGTEFTLTISSLQSEDFAVYYC | QQYNYWT | FGQGTKVEIK |

Table 32, 2

Table 33. Hybridoma Heavy Chain Analysis AB-TNFα-XG2

| CHAIN NAME | SEQ ID NO: | | FR1 | CDR1 | FR2 | CDR2 | FR3 | CDR3 | FR4 |
|---|---|---|---|---|---|---|---|---|---|
| | 278 | Germline | QVQLVESGGGVVQPGRSLRLSCAAS | GFTFSSYGMH | WVRQAPGKGLEWVA | VIWYDGSNKYYADSVKG | RFTISRDNSKNTLYLQMNSLRAEDTAVYYCAR | | WGQGTTVTVSS |
| 2.14 | 132 | VH3-33/D6-19/JH6b | QVQLVESGGGVVQPGRSLRLSCAAS | GFTFSSYGMH | WVRQAPGKGLEWVA | VIWYDGSNKYYADSVKG | RFTISRDNSKNTLYLQMNSLRAEDTAVYYCAR | ERDSSGWYYYGMDV | WGQGTTVTVSS |
| 2.13 | 128 | " | QVQLVESGGGVVQPGRSLRLSCAAS | GLIFSNVGMH | WVRQAPGKGLEWVA | VIWYDGSNKYYADSVKG | RFTISRDNSKNTLYLQMNSLRAEDTAVYYCAR | EGIAVAGPPYYYYGMDV | WGQGTTVTVSS |
| 2.10 | 124 | " | QVQLVESGGGVVQPGRSLRLSCAAS | GFTFSSYGMH | WVRQAPGKGLEWVA | VIWYDGSIKYYADSVKG | RFTISRDNSKNTLYLQMNSLRAEDTAVYYCAR | ERDSSGWYYYGMDV | WGQGTTVTVSS |
| | 279 | Germline | EVQLLESGGGLVQPGGSLRLSCAAS | GFTFSSYAMS | WVRQAPGKGLEWVS | AISGSGGSTYYADSVKG | RFTISRDNSKNTLYLQMNSLRAEDTAVYYCAK | | WGQGTLVTVSS |
| 4.23 | 262 | VH3-23/D3-22/JH4b | EVQLLESGGGLVQPGGSLRLSCAAS | GFTFSSYAMS | WVRQAPGKGLEWVS | AISGSGGSTYYADSVKG | RFTISRDNSKNTLYLQMNSLRAEDTAVYYCAK | DYYDSSGYHPFDY | WGQGTLVTVSS |
| | 280 | Germline | EVQLVESGGGLVKPGGSLRLSCAAS | GFTFSSYSMN | WVRQAPGKGLEWVS | SISSSSSYIYADSVKG | RFTISRDNAKNSLYLQMNSLRAEDTAVYYCAR# | | WGQGTLVTVSS |
| 2.21 | 158 | VH3-21/D1-20/JH6b | EVQLVESGGGLVKPGGSLRLSCAAS | GFTFSSYSMN | WVRQAPGKGLEWVS | SISSSSSYIYADSVKG | RFTISRDNAKNSLYLQMNSLRAEDTAVYYCAR | GGITGTNYYGMDV | WGQGTTVTVSS |
| | 281 | Germline | QVQLVESGGGVVQPGRSLRLSCAAS | GFTFSSYGMH | WVRQAPGKGLEWVA | VIWYDGSNKYYADSVKG | RFTISRDNSKNTLYLQMNSLRAEDTAVYYCAR | | WGQGTLVTVSS |
| 4.7 | 198 | VH3-33/D6-19/JH4b | QVQLVESGGGVVQPGRSLRLSCAAS | GFTFSSYGMH | WVRQAPGKGLEWVA | IIWYDGSNEYYGDSVKG | RFTISRDNSKNTLFLQMNSLRAEDTAVYYCAR | DPLRIVAGDPDY | WGQGTMVTVSS |
| 4.11 | 214 | " | QVQLVESGGGVVQPGRSLRLSCAAS | GFTFSSYGMH | WVRQAPGKGLEWVA | IIWYDGSNEYYGDSVKG | RFTISRDNSKNTLFLQMNSLRAEDTAVYYCAR | DPLRIVAGDPDY | WGQGTMVTVSS |
| | 282 | Germline | EVQLVESGGGLIQPGGSLRLSCAAS | GFTVSSNYMS | WVRQAPGQGLEWVS | VIYSGGSTYADSVKG | RFTISRDNSKNTLYLQMNSLRAEDTAVYYCAR | GPGAFDI | WGQGTMVTVSS |
| 3.9 | 186 | VH3-53/--/JH3b | EVQLVESGGGLIQPGGSLRLSCAAS | GFTVSSNYMS | WVRQAPGKGLEWVS | VIYSGGSTYADSVKG | RFTISRDNSKNTLYLQMNSLRAEDTAVYYCAR | GPGAFDI | WGQGTMVTVSS |
| 3.8 | 182 | " | EVQLVESGGGLIQPGGSLRLSCAAS | GFTVSNNYMH | WVRQAPGKGLEWVS | VIYSGGNFYYADSVKG | RFTISRDNSKNTLFLQMNSLKTEDTAVYYCAR | | WGQGTMVTVSS |
| | 283 | Germline | EVQLVQSGAEVKKPGESLKISCKGS | GYSFTSYWIG | WVRQMPGKGLEWMG | IIYPGDSDTRYSPSFQG | QVTISADKSISTAYLQWSSLKASDTAMYYCAR | | WGQGTTVTVSS |
| 2.4 | 100 | VH5-S1/D3-3/JH6b | EVQLVQSGAEVKKPGESLKISCKGS | GYSFTSDWIG | WVRQMPGKGLEWMG | IIYPGDSDTRYSPSFQG | QVTISADKSITTAYLQWSSLKASDTAMYYCAR | SGYGMDV | WGQGTTVTVSS |
| | 284 | Germline | QVQLVQSGAEVKKPGASVKVSCKAS | GYTFTSYGIS | WVRQAPGQGLEWMG | WISAYNGNTNYAQKLQG | RVTMTTDTSTSTAYMELRSLRSDDTAVYYCAR | | WGQGTLVTVSS |
| 3.4 | 170 | VH1-18/D6-19/JH4b | QVQLVQSGAEVKKPGASVKVSCKAS | GYTFTFYSII | WVRQAPGQGLEWMG | WISAYNDNTNYAQKLQG | RVTMTTDTSTSTAYMELRSLRSDDTAVYYCAR | TFTSGFDY | WGQGTLVTVSS |
| | 285 | Germline | QVQLVESGGGVVQPGRSLRLSCAAS | GFTFSSYGMH | WVRQAPGKGLEWVA | VIWYDGSNKYYADSVKG | RFTISRDNSKNTLYLQMNSLRAEDTAVYYCAR | | WGQGTLVTVSS |

Table 33, 1

Table 33, 2

| CHAIN NAME | SEQ ID NO: | | FR1 | CDR1 | FR2 | CDR2 | FR3 | CDR3 | FR4 |
|---|---|---|---|---|---|---|---|---|---|
| 2.3 | 96 | VH3-33/D4-23/JH4b | QVQLVESGGGVVQPGRSLRLSCAAS | GFTFSSYGMH | WVRQAPGKGLEWVA | VIWYDGSNKYYGDSVKG | RFTISRDNSKNTLYVQMNSLRAEDTAVYYCAR | ESDYGGNPYFDY | WGQGTLVTVSS |
| 4.8 | 202 | " | QVHLVESGGGVVQPGRSLRLSCAAS | GFTFSSYGMH | WVRQAPGKGLEWVA | VIWHDGSNKYYADSVKG | RFTISRDNSKNTLYLQMNSLRAEDTAVYYCTR | ESDYGYPYFDY | WGQGILATVSS |
| 4.4 | 194 | " | QVQLVESGGGVVQPGRSLRLSCAAS | GFTFSSYGMH | WVRQAPGKGLEWVA | VIWHDGSNKYYADSVKG | RFTISRDNSKNTLYLQMNSLRAEDTAVYYCTR | ESDYGGYPYFDY | WGQGILATVSS |
| 4.3 | 190 | " | QVQLVESGGGVVQPGRSLRLSCAAS | GFTFSSYGMH | WVRQAPGKGLEWVA | VIWYDGSNKYYADSVKG | RFTISRDNSKNTLYLQMNSLRAEDTAVYYCAR | ESDYGGNPYFDY | WGQGTLAAVSS |
| | 286 | Germline | EVQLVESGGGLIQPGGSLRLSCAAS | GFTVSSNYMS | WVRQAPGKGLEWVS | VIYSGGSTYYADSVKG | RFTISRDNSKNTLYLQMNSLRAEDTAVYYCAR | | WGQGTLVTVSS |
| 2.17 | 144 | VH3-53/D7-27/JH4b | EVQLVESGGGLIQPGGSLRLSCAAS | GFTVSSNYYN | WVRQAPGKGLEWVS | VIYNAGSAYYADSVKG | RFTISRDNSKNTLFLQMNSLRAEDTAVYYCAR | GTGAFDY | WGQGTLVTVSS |
| | 287 | Germline | QVQLVESGGGVVQPGRSLRLSCAAS | GFTFSSYGMH | WVRQAPGKGLEWVA | VISYDGSNKYYADSVKG | RFTISRDNSKNTLYLQMNSLRAEDTAVYYCAR | | WGQGTTVTVSS |
| 4.13 | 222 | VH3-30/D4-17/JH6b | QVQLVESGGGVVQPGRSLRLSCAAS | GFTFSSYDMH | WVRQAPGKGLEWVA | IISYDGSIKYYADSVKG | RFTISRDNSKNTLYLQMNSLRAEDTAVYYCAR | ENAVTYGGYYHYGMDV | WGQGTTVTVSS |
| | 288 | Germline | QVQLVESGGGLVKPGGSLRLSCAAS | GFTFSDYYMS | WIRQAPGKGLEWVS | YISSSGSTIYYADSVKG | RFTISRDNAKNSLYLQMNSLRAEDTAVYYCAR | | WGQGTTVTVSS |
| 1.1 | 84 | VH3-11/--/JH6b | QVQLVESGGGLVKPGGSLRLSCAAS | GFTFSDYYMS | WIRQAPGKGLEWVS | YISRSGSTIYYADSVKG | RFTISRDNAKNSLYLQMNSLRAEDTAVYYCAR | SLGGMDV | WGQGTTVTVSS |
| 2.16 | 140 | " | QVQLVESGGGLVKPGGSLRLSCAAS | GFTFSDYYMS | WIRQAPGKGLEWVS | YISRSGSTIYYADSVKG | RFTISRDNAKNSLYLQMNSLRAEDTAVYYCAR | SLGGMDV | WGQGTTVTVSS |
| 2.18 | 148 | " | QVQLVESGGGLVKPGGSLRLSCAAS | GFTFSDYYMS | WIRQAPGKGLEWVS | YISRSGSTIYYADSVKG | RFTISRDNAKNSLYLQMNSLRAEDTAVYYCAR | SLGGMDV | WGQGTTVTVSS |
| | 289 | Germline | QVQLVQSGAEVKKPGASVKVSCKAS | GFTFSSYGMH | WVRQAPGQGLEWMG | VIWYDGSNKYYADSVKG | RFTISRDNSKNTLYLQMNSLRAEDTAVYYCAR | | WGQGTTVTVSS |
| 4.12 | 218 | VH3-33/D4-17/JH6b | QVQLVQSGAEVKKPGASVKVSCKAS | GFTFSSYGMH | WVRQAPGQGLEWMG | VIWYDGSNKYYADSVKG | RFTISRDNSKNTLYLQMNSLRAEDTAVYYCAR | ETTVTKEGYYYYGMDV | WGQGTTVTVSS |
| 4.9 | 206 | " | QVQLVESGGGVVQPGRSLRLSCAAS | GFTFSSYGMH | WVRQAPGKGLEWVA | VIWYDGSNKYYADSVKG | RFTISRDNSKNTLYLQMNSLRAEDTAVYYCAR | ETTVTKEGYYYYGMDV | WGQGTTVTVSS |
| | 290 | Germline | QVQLVQSGAEVKKPGASVKVSCKAS | GYTFTSYGIS | WVRQAPGQGLEWMG | WISAYNGNTNYAQKLQG | RVTMTDTSTSTAYMELRSLRSDDTAVYYCAR | | WGQGTLVTVSS |
| 2.6 | 108 | VH1-18/D1-7/JH4b | QVQLVQSGAEVKKPGASVKVSCKAS | GYTFTSYGIS | WVRQAPGQGLEWMG | WISAYNVNTNYAQKLQG | RVTMTDTSTNTAYMELRSLRSDDTAVYYCAR | DPITETMEDYFDY | WGQGTLVTVSS |
| | 291 | Germline | EVQLVQSGAEVKKPGESLKISCKGS | GYSFTSYWIG | WVRQMPGKGLEWMG | IIYPGDSDTRYSPSFQG | QVTISADKSISTAYLQWSSLKASDTAMYYCAR | | WGQGTLVTVSS |
| 3.2 | 166 | VH5-51/D7-27/JH4b | EVQLVQSGAEVKKPGESLKISCKTS | GYSFTSYWIG | WVRQMPGKGLEWMG | IIYLGDSDTRYSPSFQG | QVTISADKSISTAYLQWSSLKASDTAMYYCAR | SNWGLDY | WGQGTLVTVSS |
| | 292 | Germline | QVQLVESGGGVVQPGRSLRLSCAAS | GFTFSSYGMH | WVRQAPGKGLEWVA | VIWYDGSNKYYADSVKG | RFTISRDNSKNTLYLQMNSLRAEDTAVYYCAR | | WGQGTTVTVSS |

| CHAIN NAME | SEQ ID NO: | | FR1 | CDR1 | FR2 | CDR2 | FR3 | CDR3 | FR4 |
|---|---|---|---|---|---|---|---|---|---|
| 4.16 | 234 | VH3-33/D2-21/JH6b | QVQLVESGGGVVQPGRSLRLSCTTS | GFTFSNYGMH | WVRQAPGKGLEWVA | VIWYDGSIKYYVDSVKG | RFTISRDNSKNTLYLQMNSLRAEDTAVYYCAR | EKDCGGDCYSHYGMDV | WGQGTTVTVSS |
| 4.15 | 230 | " | QVQLVESGGGVVQPGRSLRLSCTTS | GFTFSNYGMH | WVRQAPGKGLEWVA | VIWYDGSIKYYVDSVKG | RFTISRDNSKNTLYLQMNSLRAEDTAVYYCAR | EKDCGGDCYSHYGMDV | WGQGTTVTVSS |
| 4.14 | 226 | " | QVQLVESGGGVVQPGRSLRLSCTTS | GFTFSNYGMH | WVRQAPGKGLEWVA | VIWYDGSIKYYVDSVKG | RFTISRDNSKNTLYLQMNSLRAEDTAVYYCAR | EKDCGGDCYSHYGMDV | WGQGTTVTVSS |
| 4.17 | 238 | " | QVQLVESGGGVVQPGRSLRLSCTTS | GFTFSNYGMH | WVRQAPGKGLEWVA | VIWYDGSIKYYVDSVKG | RFTISRDNSKNTLYLQMNSLRAEDTAVYYCAR | EKDCGGDCYSHYGMDV | WGQGTTVTVSS |
| | 293 | Germline | QVQLVESGGGVVQPGRSLRLSCAAS | GFTFSSYGMH | WVRQAPGKGLEWVA | VIWYDGSNKYYADSVKG | RFTISRDNSKNTLYLQMNSLRAEDTAVYYCAR | | WGQGTTVTVSS |
| 2.1 | 88 | VH3-33/--/JH6b | QVQLVESGGDVVQPGRSLRLSCAAS | GFTFSSSGMH | WVRQAPGKGLEWVA | IIWYDGSNKYYADSVKG | RFTISRDNSKNTLYLQMNSLRAEDTAVYYCAR | DDYYYGMDV | WGQGTTVTVSS |
| | 294 | Germline | QVQLVESGGGVVQPGRSLRLSCAAS | GFTFSSYGMH | WVRQAPGKGLEWVA | VIWYDGSNKYYADSVKG | RFTISRDNSKNTLYLQMNSLRAEDTAVYYCAR | | WGQGTLVTVSS |
| 2.2 | 92 | VH3-33/D4-23/JH4a | QVQLVESGGGVVQPGRSLRLSCAAS | GFTFSSYGMH | WVRQAPGKGLEWVA | VIWYDGNNKYYADSVKG | RFTISRDNSKNTLYLQMNSLRAEDTAVYYCAR | ESDYGGNPYFDY | WGQGTLVTVSS |
| | 295 | Germline | QVQLQESGPGLVKPSETLSLTCTVS | GGSISSYYWS | WIRQPPGKGLEWIG | YIYYSGSTNYNPSLKS | RVTISVDTSKNQFSLKLSSVTAADTAVYYCAR | | WGQGTLVTVSS |
| 3.6 | 178 | VH4-59/D6-19/JH4b | QVQLQESGPGLVKPSETLSLTCTVS | GGSISSYYWS | WIRQPPGKGLEWIG | YFYYSGSTNYNPSLKS | RVTISVDTSKNQFSLKLRSVTAADTAVYYCAR | DRFTSGWPDY | WGQGTLVTVSS |
| | 296 | Germline | EVQLVESGGGLVQPGGSLRLSCAAS | GFTFSSYSMN | WVRQAPGKGLEWVS | YISSSSTIYYADSVKG | RFTISRDNAKNSLYLQMNSLRDEDTAVYYCAR | | WGQGTLVTVSS |
| 4.22 | 258 | VH3-48/D1-14/JH4b | EVQLVESGGGLVQPGGSLRLSCAAS | GFTFSNYGMH | WVRQAPGKGLRWVS | YISNSITSKYYADSVKG | RFTISRDNAKNSLYLQMNSLRDVDTAVHCAR | GPGGFDY | WGQGTLVTVSS |
| | 297 | Germline | EVQLVESGGGLIQPGGSLRLSCAAS | GFTVSSNYMS | WVRQAPGKGLEWVS | VIYSGGSTYYADSVKG | RFTISRDNSKNTLYLQMNSLRAEDTAVYYCAR | | WGQGTLVTVSS |
| 2.9 | 120 | VH3-53/--/JH4b | EVQLVESGGGLIQPGGSLRLSCAAS | GFTVSSNYMS | WVRQAPGKGLEWVS | VIYSGGGTYYADSVKG | RFTISRDNSKNTLYLQMNSLRAEDTAVYYCAR | GPGSFDY | WGQGTLVTVSS |
| | 298 | Germline | QVQLVQSGAEVKKPGASVKVSCKAS | GYTFTGYYMH | WVRQAPGQGLEWMG | WINPNSGGTNYAQKFQG | RVTMTRDTSISTAYMELSRLRSDDTAVYYCAR | | WGQGTTVTVSS |
| 3.1 | 162 | VH1-2/D6-19/JH6b | QVQLVQSGAEVKKPGASVKVSCKAS | GYTFTGYYMH | WVRQAPGQGLEWMG | WINPNSGGTNYAQKFQG | RVTMTRDTSISTAYMELSRLRSDDTAVYYCAR | APLWTVRSWYYYGMDV | WGQGTTVTVSS |
| | 299 | Germline | QVQLVESGGGVVQPGRSLRLSCAAS | GFTFSSYGMH | WVRQAPGKGLEWVA | VIWYDGSNKYYADSVKG | RFTISRDNSKNTLYLQMNSLRAEDTAVYYCAR | | WGQGTTVTVSS |
| 4.19 | 246 | VH3-33/D3-9/JH6b | QVQLVESGGGVVQPGRSLRLSCAAS | GFTFSSYGMH | WVRQAPGKGLEWVA | VIWYDGRNKYNADSVKG | RFTISRDNSKNTLNLQMNSLRAEDTAVYYCAR | DLTYDILGGMDV | WGQGTTVTVSS |
| 4.18 | 242 | " | QVQLVESGGGVVQPGRSLRLSCAAS | GFTFSSYGMH | WVRQAPGKGLEWVA | VIWYDGRNKYNADSVKG | RFTISRDNSKNTLNLQMNSLRAEDTAVYYCAR | DLTYDILGGMDV | WGQGTTVTVSS |
| 2.8 | 116 | " | QVQLVESGGGVVQPGRSLRLSCAAS | GFTFSSYGMH | WVRQAPGKGLEWVA | VIWYDGRNKYNADSVKG | RFTISRDNSKNTLNLQMNSLRAEDTAVYYCAR | DLTYDILGGMDV | WGQGTTVTVSS |

Table 33, 3

| CHAIN NAME | SEQ ID NO: | | FR1 | CDR1 | FR2 | CDR2 | FR3 | CDR3 | FR4 |
|---|---|---|---|---|---|---|---|---|---|
| 4.20 | 250 | " | QVQLVESGGGVVQPGRSLRLS CAAS | GFTFSSYGMH | WVRQAPGKGLE WVA | VIWYDGRNKYN ADSVKG | RFTISRDNSKNTLNLQMNSLR AEDTAVYYCAR | DLTYDILGGM DV | WGQGTTVTVSS |
| 2.7 | 112 | " | QVQLVESGGGVVQPGRSLRLS CAAS | GFTFSSYGMH | WVRQAPGKGLE WVA | VIWYDGRNKYN ADSVKG | RFTISRDNSKNTLNLQMNSLR AEDTAVYYCAR | DLTYDILGGM DV | WGQGTTVTVSS |
|  | 300 | Germline | EVQLVESGGGLIQPGGSLRLS CAAS | GFTVSSNYMS | WVRQAPGKGLE WVS | VIYSGGSTYYA DSVKG | RFTISRDNSKNTLYLQMNSLR AEDTAVYYCAR |  | WGQGTTVTVSS |
| 2.19 | 152 | VH3-53/--/JH6b | EVQLVESGGGLIQPGGSLRLS CAAS | GFTVSSNYMS | WVRQAPGKGLE WVS | VIYSGGSTYYA DSVKG | RFTISRDNSKNTLYLQMNSLR AEDTAVYYCAR | GEGGMDV | WGQGTTVTVSS |
| 2.15 | 136 | " | EVQLVESGGGLIQPGGSLRLS CAAS | GFTVSSNYMS | WVRQAPGKGLE WVS | VIYSGGSTYYA DSVKG | RFTISRDNSKNTLYLQMNSLR AEDTAVYYCAR | GEGGMDV | WGQGTTVTVSS |
|  | 301 | Germline | QVQLVESGGGVVQPGRSLRLS CAAS | GFTFSSYGMH | WVRQAPGKGLE WVA | VIWYDGSNKYY ADSVKG | RFTISRDNSKNTLYLQMNSLR AEDTAVYYCAR |  | WGQGTTVTVSS |
| 2.5 | 164 | VH3-33/D3-10/JH6b | QVQLVESGGGVVQPGRSLRLS CAAS | GFTFSSYDMH | WVRQAPGKGLE WVA | VIWYDGSNKYH ADSVKG | RFTISRDNSKNTLYLQMNSLR AEDTAVYYCAR | ENTMVRGGDYY YGMDV | WGQGTTVTVSS |
| 3.5 | 174 | " | QVQLVESGGGVVQPGRSLRLS CAAS | GFTFSSYDMH | WVRQAPGKGLE WVA | VIWYDGSNKYH ADSVKG | RFTISRDNSKNTLYLQMNSLR AEDTAVYYCAR | ENTMVRGGDYY YGMDV | WGQGTLVTVSS |
|  | 302 | Germline | QVQLVESGGGVVQPGRSLRLS CAAS | GFTFSSYGMH | WVRQAPGKGLE WVA | VIWYDGSNKYY ADSVKG | RFTISRDNSKNTLYLQMNSLR AEDTAVYYCAR |  | WGQGTLVTVSS |
| 4.10 | 210 | VH3-33/D4-17/JH5b | QVQLVESGGGVVQPGRSLRLS CAAS | GFTFSSYGMH | WVRQAPGKGLE WVA | VIWYDGSNKYY ADSVKG | RFTISRDNSKNTLYLQMNSLR AEDTAVYYCAR | SRYGDWGWFDP | WGQGTLVTVSS |
|  | 303 | Germline | QVQLVESGGGVVQPGRSLRLS CAAS | GFTFSSYGMH | WVRQAPGKGLE WVA | VIWYDGSNKYY ADSVKG | RFTISRDNSKNTLYLQMNSLR AEDTAVYYCAR |  | WGQGTTVTVSS |
| 4.21 | 254 | VH3-33/D6-19-D7-27/JH6b | QVQLVESGGGVVQPGRSLRLS CAAS | GFTFSSYGMH | WVRQAPGKGLE WVA | VIWYDGSNKYY ADSVKG | RFTISRDNSKNTLYLQMNSLR AEDTAVYYCAR | GNRVVVAGTRV TPANWGYYYG MDV | WGQGTTVTVSS |

Table 33, 4

Table 34. Hybridoma Light Chain Analysis AB-TNFα-XG2K

| CHAIN NAME | SEQ ID NO: | | FR1 | CDR1 | FR2 | CDR2 | FR3 | CDR3 | FR4 |
|---|---|---|---|---|---|---|---|---|---|
| 2.4 | 304 | Germline | QSVLTQPPSVSGAPGQRVTISC | TGSSSNIGAGYDVH | WYQQLPGTAPKLLIY | GNSNRPS | GVPDRFSGSKSGTSASLAITGLQAEDEADYYC | QSYDSSLSGSV | FGGGTKLTVL |
| | 102 | V1-13/JL2 | QSLLTQPPSVSGAPGQRVTISC | TGSSSNIGAGYDVH | WYQQFPGTAPKLLIY | GNSNRPS | GVPDRFSGSKSGTSASLAITGLQAEDEADYYC | QSYDSSLSGSV | FGGGTKLTVL |
| 4.7 | 200 | " | QSVLTQPPSVSGAPGLRVTISC | TGNSSNIGAGYDVH | WYQQLPGTAPKLLIY | GNSNRPS | GVPDRFSGSKSGTSASLAITGLQAEDETDYYC | QSYDSSLSGSV | FGGGTKLTVL |
| | 305 | Germline | DIQMTQSPSSLSASVGDRVTITC | RASQGIRNDLG | WYQQKPGKAPKRLIY | AASSLQS | GVPSRFSGSGSGTEFTLTISSLQPEDFATYYC | LQHNSYPLT | FGGGTKVEIK |
| 4.9 | 208 | A30/JK4 | DIQMTQSPSSLSASVGDRVTITC | RASQGIRNDLG | WYQQKPGKAPKRLIY | AASSLQS | GVPSRFSGSGSGTEFTLTISSLQPEDFATYYC | LQHNSYPLT | FGGGTKVEIK |
| 4.21 | 256 | " | DIQMTQSPSSLSASVGDRVTITC | RASQGIRNDLG | WYQQKPGKAPKCLIY | VASSLQS | GVPSRFSGSGSGTEFTLTISSLQPEDFATYYC | LQHNSYPLT | FGGGTKVEIK |
| 4.20 | 252 | " | DIQMTQSPSSLSASVGDRVTITC | RASQGIRHDLG | WYQQKPGKAPRRLIY | GASSLQS | GVPSRFSGSGSGTEFTLTISSLQPEDFATYYC | LQHNSYPLT | FGGGTKVEIK |
| 4.17 | 240 | " | DIQMTQSPSSLSASVGDRVTITC | RASQGIRNDLG | WYQQKPGKAPKRLIY | AASSLQS | GVPSRFSGSGSGTEFTLTISSLQPEDFATYYC | LQHMSLPLT | FGGGTKVEIK |
| 4.16 | 236 | " | DIQMTQSPSSLSASVGDRVTITC | RASQGIRNDLG | WYQQKPGKAPKRLIY | AASSLQS | GVPSRFSGSGSGTEFTLTISSLQPEDFATYYC | LQHMSLPLT | FGGGTKVEIK |
| 2.14 | 134 | " | DIQMTQSPSSLSASVGDRVTITC | RASQAIRNDLG | WYQQKPGKAPKRLIY | AASSLQS | GVPSRFSGSRSGTEFTLTISSLQPEDFASYYC | LQHRSYPLT | FGGGTKVEIK |
| 4.15 | 232 | " | DIQMTQSPSSLSASVGDRVTITC | RASQGIRNDLG | WYQQKPGKAPKRLIY | AASNFLS | GVPSRFSGSGSGTEFTLTISSLQPEDFTTYYC | LQHMSLPLT | FGGGTKVEIK |
| 3.9 | 188 | " | DIQMTQSPSSLSASVGDRVTITC | RASQGIRNDLG | WFQQKPGKAPKRLIY | AASSLQS | GVPSRFSGSGSGTEFTLTISSLQPEDFTTYYC | LQHNPYPPRLT | FGGGTKVEIK |
| 4.14 | 228 | " | DIQMTQSPSSLSASVGDRVTITC | RASQGIRNDLG | WYQQKPGKAPKRLIY | AASSLQS | GVPSRFSGSGSGTEFTLTISSLQPEDFTTYYC | LQHMSLPLT | FGGGTKVEIK |
| 4.13 | 224 | " | DIQMTQSPSSLSTSVGDRVTITC | RASQGIRNDLG | WYQQKPGKAPKRLIY | AASSLQS | GVPSRFSGSGSGTEFTLTISSLQPEDFTTYYC | LQHMSLPLT | FGGGTKVEIK |
| 4.12 | 220 | " | DIQMTQSPSSLSASVGDRVTITC | RASQGIRNDLG | WYQQKPGKAPKRLIY | AASSLQS | GVPSRFSGSGSGTEFTLTISSLQPEDFATYYC | LQHNSYPLT | FGGGTKVEIK |
| 2.10 | 126 | " | DIQMTQSPSSLSASVGDRVTITC | RASQGIRNDLG | WYQQKPGKAPKRLIY | AASSLQS | GVPSRFSGSGSGTEFTLTVSSLQPEDFATYYC | LQHNSLPLT | FGGGTKVEIK |
| 3.6 | 180 | " | DIQMTQSPSSLSASVGDRVTITC | RASQGIRNDLG | WYQQKPRKAPKRLIF | AASSLQS | GVPSRFSGSGSGPEFTLTISSLQPEDFATYYC | LQHNSYPLT | FGGGTKVEIK |
| 3.5 | 176 | " | DIQMTQSPSSLSASVGDRVTITC | RASQGIRNDLG | WYQQKPRKAPKRLIF | AASSLQS | GVPSRFSGSGSGPEFTLTISSLQPEDFATYYC | LQHNSYPLT | FGGGTKVEIK |

Table 34, 1

Table 34, 2

| CHAIN NAME | SEQ ID NO. | | FR1 | CDR1 | FR2 | CDR2 | FR3 | CDR3 | FR4 |
|---|---|---|---|---|---|---|---|---|---|
| 4.23 | 306 | Germline | DIQMTQSPSSLSASVGDRVTITC | RASQGISNYLA | WYQQKPGKVPKLLIY | AASTLQS | GVPSRFSGSGSGTDFTLTISSLQPEDVATYYC | QKYNSAPFT | FGPGTKVDIK |
|  | 264 | A20/JK3 | DIQMTQSPSSLSASVGDRVTITC | RASQGISNYLA | WYQQKPGKVPKFLIY | AASTLQS | GVPSRFSGSGSGTDFTLTVSSLQPEDVATYYC | QMYNSVPFT | FGPGTKVDIK |
|  | 307 | Germline | DIQMTQSPSSLSASVGDRVTITC | RASQGIRNDLG | WYQQKPGKAPKRLIY | AASSLQS | GVPSRFSGSGSGTEFTLTISSLQPEDFATYYC | LQHNSYPWT | FGQGTKVEIK |
| 4.22 | 260 | A30/JK1 | DIQMTQSPSSLSASVGDRVTITC | RASQGIRNDLG | WYQQKPGKAPKCLIY | VASSLQS | GVPSRFSGSGSGTEFTLTISSLQPEDFATYYC | LQHNSYPWT | FGQGTKVEIK |
|  | 308 | Germline | DIQMTQSPSSLSASVGDRVTITC | RASQSISSYLN | WYQQKPGKAPKLLIY | AASSLQS | GVPSRFSGSGSGTDFTLTISSLQPEDFATYYC | QQSYSTPIT | FGQGTRLEIK |
| 2.16 | 142 | O12/JK5 | DIQMTQSPSSLSASVGDRVAITC | RTSQSISSYLN | WYQQKPGKAPELLIY | AASNLQS | GVPSRFSGSGSGTDFTLTISSLQPEDFATYYC | QQSSSTLIT | FGQGTRLEIK |
| 2.19 | 156 | " | DIQMTQSPSSLSASVGDRVTITC | RTSQSISSYLN | WYQQKPGKAPEVLIY | AASNLQR | GVPSRFSGSGSGTDFTLTISSLQPEDFATYYC | QQSSSTLIT | FGQGTKLTVL |
| 2.18 | 150 | " | DIQMTQSPSSLSASVGDRVTITC | RTSQSISSYLN | WYHQKPGKAPELLIY | AAFNLQS | GVPSRFSGSGSGTDFTLTISSLQPEDFATYYC | QQSSSTLIT | FGQGTKLTVL |
| 2.21 | 160 | " | DIQMTQSPSSLSASVGDRVTITC | RTSQSISSYLN | WYQQKPGKAPELLIY | AAFNLQS | GVPSRISGSGSGTDFTLTISSLHPEDFATYYC | QQSSSTLIT | FGQGTRLEIK |
|  | 309 | Germline | QSVLTQPPSVSAAPGQKVTISC | SGSSSNIGNNYVS | WYQQLPGTAPKLLIY | DNNKRPS | GIPDRFSGSKSGTSATLGITGLQTGDEADYYC | GTWDSSLSAGV | FGGGTKLTVL |
| 3.1 | 164 | V1-19/JL3 | QSVLTQPPSMSAAPGQKVTISC | SGSSSNIGNNYVS | WYQQLPGIAPKLLIY | DNNKRPS | GIPDRFSGSKSGTSATLGITGLQTGDEADYYC | GTWDSSLSAGV | FGGGTKLTVL |
| 1.1 | 86 | " | QSVLTQPPSVSAAPGQKVTISC | SGSSSNIGNNYVS | WYQQFPGTAPKLLIY | DNNRRPS | GIPDRFSGSKSGTSATLGITGLQTGDEADYYC | GTWDSSLSAGV | FGGGTKLTVL |
|  | 310 | Germline | EIVMTQSPATLSVSPGERATLSC | RASQSVSSNLA | WYQQKPGQAPRLLIY | GASTRAT | GIPARFSGSGSGTEFTLTISSLQSEDFAVYYC | QQYNNWPIT | FGQGTRLEIK |
| 3.8 | 184 | L2/JK5 | EIVMTQSPATLSVSPGERVTLSC | RASQSATSNLA | WYQQKPGQAPRLLIY | GASTRAT | GIPARFSGSGSGTEFTLTISSLQSEDFAVYYC | QQYNWMPFT | FGQGTRLEIK |
|  | 311 | Germline | QSVLTQPPSVSAAPGQKVTISC | SGSSSNIGNNYVS | WYQQLPGTAPKLLIY | DNNKRPS | GIPDRFSGSKSGTSATLGITGLQTGDEADYYC | GTWDSSLSAGV | FGGGTKLTVL |
| 2.1 | 90 | V1-19/JL2 | QSALTQPPSVSAAPGQKVTISC | SGSSSNIGSNYVS | WCQQLRTAPKLLIY | DNNKRPS | GIPDRFSGSKSGTSATLVITGLQTGDEADYYC | GAWDSSLSAGV | FGGGTKLTVL |
|  | 312 | Germline | DIQMTQSPSSASVGDRVTITC | RASQGISSWLA | WYQQKPGKAPKLLIY | AASSLQS | GVPSRFSGSGSGTDFTLTISSLQPEDFATYYC | QQANSPWT | FGQGTKVEIK |
| 2.9 | 122 | L5/JK1 | DIQMTQSPSSVSASVGDRVTITC | RASQGISSWLA | WYQQKPGKAPKLLIY | AASSLQS | GVPSRFSGSGSGTDFTLTISSLQPEDFASYYC | QQANSPWT | FGQGTKVEIK |

| CHAIN NAME | SEQ ID NO: | | FR1 | CDR1 | FR2 | CDR2 | FR3 | CDR3 | FR4 |
|---|---|---|---|---|---|---|---|---|---|
| | 313 | Germline | EIVMTQSPATLSVSPGERATLSC | RASQSVSSNLA | WYQQKPGQAPRLLIY | GASTRAT | GIPARFSGSGSGTEFTLTISSLQSEDFAVYYC | QQYNNWPLT | FGGGTKVEIK |
| 4.11 | 216 | L2/JK4 | EIVMTQSPATLSVSPGERATLSC | RASQSVISNLA | WYQQQPGQAPRLLIY | GASTRAT | GFPARFSGSGSGTEFTLTISSLQSEDFAVYYC | QQYNNWPLT | FGGGTKVEIK |
| 2.17 | 146 | " | EIVMTQSPATLSVSPGERATLSC | RASQSVSSNLA | WYQQKPGQAPRLLIY | GASTRAT | GIPARFSGSGRTGTEFTLTISSLQSEDFAVYYC | QQYNNWPLT | FGGGTKVEIK |
| | 314 | Germline | EIVMTQSPATLSVSPGERATLSC | RASQSVSSNLA | WYQQKPGQAPRLLIY | GASTRAT | GIPARFSGSGSGTEFTLTISSLQSEDFAVYYC | QQYNNWPFT | FGPGTKVDIK |
| 4.18 | 244 | L2/JK3 | EIVMTQSPATLSVSPGERATLSC | RASQSVTSNLA | WYQQKPGQAPRLLIY | GASTRAT | GIPARFSGSGSGTEFTLTISSLPSEDFAVYYC | QQYHTWPFT | FGPGTKVDIK |
| 2.15 | 138 | " | EIVMTQSPSTLSVSPGERATLSC | RASQSVSSNLA | WYQQKPGQAPRLLIY | GASIRAT | GIPARFSGSGSGTEYTLTISSLQSEDFAVYYC | QQYNNWPFT | FGPGTKVDIK |
| 4.19 | 248 | " | EIVMTQSPSTLSVSPGERATLSC | RASQSVTSNLA | WYQQKPGQAPRLLIY | GASTRAT | GIPARFSGSGSGTEFTLTISSLPSEDFAVYYC | QQYHTWPFT | FGPGTKVDIK |
| | 315 | Germline | QSVLTQPPSASGTPGQRVTISC | SGSSSNIGSNTVN | WYQQLPGTAPKLLIY | SNNQRPS | GVPDRFSGSKSGTSASLAISGLQSEDEADYYC | AAWDDSLNGPV | FGGGTKLTVL |
| 4.10 | 212 | V1-16/JL3 | QSVLTQPPSASGTPGQRVTISC | SGSSSNIGSNTVN | WYQQLPGTAPKLLIY | SNNQRPS | GVPDRFSGSKSGTSASLAISGLQSEDEADYYC | AAWDDSLNGPV | FGGGTKLTVL |
| | 316 | Germline | SSELTQDPAVSVALGQTVRITC | QGDSLRSYYAS | WYQQKPGQAPVLVIY | GKNNRPS | GIPDRFSGSSSGNTASLTITGAQAEDEADYYC | NSRDSSGNHLV | FGGGTKLTVL |
| 2.5 | 106 | V2-13/JL3 | SSELTQDPAVSVALGQTVRITC | QGDSLRRYYAS | WYQQKPGQAPILVIY | GKNNRPS | GIPDRFSGSSSGNTASLTITGAQAEDEADYYC | NSRDSSGNHLV | FGGGTKLTVL |
| 3.4 | 172 | " | SSELTQDPAVSVALGQTVRITC | QGDSLRRYYAS | WYQQKPGQAPILVIY | GKNNRPS | GIPDRFSGSSSGNTASLTITGAQAEDEADYYC | NSRDSSGNHLV | FGGGTKLTVL |
| | 317 | Germline | SYELTQPPSVSVSPGQTARITC | SGDALPKKYAY | WYQQKSGQAPVLVIY | EDSKRPS | GIPERFSGSSSGTMATLTISGAQVEDEADYYC | YSTDSSGNHVV | FGGGTKLTVL |
| 2.19 | 154 | V2-7/JL2 | SYELTQPPSVSVSPGQTARITC | SGDALPKKYVY | WYQQKSGQAPVLVIY | EDSKRPS | GIPERFSGSSSGTMATLTINGAQVEDEADYYC | YSTDSSGNHVV | FGGGTKLTVL |
| | 318 | Germline | DIQMTQSPSSLSASVGDRVTI TC | QASQDISNYLN | WYQQKPGKAPKLLIY | DASNLET | GVPSRFSGSGSGTDFTFTISSLQPEDIATYYC | QQYDNLPIT | FGQGTRLEIK |
| 2.13 | 130 | O18/JK5 | DIQMTQSPSSLSASVGDRVTI TC | QASQDISNYLN | WYQQKPGKAPKLLIY | DASNLET | GVPSRFSGSGSGTDFTFTISSLQPEDIATYYC | HQCDNLPH | FGQGTRLEIK |
| | 319 | Germline | SSELTQDPAVSVALGQTVRITC | QGDSLRSYYAS | WYQQKPGQAPVLVIY | GKNNRPS | GIPDRFSGSSSGNTASLTITGAQAEDEADYYC | NSRDSSGNHVV | FGGGTKLTVL |
| 2.3 | 98 | V2-13/JL2 | SSELTQDPAVSVALGQTVRITC | QGDSLRIYYAS | WYQQKPGQAPVLVIY | GKNNRPS | GIPDRFSGSSSGNTASLTVTGAQAEDEADYYC | KSRDSSFNHVT | FGGGTKLTVL |
| 2.6 | 110 | " | SSELTQDPAVSVALGQTVRITC | QGDSLRMYYAS | WYQQKPGQAPILVIY | GKNNRPS | GIPDRFSGSSSGNTASLTITGAQAEDEADYYC | NSRDSSGNHVT | FGGGTKLTVL |
| 4.3 | 192 | " | SSELTQDPAVSVALGQTVRITC | QGDSLRSYYAS | WYQQKPGQAPVLVIY | GKNNRPS | GIPDRFSGSSSENTASLTITGAQAEDEADYYC | KSRDSSFNHVT | FGGGTKLTVL |

Table 34, 3

| CHAIN NAME | SEQ ID NO: | | FR1 | CDR1 | FR2 | CDR2 | FR3 | CDR3 | FR4 |
|---|---|---|---|---|---|---|---|---|---|
| 4.8 | 204 | " | SSELTQDPAVSVALGQTVRITC | QGDILRSYYAS | WYQQKPGQAPILVIY | GKNNRPS | GIPDRFSGSSSGNTASLTITGAQAEDEADYYC | KSRDSSYNHVT | FGGGTKLTVL |
| 2.8 | 118 | " | SSELTQDPAVSVALGQTVRITC | QGDSLRRYYAS | WYQQKPGQAPIVVIY | GKKNRPS | GIPDRFSGSSSGNTASLTITGAQAEDEADYYC | KSRDSSGNHVT | FGGGTKLTVL |
| 2.2 | 94 | " | SSELTQDPAVSVALGQTVRITC | QGDSLRSYYAS | WYQQRPGQAPVLVIY | GRNNRPS | GIPDRFSGSSSGLTASLTVTGAQAEDEADYYC | NSRDSSYNHVA | FGGGTKLTVL |
| 4.4 | 196 | " | SSELTQDPAVSVALGQTVRITC | QGDILRSYYAS | WYQQKPGQAPVLVIY | GKNNRPS | GIPDRFSGSSSGNTASLTITGAQAEDEADYYC | KSRDSSYNHVT | FGGGTKLTVL |
| | 320 | Germline | QSVLTQPPSVSGAPGQRVTISC | TGSSSNIGAGYDVH | WYQQLPGTAPKLLIY | GNSNRPS | GVPDRFSGSKSGTSASLAITGLQAEDEADYYC | QSYDSSLSGSV | FGGGTKLTVL |
| 3.2 | 168 | V1-13/JL3 | QSVLTQPPSVSGAPGQRVTISC | TGSSSNIGAGYDVH | WYQQFPGTAPKLLIQ | GNSNRPS | GVPDRFSGSKSGTSASLAITGLQAEDEADYYC | QSYDSSLSGSV | FGGGTKLTVL |
| 2.7 | 114 | " | QSVLTQSPSVSGAPGQRVTISC | TGSSSNIGAGYDVH | WYQQLPGTAPRLLIY | GNNNRPS | GVPDRFSGSKSGTSASLAITGLQAEDEADYYC | QSYDSSLSGSV | FGGGTKLTVL |

Table 34, 4